United States Patent [19]
Guthrie et al.

[11] Patent Number: 5,344,843
[45] Date of Patent: Sep. 6, 1994

[54] CAT-1 INHIBITORS, PHARMACEUTICAL COMPOSITIONS AND METHODS OF USE

[75] Inventors: Robert W. Guthrie, Saddle Brook; John G. Mullin, Jr., Hawthorne, both of N.J.; David F. Kachensky, Milford, Pa.; Richard W. Kierstead, North Caldwell, N.J.; Jefferson W. Tilley, North Caldwell, N.J.; Guy P. Heathers, Morristown, N.J.; Alan J. Higgins, Upper Montclair, N.J.; Ronald A. LeMahieu, North Caldwell, N.J.

[73] Assignee: Hoffman-La Roche Inc., Nutley, N.J.

[21] Appl. No.: 850,620

[22] Filed: Mar. 13, 1992

Related U.S. Application Data

[63] Continuation-in-part of Ser. No. 698,014, May 9, 1991, abandoned.

[51] Int. Cl.⁵ .................... A61K 31/19; A61K 31/38; C07C 65/40; C07D 333/32
[52] U.S. Cl. .................... 514/473; 514/277; 514/306; 514/307; 514/336; 514/337; 514/461; 514/471; 514/472; 514/561; 514/562; 514/563; 514/570; 514/571; 546/143; 546/147; 546/167; 546/171; 546/172; 546/174; 546/284; 546/300; 546/301; 549/64; 549/65; 549/66; 549/68; 549/69; 549/72; 549/77; 549/79; 562/435; 562/443; 562/444; 562/449; 562/450; 562/452; 562/463; 562/460; 562/490; 562/492; 562/495; 562/496
[58] Field of Search ............ 549/65, 68, 69, 494, 549/63, 64, 478, 479, 480, 488, 483, 484; 560/39; 562/443, 441, 459, 463, 464, 435, 444, 450, 452, 460, 490, 492, 495, 496; 514/465, 538, 539, 471, 473, 471, 472, 277, 306, 307, 336, 337; 546/147, 167, 174

[56] References Cited

U.S. PATENT DOCUMENTS

| | | | |
|---|---|---|---|
| 3,969,119 | 7/1976 | Muzyczko et al. | 96/115 R |
| 4,018,921 | 4/1977 | Gleason | 424/246 |
| 4,304,930 | 12/1981 | Palosi et al. | 562/465 |
| 4,393,008 | 7/1983 | Palosi et al. | 260/465 D |
| 4,675,439 | 6/1987 | Mita et al. | 562/444 |
| 4,814,339 | 3/1989 | Rotondo | 514/332 |
| 5,004,817 | 4/1991 | Bastioli et al. | 549/557 |
| 5,070,087 | 12/1991 | Teng et al. | 514/212 |

FOREIGN PATENT DOCUMENTS

| | | |
|---|---|---|
| 2027306 | 4/1991 | Canada . |
| 331085 | 9/1989 | European Pat. Off. . |
| 0422597 | 4/1991 | European Pat. Off. . |
| 2950608 | 10/1980 | Fed. Rep. of Germany . |

OTHER PUBLICATIONS

Elkaschief et al., Chemical Abstracts, vol. 83 (1975) 429944e.

Chemical Abstracts, vol. 88 (1977) 104914j.

*Primary Examiner*—Richard L. Raymond
*Attorney, Agent, or Firm*—George M. Gould; George W. Johnston; Robert A. Silverman

[57] ABSTRACT

The invention relates to compounds of the formula

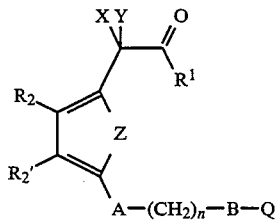

I wherein $R_1$, $R_2$, $R_2'$ X, Y, Z, A, B, Q and n are as described herein. Their pharmaceutically acceptable salts, and when appropriate, enantiomers, racemates, diastereomers or mixtures thereof or geometric isomer or mixtures thereof, and pharmaceutically acceptable salts thereof. The compounds of formula I inhibit enzyme carnitine acyltransferase 1 (CAT-1) and are therefore useful in the prevention of injury to ischemic tissue, and can limit infarct size, improve cardiac function and prevent arrhythmias during and following a myocardial infarction.

38 Claims, No Drawings

OTHER PUBLICATIONS

Bouzard et al., Chemical Abstracts, vol. 88 (1977) 105365t.
Cross et al., Chemical Abstracts, vol. 95 (1981) 169183j.
Hilball et al., Chemical Abstracts, vol. 98 (1983) 198224r.
Domagala, Tetrahedron Letters, vol. 21 (1980) pp. 4997–5000.
W. Foye, "Principles of Medicinal Chemistry" 2nd ed., p. 80, Lea & Febiger, Philadelphia (1981).
Patent Abstract of Japan, vol. 12, No. 333 (C-526)(3180) for JP-A-63 096 152 (Canon Inc.) Apr. 27, 1988.
J. Mol. Cell Cardiol., 19 509–520 (1987).
Am. J. Cardiol. 48: 702–710.
Life Science vol. 27, pp. 963–970.
Basic Res. Cardiol. 81: 258–266 (1986).
Biochem. Biophys. Res. Commun: 100,, 291–296 (1981).
Proceedings of the B.P.S. Apr. 4th–6th 1979, 443P–444P.
Life Sciences, vol. 29, pp. 1847–1853 (1980).
Naunyn–Schmiedeberg's Arch. Pharmacol. (1984) 327: 70–74.
J. Med. Cell Cardiol 17, 619–625 (1985).
Research Commun. in Chem. Path. and Pharmacology vol. 26, No. 3, Dec. 1979.
Basic Res. Cardiol. 78, 19–27 (1983).
J. Moll Cell. Cardiol 20, 277–282 (1988).
G. M. Salituro et al., J. Am. Chem. Soc., Total Synthesis of (−) —Nocardicins A–G; A Biogenetic Approach 112(2) pp. 760–770 (1990).
W. D. Sprung et al., Pharmazie, Zur Synthese p-substitiuester DL-2-Phenylglycinocyylester, 44 (48), pp. 540–542 (1989).
T. W. Greene, Protective Groups in Organic Synthesis, pp. 249 and 330, John Wiley & Sons, New York (1981).
I. T. Barnish et al., *J. Med. Chem.*, Promotion of Carbohydrate Oxidation in the Heart by Some Phenylglyoxylic Acids, 24, pp. 399–404 (1981).
E. M. Gordon et al., *J. Org. Chem.*, 44, No. 8, pp. 1218–1221 (1979).

CAT-1 INHIBITORS, PHARMACEUTICAL COMPOSITIONS AND METHODS OF USE

CROSS REFERENCE TO RELATED APPLICATIONS

This application is a continuation-in-part of U.S. application Ser. No. 07/698,014, filed May 9, 1991 now abandoned.

BRIEF SUMMARY OF THE INVENTION

The invention relates to compounds of the formula

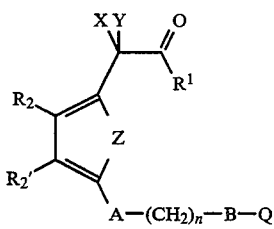

wherein $R_1$ is hydroxy, $OR_3$ or

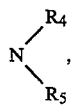

wherein one of $R_4$ or $R_5$ is hydrogen, lower alkyl or hydroxy-lower alkyl, and the other is hydrogen, hydroxy, lower alkyl or lower alkoxy, and wherein $R_3$ is

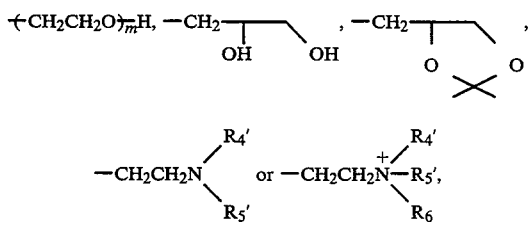

and wherein $R_4'$, $R_5'$, and $R_6$ are, independently, hydrogen, lower alkyl or hydroxy lower alkyl, and wherein m is an integer from 1 to 4;

$R_2$ and $R_2'$, independently, are hydrogen, lower alkyl, aryl, aryl-lower alkyl, lower alkoxy, hydroxy, amino, lower alkylamino and di-lower alkylamino, cyano, halogen, mercapto, lower alkylthio, lower alkylsulfinyl, lower alkylsulfonyl, trihalo-lower alkyl, acyl or nitro;

A is a bond,

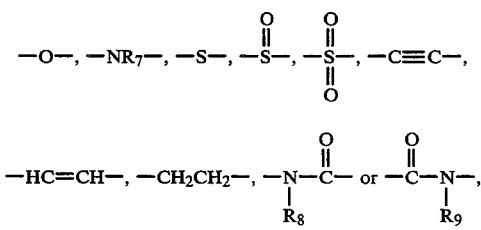

wherein $R_7$ is hydrogen, lower alkyl or acyl and $R_8$ and $R_9$ are, independently, hydrogen or lower alkyl; n is an integer from 0 to 10;

B is a bond,

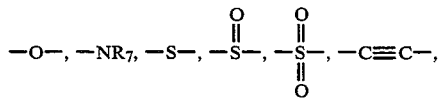

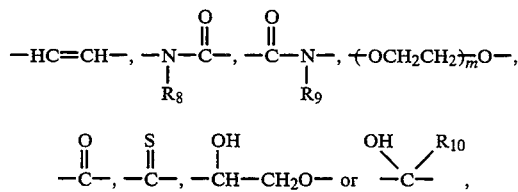

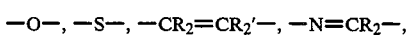

wherein $R_7$, $R_8$, $R_9$ and m are defined as above and $R_{10}$ is hydrogen or lower alkyl;

Z is $$-O-, -S-, -CR_2=CR_2'-, -N=CR_2-,$$

$$-CR_2=N- \text{ or } \diagdown N-R_{11}\diagup$$

wherein $R_{11}$ is hydrogen or lower alkyl;

X and Y taken together are O=, S=, hydroxyimino, alkyloxyimino, alkenyloxyimino, arylalkoxyimino, hydrazono, mono-lower alkyl hydrazono, di-lower alkyl hydrazono or semicarbazono, or, independently, when one of X or Y is halogen, the other is hydrogen, halogen, lower alkyl or aryl-lower alkyl; or when one of X or Y is amino, lower alkylamino or di-lower alkylamino, the other is hydrogen, lower alkyl or aryl-lower alkyl; or when one of X or Y is hydroxy, alkoxy or aryl-lower alkoxy, the other is hydrogen, hydroxy, lower alkyl, lower alkoxy or aryl-lower alkoxy; Q is a cycloalkyl, aryl or heterocyclic radical; provided that, when A is oxygen (O) and B is a bond, sulfur (S) or oxygen (O), then n is 2–10; and, when a basic or acidic group is present, their pharmaceutically acceptable salts, and, when appropriate, enantiomers, racemates, diastereomers or mixtures thereof or geometric isomers or mixtures thereof, and pharmaceutically acceptable salts thereof.

The compounds of formula I inhibit the enzyme carnitine acyltransferase 1 (CAT-1) and are therefore useful in the prevention of injury to ischemic tissue, and can limit infarct size, improve cardiac function and prevent arrhythmias during and following a myocardial infarction.

In another aspect, the invention relates to pharmaceutical compositions and methods of use comprising the compounds of formula I.

BACKGROUND OF THE INVENTION

The enzyme carnitine acyltransferase 1 (CAT-1) resides on the inner face of the outer mitochondrial membrane and is responsible for converting acyl-CoA into carnitine esters for the purpose of transporting acyl groups into the mitochondria for beta-oxidation. During ischemia or hypoxia, beta-oxidation is inhibited by the high mitochondrial redox potential, which results in a build-up of long-chain acylcarnitines (LCA) in the cytosol. LCA, in turn, has been shown to mediate a number of deleterious events in ischemic tissue. These include activation of calcium channels, increase in cytosolic calcium and electrophysiological derangements resulting from their incorporation into the sarcolemma of the cardiac myocyte. Thus CAT-I inhibitors can prevent injury to ischemic tissue, i.e., can limit infarct size, improve cardiac function and prevent arrhythmias during and following a myocardial infarction.

DETAILED DESCRIPTION OF THE INVENTION

The invention relates to compounds of the formula

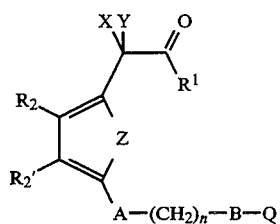

wherein $R_1$ is hydroxy, $OR_3$ or wherein one of $R_4$ or $R_5$ is hydrogen, lower alkyl or hydroxy-lower alkyl, and the other is hydrogen, hydroxy, lower alkyl or lower alkoxy, and wherein $R_3$ is wherein $R_4'$, $R_5'$, and $R_6$ are independently, hydrogen, lower alkyl or hydroxy lower alkyl, and wherein m is an integer from 1 to 4;

$R_2$ and $R_2'$, independently, are hydrogen, lower alkyl, aryl, aryl-lower alkyl, lower alkoxy, hydroxy, amino, mono- and disubstituted amino, cyano, halogen, mercapto, lower alkylthio, lower alkylsulfinyl, lower alkylsulfonyl, trihalo-lower alkyl, acyl or nitro;

A is a bond,

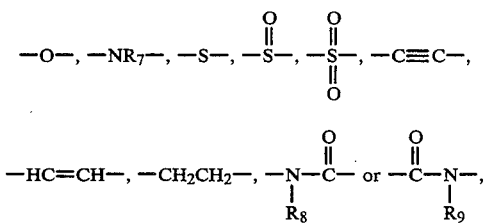

wherein $R_7$ is hydrogen, lower alkyl or acyl and $R_8$ and $R_9$ are, independently, hydrogen or lower alkyl; n is an integer from 0 to 10;

B is a bond, wherein $R_7$, $R_8$, $R_9$ and m are defined as above and $R_{10}$ is hydrogen or lower alkyl;

Z is wherein $R_{11}$ is hydrogen or lower alkyl;

X and Y taken together are O=, S=, hydroxyimino, alkyloxyimino, alkenyloxyimino, arylalkoxyimino, hydrazono, mono-lower alkyl hydrazono, di-lower alkyl hydrazono or semicarbazono, or, independently, when one of X or Y is halogen, the other can be hydrogen, halogen, lower alkyl or aryl-lower alkyl; or when one of X or Y is amino, lower alkylamino or di-lower alkylamino, the other can be hydrogen, lower alkyl or aryl-lower alkyl; or when one of X or Y is hydroxy, alkoxy or aryl-lower alkoxy, the other is hydrogen, hydroxy, lower alkyl, lower alkoxy or aryl-lower alkyl; Q is a cycloalkyl, aryl or heterocyclic radical; provided that, when A is oxygen (O) and B is a bond, sulfur (S) or oxygen (O), then n is 2-10; and, when a basic or acidic group is present, their pharmaceutically acceptable salts, and, where appropriate, enantiomers, racemates, diastereomers or mixtures thereof or geometric isomer or mixtures thereof, and pharmaceutically acceptable salts thereof.

As used herein, the term "alkyl" denotes a straight or branched chain saturated hydrocarbon containing 1 to 16 carbon atoms, preferably from 1 to 10 carbon atoms, for example, methyl, ethyl, propyl, isopropyl, butyl, t-butyl, neopentyl, pentyl, hexyl, heptyl, octyl, nonyl, decyl, undecyl, dodecyl, tridecyl, tetradecyl, pentadecyl, hexadecyl and the like. The term "lower alkyl" denotes a straight or branched chain saturated hydrocarbon containing 1 to 7 carbon atoms. In the term "hydroxyalkyl", the alkyl group is as described above. The term "alkoxy" denotes an alkyl ether group in which the alkyl group is as described above, for example, methoxy, ethoxy, propoxy, pentoxy, hexoxy, heptoxy, octoxy, nonoxy, decoxy, undecoxy, tridecoxy, tetradecoxy, hexadecoxy and the like. The term "lower alkoxy" denotes an alkyl ether group in which the alkyl group contains 1 to 7 carbon atoms. In the term "hydroxyalkoxy", the alkoxy group is as described above. In the term "alkoxyalkyl", the alkoxy and alkyl groups are as described above. The term "lower alkylthio" denotes a lower alkylthio ether group in which the lower alkyl group is as described, for example, methylthio, ethylthio, isopropylthio, propylthio, butylthio, pentylthio, heptylthio and the like. The term "alkenyl" denotes a straight or branched olefinic hydrocarbon containing 2 to 12 carbon atoms, preferably from 2 to 6 carbon atoms, for example, vinyl, allyl, butenyl, pentenyl, nonenyl, dodecenyl and the like. The term "alkenyloxy" denotes an alkenyl ether group, wherein the alkenyl group is as previously described, for example, allyloxy, pentenyloxy, octenyloxy and the like. The term "aryl" preferably denotes a mono-, bi- or tricyclic aromatic hydrocarbon radical, for example, phenyl, naphthyl, 1,1'-biphenyl, anthracenyl, phenanthrenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl and the like, which radical may be unsubstituted or mono-, di- or tri-substituted, independently, by a radical selected from alkyl, alkoxy, acyloxy, halogen, acyloxyalkyl, alkoxyalkyl, arylalkyl, arylalkoxy, aryloxyalkyl, aryloxy, alkoxy, alkoxyalkoxy, hydroxy, hydroxyalkyl, hydroxyalkoxy, amino, lower alkylamino or di-lower alkylamino, cyano, nitro, mercapto, alkylthio, alkylsulfinyl, alkylsulfonyl, trihaloalkyl, sulfamoyl, N-alkylsulfamoyl, N,N-dialkylsulfamoyl, carboxycarbonyl, alkoxalyl (which has the formula $R_{12}O-C(O)-C(O)-$, wherein $R_{12}$ is alkyl as described earlier), phenyl or phenyl mono-, di-or tri-substituted, independently, by a radical selected from lower alkyl, lower alkoxy, halogen and trifluoromethyl. Exemplary of such aryl radicals are unsubstituted phenyl, naphthyl or 1,1'-biphenyl or, mono-, di- or trisubstituted independently, by a radical select from halogen, alkyl, alkoxy, acyloxyalkyl, phenyl and substituted phenyl, and trihaloalkyl. The term "aryloxy" denotes an unsubstituted or substituted aromatic hydrocarbon ether, in which the aryl group is defined as above. In the terms "arylalkyl", "arylalkoxy", "aryloxyalkyl" and "aryloxyalkoxy", the aryl, aryloxy, alkyl and alkoxy groups are as described above. The term "halogen" denotes all the halogen, that is, bromine, chlorine, flourine and iodine.

The term "acyl" denotes an "alkanoyl" group, derived from an aliphatic carboxylic acid of 1 to 7 carbon atoms, for example, formyl, acetyl, propionyl and the like; or an "aroyl" group derived from an aromatic carboxylic acid, such as, benzoyl and the like. The term "acyloxy" denotes an "alkanoyloxy" group, derived from an aliphatic carboxylic acid of 1 to 7 carbon atoms, for example, formyloxy, acetyloxy, propionyloxy and the like. In the term "acyloxyalkyl", the terms acyloxy and alkyl are as described above. The term "cycloalkyl" denotes a cyclic radical of 3 to 10 carbon atoms, for example, cyclopropyl, cyclobutyl, cyclohexyl, cycloheptyl, cyclooctyl, adamantyl and the like. The term "heterocyclic radical" denotes a monocyclic 5-, 6- or 7-membered heterocyclic or bi- or tricyclic heterocyclic radical containing one or more hetero atoms selected from nitrogen, oxygen or sulfur, which radical may be unsubstituted or substituted, independently, by one or more groups selected from alkyl, alkoxy, acyloxy, halogen, acyloxyalkyl, alkoxyalkyl, arylalkyl, arylalkoxy, aryloxyalkyl, aryloxyalkoxy, alkoxyalkoxy, hydroxy, hydroxyalkyl, hydroxyalkoxy, amino, lower alkylamino or di-lower alkylamino, cyano, nitro, mercapto, alkylthio, alkylsulfinyl, alkylsulfonyl, trihaloalkyl, sulfamoyl, N-alkylsulfamoyl, N,N-dialkylsulfamoyl, carboxycarbonyl, alkoxalyl (which has the formula $R_{12}O-C(O)-C(O)-$, wherein $R_{12}$ is alkyl, as described earlier), phenyl or phenyl mono-, di- or tri-substituted, independently, by a radical selected from lower alkyl lower alkoxy, halogen and trifluoromethyl and the like. Exemplary of such heterocyclic radicals are pyridinyl, pyrimidyl, imidazolinyl, piperidinyl, morpholinyl, thienyl, furanyl, quinolyl, isoquinolyl, benzothienyl, indolyl, benzofuranyl, carbazolyl, chromanyl, isochromanyl, chromenyl, isochromenyl, naphthothienyl, phenothiazinyl, xanthenyl and the like.

A preferred group of compounds of formula I is one wherein $R_1$ is as previously described;

$R_2$ and $R_2'$, independently, are hydrogen, alkyl, aryl, alkoxy, hydroxy, halogen, alkanoyl, aroyl or nitro;

A is a bond, $$-O-, -NR_7-, -S-, -\overset{O}{\underset{\|}{S}}-, -\overset{O}{\underset{\underset{\|}{O}}{S}}-, -C{\equiv}C-,$$

$$-HC{=}CH-, -CH_2CH_2-, -\underset{R_8}{\overset{O}{\underset{\|}{N-C}}}- \text{ or } -\underset{R_9}{\overset{O}{\underset{\|}{C-N}}}-,$$

wherein $R_7$ is hydrogen, lower alkyl or acyl and $R_8$ and $R_9$ are independently hydrogen or lower alkyl;

B is a bond $$-O-, -NR_7-, -S-, -C{\equiv}C-, -HC{=}CH-,$$

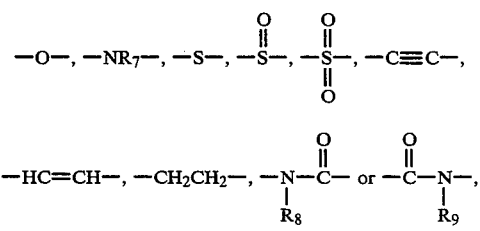

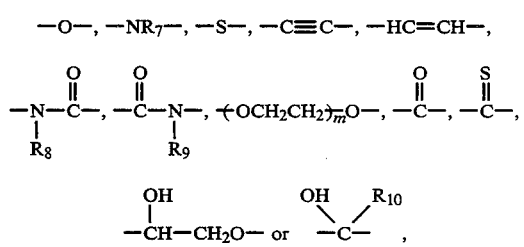

wherein $R_7$, $R_8$, $R_9$ and m are as previously described and $R_{10}$ is hydrogen;

n is an integer from 1 to 6, with the proviso that when A and B are, independently, a bond or one of the following groups,

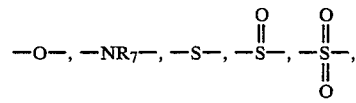

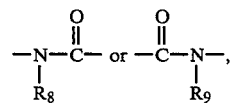

then n is an integer from 2 to 6;

Z is $-S-$, $-CR_2{=}CR_2'-$, $-N{=}CR_2-$ or $-CR_2{=}N-$;

X and Y taken together are $O{=}$, hydroxyimino, alkyloxyimino, alkenyloxyimino, arylalkoxyimino, hydrazono, mono-lower alkyl hydrazono, di-lower alkyl hydrazono or semicarbazono, or, independently, when one of X or Y is halogen, the other can be hydrogen or halogen; or when one of X or Y is amino, the other is hydrogen; or when one of X or Y is hydroxy or alkoxy, the other is hydrogen, or hydroxy;

Q is a cycloalkyl, aryl or heterocyclic radical, for example, phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups; alkyl, alkoxy, acyloxy, halogen, acyloxyalkyl, alkoxyalkyl, aryloxyalkoxy, hydroxy, hydroxyalkyl, hydroxyalkoxy, phenyl, trihaloalkyl, sulfamoyl, carboxycarbonyl or alkoxalyl.

A more preferred group of compounds of formula I is one wherein $R_1$ is as previously described; $R_2$ and $R_2'$, independently, are hydrogen, alkyl, alkoxy, hydroxy or halogen;

A is a bond,

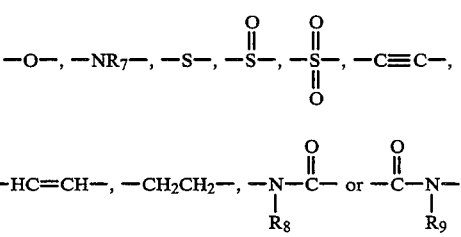

wherein $R_7$ is hydrogen or lower alkyl and $R_8$ and $R_9$ are hydrogen;

B is a bond,

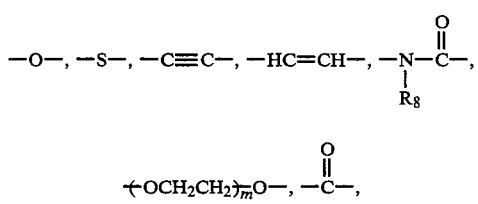

wherein m is 1 or 2 and $R_8$ is hydrogen; n is an integer from 1 to 6, with the proviso that when A and B are, independently, a bond or one of the following groups,

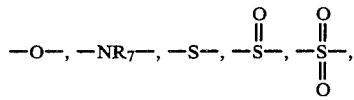

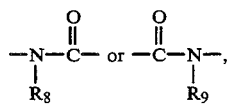

then n is an integer from 2 to 6;

Z is —S—, or —CR$_2$=CR$_2'$—,

X and Y taken together are O=, hydroxyimino, alkyloxyimino or alkenyloxyimino, or, independently, when one of X or Y is halogen, the other is halogen; or when one of X or Y is amino, the other is hydrogen; or when one of X or Y is hydroxy, the other is hydrogen or hydroxy;

Q is phenyl, cyclohexyl, clyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups; alkyl, alkoxy, acyloxy, halogen, acyloxyalkyl, alkoxyalkyl, aryloxyalkoxy, hydroxy, hydroxyalkyl, hydroxyalkoxy, phenyl, trihaloalkyl, sulfamoyl carboxycarbonyl or alkoxalyl.

A still more preferred group of compounds of formula I is one wherein R$_1$ is hydroxy
wherein one of R$_4$ and R$_5$ is hydrogen, lower alkyl or hydroxy-lower alkyl, and the other is hydroxy;

R$_2$ and R$_2'$ are hydrogen;

A is —O—, —NR$_7$— or —S—, wherein R$_7$ is hydrogen;

B is a bond,

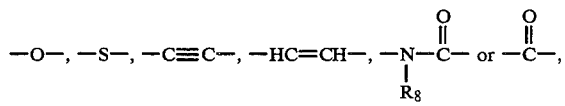

wherein R$_8$ is hydrogen;

n is an integer from 1 to 4, with the proviso that when B is a bond or one of the following groups,

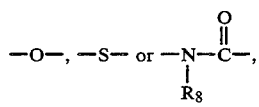

then n is an integer from 2 to 4;

Z is —S— or —CR$_2$=CR$_2'$—;

X and Y taken together are O=, hydroxyimino, alkyloxyimino or alkenyloxyimino, or, independently, when one of X or Y is fluoro, the other is fluoro; or when one of X or Y is amino, the other is hydrogen; or when one of X or Y is hydroxy, the other is hydroxy; Q is phenyl, cyclohexyl, cyclooctyl, adamantyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, of which phenyl or naphthalenyl can be substituted by one or more of the following groups, lower alkyl, phenyl, acyloxy, acyloxyalkyl or hydroxyalkyl.

Preferred compounds of formula I are:

(S)-alpha-amino-4-[[2-(cyclooctyloxy)ethyl]oxy]benzeneacetic acid hydrochloride;

3-fluoro-4-[2-(2-naphthalenyloxy)ethoxy]-alpha-oxobenzeneacetic acid;

4-[2-(1-naphthalenyl)-2-oxoethoxy]-alpha-oxobenzeneacetic acid;

4-[[2-(2-naphthhalenyloxy)ethyl]oxy]-alpha-oxobenzeneacetic acid 2-(dimethylamino)ethyl ester, (E)-4-[3-[2-[(2,2-dimethyl-1-oxobutoxy)methyl]-6-methylphenyl]-2-propenyloxy]-alphaoxobenzeneacetic acid(1:1) morpholine salt;

4-[[2-(2-naphthalenyloxy)ethyl]oxy]-alpha-oxobenzeneacetic acid;

4-[[2-(2-naphthalenyloxy)ethyl]thio]-alpha-oxobenzeneacetic acid;

4-[[2-(2-naphthalenythio)ethyl]oxy]-alpha-oxobenzeneacetic acid;

4-[[2-cyclooctyloxy)ethyl]oxy]-alpha-oxobenzeneacetic acid;

4-[3-(4-acetyl-3-hydroxy-2-propylphenoxy)propoxy]-alpha-oxobenzeneacetic acid;

N-hydroxy-N-methyl-4-[2-(2-naphthalenyloxy)ethoxy]-alpha-oxobenzeneacemmide;

(Z)-alpha-(hydroxyimino)-5-[2-(2-naphthalenyloxy)ethoxy]-2-thiopheneacetic acid;

5-[[2-(2-naphthalenyloxy)ethyl]oxy]-alpha-oxo-2-thiopheneacetic acid;

alpha-oxo-4-[[2-(phenoxy)ethyl]oxy]benzeneacetic acid;

(Z)-alpha-(ethoxyimino)-5-[2-(2-naphthalenyloxy)ethoxy]-2-thiopheneacetic acid;

rac.-5-[[2-(2-naphthalenyloxy)ethyl]oxy]-alpha-oxo-2-thiopheneacetic acid 2,3-dihydroxypropyl ester;

(S)-alpha-amino-4-[2-[2-[(2,2-dimethyl-1 -oxobutoxy)-methyl]-6-methylphenoxy]ethoxy]benzeneacetic acid;

(E)-4-[[3-(2-naphthalenyl)-2-propenyl]oxy]-alpha-oxobenzeneacetic acid;

4-[[2-[2-[(2,2-dimethyl-1-oxobutoxy)methyl]-6-methylphenoxy]ethyl]oxy]-alphaoxobenzeneacetic acid (2:1) hydrate; and 4-[[4-(2-naphthalenyloxy)butyl]oxy]-alpha-oxobenzeneacetic acid.

Exemplary of other compounds of formula I of the invention are:

4-[2-(6-hydroxy-2-naphthalenyloxy)ethoxy]-alpha-oxobenzeneacetic acid;

4-[2-(8-hydroxy-2-naphthalenyloxy)ethoxy]-alpha-oxobenzeneacetic acid;

6-[2-(2-naphthalenyloxy)ethoxy]-alpha-oxo-3-pyridineacetic acid;

4-[2-[2,4-dichloro-6-[(2,2-dimethyl-1-oxobutoxy)methyl]phenoxy]ethoxy]-alphaoxobenzenea acid;

4-[2-[2,4-dimethyl-6-[(2,2-dimethyl-1-oxobutoxy)methyl]phenoxy]ethoxy]-alphaoxobenzeneac acid;

4-[2-[2-[[[(4-fluorophenyl)carbonyl]oxy]methyl]-phenoxy]ethoxy]-alpha-oxo-2-thiopheneacetic acid;

5-[2-[2-[[[(4-fluorophenyl)carbonyl]oxy]methyl]-phenoxy]ethoxy]-alpha-oxo-2-thiopheneacetic acid;

5-[2-[2-(methoxycarbonyl)-6-methyl]phenoxy]ethoxy]-alpha-oxo-2-thiopheneacetic acid;

(E)-4-[[3-(4-bromophenyl)-2-propenyl]oxy]-alpha-oxo-3-pyridineacetic acid;

(E)-4-[[4-(4-fluorophenyl)-2-butenyl]oxy]-alpha-oxobenzeneacetic acid;

(E)-alpha-oxo-4-[(3-phenyl-2-propenyl)oxy]thiopheneacetic acid;

(S)-alpha-amino-4-[[2-(2-naphthalenyloxy)ethyl]oxy]-benzeneacetic acid;
(S)-alpha-amino-4-[[2-(phenoxy)ethyl]oxy]benzeneacetic acid hydrochloride;
(S)-alpha-amino-alpha-methyl-4-[[2-(2-naphthalenyloxy)ethyl]oxy]benzeneacetic acid;
(Z)-alpha-oxo-5-[(3-phenyl-2-propenyl)oxy]-2-thiopheneacetic acid;
(E)-4-[[3-(1-naphthalenyl)-2-propenyl]oxy]-alpha-oxobenzeneacetic acid;
alpha-oxo-5-[4-(3-pyridinyl)butoxy]-2-thiopheneacetic acid;
alpha-oxo-4-[2-(4-pyridinyl)ethoxy]benzeneacetic acid;
alpha-oxo-4-[[7-(phenoxy)heptyl]oxy]benzeneacetic acid;
alpha-oxo-4-[[8-(phenoxy)octyl]oxy]benzeneacetic acid;
alpha-oxo-5-[[2-(4-phenoxyphenoxy)ethyl]oxy]-2-furanacetic acid;
alpha-oxo-4-[[3-(4-quinolyloxy)propyl]oxy]benzeneacetic acid;
2-[[4-[[4-(1-naphthalenyloxy)butyl]oxy-alpha-oxobenzeneacetyl]oxy]-N,N,N-trimethylethanaminium iodide;
5-[3-(2-naphthalenyloxy)propyl]-alpha-oxo-2-thiopheneacetic acid;
4-[[4-(1-naphthalenyloxy)butyl]oxy]-alpha-oxobenzeneacetic acid;
4-[[2-(2-chlorophenoxy)ethyl]oxy]-alpha-oxobenzeneacetic acid;
4-[[2-(2-fluorophenoxy)ethyl]oxy]-alpha-oxo-3-pyridineacetic acid;
4-[[2-(2-naphthalenyl)ethyl]amino]-alpha-oxobenzeneacetic acid;
5-[[2-(2-naphthalenyloxy)ethyl]oxy]-alpha-oxo-2-thiopheneacetamide;
4-[[3-(2-naphthalenyloxy)propyl]sulfonyl]-alpha-oxobenzeneacetic acid;
4-[[3-(2-naphthalenylthio)propyl]oxy]-alpha-oxobenzeneacetic acid;
5-[[2-(3,4,5-trimethoxyphenoxy)ethyl]oxy]-alpha-oxo-2-furanacetic acid;
4-[[2-(6-methoxy-2-naphthalenyloxy)ethyl]oxy]-alpha-oxobenzeneacetic acid;
4-[[2-(3-naphtho[2,3-b]thienyloxy)ethyl]oxy]-alpha-oxobenzeneacetic acid;
4-[[2-(7-isoquinolyl)ethyl]oxy]-alpha-oxobenzeneacetic acid;
4-[[3-(cyclohexyl)propyl]oxy]-alpha-oxobenzeneacetic acid;
4-[[3-(cyclooctyloxy)propyl]oxy]-alpha-oxobenzeneacetic acid;
4-[[2-[2-(hydroxymethyl)phenoxy]ethyl]oxy]-alpha-oxobenzeneacetic acid;
4-[[2-[2-[(2,2-dimethyl-1-oxopropoxy)methyl]-6-methylphenoxy]ethyl]oxy]-alphaoxobenzeneacetic acid;
4-[[2-[4-(methylarninosulfonyl)phenoxy]ethyl]oxy]-alpha-oxobenzeneacetic acid
4-[[2-[8-(2,2-dimethyl-1-oxopropoxy)-2-naphthalenyloxy]ethyl]oxy]-alphaoxobenzeneacetic acid;
4-[[3-(2-dimethylaminophenyl)propyl]oxy]-alpha-oxobenzeneacetic acid:
5-[[4-(2-naphthalenyl)butyl]oxy]-alpha-oxo-2-thiopheneacetic acid;
4-[[3-(4-cyanophenyl)propyl]oxy]-alpha-oxobenzeneacetic acid
4-[[3-(4-nitrophenoxy)propyl]oxy]-alpha-oxobenzeneacetic acid;
4-[[3-[2-(trifioromethyl)phenyl]propyl]oxy]-alpha-oxobenzeneacetic acid;
4-[[3-[4-(N,N-dimethylsulfamoyl)phenoxy]ethyl]oxy]-alpha-oxobenzeneacetic acid;
4-[[3-[4-(N-ethylsuffamoyl)phenoxy]ethyl]oxy]-alpha-oxobenzeneacetic acid;
alpha-oxo-4-[[4-(phenylthio)butyl]oxy]benzeneacetic acid;
alpha-oxo-4-[[4-(2-pyrimidyl)butyl]oxy]benzeneacetic acid;
4-[[4-(3-fluorophenoxy)butyl]oxy]-alpha-oxobenzeneacetic acid;
4-[[5-(4-fluorophenoxy)pentyl]oxy]-alpha-oxobenzeneacetic acid;
4-methyl-5-[[2-(2-naphthalenyloxy)ethyl]oxy]-alpha-oxo-2-thiopheneacetic acid;
5-[(phenylmethyl)oxy]-alpha-oxo-2-furanacetic acid;
5-[[2-(2-naphthalenyloxy)ethyl]oxy]-alpha-oxo-2-thiopheneacetic acid 2-(dimethylamino)ethyl ester,
5-[[2-(3-carbazolyloxy)ethyl]oxy]-alpha-oxo-2-thiopheneacetic acid;
5-[[2-(cyclooctyloxy)ethyl]thio]-alpha-oxo-2-thiopheneacetic acid;
5-[[3-(cycloheptyloxy)propyl]oxy]-alpha-oxo-2-thiopheneacetic acid potassium salt;
alpha, alpha-difluoro-4-[[2-(3-methylphenoxy)ethyl]oxy]benzeneacetic acid;
alpha, alpha-difluoro-4-[[2-(3-naphtho[2,3-b]thienyloxy)ethyl]oxy]benzeneacetic acid;
alpha, alpha-dimethoxy-4-[[2-(phenoxy)ethyl]oxy]benzeneacetic acid
alpha-oxo-4-[(3-phenyl-2-propynyl)oxy]thiopheneacetic acid;
alpha-oxo-4-[[2-(2-xanthenyloxy)ethyl]oxy]benzeneacetic acid (1:1 ) diethanolamine salt;
alpha-oxo-4-[[2-(4-trifluoromethylphenoxy)ethyl]oxy]-2-furanacetic acid;
alpha-oxo-4-[[6-(phenoxy)hexyl]oxy]benzeneacetic acid;
4-[[2-(3-benzo[b]thienyloxy)ethyl]oxy]-alpha-oxobenzeneacetic acid
rac.-5-[[2-(3-indolyloxy)ethyl]oxy]-alpha-oxo-2-thiopheneacetic acid 2,3-dihydroxypropyl ester,
rac.-alpha-chloro-alpha-methyl-4-[[2-(phenoxy)ethyl]oxy]benzeneacetic acid;
rac.-alpha-ethoxy-4-[(2-phenylethyl)oxy]benzeneacetic acid;
rac.-alpha-oxo-4-[[2(1,2,3,4-tetrahydro-2-naphthalenyloxy)ethyl]oxy]benzeneacetic acid and the like;

The compounds of formula I can be prepared as hereinafter described in Reaction Schemes I–XV.

Reaction Scheme I

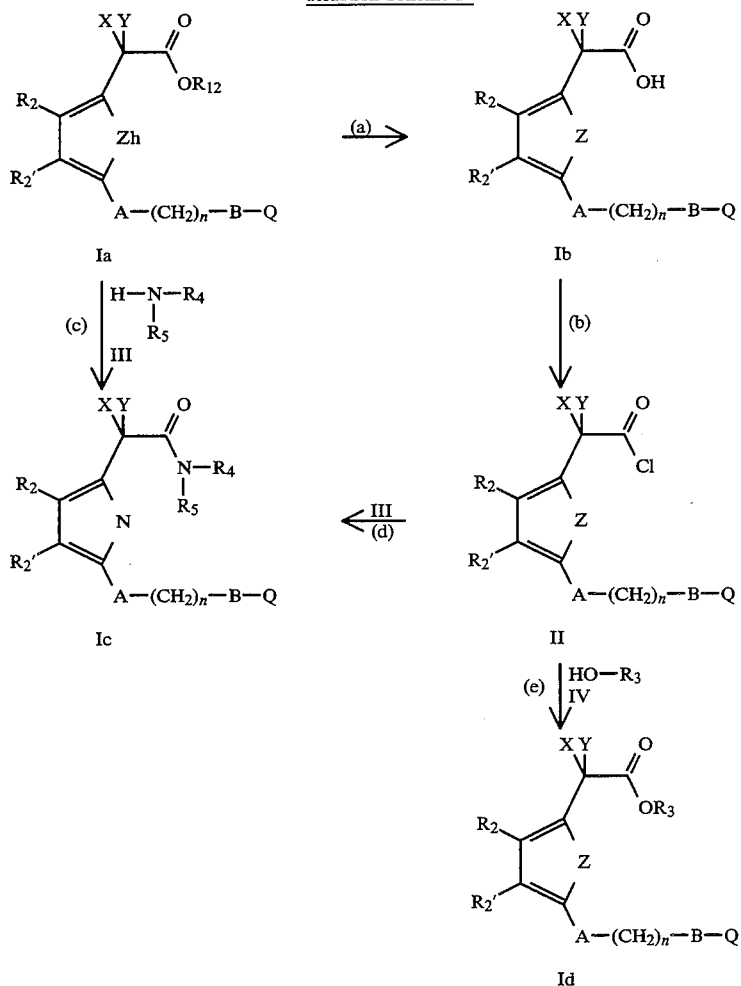

wherein A, B, Q, $R_2$, $R_2'$, $R_3$, $R_4$, $R_5$, X, Y and n are as previously described and $R_{12}$ is lower alkyl.

In Reaction Scheme I, step (a), an ester of formula Ia, which are prepared by methods herein after described, which includes as appropriate, its enantiomeric, diastereoisomeric or geometric isomers and/or mixtures thereof is reacted with an excess of an alkali metal hydroxide in a solvent mixture, preferably methanol-water or methanol-tetrahydrofuranwater, at a temperature of from 0° C. to reflux. The resulting carboxylic acid of formula Ib which includes as appropriate, its enantiomeric, diastereoisomeric or geometric isomers and/or mixtures thereof may be isolated utilizing conventional methods such as crystallization, crystallization of salts, chromatography and the like.

In step (b), a carboxylic acid of formula Ib, which includes as appropriate, its enantiomeric, diastereoisomeric or geometric isomers and/or mixtures thereof, is dissolved in a suitably inert solvent, for example, dichloromethane or toluene, optionally containing a catalytic amount of dimethylformamide, and treated with a carboxylic acid halide forming reagent such as oxalyl chloride at a temperature of from −80° C. to the reflux temperature of the mixture. The resulting carboxylic acid chloride of formula II which includes as appropriate, its enantiomeric, diastereoisomeric or geometric isomers and/or mixtures thereof, may be isolated utilizing conventional methods such as distillation, crystallization and the like, but, most conveniently, after removal of the reaction solvent, the crude product of formula II can be used per se in subsequent steps.

In step (c), a carboxylic acid ester of formula Ia, which includes as appropriate, its enantiomeric, diastereoisomeric or geometric isomers and/or mixtures thereof, is reacted with an excess of the amine of formula III, optionally in a mixture of solvents, preferably a lower alkanol-tetrahydrofuran, such as methanol-tetrahydrofuran, at a temperature of from room temperature to the reflux temperature of the mixture. The resulting carboxylic acid amide of formula Ic which include as appropriate, its enantiomeric or diastereoisomeric isomers or mixture thereof or geometric isomers or mixture thereof may be isolated utilizing conventional methods such as crystallization, crystallization of salts, chromatography and the like.

Alternatively, in step (d), a solution of the carboxylic acid chloride of formula II, which includes as appropriate, its enantiomeric, diastereoisomeric or geometric isomers and/or mixtures thereof in an inert solvent, for example, a chlorinated hydrocarbon, such as dichloromethane, is added to a solution of an excess of the amine of formula III in an inert solvent, for example, dichloromethane, optionally in the presence of a proton acceptor, for example triethylamine, at a temperature in the range of from −78 ° C. to room temperature. The resulting carboxylic acid amide of formula Ic which include, as appropriate, its enantiomeric, diastereoisomeric or geometric isomers and/or mixtures thereof may be isolated utilizing conventional methods such as crystallization, crystallization of salts, chromatography and the like.

In step (e), a solution of the carboxylic acid chloride of formula II, which includes as appropriate, its enantiomeric, diastereoisomeric or geometric isomers and/or mixtures thereof in an inert solvent, for example dichloromethane, is added to a solution of an excess of the alcohol of formula IV, an inert solvent, for example, dichloromethane, in the presence of a proton acceptor, for example, triethylamine, at a temperature of from −78° C. to room temperature. The resulting carboxylic acid ester of formula Id which include as appropriate, its enantiomeric, diastereoisomeric or geometric isomers and/or mixtures thereof may be isolated utilizing conventional methods such as crystallization, crystallization of salts, chromatography and the like.

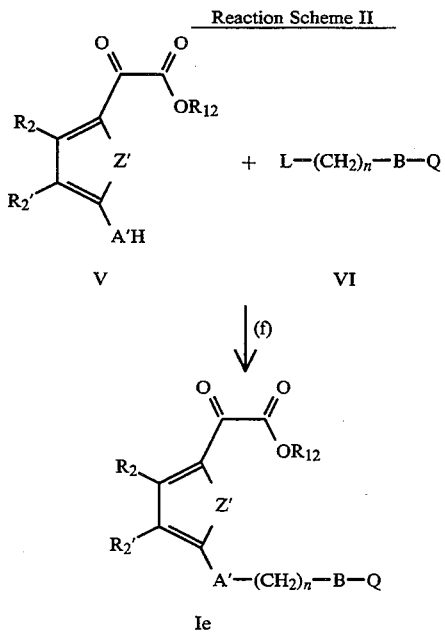

wherein n, B, Q, $R_2$, $R_2'$ and $R_{12}$ are as previously described, A' is O or S and Z' is —$CR_2$=$CR_2'$— and L is a leaving group such as chloro, bromo, iodo, alkylsulfonyloxy or arylsulfonyloxy.

In Reaction Scheme II, step (f), a phenol or thiophenol of formula V which are known or can be made by known methods, is reacted with a compound of formula VI, which are known or can be made by known methods, and which includes as appropriate, its enantiomeric, diastereoisomeric or geometric isomers and/or mixtures thereof, in the presence of an alkali metal hydride, for example, sodium hydride, in an inert solvent, preferably dimethylformamide or dimethylsulfoxide, at a temperature of from 0° C. to 100° C. The resulting compound of formula Ie which includes its enantiomeric or geometric isomers and/or mixtures thereof may be isolated utilizing conventional methods such as crystallization, chromatography and the like.

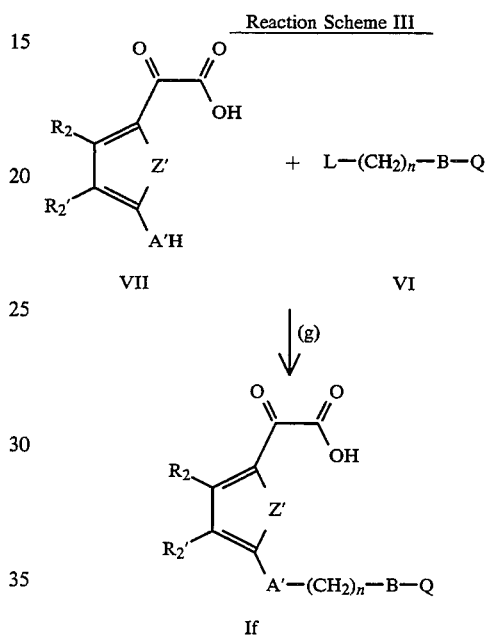

wherein n, $R_2$, $R_2'$, A', Z', B, Q, and L are as previously described.

In Reaction Scheme III, step (g), a phenol or thiophenol of formula VII which are known or can be made by known methods, is reacted with a compound of formula VI, in the presence of an alkali metal hydroxide, for example sodium hydroxide, in an inert solvent mixture, for example dimethylsulfoxide-water, at a temperature of from 0° C. to 100° C. The resulting compound of formula If which includes as appropriate, its enantiomeric, diastereoisomeric or geometric isomers and/or mixtures thereof, may be isolated utilizing conventional methods such as crystallization, crystallization of salts, chromatography and the like.

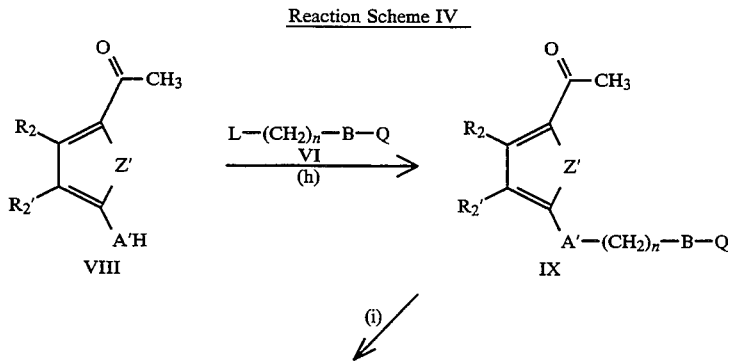

Reaction Scheme IV

-continued

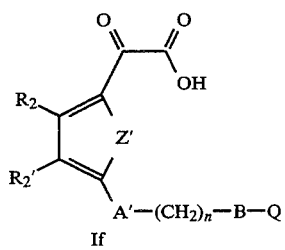

If wherein A', n, B, Q, $R_2$, $R_2'$, Z' and L are as previously described.

In Reaction Scheme IV, step (h), a phenol or thiophenol of formula VIII, which are known or can be made by known methods, is reacted with an alkylating agent of formula VI, in the presence of an alkali metal hydride in an inert solvent, for example dimethylformamide, at a temperature of from 0° C. to 100° C. The resulting compound of formula IX which include as appropriate, its enantiomers, diastereoisomers or geometric isomers and/or mixtures thereof, may be isolated utilizing conventional methods such as crystallization, chromatography and the like.

In step (i), an aryl methyl ketone of formula IX is reacted with an excess of an oxidizing agent, preferably selenium dioxide in the presence of a tertiary amine, preferably pyridine, at a temperature of from 60° C. to 100° C. to give the alpha-ketocarboxylic acid of formula If which includes as appropriate, its enantiomeric, diastereoisomeric or geometric isomers and/or mixtures thereof. The compound may be isolated utilizing conventional methods such as crystallization, crystallization of salts, chromatography and the like.

wherein n, B, Q, $R_2$, $R_2'$, $R_8$ and Z' are as previously described.

In Reaction Scheme V, step (j) an amine of formula X, which are known or can be prepared by known methods, is reacted with an excess of the carboxylic acid chloride of formula XI, which are known prepared by known methods and which includes as appropriate, its enantiomeric, diastereoisomeric or geometric isomers and/or mixtures thereof, in the presence of a proton acceptor, preferably pyridine, or triethylamine, in a suitably inert solvent such as dichloromethane at a temperature of from −78° C. to ambient temperature. The resulting carboxamide of formula XII which include as appropriate, its enantiomeric, diastereoisomeric or geometric isomers and/or mixtures thereof, may be isolated utilizing conventional methods such as crystallization, chromatography and like.

The compound of formula XII is transformed under conditions previously described in step (i) into the alpha-ketocarboxylic acid of formula Ig. The resulting compound of formula Ig which includes as appropriate, its enantiomeric, diastereoisomeric or geometric isomers and/or mixtures thereof, may be isolated utilizing conventional methods such as crystallization, crystallization of salts, chromatography and the like.

Reaction Scheme V

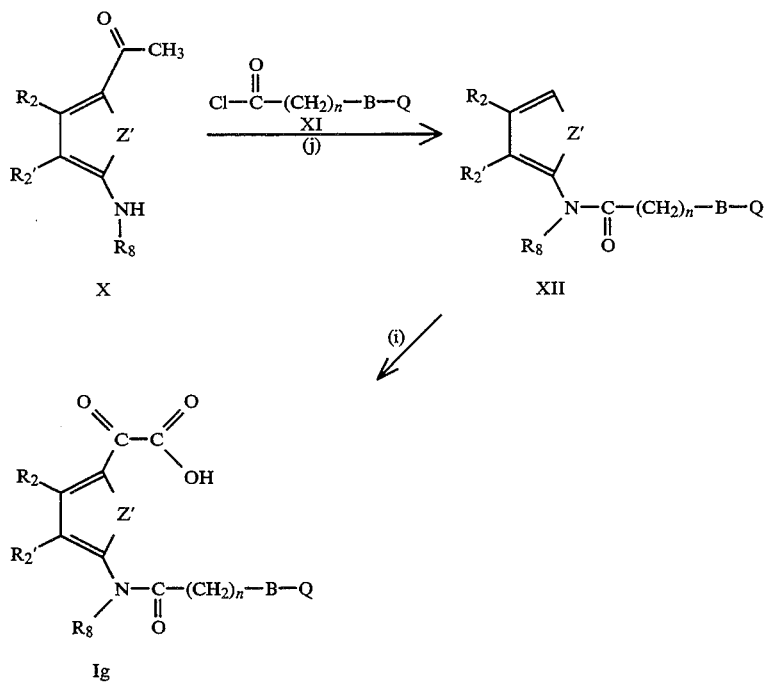

Reaction Scheme VI

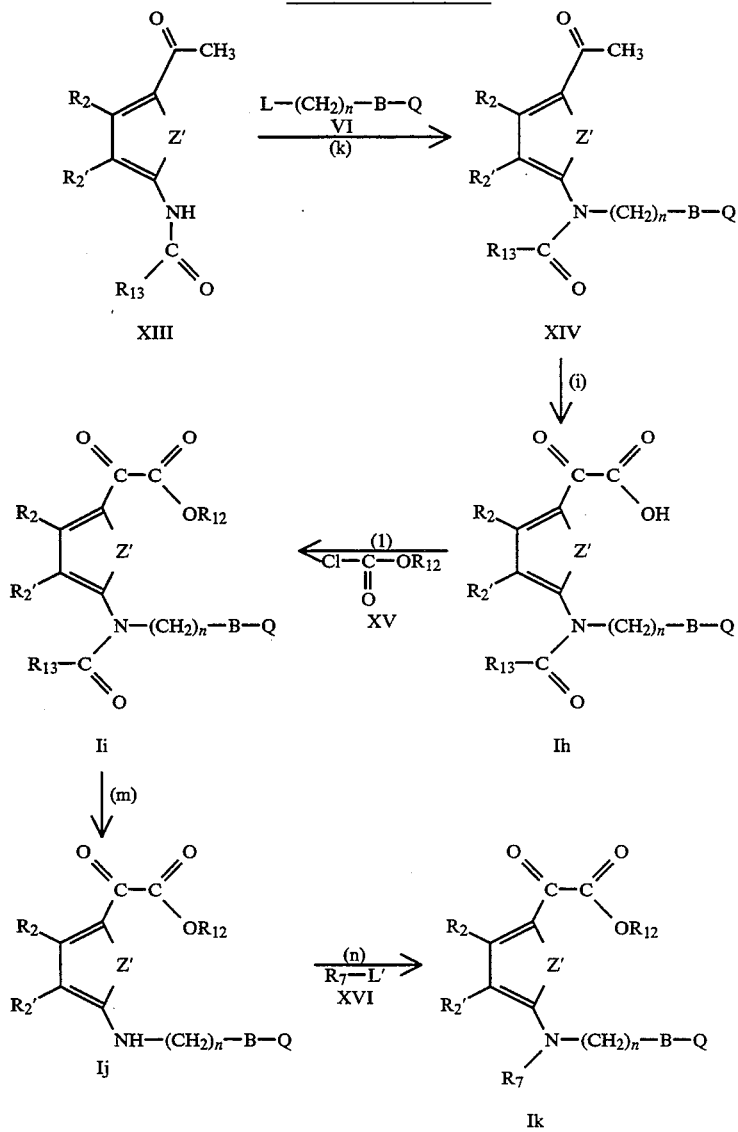

wherein n, B, L, Q, $R_2$, $R_2'$, $R_7$, $R_{12}$ and $Z'$ are as previously described, $L'$ is chloro or bromo and $R_{13}$ is hydrogen, lower alkyl or arylalkyl.

In Reaction Scheme VI, step (k), an N-acylated compound of formula XIII, which are known or can be prepared by known methods, is reacted with a compound of formula VI, in the presence of an alkali metal hydride in an inert solvent, preferably dimethylformamide, at a temperature of from 0° C. to 100° C. The resulting compound of formula XIV which includes as appropriate its enantiomeric, diastereoisomeric or geometric isomers and/or mixtures thereof may be isolated utilizing conventional methods such as crystallization, crystallization of salts, chromatography and the like.

The compound of formula XIV is transformed under conditions previously described in step (i) into a alpha-keto carboxylic acid of formula Ih. The resulting compound of formula Ih which includes as appropriate, its enantiomeric, diastereoisomeric or geometric isomers and/or mixtures thereof, may be isolated utilizing conventional methods such as crystallization, crystallization of salts, chromatography and the like. Optionally, the reaction mixture containing the alpha-ketocarboxylic acid of formula Ih may be treated in step (l) directly with an aryl or alkyl chloroformate (XV), for example, methyl chloroformate. The resulting alpha-ketocarboxylic acid ester of formula Ii which includes as appropriate, its enantiomeric, diastereoisomeric or geometric isomers and/or mixtures thereof, may be isolated utilizing conventional methods such as crystallization, chromatography and the like.

In step (m), the compound of formula Ii is deacylated by treatment with an excess of aqueous mineral acid, for example, hydrochloric acid or sulfuric acid optionally in the presence of an inert solvent, such as methanol or glyme, at a temperature of from 50° C. to 100° C. The resulting amine of formula Ij which includes as appropriate, its enantiomeric, diastereoisomeric or geometric isomers and/or mixtures thereof, may be isolated utilizing conventional methods such as crystallization, crystallization of salts, chromatography and the like.

In step (n), the secondary amine of formula Ij is reacted with an alkylating agent XVI, for example, methyl iodide, in the presence of an inert solvent, for example, diethyl ether or methanol, at a temperature of from room temperature to reflux. The resulting tertiary amines of formula Ik which includes as appropriate, its enantiomeric, diastereoisomeric or geometric isomers and/or mixtures thereof, may be isolated utilizing conventional methods such as crystallization, crystallization of salts, chromatography and the like.

that will absorb lower alkanols from the reaction mixture as they are formed, for example, 4A or 5A molecular sieves, at a temperature of from room temperature to reflux. The resulting ether of formula XIX, which include as appropriate, its enantiomeric, diastereoisomeric or geometric isomers and/or mixtures thereof,

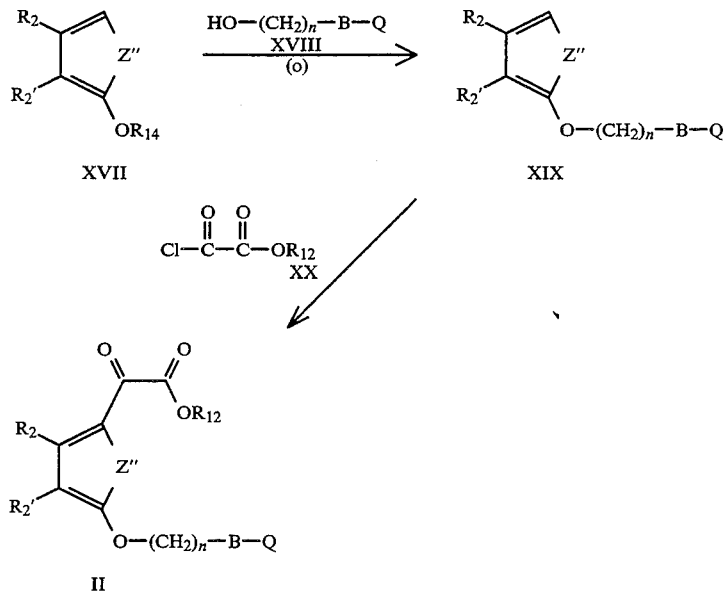

Reaction Scheme VII wherein n, B, Q, $R_2$, $R_2'$ and $R_{12}$ are as previously described, $R_{14}$ is methyl or ethyl and $Z''$ is O or S.

In Reaction Scheme VII, step (o), a 2-furanyl or 2-thienyl ether, unsubstituted in position 5, of formula XVII, which are known or can be prepared by known methods, is reacted with an alcohol of formula XVIII, which are known or can be prepared by known methods, and which includes as appropriate, its enantiomeric, diastereoisomeric or geometric isomers or mixture thereof, in an inert solvent, for example, dichloromethane or benzene in the presence of a catalytic amount of an aryl- or alkylsulfonic acid, for example, p-toluenesulfonic acid and in the presence of an agent may be isolated utilizing conventional methods such as crystallization, chromatography and the like.

In step (p), the compound of formula XIX is reacted with an excess of an oxalyl chloride ester of formula XX, in the presence of a tertiary amine base, preferably pyridine, in a suitably inert solvent, such as, dichloromethane at a temperature of from 0° C. to reflux. The resulting compound of formula II, which includes as appropriate, its enantiomeric, diastereoisomeric or geometric isomer or mixture thereof, may be isolated utilizing conventional methods such as crystallization, chromatography and the like.

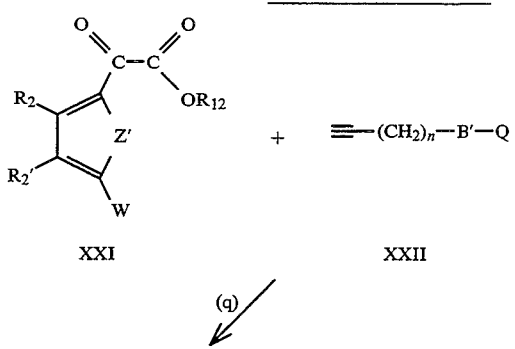

Reaction Scheme VIII

Reaction Scheme VIII

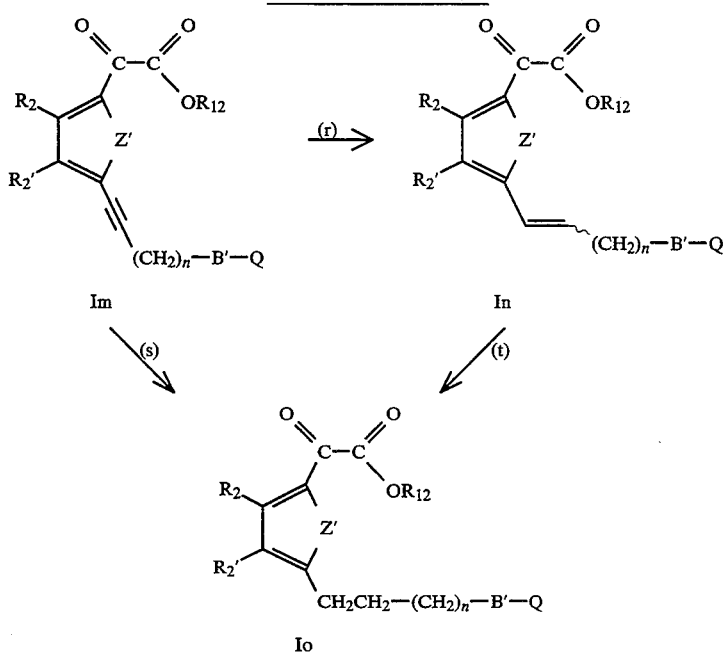

wherein n, Q, $R_2$, $R_2'$, $R_{12}$ and $Z'$ are as previously described, and $B'$ is other than —C≡C— or —HC=CH— and W is bromo, iodo or a perfluoroalkylsulfonate.

In Reaction Scheme VIII, step (q), a compound of formula XXI, which are known or can be prepared by known methods, is reacted with an acetylene of formula XXII, a compound which is known or can be prepared by known methods and which includes, as appropriate, its enantiomeric, diastereoisomeric or geometric isomers and/or mixtures thereof, in the presence of an excess of a proton acceptor, for example triethylamine, and a suitable palladium catalyst, for example bis(triphenylphosphine)palladium dichloride, optionally in an inert solvent, for example, dichloromethane or dimethylformamide, at a temperature of from room temperature to 100° C. The resulting compound of formula Im, which includes as appropriate, its enantiomeric, diastereoisomeric or geometric isomers and/or mixtures thereof, may be isolated utilizing conventional methods such as crystallization, chromatography and the like.

In step (r), the acetylene of formula Im, is dissolved in an inert solvent, for example, benzene or tetrahydrofuran, and hydrogenated over a suitably deactivated palladium catalyst, for example, Lindlar catalyst or the like, and hydrogenated at ambient temperature and at from one to three atmospheres pressure until one equivalent of hydrogen is absorbed. The resulting olefin of formula In, which includes as appropriate, its enantiomeric, diastereoisomeric or geometric isomers and/or mixtures thereof, may be isolated utilizing conventional methods such as crystallization, chromatography and the like.

In step (s), the acetylene of formula Im, is dissolved in an inert solvent, for example methanol or tetrahydrofuran, and hydrogenated over a suitable catalyst, for example, palladium on carbon or platinum oxide, at from one to five atmospheres pressure, preferably at ambient temperature until the uptake of hydrogen had ceased. The resulting compound of formula Io, which includes as appropriate, its enantiomeric, diastereoisomeric or geometric isomers and/or mixtures thereof, may be isolated utilizing conventional methods such as crystallization, chromatography and the like.

In step (t), the olefin of formula In, which includes as appropriate, its enantiomeric, diastereoisomeric or geometric isomers and/or mixtures thereof, is dissolved in an inert solvent, for example, methanol or tetrahydrofuran, and hydrogenated over a suitable catalyst, for example, palladium on carbon or platinum oxide, at from one to five atmospheres pressure, preferably at ambient temperature until the uptake of hydrogen had ceased. The resulting compound of formula Io may be isolated utilizing conventional methods such as crystallization, chromatography and the like.

Reaction Scheme IX

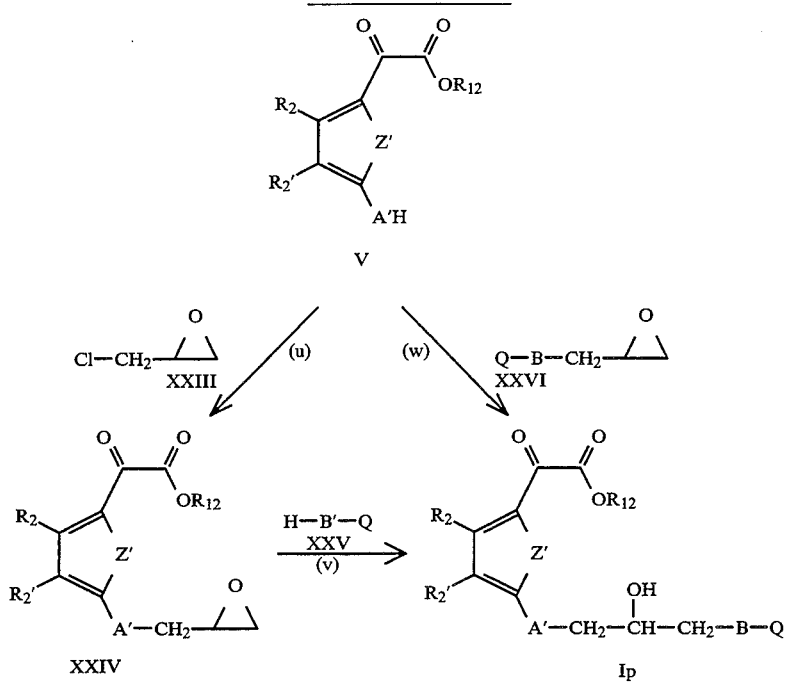

wherein n, A′, B, Q, $R_2$, $R_2'$, $R_{12}$ and Z′ are as previously described and B′ is O, S or $NR_7$ wherein $R_7$ is as previously described.

In Reaction Scheme IX, step (u) a phenol or thiophenol of formula V is reacted with a compound of formula XXIII, epichlorohydrin, which includes its enantiomers and/or mixtures thereof, in the presence of an alkali metal hydride, for example sodium hydride in an inert solvent, for example, dimethylformamide, at a temperature of from room temperature to 100° C. The resulting epoxide of formula XXIV, which includes its enantiomers and/or mixtures thereof, may be isolated utilizing conventional methods such as crystallization, chromatography and the like.

In step (v), the compound of formula XXIV, is optionally dissolved in an inert solvent, and reacted with a compound of formula XXV, which are known or can be prepared by known methods, and which includes, as appropriate, its enantiomeric, diastereoisomeric or geometric isomers or mixtures thereof, in the presence of a proton acceptor, preferably a tertiary amine, for example pyridine, at a temperature of from 40° C. to 100° C. The resulting compound of formula Ip, which includes its enantiomers, and, as appropriate, its diastereoisomeric or geometric isomers and/or mixtures thereof, may be isolated utilizing conventional methods such as crystallization, crystallization of salts, chromatography and the like.

Alternatively, in step (w), a phenol or thiophenol of formula V is reacted with an epoxide of formula XXVI, which are known or can be prepared by known methods, which includes, as appropriate, its enantiomeric, diastereoisomeric or geometric isomers and/or mixtures thereof, in the presence of a catalytic mount of an alkali metal hydroxide, for example potassium hydroxide, or an alkali metal alkoxide, for example sodium methylate, in an inert solvent, for example dimethylformamide, at a temperature of from room temperature to 100° C. The resulting compound of formula Ip, which includes, as appropriate its enantiomeric, diastereoisomeric or geometric isomers and/or mixtures thereof, may be isolated utilizing conventional methods such as crystallization, chromatography and the like.

Reaction Scheme X

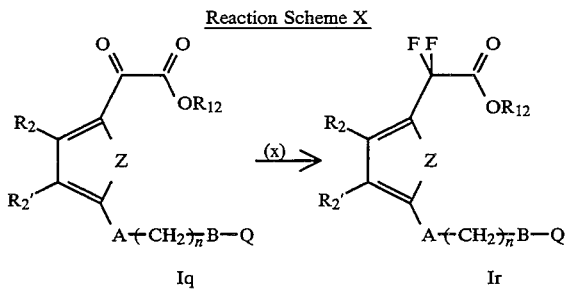

wherein A, B, Q, $R_2$, $R_2'$, $R_{12}$, Z and n are as previously described.

In Reaction Scheme X, step (x), an alpha-ketocarboxylic acid ester of formula Iq, which are or can be prepared according to one of the methods described herein, for example, Scheme II, VI, VII, VIII or IX, and which includes, as appropriate, its enantiomeric, diastereoisomeric or geometric isomers and/or mixtures thereof, is reacted with an excess of diethylaminosulfur trifluoride in an inert solvent for example 1,2-dichloroethane, at a temperature of from room temperature to reflux. The compound of formula Ir which includes its diastereoisomeric or geometric isomers and/or mixtures thereof, may be isolated utilizing conventional methods such as crystallization, crystallization of salts, chromatography and the like.

Reaction Scheme XI

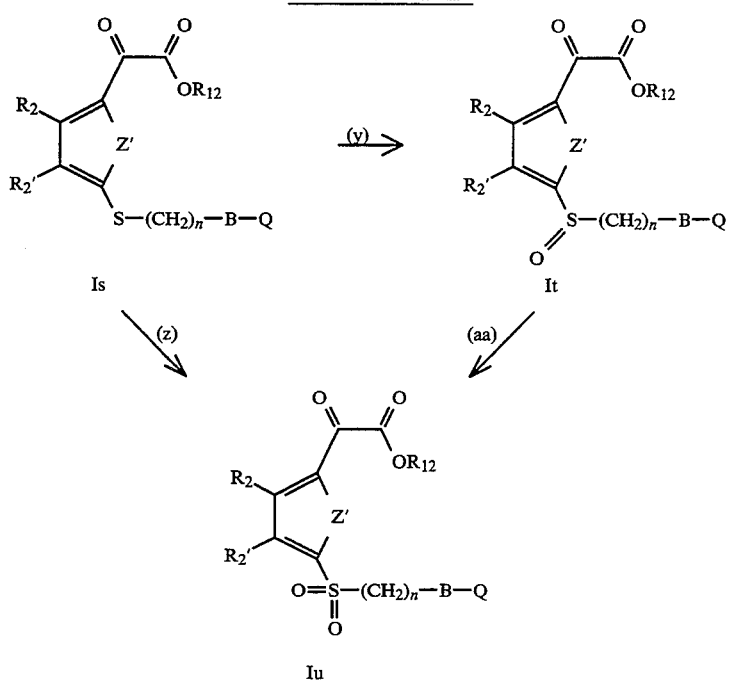

wherein A, B, Q, $R_2$, $R_2'$, $R_{12}$, Z and n are as previously described.

In Reaction Scheme XI, step (y), a sulfide of formula Is, which are or can be prepared according to the methods described herein, for example, Scheme II which includes, as appropriate, its enantiomeric, diastereoisomeric or geometric isomers and/or mixtures thereof, is reacted with one equivalent of a peracid, preferably m-chloroperbenzoic acid in an inert solvent, for example dichloromethane, at a temperature of from −20° C. to 0° C. The resulting sulfoxide of formula It, which includes, as appropriate, its enantiomeric, diastereoisomeric or geometric isomers and/or mixtures thereof, may be isolated utilizing conventional methods such as crystallization, crystallization of salts, chromatography and the like.

In step (z), a sulfide of formula Is, which includes, as appropriate, its enantiomeric, diastereoisomeric or geometric isomers and/or mixtures thereof, is reacted with an excess i.e. > two equivalents of a peracid, preferably m-chloroperbenzoic acid in an inert solvent, for example dichloromethane, at a temperature of from 0° C. to room temperature. The resulting sulfone of formula Iu, which includes, as appropriate, its enantiomeric, diastereoisomeric or geometric isomers and/or mixtures thereof, may be isolated utilizing conventional methods such as crystallization, crystallization of salts, chromatography and the like.

Alternatively, in step (aa) a sulfoxide of formula It, is reacted with an excess of a peracid, preferably m-chloroperbenzoic acid in an inert solvent, for example, dichloromethane at a temperature of from 0° C. to room temperature to give the sulfone of formula Iu.

Reaction Scheme XII

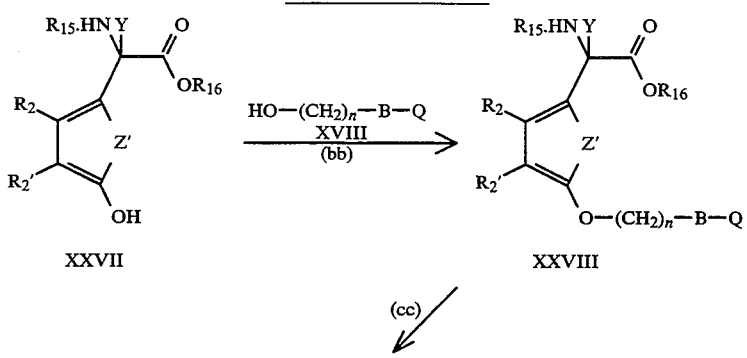

Reaction Scheme XII

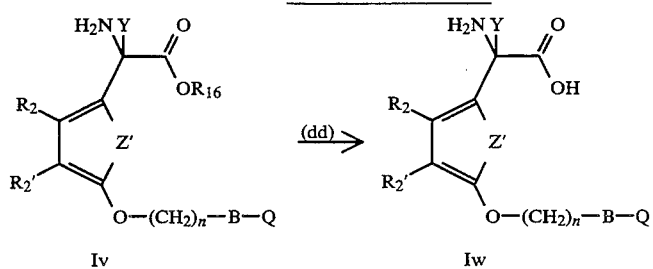

wherein B, Q, $R_2$, $R_2'$, Y, Z' and n are as previously described, $R_{15}$ is a suitable amino acid N-protecting group and $R_{16}$ is a suitable amino acid O-protecting group.

In Reaction Scheme XII, step (bb) an appropriately O,N-diprotected amino acid of formula XXVII, which are known or can be prepared by known methods, and which includes its enantiomers and/or mixtures thereof, is reacted with an alcohol of formula XVIII, in the presence of a triaryl or trialkylphosphine, for example, triphenylphosphine and a coupling reagent, for example diethyl azodicarboxylate, in an inert solvent, for example tetrahydrofuran, at a temperature of from 0° C. to room temperature. The resulting compound of formula XXVIII, which includes, as appropriate, its enantiomeric, diastereoisomeric or geometric isomers and/or mixtures thereof, may be isolated utilizing conventional methods such as crystallization, crystallization of salts, chromatography and the like.

In step (cc), the N-protected amino carboxylic acid ester of formula XXVIII, preferably N-tert-butyloxycarbonylamino carboxylic acid ester, which includes as appropriate, its enantiomeric, diastereoisomeric or geometric isomers and/or mixtures thereof, is treated with a strong acid, for example trifluoroacetic acid, in a suitably inert solvent, for example dichloromethane, to give the resulting N-deprotected amino carboxylic acid ester of formula Iv, which includes as appropriate, its enantiomeric, diastereoisomeric or geometric isomers and/or mixtures thereof. A compound of formula Iv may be isolated utilizing conventional methods such as crystallization, chromatography and the like but is generally used without further purification in the next step.

In step (dd), the aminocarboxylic acid ester of formula Iv, preferably an amino carboxylic acid benzyl ester, is dissolved in a solvent, preferably a lower alcohol, optionally containing an acid, preferably acetic acid, and hydrogenolyzed at ambient temperature and at a hydrogen pressure of from one to five atmospheres over a noble metal catalyst, for example, palladium on carbon. The resulting amino acid of formula Iw, which includes as appropriate, its enantiomeric, diastereoisomeric or geometric isomers and/or mixtures thereof, may be isolated utilizing conventional methods such as crystallization, crystallization of acid addition salts and the like.

Reaction Scheme XIII

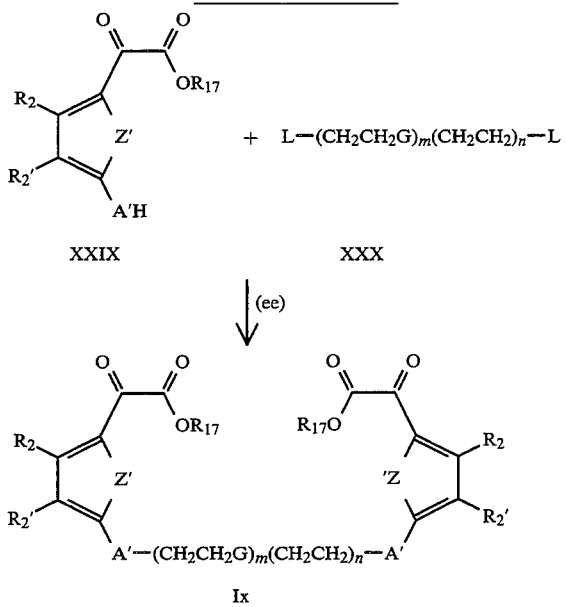

wherein m, n, A', B, L, Q, $R_2$, $R_2'$ and Z' are as previously described, $R_{17}$ is hydrogen or lower alkyl and G is O, S or a bond.

In Reaction Scheme XIII, step (ee) a phenol or thiophenol carboxylic acid ester of formula XXIX, which are known or can be prepared by known methods, and which includes as appropriate, its enantiomers and/or mixtures thereof, is reacted with a dialkylating agent of formula XXX, which are known or can be made by known methods, in the presence of an alkali metal hydride, for example, sodium hydride, in an inert solvent, preferably dimethylformamide, at a temperature of from 0° C. to 100° C. Alternatively, a phenol or thiophenol carboxylic acid of formula XXIX may be reacted with a dialkylating agent of formula XXX, in the presence of an alkali metal hydroxide, for example sodium hydroxide, in an inert solvent mixture, preferably dimethylsulfoxidewater, at a temperature of from 0° C. to 100° C. The resulting compound of formula Ix which includes, as appropriate, its diastereoisomeric isomers and/or mixtures thereof may be isolated utilizing conventional methods such as crystallization, crystallization of salts, chromatography and the like.

Reaction Scheme XIV

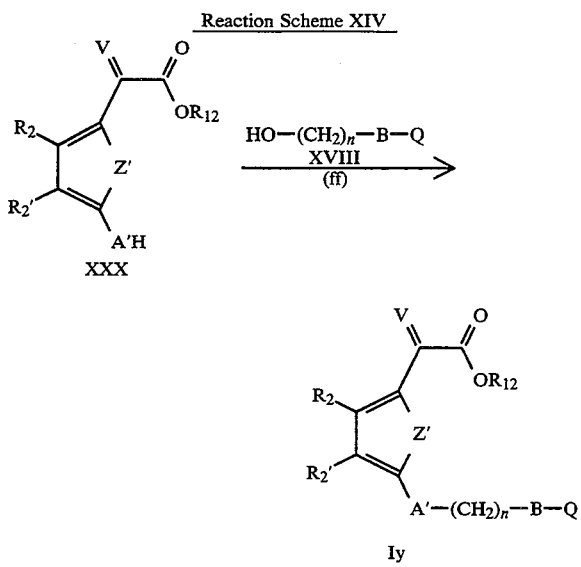

wherein A', B, Q, $R_2$, $R_2'$, $R_{12}$, Z' and n are as previously described and V is hydroxyimino, alkyloxyimino, alkenyloxyimino, arylalkoxyimino, hydrazono, mono-lower alkyl hydrazono, di-lower alkyl hydrazono or semicarbazono.

In Reaction Scheme XIV, step (ff) a phenol or thiophenol carboxylic acid ester of formula XXX, which includes as appropriate, all geometric forms and/or mixtures, is reacted with an alcohol of formula XVIII, which include as appropriate, all enantiomeric, diastereoisomeric or geometric isomers and/or mixtures thereof, in the presence of a triaryl or trialkylphosphine, for example, triphenylphosphine and a coupling reagent, for example diethyl azodicarboxylate, in an inert solvent, for example tetrahydrofuran, at a temperature of from 0° C. to room temperature. The resulting compounds of formula Iy which include all diastereoisomeric or geometric isomers and/or mixtures thereof may be isolated utilizing conventional methods such as crystallization, crystallization of salts, chromatography and the like.

Reaction Scheme XV

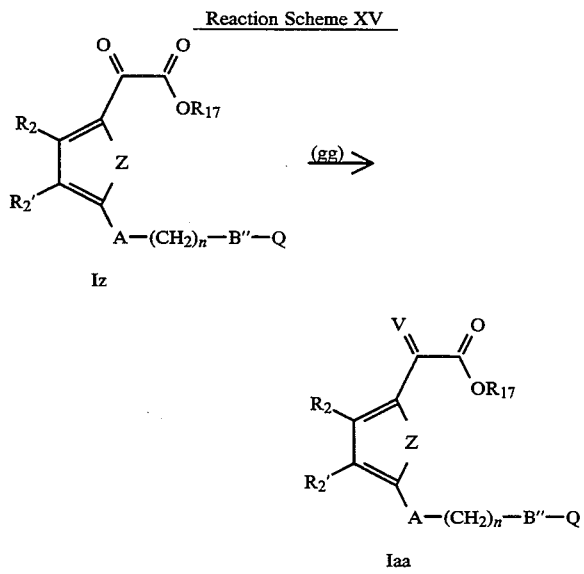

wherein A, Q, $R_2$, $R_2'$, $R_{17}$, V, Z and n are as previously described and B" is other than

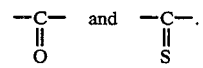

In Reaction Scheme XV, step (gg), an alpha-ketocarboxylic acid ester of formula Iz, which are or can be prepared according to one of the methods described herein, for example, Scheme II, VI, VII, VIII or IX, and which includes, as appropriate, its enantiomeric, diastereoisomeric or geometric isomers and/or mixtures thereof, is reacted with an excess of an O-alkyloxy- or O-alkenyloxy- or O-arylalkyloxyamine hydrochloride, or alternatively semicarbazide hydrochloride, in an inert basic solvent for example pyridine, at a temperature of from room temperature to 50° C. The compound of formula Iaa which includes its diastereoisomeric or geometric isomers and/or mixtures thereof, may be isolated utilizing conventional methods such as crystallization, crystallization of salts, chromatography and the like.

Alternatively, in step (gg), an alpha-ketocarboxylic acid ester of formula Iz, is reacted with an excess of an N-alkyl or N,N-dialkylhydrazine and a catalytic amount of an acid, preferably acetic acid, in an inert solvent for example methanol, optionally containing tetrahydrofuran, at a temperature of from room temperature to reflux. The compound of formula Iaa which includes its diastereoisomeric or geometric isomers and/or mixtures thereof, may be isolated utilizing conventional methods such as crystallization, crystallization of salts, chromatography and the like.

Alternatively, in step (gg), an alpha-ketocarboxylic acid of formula Iz, is reacted with a hydroxylamine in an inert solvent for example dimethylformamide at a temperature of from room temperature to 100° C. The compound of formula Iaa which includes its diastereoisomeric or geometric isomers and/or mixtures thereof, may be isolated utilizing conventional methods such as crystallization, crystallization of salts, chromatography and the like.

The invention also relates to salts of the compounds of formula I when they contain a basic or acidic functionality which lends itself for salt formation with either an acid or base. Salts of the compounds of formula I which have a carboxy group are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates, and the like, for example, calcium hydroxide, sodium hydroxide, sodium carbonate, potassium carbonate and the like, ammonia, primary, secondary and tertiary amines, such as monoalkylamines, dialkylamines, trialkylamines, for example, methylamine, diethylamine, triethylamine and the like, nitrogen containing heterocyclic amines, for example, piperidine and the like. A salt thus produced is the functional equivalent of the corresponding compound of formula I wherein R is hydrogen and one skilled in the art will appreciate that the variety of salts embraced by the invention is limited only by the criterion that a base employed in forming the corresponding salts be both nontoxic and physiologically acceptable.

Salts of the compounds of formula I which have a basic functionality, for example, amino, pyridyl, amino lower alkyl, or the like are prepared by the reaction of an appropriate compound of formula I with a non-toxic pharmacologically or pharmaceutically acceptable acid. In general, the referred to compounds of formula I form pharmaceutically acceptable addition salts with, for example, both pharmaceutically acceptable organic and inorganic acids, such as, acetic acid, succinic acid, formic acid, methanesulfonic acid, p-toluenesulfonic acid, hydrochloric acid, nitric acid, phosphoric acid, sulfuric acid and the like.

The compounds of Formula I exhibit activity as carnitine acyl transferase 1 (CAT-1) inhibitors and as such are therefore useful in disease states characterized by excessive production of the product of the reaction catalyzed by CAT-1. CAT-1 resides on the inner face of the outer mitochondrial membrane and is responsible for formation of long chain acyl carnitines from carnitine and the corresponding acyl CoA esters. These acylcarnitines may cross the inner mitochondrial membrane where they are reconverted to CoA esters through the action of a second carnitine acyl transferase (CAT-II). CAT-I is thought to represent the rate limiting step in mitochondrial fatty acid oxidation. Myocardial ischemia and the accompanying decrease in oxidative metabolism leads to an increase in cytosolic long chain acyl carnitines which, in turn, can cause electrophysiological disturbances and arrhythmias leading to sudden death. Thus, potent and cardioselective inhibitors of CAT-1 would prevent this increase in long chain acyl carnitines and are therefore useful in the improvement of cardiac function, in limiting infarct size and in the prevention of arrhythmias during and following infarction.

The useful activity of the compounds of formula I can be demonstrated by the following procedures:

1. Primary Screen—Inhibitors of CAT-1 in 1Mitochondria (a). Preparation of Mitochondria The heart is rapidly removed from an anesthetized rat (sodium pentabarbitol) and placed in ice-cold homogenization buffer (sucrose, 250 mM; Tris, 10 mM; EDTA, 1 mM; BSA, 0.01%; pH=7.4). The atria and extraneous tissue are removed and the remainder is chopped with scissors. The pieces are rinsed in homogenization buffer before being homogenized in 10 mL of the same buffer for 5–7 seconds. The homogenate is then diluted with homogenization buffer (40 total volume) and centrifuged at 200 g for 20 minutes. The supernatant is withdrawn and centrifuged at 7000 g for 20 minutes and the resulting pellet is isolated, resuspended in 40 mL of homogenization buffer and centrifuged once more at 7000 g for 20 minutes. The isolated pellet is resuspended in 10 mL of homogenization buffer and stored at 4° C. until use. This preparation is used as the isolated mitochondrial preparation.

(b). Inhibition of CAT-1 assay

Isolated mitochondria (20 $\mu$L) are incubated with 60 $\mu$L of Tris/sucrose buffer (sucrose, 500 mM; Tris, 20 mM; KCl, 100 mM; EDTA, 2 mM; pH=7.0 plus 83 $\mu$M palmitoyl CoA, and BSA, 0.8 mg/mL and $10^{-4}$ to $10^{-10}$M of the drug to be tested. After 10 minutes at 30° C., the reaction is started by addition of 10 $\mu$L of $^3$H-carnitine (final concentration=250 $\mu$M). After 5 minutes, the reaction is terminated by the addition of ice cold 70% perchloric acid (PCA). The precipitated solids so formed, containing the insoluble product of the enzyme palmitoyl carnitine, are captured on filter paper. The filter paper is washed with 7% PCA, then dried and placed in scintillation vials with 10 mL of scintillant (Aquasol, New England Nuclear) and counted for radioactivity. The rate of the reaction is assessed by the difference in radioactivity between zero time and five minutes in the absence of test compound. The ability of test compounds at selected concentrations to inhibit CAT-1 is determined by their ability to reduce the formation of the radioactive product. The IC$_{50}$ of the test compound is the concentration of test compound that reduces the formation of radioactive product by 50%.

Results of this assay are reported in Table I, under the heading "Primary Screen".

2. Secondary Screen—Inhibition of CAT-1 in intact Cardiac Myocytes (a) Preparation of Isolated Rat Cardiac Myocytes Four hearts are excised from anesthetized rats and perfused retrogradly via the Langendorf technique. Each heart receives 100 mL of Krebs (NaCl, 118.4 mM; KCL, 4.6 mM; NaH$_2$PO$_4$, 1.0 mM; NaHCO$_3$, 20 mM; MgSO$_4$, 2 mM; CaCl$_2$, 50 $\mu$M; glucose, 11.0 mM), 100 mL of Ca++ free Krebs and finally 100 mL of 0.5% collagenase (Boehringer Mannheim, type 1) in Hepes (NaCl, 115 mM; KCl, 5 mM; sucrose, 35 mM; glucose, 10 mM; Hepes, 10 mM; taurine, 4 mM; MgSO$_4$, 2 mM; CaCl$_2$, 50 $\mu$M). After these perfusions, the hearts are chopped into pieces, approx. 0.5 cm$\times$0.5 cm and placed in four 125 mL plastic bottles along with 25 mL of collagenase/Hepes situated in a water bath maintained at 35° C. The pieces of cardiac tissue in each bottle are agitated by using a Harvard respirator connected to four glass syringes, which sucks the tissue up and down each tube during each respiratory cycle. After fifteen minutes, the collagenase/Hepes is removed and replaced with fresh collegenase/Hepes and the process repeated. The collegenase/Hepes from the subsequent fifteen minute harvests are centrifuged at 500 g to pellet the cells which are then resuspended in Hepes buffer. After six harvests, all cells are pelleted, resuspended in 2$\times$26.5 mL of Hepes plus BSA (350 mg) and layered on top of 2$\times$percoll gradients (21.15 mL percoll, 2.35 mL NaCl, 6 drops acetic acid). This is centfifuged at 3000 g for eight minutes forming a percoll gradient which results in viable cells being separated from damaged cells. The viable cells are removed, washed with Hepes and finally resuspended in 25 mL of Hepes. The concentration of calcium is slowly increased to 500 $\mu$M by small additions of CaCl$_2$ over two hours.

(b). Cellular Assay

The isolated cardiac myocytes (2 mL; approximately 1$\times$10$^6$ cells) are separated into six glass pods. Into four of these are placed selected concentrations of the compound to be tested, and the cells are incubated for twenty minutes, after which the pods are centrifuged at 300 g for three minutes. 300 $\mu$L of normoxic Hepes is placed in one of the pods not containing compound and then all pods are placed in a hypoxic chamber (N$_2$ atmosphere). Oxygen is fed via small bore steel tubes to the pod containing the normoxic buffer, while the other five pods receive pre-purified argon (99.998% pure). After two minutes, Hepes (pre-gassed with argon for at least twelve hours) is fed into the five hypoxic pods. This hypoxic environment (pO$_2$<10 mm Hg) is maintained for twenty minutes, after which the cells and pods are frozen by contact with a metal block precooled in liquid N₂. The pods are then removed from the chamber and stored at −70° C. The carnitine assay is performed, as described below in (c), to determine the amount of long-chain acylcarnitine in the cells from the normoxic, hypoxic and hypoxic plus compound samples. The hypoxic condition causes the long-chain acylcarnitines to increase threefold. The presence of the CAT-1 inhibitors inhibit this increase if they penetrate the cell membrane. Thus the IC$_{50}$ in this screen is the concentration of test compound which produces a 50% inhibition of the hypoxia-induced increase in long-chain acylcarnitines.

Results of this assay are reported in Table I, under the heading "Secondary Screen".

(c) Long-chain Acylcarnitine Assay.

The frozen cell samples are thawed, mixed and homogenized with 40 μL of 70% PCA. The homogenate is transferred to eppendorf tubes while the homogenization tube and the glass pod is rinsed with 500 μL of 7% PCA, with the rinse being added to the eppendorf tube. This is then centrifuged at 1000 g for two minutes to pellet the precipitate (containing the long-chain acylcarnitine) and the supernatant is discarded. The pellet is washed twice with 500 μL of 7% PCA, the supernatants being discarded. The pellet is then hydrolyzed (to separate the acyl unit from carnitine to yield free carnitine) by the addition of 200 μL of aleionized H₂O and 50 μL of 5N KOH and incubated at 70° C. for ninety minutes. Following hydrolysis, the samples are neutralized by the addition of 500 μL of 0.83M Hepes (pH=7.4) and 10 μL of 70% PCA. After the tubes are centrifuges, the supernatants are transferred into eppendorf tubes. The pellets are washed with 250 μL of 0.83M Hepes and the washes are added to the eppendorf tube. To measure the level of carnitine in the samples, 300 μL of the supernatant in the eppendorf tubes is incubated with 300 μL of deionized H₂O, 400 μL of (0.83M Hepes; 50 mM EDTA: 10 mM N-ethylmaleimide; 10 μM ³H-acetyl CoA; 10 μL carnitine acyltransferase, Sigma, 45 units). The tubes are vortexed and incubated for ninety minutes at 35° C. Standards are also incubated containing known amounts of carnitine (from 5 to 500 pmoles). The ³H-acetyl carnitine so formed is separated from the ³H-acetyl CoA by passing the samples through a Dowex 1-8× anion exchange resin (100–200 mesh, chloride form) and the eluate (containing the ³H-acetyl carnitine) is captured in mini-vials. The resin is washed with 300 μL of deionized H₂O and the eluate is again captured in the vial 5 mL of scintillant (Aquasol 2, New England Nuclear) is added and the amount of radioactivity is determined. The amount of carnitine in each sample and hence LCA is determined from comparison with the standard curve.

| | | Inhibition of CAT-1 | |
|---|---|---|---|
| Example | Name | Primary Screen IC$_{50}$(μM) | Secondary Screen IC$_{50}$(μM) |
| 4 | 5-[[2-(2-Naphthalenyloxy)ethyl]oxy]-alpha-oxo-2-thiopheneacetic acid | 0.05 | 1 |
| 5 | rac.-5-[[2-(2-Naphthalenyloxy)ethyl]=oxy]-alpha-oxo-2-thiopheneacetic acid 2,3-dihydroxypropyl ester | 0.04 | 0.25 |
| 6 | 5-[[2-(2-Naphthalenyloxy)ethyl]=oxy]-alpha-oxo-2-thiopheneacetic acid 2-(dimethylamino)ethyl ester. | 0.04 | 0.3 |
| 7 | 2-[[5-[[2-(2-Naphthalenyloxy)ethyl]=oxy]-alpha-oxo-2-thiopheneacetyl]oxy]-N,N,N-trimethylethanaminium iodide. | 0.03 | 0.1 |
| 9 | 5-[[2-(Cyclooctyloxy)ethyl]oxy]-alpha-oxo-2-thiopheneacetic acid (5:3) hydrate. | 1.8 | 8 |
| 11 | alpha, alpha-Difluoro-4-[[2-(phenoxy)ethyl]oxy]benzeneacetic acid | 18 | — |
| 13 | alpha, alpha-Difluoro-4-[[2-(2-naphthalenyloxy)ethyl]oxy]benzene=acetic acid | 1.75 | 3.8 |
| 18 | (S)-alpha-Amino-4-[[2-(cyclooctyl=oxy)ethyl]oxy]benzeneacetic acid hydrochloride | 37.4 | 5 |
| 19 | 4-[(Phenylmethyl)oxy]-alpha-oxobenzeneacetic acid | 90 | — |
| 21 | 4-[(2-Phenylethyl)oxy]-alpha-oxobenzeneacetic acid | 12 | — |
| 23 | 4-[(3-Phenylpropyl)oxy]-alpha-oxobenzeneacetic acid | 0.5 | 37 |
| 25 | 4-[(4-Phenybutyl)oxy]-alpha-oxobenzeneacetic acid | 2 | 12 |
| 27 | 4-[[3-(4-Fluorophenyl)propyl]=oxy]-alpha-oxobenzeneacetic acid | 3 | — |
| 29 | (E)-4-[[3-(4-Fluorophenyl)-2-propenyl]=oxy]-alpha-oxobenzeneacetic acid | 0.25 | — |
| 31 | (E)-alpha-Oxo-4-[(3-phenyl-2-propenyl)oxy]benzeneacetic acid | 0.1 | — |
| 33 | (Z)-alpha-Oxo-4-[(3-phenyl-2-propenyl)oxy]benzeneacetic acid | 1.0 | — |
| 35 | alpha-Oxo-4-[(3-phenyl-2-propynyl)oxy]benzeneacetic acid | 0.4 | — |
| 37 | alpha-Oxo-4-[[2-(phenoxy)=ethyl]oxy]benzeneacetic acid | 2 | 37 |
| 39 | 4-[[2-(2-Fluorophenoxy)ethyl]=oxy]-alpha-oxobenzeneacetic acid | 0.6 | — |

-continued

| | | Inhibition of CAT-1 | |
|---|---|---|---|
| Example | Name | Primary Screen IC$_{50}(\mu M)$ | Secondary Screen IC$_{50}(\mu M)$ |
| 41 | 4-[[2-(3-Fluorphenoxy)ethyl]=oxy]-alpha-oxobenzeneacetic acid | 1 | — |
| 43 | 4-[[2-(4-Fluorophenoxy)ethyl]=oxy]-alpha-oxobenzeneacetic acid | 0.8 | — |
| 45 | 4-[[2-(4-Chlorophenoxy)ethyl]=oxy]-alpha-oxobenzeneacetic acid | 0.3 | — |
| 47 | 4-[[2-(4-Nitrophenoxy)ethyl]oxy]-alpha-oxobenzeneacetic acid | 3 | — |
| 49 | 4-[[2-(4-Methylphenoxy)ethyl]oxy]-alpha-oxobenzeneacetic acid | 4 | — |
| 51 | alpha-Oxo-4-[[2-(4-trifluoromethyl=phenoxy)ethyl]oxy]benzeneacetic acid | 0.8 | — |
| 53 | 4-[[2-(Aminosulfonyl)phenoxy]=ethyl]oxy]-alpha-oxobenzeneacetic acid (4:1) molar hydrate | 4 | — |
| 55 | 4,4'-[1,2-Ethanediylbis(oxy)bis(alpha-oxobenzeneacetic acid (4:1) molar hydrate | 6 | — |
| 57 | 4-[[2-[4-(1,1'-Biphenyl)oxy]ethyl]oxy]-alpha-oxobenzeneacetic acid (4:1) molar hydrate | 5 | — |
| 59 | alpha-Oxo-4-[[2-(4-phenoxyphen=oxy)ethyl]oxy]benzeneacetic acid | 10 | — |
| 61 | 4-[[2-(4-Methoxyphenoxy)ethyl]=oxy]-alpha-oxobenzeneacetic acid | 2 | — |
| 63 | 4-[[2-(3,4- Dimethoxyphenoxy)=ethyl]oxy]-alpha-oxobenzene=acetic acid | 3 | — |
| 65 | 4-[[2-(3,4,5-Trimethoxyphenoxy)=ethyl]oxy]-alpha-oxobenzeneacetic acid | 3 | — |
| 67 | alpha-Oxo-4-[[(phenoxy)methyl]=oxy]benzeneacetic acid (5:1) molar hydrate | 15 | — |
| 69 | alpha-Oxo-4-[[(3-phenoxy)propyl]=oxy]benzeneacetic acid | 2 | — |
| 71 | alpha-Oxo-4-[[(4-phenoxy)butyl]=oxy]benzeneacetic acid | 0.4 | 20 |
| 73 | alpha-Oxo-4-[[(5-phenoxy)pentyl]=oxy]benzeneacetic acid | 5 | — |
| 75 | alpha-Oxo-4-[[(6-phenoxy)hexyl]=oxy]benzeneacetic acid | 10 | — |
| 77 | 4-[[2-[[2-(Phenoxy)ethyl]oxy]=ethyl]oxy]-alpha-oxobenzene=acetic acid | 2 | — |
| 78 | 4,4'-[Oxybis(2,1-ethanediyloxy)]=bis(alpha-oxobenzeneacetic acid) | 2 | — |
| 80 | rac.-4-[[(2-Hydroxy-3-phenoxy)=propyl]oxy]-alpha-oxobenzene=acetic acid | 8 | — |
| 82 | alpha-Oxo-4-[[2-(phenylthio)ethyl]=oxy]benzeneacetic acid | 0.3 | 17.5 |
| 84 | 4-[[2-(1-Naphthalenyloxy)ethyl]=oxy]-alpha-oxobenzeneacetic acid | 0.08 | 4.0 |
| 86 | 4-[[2-(2-Naphthalenyloxy)ethyl]=oxy]-alpha-oxobenzeneacetic acid | 0.08 | 3 |
| 88 | 4-[[4-(2-Naphthalenyloxy)butyl]=oxy]-alpha-oxobenzeneacetic acid | 0.17 | 3.5 |
| 90 | 4-[[2-(2-Naphthalenylthio)ethyl]=oxy]-alpha-oxobenzeneacetic acid | 0.27 | 28 |
| 92 | 4-[[4-(2-Naphthalenylthio)butyl]oxy]-alpha-oxobenzeneacetic acid | 3.5 | — |
| 94 | 4-[[3-(2-Naphthalenyl)propyl]oxy]-alpha-oxobenzeneacetic acid | 0.08 | 12 |
| 96 | (E)-4-[[3-(2-Naphthalenyl)-2-propenyl]oxy]-alpha-oxo=benzeneacetic acid | 0.065 | 7 |
| 97 | 4-[[2-(Methoxy)ethyl]oxy]-alpha-oxobenzeneacetic acid | 30 | — |
| 99 | 4-[[2-(Cyclohexyloxy)ethyl]oxy]-alpha-oxobenzeneacetic acid | 0.9 | 20 |
| 101 | 4-[[2-(Cyclooctyloxy)ethyl]oxy]-alpha-oxobenzeneacetic acid | 0.9 | 50 |
| 103 | alpha-Oxo-4-[[2-tricyclo(3.3.1.1-3,7)dec-1-yloxy]ethyl]oxy]benzene=acetic acid | 1.5 | 40 |
| 104 | rac.-4-[[2-(2-Naphthalenyloxy)ethyl]=oxy]-alpha-oxobenzeneacetic acid 2,3-dihydoxypropyl ester | 0.04 | 1.2 |

-continued

Inhibition of CAT-1

| Example | Name | Primary Screen IC$_{50}$($\mu$M) | Secondary Screen IC$_{50}$($\mu$M) |
|---|---|---|---|
| 105 | 4-[[2-(2-Naphthalenyloxy)ethyl]oxy]-alpha-oxobenzeneacetic acid 2-[2-(2-hydroxyethoxy)ethoxy]ethyl ester | 0.04 | 75 |
| 106 | 4-[[2-(2-Naphthalenyloxy)ethyl]=oxy]-alpha-oxobenzeneacetic acid 2-(dimethylamino)ethyl ester | 0.09 | 1 |
| 108 | 4-[[2-(2-Anthracenyloxy)ethyl]=oxy]-alpha-oxobenzeneacetic acid | 0.2 | — |
| 110 | alpha-Oxo-4-[[2-(9-phenanthren=yloxy)ethyl]oxy]benzeneacetic acid | 0.1 | — |
| 112 | alpha-Oxo-4-[[2-(5,6,7,8-tetrahydro-2-naphthalenyloxy)ethyl]benzene=acetic acid | 0.2 | — |
| 114 | rac.-alpha-Oxo-4-[[2-(1,2,3,4-tetra=hydro-2-naphthalenyloxy)ethyl]=oxy]benzeneacetic acid | 2.8 | — |
| 116 | alpha-Oxo-4-[[2-[3-(2-phenoxyethoxy)-2-naphthalenyloxy]ethyl]oxy]benzene=acetic acid | 0.65 | — |
| 118 | 4-[[2-[3-(2-Hydroxyethoxy)-2-naphthalenyloxy[ethyl]oxy]-alpha-oxobenzeneacetic acid | 0.25 | — |
| 121 | 4-[[2-(3-Hydroxy-2-napthalenlenyl=oxy)ethyl]oxy]-alpha-oxo=benzeneacetic acid | 0.3 | — |
| 123 | alpha-Oxo-4-[4-(3-pyridinyl)but=oxy]benzeneacetic acid | 1.5 | — |
| 125 | alpha-Oxo-4-[4-(4-pyridinyl)but=oxy]benzeneacetic acid | 2.0 | — |
| 127 | alpha-Oxo-4-[[2-(7-quinolyloxy)=ethyl]oxy]benzeneacetic acid monohydrate | 0.26 | — |
| 129 | 4-[[2-(7-Isoquinolyloxy)ethyl]=oxy]-alpha-oxobenzeneacetic acid (5:2) molar hydrate | 0.44 | — |
| 131 | alpha-Oxo-4-[[2-(4-quinolyloxy)=ethyl]oxy]benzeneacetic acid | 0.96 | — |
| 133 | 4-[[2-[8-(2,2-Dimethyl-1-oxobutoxy)-2-naphthalenyloxy]ethyl]oxy]-alpha-oxobenzeneacetic acid methyl ester | 35 | — |
| 134 | 4-[[2-[8-(2,2-Dimethyl-1-oxobutoxy)-2-naphthalenyloxy]ethyl]oxy]-alpha-oxobenzeneacetic acid | 0.6 | 0.4 |
| 136 | 4-[[2-[2-[(2,2-Dimethyl-1-oxobutoxy)=methyl]-6-methylphenoxy]ethyl]oxy]-alpha-oxobenzeneacetic acid (2:1) hydrate | 7.7 | 0.9 |
| 138 | 4-[[2-[6-(Acetyloxy)-2-naphthalen=yloxy]ethyl]oxy-alpha-oxobenzene=acetic acid methyl ester | 8.9 | — |
| 140 | 4-[[3-(2-Naphthoylamino)propyl]=oxy]-alpha-oxobenzeneacetic acid | 0.15 | — |
| 141 | 4-[[2-Benzofuranyl)methoxy]-alpha-oxobenzeneacetic acid | 0.7 | — |
| 142 | 4-[3-(2-Naphthalenyloxy)-1-propynyl]-alpha-oxobenzene=acetic acid | 1.8 | 20 |
| 143 | 4-[3-(2-Naphthalenyloxy)propyl]-alpha-oxobenzeneacetic acid | 2.7 | 12 |
| 146 | 4-[3-[[(2-Naphthalenyl)carbonyl]=amino]-1-propynyl]-alpha-oxo=benzeneacetic acid | 5.5 | — |
| 147 | 4-[3-[[(2-Naphthalenyl)carbonyl]=amino]propyl]-alpha-oxobenzene=acetic acid | 6.2 | — |
| 149 | 4-[[2-(2-Naphthalenyloxy)ethyl]=thio]-alpha-oxobenzeneacetic acid | 0.08 | — |
| 151 | rac.-4-[[2-(2-Naphthalenyloxy)ethyl]sulfinyl]-alpha-oxo=benzeneacetic acid | 5.5 | — |
| 153 | 4-[[2-(2-Naphthalenyloxy)acetyl]=amino]-alpha-oxobenzene=acetic acid | 0.93 | — |
| 155 | 4-[(2-Naphtahlenyl)methoxy]-alpha-oxobenzeneacetic acid | 0.22 | — |
| 157 | 4-[2-(2-Naphthalenyl)-2-oxoethoxy[-alpha-oxobenzeneacetic acid | 0.05 | 0.3 |
| 159 | 4-[(2-Quinolinyl)methoxy]-alpha-oxo-benzeneacetic acid | 5.1 | — |

-continued

Inhibition of CAT-1

| Example | Name | Primary Screen IC$_{50}$($\mu$M) | Secondary Screen IC$_{50}$($\mu$M) |
|---|---|---|---|
| 163 | N,N-Bis(2-hydroxyethyl)-4-[[2-(2-naphthalenyloxy)ethyl]oxy]-alpha-oxobenzeneacetamide | 3.5 | — |
| 164 | N-[2-(Dimethylamino)ethyl]-4-[[2-(2-naphthalenyloxy)ethyl]oxy]-alpha-oxobenzeneacetamide | — | — |
| 168 | 4-[[2-(2-Naphthalenyloxy)ethyl]amino]-alpha-oxobenzeneacetic acid | 0.7 | — |
| 169 | rac.-4-[[2-(2-Naphthalenyloxy)ethyl]oxy]-alpha-oxobenzeneacetic acid (2.2-dimethyl-1,3-dioxolan-4-yl)methyl ester | 3.5 | — |
| 171 | 4-[[2-(2-Naphthalenyloxy)ethyl]=sulfonyl]-alpha-oxobenzeneacetic acid | 28% @ 10 mM | — |
| 173 | (4-[[2-(Cyclooctyloxy)ethyl]thio]-alpha-oxobenzeneacetic acid | 0.8 | 0.3 |
| 175 | (4-[[2-[2-[(2,2-Dimethyl-1-oxobut=oxy)methyl]-6-methylphenoxy]ethyl]=thio]-alpha-oxobenzeneacetic acid | 0.5 | 0.2 |
| 177 | 4-[[[2-(2-Naphthalenyloxy)ethyl]=amino]carbonyl]-alpha-oxobenzene=acetic acid | 0.4 | 25 |
| 179 | 4-[2-(2-Naphthalenyloxy)ethoxy]-3-nitro-alpha-oxobenzeneacetic acid | 0.2 | 8 |
| 181 | 3-Methyl-4-[2-(2-naphthalenyloxy)=ethoxy]-alpha-oxobenzeneacetic acid | 0.4 | 7.5 |
| 183 | 2-Methyl-4-[2-(2-naphthalenyloxy)=ethoxy]-alpha-oxobenzeneacetic acid (4:1) hydrate | 4.7 | — |
| 185 | 3-Chloro-4-[2-(2-naphthalenyloxy)=ethoxy]-alpha-oxobenzeneacetic acid | 0.08 | 12 |
| 187 | 2-Chloro-4-[2-(2-naphthalenyloxy)=ethoxy]-alpha-oxobenzeneacetic acid | 0.3 | 9 |
| 189 | 3,5-Dichloro-4-[2-(2-naphthalenyloxy)=ethoxy]-alpha-oxobenzeneacetic acid | 28% @ 10 mM | — |
| 191 | 2,6-Dichloro-4-[2-(2-naphthalenyloxy)=ethoxy[-alpha-oxobenzeneacetic acid | 6.7 | — |
| 195 | 2,6-Dimethoxy-4-[2-(2-naphthalenyl=oxy)ethoxy]-alpha-oxobenzeneacetic acid | 24% @ 10 mM | — |
| 197 | 2-Fluoro-4-[2-(2-naphthalenyloxy)=ethoxy]-alpha-oxobenzeneacetic acid | 0.16 | 6 |
| 199 | 3-Fluoro-4-[2-(2-naphthalenyloxy)=ethoxy]-alpha-oxobenzeneacetic acid | 0.17 | 0.6 |
| 201 | 2,6-Difluoro-4-[2-(2-naphthalenyloxy)=ethoxy]-alpha-oxobenzeneacetic acid | 0.83 | 7 |
| 203 | 3,5-Difluoro-4-[2-(2-naphthalenyloxy)=oxy)ethoxy]-alpha-oxobenzeneacetic acid | 37% @ 10 mM | — |
| 205 | 2,3,5,6-Tetrafluoro-4-[2-(2-naphthalenyl=oxy)ethoxy]-alpha-oxobenzeneacetic acid | 7.2 3 | 5% @ 25 $\mu$M |
| 212 | 4-[3-[2-(2,2-Dimethyl-1-oxobutoxy)=methyl]-6-methylphenyl]-2-propynyl=oxy]-alpha-oxobenzeneacetic acid (1:1) morpholine salt | 0.47 | 47% @ 25 mM |
| 215 | (Z)-4-[3-[2-(2,2-Dimethyl-1-oxobutoxy)=methyl]-6-methylphenyl]-2-propenyloxy]-alpha-oxobenzeneacetic acid (1:1) morpholine salt | 2 | 9 |
| 220 | (E)-4-[3-[2-[(2,2-Dimethyl-1-oxobutoxy)=methyl]-6-methylphenyl]-2-propenyloxy]-alpha-oxobenzeneacetic acid (1:1) morpholine salt | 1.6 | 0.09 |
| 223 | 4-[3-[2-(2,2-Dimethyl-1-oxobutoxy)=methyl]-6-methylphenyl]propoxy]-alpha-oxobenzeneacetic acid (1:1) morpholine salt | 1.1 | 0.09 |
| 229 | (E)-4-[3-[4'-Fluoro-3-(1-methylethyl)[1,1'-biphenyl]-2-yl]-2-propenyloxy]-alpha-oxbenzeneacetic acid | 9 | 1 |
| 234 | 4-[2-[4'-Fluoro-3-(1-methylethyl)[1,1'-biphenyl]-2-yloxy]ethoxy]-alpha-oxo=benzeneacetic acid | — | 90% @ 25 mM |
| 241 | (E)-4-[3-[3-(4-Fluorophenyl)-1-(1-methylethyl)-1H-indol-2-yl]-2-propen=yloxy]-alpha-oxobenzeneacetic acid (1:1) morpholine salt | 38% @ 10 mM | 12 |
| 243 | (E)-4-[3-[1-(4-Fluorophenyl)-4-(1- | 35% @ 10 mM | 7 |

-continued

| | | Inhibition of CAT-1 | |
|---|---|---|---|
| Example | Name | Primary Screen IC$_{50}$($\mu$M) | Secondary Screen IC$_{50}$($\mu$M) |
| | methylethyl)-2-phenyl-1H-imidazol-5-yl]-2-propenyloxy-alpha-oxobenzene= acetic acid (1:1) morpholine salt | | |
| 245 | 4-[2-Oxo-2-(4-phenyl-1-piperidinyl)= ethoxy]-alpha-oxobenzeneacetic acid | 0.06 | 33% @ 25 mM |
| 247 | 4-[2-(Cyclooctylamino)-2-oxoethoxy]-alpha-oxobenzeneacetic acid | 0.4 | 30 |
| 249 | 4-[2-Oxo-2-(4-phenyl-1-piperazinyl)= ethoxy]-alpha-oxobenzeneacetic acid | 10 | — |
| 251 | 4-[2-Oxo-2-(1,2,3,4-tetrahydro-2-isoquinolinyl)ethoxyl]-alpha-oxobenzeneacetic acid | 0.4 | — |
| 253 | alpha-Oxo-4-[2-oxo-2-[4-[2-[2-(tri= fluoromethyl)phenyl]ethyl]-1-piperazin= yl]ethoxy]benzeneacetic acid hydrochloride salt | 0.5 | — |
| 255 | 4-[2-(4-Morpholinyl)-2-oxoethoxy]-alpha-oxobenzeneacetic acid | 12 | — |
| 257 | 4-[3-(4-Acetyl-3-hydroxy-2-propylphen= oxy)propoxy]-alpha-oxobenzeneacetic acid | 0.38 | 0.1 |
| 259 | 4-[6-[2,3-bis(Phenylmethoxy)phenyl]= hexyloxy]-alpha-oxobenzeneacetic acid | 1.2 | — |
| 260 | 4-[6-(2,3-Dihydroxyphenyl)hexyloxy]-alpha-oxobenzeneacetic acid | 4 | 94% @ 25 mM |
| 262 | 4-[3-(5,6-Dihydro-6-oxo-5-phenanthrid= inyl)propoxy]-alpha-oxobenzeneacetic acid | 1 | 99% @ 25 mM |
| 264 | 4-[3-(1,2-Dihydro-2-oxo-1-quinolinyl)= propoxy]-alpha-oxobenzeneacetic acid | 12 | — |
| 266 | 4-[5-[3,5-bis(1,1-Dimethylethyl)-4-hydroxyphenyl]-5-oxopentyloxy]-alpha-oxobenzeneacetic acid | 48% @ 10 $\mu$M | — |
| 268 | 4-[3-[3-Hydroxy-4-(methoxycarbonyl)-2-propylphenoxy)propoxy]-alpha-oxo= benzeneacetic acid | 0.23 | — |
| 269 | 4-[3-[4-Carboxy-3-hydroxy-2-propyl= phenoxy)propoxy]-alpha-oxobenzene= aceticacid | 1.8 | — |
| 271 | 4-[3-[4-Acetyl-3-methoxy-2-propylphen= oxy)propoxy]-alpha-oxobenzeneacetic acid | 0.46 | — |
| 273 | 4-[3-(4-Acetyl-3-hydroxyphenoxy)prop= oxy]-alpha-oxobenzeneacetic acid | 0.73 | — |
| 275 | 4-[3-[[3,5-bix(1,1-Dimethylethyl)-4-hydroxyphenyl]thio]propoxy]-alpha-oxobenzeneacetic acid | 0.57 | — |
| 280 | rac-4-[4-Hydroxy-4-(2-naphthalenyl)= butoxy]-alpha-oxobenzeneacetic acid | 0.2 | 2 |
| 282 | 4-[[4-(2-Naphthalenyl)-4-oxobutyl]oxy]-alpha-oxobenzeneacetic acid | 0.4 | 8 |
| 284 | 4-[2-(1-Naphthalenyl)-2-oxoethoxy]-alpha-oxobenzeneacetic acid | 0.03 | 0.8 |
| 286 | 4-[2-[4-(1,1-Dimethylethyl)phenyl-2-oxo= ethoxy]-alpha-oxobenzeneacetic acid | 0.3 | 1.2 |
| 288 | 4-[2-[[1,1'-Biphenyl]-2-yl]-2-oxoethoxy] alpha-oxobenzeneacetic acid | 1.4 | — |
| 290 | 4-[2-(Cyclooctyl)02ooxoethoxy]-alpha-oxobenzeneacetic acid | 1 | — |
| 292 | 4-[2-Oxo-2-(2,4,6-trimethylphenyl)eth= oxy]-alpha-oxobenzeneacetic acid | 4.5 | — |
| 294 | 4-[3-[4-(2-Chlorophenyl)-9-methyl-6H-thienol[3,2-f][1,2,4]triazolo[4,3-a][1,4] diazepin-2-yl]-2-propoxy]-alpha-oxo= benzeneacetic acid (20:9) dichloro= methane solvate | 0.3 | 37% @ 25 mM |
| 296 | 4-[3-[4-(2-Chlorophenyl)-9-methyl-6H-thieno[3,2-f][1,2,4]triazolo[4,3-a][1,4] diazepin-2-yl]-2-propoxy]-alpha-oxo= benzeneacetic acid (10:7) hydrate (25:2) dichloromethane solvate | 10 | — |
| 298 | (S)-alpha-Amino-4-[2-[2,2-dimethyl-1-oxobutoxy)methyl]-6-methylphenoxyl] ethoxy]benzeneacetic acid | 2.5 | 30 |
| 299 | N-Hydroxy-N-methyl-4-[2-(2-naphth= alenyloxy)ethoxy]-alpha-oxobenzene= acetamide | 1.9 | 8 |
| 300 | N-Hydroxy-4-[2-(2-naphthalenyloxy)eth= | 2.1 | 5 |

-continued

| | Inhibition of CAT-1 | | |
|---|---|---|---|
| Example | Name | Primary Screen IC$_{50}$($\mu$M) | Secondary Screen IC$_{50}$($\mu$M) |
| 301 | oxy]-alpha-oxo-2-thiopheneacetamide (Z)-alpha-(Hydroxyimino)-4-[2-(2-naphthalenyloxy)ethoxy]benzeneacetic acid | 0.58 | 2 |
| 302 | (Z)-alpha-(Hydroxyimino)-5-[2-(2-naphthalenyloxy)ethoxy]-2-thiopheneacetic acid | 0.24 | 0.9 |
| 304 | (Z)-4-[2-[2-[(2,2-Dimethyl-1-oxobutoxy)methyl]-6-methylphenyloxy]ethoxy]-alpha-methoxyiminobenzeneacetic acid | 3.3 | 5 |
| 306 | (Z)-alpha-(Methoxyimino)-5-[2-(2-naphthalenyloxy)ethoxyl]-2-thiopheneacetic acid hemihydrate | 0.3 | 7 |
| 307 | (E)-alpha-(Methoxyimino)-5-[2-(2-naphthalenyloxy)ethoxyl]-2-thiopheneacetic acid | 1.5 | 5 |
| 309 | (Z)-alpha-(Ethoxyimino)-5-[2-(2-naphthalenyloxy)ethoxy]-2-thiopheneacetic acid | 0.02 | — |
| 310 | (E)-alpha-(Ethoxyimino)-5-[2-(2-naphthalenyloxy)ethoxy]-2-thiopheneacetic acid | 0.24 | — |
| 312 | (Z)-5-[2-(2-Naphthalenyloxy)ethoxy]-alpha-[(2-propenyloxy)imino]-2-thiopheneacetic acid | 0.1 | — |
| 313 | (E)-5-[2-(2-Naphthalenyloxy)ethoxy]-alpha-[(2-propenyloxy)imino]-2-thiopheneacetic acid | 0.27 | — |
| 315 | (Z)-5-[2-(2-Naphthalenyloxy)ethoxy]-alpha-[(phenylmethoxy)imino]-2-thiopheneacetic acid | 0.14 | — |
| 316 | (E)-5-[2-(2-Naphthalenyloxy)ethoxy]-alpha-[(phenylmethoxy)imino]-2-thiopheneacetic acid | 0.5 | — |
| 320 | (E)-alpha-(Dimethylhydrazono)-4-[2-(2-naphthalenyloxy)ethoxy]benzeneacetic acid | 1.8 | |
| 321 | (Z)-alpha-(Dimethylhydrazono)-4-[2-(2-naphthalenyloxy)ethoxy]benzeneacetic acid | 6.5 | — |

A compound of formula I, an enantiomer thereof or a salt thereof or a composition containing a therapeutically effective amount of a compound of formula I or a salt thereof can be administered by methods well known in the art. Thus, a compound of formula I or a salt thereof can be administered either singly or with other pharmaceutical agents, orally, parenterally, rectally, or by inhalation, for example, in the form of an aerosol, micropulverized powder or nebulized solution. For oral administration the described compound can be administered in the form of tablets, capsules, for example, in admixture with talc, starch, milk sugar or other inert ingredients, that is, pharmaceutically acceptable carriers, in the form of aqueous solutions, suspensions, elixirs or aqueous alcoholic solutions, for example, in admixture with sugar or other sweetening agents, flavoring agents, colorants, thickeners and other conventional pharmaceutical excipients, or beadlets for oral administration. For parenteral administration, the desired compound can be administered in solutions or suspension, for example, as an aqueous or peanut oil solution or suspension using excipients and carders conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition. For rectal administration, the desired compound can be administered in the form of suppositories utilizing an inert carder material cocoa butter and the like. For topical administration, the compounds of formula I can be incorporated into ointments, creams, lotions, gels, and the like. In general, the solutions, ointments and creams which are useful in accordance with this invention include formulations having absorbable, water soluble or emulsion-type bases, such as petrolatum, lanolin, polyethylene glycols, or the like.

Suitable solutions will contain the compounds of formula I dissolved in a pharmaceutically acceptable solvent, such as polyethylene glycol, or the like.

Suitable lotions include, true solutions to aqueous or hydroalcoholic formulations containing finely divided particles. Lotions can contain suspending or dispersing agents such as cellulose derivatives, for example, methyl cellulose, ethyl cellulose, or the like. Gels will typically be semi-solid preparations made by gelling a solution or suspension of a compound of formula I in a suitable hydrous or anhydrous vehicle, using a gelling agent such as carboxy polymethylene, or the like, and thereafter neutralizing it to proper consistency with an alkali metal hydroxide, for example, sodium hydroxide, and an amine, for example, polyethylenecocoamine. Topical pharmaceutical compositions containing a compound of formula I can also be formulated to include conventional ingredients such as preservatives, stabilizers, wetting agents, emulsifying agents, buffers, and the like, in conventional amounts adjusted for particular requirements and which are readily determinable by those skilled in the art.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 1 to about 2000 mg per day, preferably about 25 to about 500 mg either as a single dose or in divided doses.

The compounds of formula I of the invention may possess one or more asymmetric carbon atoms, they can thus be obtained as enantiomers or as racemic mixtures. The resolution of racemates into the optically active isomers can be carried out by known procedures. Some racemic mixtures can be precipitated as eutectics and can thereafter be separated. Chemical resolution of the starting material is, however, preferred if an enantiomer of formula I is to be prepared. By this method, diastereomeric salts are formed from the reacemic mixture, for example, of a precursor of a compound of formula VI, with an optically active resolving agent, for example, an optically active base, such as R-(+)-α-methylbenzylamine, which can be reacted with a carboxyl group. The formed diastereomers are separated by selective crystallization and converted to the corresponding optical isomer. Thus, the invention covers the racemates of the compounds of formula I as well a their optically active isomers (enantiomers).

The examples that follow also further illustrate the invention. Melting points of compounds were determined on a Thomas-Hoover capillary melting point apparatus and are uncorrected. The proton NMR spectra were recorded on a Varian XL-100, XL-200 or XL-400 spectrometer, IR spectra were obtained on a Beckman IR-9 or IR-12 spectrometer. NMR and IR spectra were recorded for each new compound reported herein and were consistent with the assigned structures. Preparative high-pressure liquid chromatography (HPLC) was performed on silica gel Prep-Pak 500 cartridges with a Waters Associates Prep LC 500A instrument. Hash chromatography was performed with a loading ratio most often in the range of 50–100 g of sorbent to 1 g of compound, using a column pressure of 3–5 psi on Kieselgel 60,230–400 mesh, obtained from the same supplier. Column chromatography was accomplished on Kieselgel 60, 35–70 mesh, from E. Merck, Darmstadt. Kieselgel 60 $F_{254}$ plates from E. Merck were used for TLC, and compounds were visualized with UV light or iodine vapor. Dimethylformamide was dried over Linde 3A sieves.

EXAMPLE I

Preparation of
2-[[2-(2-naphthalenyloxy)ethyl]oxy]thiophene

A solution of 2-methoxythiophene (2.28 g) and 2-(2-naphthalenyloxy)ethanol (4.0 g) in benzene (35 mL) containing para-toluenesulfonic acid (0.02 g) was stirred at reflux for 3 days in a flask equipped with a Soxhlet extractor charged with 4 Å molecular sieves. The mixture was cooled, washed with 0.5N sodium hydroxide solution, dried over anhydrous magnesium sulfate (MgSO4) and evaporated. Crystallization of the residual material from ethanol (30 mL) provided 2.68 g of 2-[[2-(2-naphthalenyloxy)ethyl]oxy]thiophene as colorless flakes, mp 129°–130 ° C.

Analysis Calculated for $C_{16}H_{14}O_2S$: C, 71.09; H, 5.22; S, 11.86. Found: C, 70.85; H, 5.14; S, 11.73.

EXAMPLE 2

Preparation of
2-[[2-(cyclooctyloxy)ethyl]oxy]thiophene

As in Example 1, a solution of 2-methoxythiophene (11.4 g) and 2-(cyclooctyloxy) ethanol (13.78 g) in benzene (200 mL) containing para-toluenesulfonic acid (0.1 g) was stirred at reflux for 3 days in a flask equipped with a Soxhlet extractor charged with 4 Å molecular sieves. After the reaction was worked up in the usual manner, the crude product was purified by HPLC (hexane-diethyl ether; 2.4: 1) to give 12.6 g of 2-[[2-(cyclooctyloxy) ethyl]oxy]thiophene as a colorless oil. A small portion was distilled in a Kugelrohr apparatus (~130 ° C./0.02 mm) to furnish the analytical specimen.

Analysis Calculated for $C_{14}H_{22}O_2S$: C, 66.10; H, 8.72; S, 12.60. Found: C, 66.30; H, 8.72; S, 12.40.

EXAMPLE 3

Preparation of
5-[[2-(2-naphthalenyloxy)ethyl]oxy]-alpha-oxo-2-thiopheneacetic acid ethyl ester Ethyl oxalyl chloride (3 mL) was added dropwise with stirring to a chilled solution of 2-[[2-(2-naphthalenyloxy)ethyl]oxy]thiophene (2.027 g) in dichloromethane (15 mL) containing pyridine (0.75 mL). After the solution was stirred at 35 ° C. for 5 hours, it was then cooled and poured into a saturated aqueous sodium bicarbonate solution. The mixture was stirred for 10 minutes, then the phases were separated and the organic layer was washed in turn with brine, 0.5 N hydrochloric acid and brine. The aqueous layer and washes were back-extracted in turn with dichloromethane, then the combined extracts were dried (MgSO4) and evaporated. The residual material was crystallized from dichloromethane-diethyl ether to provide 1.96 g of 5-[[2-(2-naphthalenyloxy)ethyl]oxy]-alpha-oxo-2-thiopheneacetic acid ethyl ester as a yellow crystalline solid, mp 98°–100 ° C. A sample was re, crystallized from the same solvents to give the analytical specimen, mp 98°–100° C.

Analysis Calculated for $C_{20}H_{18}O_5S$: C, 64.85; H, 4.90; S, 8.65. Found: C, 65.00; H, 4.83; S, 8.46.

EXAMPLE 4

Preparation of
5-[[2-(2-naphthalenyloxy)ethyl]oxy]-alpha-oxo-2-thiopheneacetic acid In potassium hydroxide solution (3.1 mL) was added dropwise with stirring to a chilled solution of 5-[[2-(2-naphthalenyloxy)ethyl]oxy]-alpha-oxo-2-thiopheneacetic acid ethyl ester (1.13 g) in methanol (7 mL). Almost immediately the potassium salt precipitated from the solution as a colorless solid which was filtered off and washed with methanol. The solid was partitioned between dichloromethane (100 mL) and 0.1N hydrochloric acid (35 mL) and after all solids had dissolved, the organic layer was washed with water, dried over anhydrous sodium sulfate (Na$_2$SO$_4$) and evaporated to yield 0.94 g of 5-[[2-(2naphthalenyloxy)ethyl]oxy]-alpha-oxo-2-thiopheneacetic acid as a yellow-orange solid. Crystallization of the acid from benzene-hexane furnished the title compound as a yellow solid, mp 152°–154 ° C.

Analysis Calculated for C$_{18}$H$_{14}$O$_5$S: C, 63.15; H, 4.12; S, 9.36. Found: C, 63.18; H, 4.11; S, 9.09.

EXAMPLE 5

Preparation of rac.-5-[[2-(2-naphthalenyloxy)ethyl]oxy]-alpha-oxo-2-thiopheneacetic acid 2,3-dihydroxypropyl ester A solution of the acid chloride, prepared from 1.027 g of 5-[[2-(2-naphthalenyloxy)ethyl]oxy]-alpha-oxo-2-thiopheneacetic acid as described in Example 6, in tetrahydrofuran -dimethylforrnamide (3:1; 35 mL) was added dropwise with stirring to a chilled (-70 ° C.) solution of glycerol (1.824 g) and triethylamine (0.47 mL) in tetrahydrofurandirnethylformamide (3:1; 60 reL). The cooling bath was removed and the reaction was stirred at room temperature for 2 hours, then was diluted with dichloromethane and washed in turn with saturated sodium bicarbonate solution and brine. The aqueous layers were backwashed with dichloromethane, then the combined organic extracts were dried (Na$_2$SO$_4$) and evaporated. The resulting solid was crystallized from dichloromethane to furnish 0.67 g of rac.-5-[[2-(2-naphthalenyloxy)etyloxy]-alpha-oxo-2-thiopheneacetic acid 2,3-dihydroxypropyl ester, mp 113°–115 ° C.

Analysis Calculated for C$_{21}$H$_2$O$_7$S: C, 60.57; H, 4.84; S,7.70. Found: C, 60.29; H, 4.80; S,7.57.

EXAMPLE 6

Preparation of 5-[[2-(2-naphthalenyloxy)ethyl]oxy]-alpha-oxo-2-thiopheneacetic acid 2-(dimethylamino)ethyl ester Oxalyl chloride (1 mL) was added dropwise with stirring to a chilled (−70° C.) solution of 2-[[2-(2-naphthalenyloxy)ethyl]oxy]-alpha-oxo-2-thiopheneacetic acid (1.027 g) in dichloromethane (20 mL) containing a catalytic mount of dimethylforrnamide. After the addition was complete, the cooling bath was removed and the mixture was stirred at room temperature for 1 hour. The solvent was then removed in vacuo to give the crude acid chloride as a yellow-orange solid.

A solution of the above acid chloride in dichloromethane (15 mL) was added dropwise with stirring to a chilled (270° C.) solution of 2-(dimethylamino)ethanol (0.357 g) and triethylamine (0.47 mL) in dichloromethane (10 mL). The cooling bath was removed and the reaction was stirred at room temperature for 2 hours, then was diluted with dichloromethane and washed in turn with saturated sodium bicarbonate solution and with brine twice. After the dried (Na$_2$SO$_4$) organic layer was evaporated, the gummy residue was triturated with diethyl ether, filtered to remove some insolubles, and the filtrate concentrated to dryness. The resulting solid was crystallized from ethyl acetate-hexane to yield 0.7 g of 5-[[2-(2-naphthalenyloxy) ethyl]oxy]-alpha-oxo-2-thiopheneacetic acid 2-(dimethylamino)ethyl ester as an off-white crystalline solid, mp 76°–77 ° C.

Analysis Calculated for C$_{22}$H$_{23}$NO$_5$$_5$S: C, 63.91; H, 5.61; N, 3.39; S, 7.75. Found: C, 63.62; H, 5.57; N, 3.46; S, 7.58.

EXAMPLE 7

Preparation of 2-[[5-[[2-(2-naphthalenyloxy)ethyl]oxy]-alpha-oxo-2-thiopheneacetyl]oxy]-N,N,N-trimethylethanaminium iodide A solution of 5-[[2-(2-naphthalenyloxy)ethyl]oxy]-alpha-oxo-2-thiopheneacetic acid 2-(dimethylamino)ethyl ester (0.4 g) and methyl iodide (0.15 g) in acetone (7 mL) was stirred overnight at room temperature. The resulting yellow crystalline solid was filtered off, washed with acetone and then crystallized from methanol to afford 0.36 g of 2-[[5-[[2-(2naphthalenyloxy)ethyl]oxy]-alpha-oxo-2-thiopheneacetyl]oxy]-N,N,N-trimethylethanaminium iodide, mp 169°–170 ° C.

Analysis Calculated for C$_{23}$H$_{26}$INO$_5$S: C, 49.74; H, 4.72; I, 22.85; N, 2.52; S, 5.77. Found: C, 49.68; H, 4.60; I, 22.67; N, 2.57; S, 6.06.

EXAMPLE 8

Preparation of 5-[[2-(cyclooctyloxy)ethyl]oxy]-alpha-oxo-2-thiopheneacetic acid ethyl ester As described in Example 3, ethyl oxalyl chloride (16 mL) was added dropwise with stirring to a chilled solution of 2-[[2-(cyclooctyloxy)ethyl]oxy]thiophene (10.18 g) in dichloromethane (80 mL) containing pyridine (4.0 mL). After the solution was stirred at 35° C. for 5 hours, the product was isolated in the usual way and was purified by HPLC (hexane-diethyl ether; 3: 1) to give 9.7 g of 5-[[2-(cyclooctyloxy)ethyl]oxy]-alpha-oxo-2-thiopheneacetic acid ethyl ester as a yellow liquid. A sample was distilled in a Kugelrohr apparatus (∼210° C./0.02 mm) to furnish the analytical sample.

Analysis Calculated for C$_{18}$H$_{26}$O$_5$S: C, 60.99; H, 7.39; S, 9.05. Found: C, 60.80; H, 7.40; S, 8.86.

EXAMPLE 9

Preparation of 5-[[2-(cyclooctyloxy)ethyl]oxy]-alpha-oxo-2-thiopheneacetic acid (5:3) hydrate 1N Potassium hydroxide solution (10 mL) was added dropwise to a chilled solution of 5-[[2-(cyclooctyloxy)ethyl]oxy]-alpha-oxo-2-thiopheneacetic acid ethyl ester (4.43 g) in methanol (50 mL). After the reaction was stirred at 0°–5° C. for 15 minutes, the product was isolated as described in Example 6 to furnish 3.9 g of 5-[[2-(cyclooctyloxy)ethyl]oxy]-alpha-oxo-2-thiopheneacetic acid as a yellow-orange oil. Crystallization of the product from wet benzene-hexane furnished 3.1 g of the hydrated acid as a pale yellow crystalline solid, mp 60°–62 ° C.

Analysis Calculated for C$_{16}$H$_{22}$O$_5$S0.6 H$_2$O: C, 56.99; H, 6.93; S, 9.50; H$_2$O, 3.20. Found:.C, 58.73; H, 6.89; S, 9.45: H$_2$O, 3.11.

EXAMPLE 10

Preparation of alpha, alpha-difluoro-4-[[2-(phenoxy)ethyl]oxy]benzeneacetic acid methyl ester To a solution of alpha-oxo-4-[(2-phenoxy)ethyl]oxy]-benzeneacetic acid methyl ester (0.7 g) in 1,2-dichloroethane (30 mL) was added diethylaminosulfur trifluoride (3.08 mL) dropwise. The reaction mixture was heated to a bath temperature of 60°–65 ° C. for 18 hours and was cooled in an ice bath. The mixture was poured carefully onto a mixture of ice and water (40 mL) and the layers were separated. The aqueous layer was extracted with dichloromethane (3 x 20 mL) and the combined organic layers were washed with brine (2×25 mL) and dried (MgSO4). Concentration of the extracts afforded 0.99 g of crude product which was purified by chromatography over 100 g of silica gel (hexane-dichloromethane; 3:7) followed by crystallization to give 0.39 g of alpha, alpha-difluoro-4-[[2(phenoxy)ethyl]oxy]benzeneacetic acid methyl ester, mp 76°–78 ° C.

Analysis Calculated for $C_{17}H_{16}F_2O_4$: C, 63.35; H, 5.00; F, 11.79. Found: C, 63.19; H, 5.02; F, 11.73.

EXAMPLE 11

Preparation of alpha, alpha-difluoro-4-[[2-(phenoxy)ethyl]oxy]benzeneacetic acid A solution of alpha, alpha-difluoro-4- [[2-(phenoxy)ethyl]oxy]benzeneacetic acid methyl ester (0.35 g) in methanol (8 mL) was treated with 1N sodium hydroxide (2.5 mL) and was heated on a steam bath for 10 minutes. The mixture was allowed to cool, then was acidified with excess 2N hydrochloric acid and extracted with ethyl acetate. The combined organic layers were washed with water and brine. Concentration of the dried (MgSO4) extracts afforded 0.39 g of a solid which was crystallized from ethyl acetate-hexane to give 0.26 g of alpha, alpha-difluoro-4- [[2-(phenoxy)ethyl]oxy]benzeneacetic acid, mp 143°–144° C.

Analysis Calculated for $C_{16}H_{14}F_2O_4$: C, 62.33; H, 4.58; F, 12.33. Found: C, 62.12; H, 4.55; F, 12.27.

EXAMPLE 12

Preparation of alpha, alpha-difluoro-4-[[2-(2-naphthalenyloxy)ethyl]oxy]benzeneacetic acid methyl ester To a solution of 4-[[2-(2-naphthalenyloxy)ethyl]oxy]-alpha-oxobenzeneacetic acid methyl ester (1.0 g) in 1,2-dichloroethane (35 mL) was added diethylaminosulfur trifluoride (3.77 mL) dropwise. The reaction mixture was heated to a bath temperature of 60°–65 ° C. for 18 hours. After the cooled mixture was poured carefully onto 40 mL of ice and water, the layers were separated and the aqueous layer was extracted with 3 portions of dichloromethane. The combined organic layers were washed with brine, dried (MgSO4) and evaporated to afford 1.26 g of a tan solid. The crude product was purified by chromatography over silica gel (100 g; hexane-dichloromethane, 1:3) followed by crystallization from ethyl acetate to give 0.59 g of alpha, alpha-difluoro-4-[[2-(2naphthalenyloxy)ethyl]oxy]benzeneacetic acid methyl ester, mp 123°–125 ° C. The mother liquors were diluted with hexane to give an additional 0.16 g mp 123°–124.5 ° C.

Analysis Calculated for $C_{21}H_{18}F_2O_4$: C, 67.73; H, 4.87; F, 10.21. Found: C, 67.64; H, 5.11; F, 10.50.

EXAMPLE 13

Preparation of alpha, alpha-difluoro-4-[[2-(2-naphthalenyloxy)ethyl]oxy]benzeneacetic acid A suspension of alpha, alpha-difluoro-4-[[2-(2-naphthalenyloxy)ethyl]oxy]benzeneacetic acid methyl ester (0.65 g) in methanol (4 mL) and 1N sodium hydroxide (4 mL) was heated on a steam bath as methanol (150 mL), followed by acetone (350 mL) were added and the mixture was filtered hot. The resulting solid was taken up in 2N hydrochloric acid and was extracted with ethyl acetate. The organic layers were washed with brine and were dried over MgSO4. The methanol-acetone filtrate from the reaction mixture was concentrated, acidified with excess 2N hydrochloric acid and was extracted with ethyl acetate as above. The combined organic layers from both extractions were concentrated and the residue crystallized from ethyl acetate-hexane to give 0.45 g of alpha, alpha-difluoro-4-[[2-(2-naphthalenyloxy)ethyl]oxy]benzeneacetic acid, mp 173°–175 ° C.

Analysis Calculated for $C_{20}H_{16}F_2O_4$: C, 67.03; H, 4.50; F, 10.60. Found: C, 66.87; H, 4.47; F, 10.80.

EXAMPLE 14

Preparation of (S)-alpha-amino-N-[[(1,1-dimethyethyl)oxy]carbonyl]-4-hydroxybenzeneacetic acid benzyl ester Di-tert-butyl dicarboxylate (31.44 g) was added dropwise to a stirred solution of (S)-4hydroxyphenylglycine (24 g) and triethylamine (19.92 mL) in tetrahydrofuran-water (1:1; 720 mL). After the mixture was allowed to stir overnight at room temperature, ethyl acetate (600 mL) was added and the phases separated. The aqueous layer was adjusted to pH 3.0–3.5 by the addition of 6N hydrochloric acid, then was extracted with ethyl acetate (6 x 250 H mL). The combined extracts were washed with brine, dried (MgSO4), evaporated and the residual oil was triturated with hexane. The resulting solid was filtered off to give 35.9 g (S)-alpha-amino-N-[[( 1,1 -dimethyethyl)oxy]carbonyl]-4-hydroxybenzeneacetic acid. A portion of the above acid (10 g) and benzyl bromide (6.4 g) was dissolved in dry dimethylformamide (150 mL). After the addition of potassium bicarbonate (3.75 g), the heterogeneous mixture was stirred overnight at room temperature and then the solvent was removed in vacuo. The residual material was partitioned between ethyl acetate and water, and the separated organic layer was washed in turn with saturated sodium bicarbonate solution, water (twice) and brine. Evaporation of the dried (MgSO4) extract and trituration of the resulting residue with hexane furnished 11.7 g of (S)-alpha-amino-N-[[(l,1dimethyethyl)oxy]carbonyl]-4-hydroxybenzeneacetic acid benzyl ester as a colorless solid, mp 104°–106° C. Crystallization of a portion from diethyl ether-hexane provided the analytical specimen, mp 105°–106° C., $[\alpha]_D + 65.09°$ (c, 0.994, methanol).

Analysis Calculated for $C_{20}H_{23}NO_5$: C, 67.21; H, 6.49; N, 3.92. Found: C, 67.35; H, 6.39; N, 3.74.

EXAMPLE 15

Preparation of (S)-alpha-amino-N-[[(1,1-dimethyethyl)oxy]carbonyl]-4-[[2-(cyclohexyloxy)ethyl]oxy]benzeneacetic acid benzyl ester A solution of diethyl azodicarboxylate (1.37 g) in dry tetrahydrofuran (10 mL) was added dropwise with stirring to a chilled (0°–5 ° C.) solution of (S)-alpha-amino-N-[[(1,1dimethyethyl)oxy]carbonyl]-4-hydroxybenzeneacetic acid benzyl ester (2.25 g), 2(cyclohexyloxy)ethanol (1 g) and triphenylphosphine (2.07 g) in dry tetrahydrofuran (25 mL). After the reaction mixture was stirred at 0°–5° C. for 4 hours then at room temperature overnight, the solvents were removed under reduced pressure and the residue triturated with ethyl acetate-hexane (1:3). The solids (triphenylphosphine oxide) were filtered off and the filtrate was evaporated. Purification of the residue by HPLC (ethyl acetate-hexane; 1:7) furnished 2.15 g of (S)-alpha-amino-N-[[(1,1-dimethyethyl)oxy]carbonyl]-4-[[2-(cyclohexyloxy)ethoxy] benzeneacetic acid benzyl ester as an oil, $[\alpha]_D +48.07°$ (c, 1.19, methanol).

EXAMPLE 16

Preparation of (S)-alpha-amino-N- [[(1,1-dimethyethyl)oxy]carbonyl]-4-[[2-(cyclooctyloxy)ethyl]oxy]benzeneacetic acid benzyl ester As described in Example 15, a solution of diethyl azodicarboxylate (2.057 g) in dry tetrahydrofuran (10 mL) was added to a chilled (0°–5° C.) solution of (S)-alpha-amino-N[[(1,1-dimethyethyl)oxy]carbonyl]-4-hydroxybenzeneacetic acid benzyl ester (3.37 g), 2(cyclooctyloxy)ethanol (1.77 g) and triphenylphosphine (3.105 g) in dry tetrahydrofuran (30 mL). After the reaction mixture was stirred at 0°–5° C. for 4 hours then at room temperature overnight, the reaction was worked up in the usual manner. Purification of the crude product by HPLC (ethyl acetate-hexane; 1:7) followed by crystallization from hexane afforded 3.56 g of (S)-alpha-amino-N-[[( 1,1 -dimethyethyl)oxy]carbonyl]-4-[[2(cyclooctyloxy)ethyl]oxy]benzeneacetic acid benzyl ester as a colorless solid, mp 71°–73° C.; $[\alpha]_D +48.94°$ (c, 0.993, ethanol).

Analysis Calculated for $C_{30}H_{41}NO_6$: C, 70.42; H, 8.08; N, 2.74. Found: C, 70.33; H, 8.12; N, 2.82.

EXAMPLE 17

Preparation of (S)-alpha-amino-4-[[2-(cyclohexyloxy)ethyl]oxy]benzeneacetic acid A solution of (S)-alpha-amino-N-[[( 1,1 -dimethyethyl)oxy]carbonyl]-4-[[2-(cyclohexyloxy) ethyl]oxy]-benzeneacetic acid benzyl ester (2.15 g) in dichloromethane (15 mL) containing trifluoroacetic acid (15 mL) was stirred at room temperature for 1 hour. After the solvents were removed under reduced pressure, the residue was dissolved in ethyl acetate and the mixture was basified to ~pH 9.5 with concentrated ammonium hydroxide. The organic layer was washed in turn with ammonium bicarbonate solution and brine, then was dried over anhydrous potassium carbonate ($K_2CO_3$) and evaporated to give 1.3 g of (S)-alpha-amino-4-[[2-(cyclohexyloxy)ethyl]oxy]benzeneacetic acid benzyl ester. A solution of the crude ester (1.25 g) in methanol (50 mL) was hydrogenated over 10% Pd/C at ambient temperature and pressure until the uptake of hydrogen had ceased. The reaction was diluted with methanol (100 ml), heated to reflux for five minutes, then the catalyst was filtered off through a bed of Celite, and washed with hot methanol (3×30 mL). The combined filtrates were concentrated at reflux to ~50 mL, then were cooled and the solids collected by filtration to yield 0.65 g of (S)-alpha-amino-4-[[2(cyclohexyloxy)ethyl]oxy]benzeneacetic acid, mp 219°–220° C.

EXAMPLE 18

Preparation of (S)-alpha-amino-4-[[2-(cyclooctyloxy)ethyl]oxy]benzeneacetic acid hydrochloride As in Example 17, a solution of (S)-alpha-amino-N-[[(1,1-dimethyethyl) oxy]carbonyl]-4-[[2-(cyclooctyloxy)ethyl]oxy]benzeneacetic acid benzyl ester (3.5 g) in dichloromethane (12 mL) containing trifluoroacetic acid (12 mL) was stirred at room temperature for 45 minutes. The crude product was isolated in the previously described manner, was purified by HPLC (ethyl acetate-hexane; 1:1 ) to furnish 1.97 g of (S)-alpha-amino-4-[[2-(cyclooctyloxy)ethyl]oxy]benzeneacetic acid benzyl ester as an oil. A solution of the benzyl ester (1.9 g) in methanol (50 mL) containing one drop of acetic acid was hydrogenated over 10% Pd/C (0.2 g) at ambient temperature and pressure for 16 hours. The reaction was diluted with methanol (100 ml), heated to reflux for five minutes, then the catalyst was filtered off through a bed of Celite, and washed with hot methanol (3×30 mL). The combined filtrates were evaporated to yield 1.4 g of (S)-alpha-amino-4-[[2(cyclooctyloxy)ethyl]oxy]benzeneacetic acid as an off-white solid. A stirred slurry of the amino acid (0.35 g) in diethyl ether (6 mL) was treated with 3.5M ethanolic HCl (0.25 mL) to give 0.28 g of S)-alpha-amino-4-[[2-(cyclooctyloxy)ethyl]oxy]benzeneacetic acid hydrochloride as a colorless solid, mp 210° C., $[\alpha]_D +83.21°$ (c, 1.092, methanol)

Analysis Calculated for $C_{18}H_{28}NO_4.HCl$: C, 60.4!; H, 7.89; Cl, 9.91; N, 3.91. Found: C, 60.16; H, 7.71; Cl, 9.68; N, 3.70.

EXAMPLE 19

Preparation of 4-[(phenylmethyl)oxy]-alpha-oxobenzeneacetic acid

A mixture of 4-[(phenylmethyl)oxy]-alpha-oxobenzeneacetic acid methyl ester (0.53 g) in methanol (5 mL) and 0. SN sodium hydroxide (8 mL) were heated on the steam bath for 0.5 hours while methanol was distilled out. The resulting mixture containing solid sodium salt was cooled, concentrated to remove the organic solvents, acidified with 1N hydrochloric acid (4 mL), and extracted with diethyl ether (3×25 mL). The organic layers were washed in turn with water (2×10 mL) and the combined organic layers were dried ($Na_2SO_4$), filtered, and evaporated to give 0.5 g of crude product. Crystallization from benzene-hexane provided 0.45 g of 4-[(phenylmethyl)oxy]-alpha-oxobenzeneacetic acid, mp 97°–98° C.

Analysis Calculated for $C_{15}H_{12}O_4$: C, 70.31; H, 4.72. Found: C, 70.44; H, 4.64.

EXAMPLE 20

Preparation of 4-[(2-phenylethyl)oxy]-alpha-oxobenzeneacetic acid methyl ester

A stirred mixture of 4-hydroxy-alpha-oxobenzeneacetic acid methyl ester (0.724 g) in dimethylformamide (10 mL) under argon was treated with 55% sodium hydride dispersion in mineral oil (0. 175 g) and stirred for 15 minutes. The mesylate of phenethyl alcohol (1.28 g) was added and the mixture was stirred and heated under argon at 60° C. overnight. The cooled mixture was treated with glacial acetic acid (3 drops) and the volatiles were removed under vacuum. The residue was mixed with water, the product was extracted with diethyl ether (3×50 mL) and the organic layers were washed in turn with water. The combined organic layers were dried (Na$_2$SO$_4$), filtered, and evaporated to give crude product. The material was purified by HPLC (dichloromethane-hexane; 3:1) to provide 0.4 g of 4-[(2-phenylethyl)oxy]-alpha-oxobenzeneacetic acid methyl ester as a colorless oil.

Analysis Calculated for C$_{17}$H$_{16}$O$_4$: C, 71.82; H, 5.67. Found: C, 72.12; H, 5.93.

EXAMPLE 21

Preparation of 4-[(2-phenylethyl)oxy]-alpha-oxobenzeneacetic acid

A mixture of 4-[(2-phenylethyl)oxy)]-alpha-oxobenzeneacetic acid methyl ester (0.4 g) in methanol and 0.5N sodium hydroxide (8 mL) was treated as in Example 19 and the crude product was crystallized from benzene-hexane to give 0.37 g of 4-[(2-phenylethyl)oxy]-alpha-oxobenzeneacetic acid as a colorless solid, mp 72°-73° C.

Analysis Calculated for C$_{16}$H$_{14}$O$_4$: C, 71.10; H, 5.22. Found: C, 70.86, H, 5.12.

EXAMPLE 22

Preparation of 4-[(3-phenylpropyl)oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with 3-bromo-1-phenylpropane. The mixture was heated at 60° C. overnight and worked up as in Example 20. The material was purified by HPLC (dichloromethane-hexane; 4:1) to provide 0.65 g of 4-[(3-phenylpropyl)oxy]-alpha-oxobenzeneacetic acid methyl ester as a colorless oil.

Analysis Calculated for C$_{18}$H$_{18}$O$_4$: C, 72.47; H, 6.08. Found: C, 72.19; H, 6.23.

EXAMPLE 23

Preparation of 4-[(3-phenylpropyl)oxy]-alpha-oxobenzeneacetic acid

A mixture of 4-[(3-phenylpropyl)oxy]-alpha-oxobenzeneacetic acid methyl ester (0.65 g) in methanol and 0.5N sodium hydroxide (8 mL) was treated as in Example 19. Extraction provided 0.6 g which solidified and was crystallized from benzene-hexane to give 0.45 g of colorless 4-[(3-phenylpropyl)oxy]-alpha-oxobenzeneacetic acid, mp 58°-59° C.

Analysis Calculated for C$_{17}$H$_{16}$O$_4$: C, 71.82; H, 5.67. Found: C, 71.66; H, 5.78.

EXAMPLE 24

Preparation of 4-[(4-phenybutyl)oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 4-phenylbutanol (1.37 g). The mixture was heated at 60° C. overnight and worked up as in Example 20. The material was purified by HPLC (dichloromethane-hexane; 2:1) to provide 0.64 g of 4-[(4-phenybutyl)oxy]-alpha-oxobenzeneacetic acid methyl ester as a colorless oil.

Analysis Calculated for C$_{19}$H$_{20}$O$_4$: C, 73.06; H, 6.45. Found: C, 72.93; H, 6.55.

EXAMPLE 25

Preparation of 4-[(4-phenybutyl)oxy]-alpha-oxobenzeneacetic acid

A mixture of analytically pure 4;[(4-phenybutyl)oxy]-alpha-oxobenzeneacetic acid methyl ester (0.575 g) in methanol and 0.5N sodium hydroxide (8 mL) was treated as in Example 19. Extraction provided 0.53 g of analytically pure 4-[(4-phenybutyl)oxy]-alpha-oxobenzeneacetic acid which would not solidify.

Analysis Calculated for C$_{18}$H$_{18}$O$_4$: C, 72.47; H, 6.08. Found: C, 72.50; H, 6.00.

EXAMPLE 26

Preparation of 4-[[3-(4-fluorophenyl)propyl]oxy]-alpha-oxobenzeneacetic acid methyl ester A stirred mixture of 4-hydroxy-alpha-oxobenzeneacetic acid methyl ester (1.63 g) in dimethylformamide (20 mL) under argon was treated with 55% sodium hydride (0.394 g), stirred for 15 minutes and treated with 4-fluorophenylpropyl bromide (1.25 g). The mixture was heated at 60° C. overnight and worked up as in Example 20. The material was purified on HPLC (dichloromethane-hexane; 4:1) and crystallized from diethyl etherhexane to provide 0.67 g of 4-[[3-(4-fluorophenyl)propyl]oxy]-alpha-oxobenzeneacetic acid methyl ester, mp 42°-43° C.

Analysis Calculated for C$_{18}$H$_{17}$FO$_4$: C, 68.35; H, 5.42; F, 6.01. Found: C, 68.22; H, 5.52; F, 6.31.

EXAMPLE 27

Preparation of 4-[[3-(4-fluorophenyl)propyl]oxy]-alpha-oxobenzeneacetic acid A mixture of 4-[[3-(4-fluorophenyl)propyl]oxy]-alpha-oxobenzeneacetic acid methyl ester (0.58 g) in methanol and 0.5N sodium hydroxide (8 mL) was treated as in Example 19. Extraction provided 0.55 g which solidified and was crystallized from diethyl etherhexane to give 0.43 g of colorless 4-[[3-(4-fluorophenyl)propyl]oxy]-alpha-oxobenzeneacetic acid, mp 77°-78° C.

Analysis Calculated for C$_{17}$H$_{15}$FO$_4$: C, 67.54; H, 5.00; F, 6.28. Found: C, 67.32; H, 5.07; F, 6.53.

EXAMPLE 28

Preparation of (E)-4-[[3-(4-fluorophenyl)-2-propenyl]oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with 1-(3-chloro-1-propenyl)-4-fluorobenzene (0.85 g). The mixture was heated at 60° C. overnight and worked up as in Example 20. Crystallization from diethyl etherhexane provided 0.9 g of (E)-4-[[3-(4-fluorophenyl)-2-propenyl]oxy]-alpha-oxobenzeneacetic acid methyl ester, mp 84°-85° C.

Analysis Calculated for C$_{18}$H$_{15}$FO$_4$: C, 68.78; H, 4.81; F, 6.04. Found: C, 68.70; H, 5.08; F, 6.09.

EXAMPLE 29

Preparation of
(E)-4-[[3-(4-fluorophenyl)-2-propenyl]oxy]-alpha-oxobenzeneacetic acid A mixture of (E)-4-[[3-(4-fluorophenyl)-2-propenyl]oxy]-alpha-oxobenzeneacetic acid methyl ester (0.5 g) in methanol and 0.5N sodium hydroxide (8 mL) was treated as in Example 19. Extraction provided solids which were crystallized from diethyl ether-hexane to give 0.43 g of colorless (E)-4-[[3-(4-fluorophenyl)-2-propenyl]oxy]-alpha-oxobenzeneacetic acid, mp 132°-133° C.

Analysis Calculated for $C_{17}H_{13}FO_4$: C, 68.00; H, 4.36; F, 6.33. Found: C, 67.92; H, 4.39; F, 6.03.

EXAMPLE 30

Preparation of
(E)-alpha-oxo-4-[(3-phenyl-2-propenyl)oxy]benzeneacetic acid methyl ester 0.1 molar hydrate A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (E)-(3-chloro-1-propenyl)benzene (0.763 g). The mixture was heated at 60° C. overnight and worked up as in Example 20. The material was purified by HPLC (dichloromethane-hexane; 3:1) and crystallized from diethyl etherhexane to provide 0.8 g of (E)-alpha-oxo-4-[(3-phenyl-2-propenyl)oxy]benzeneacetic acid methyl ester 0.1 molar hydrate, mp 80°-82° C.

Analysis Calculated for $C_{18}H_{16}O_4.0.1\ H_2O$: C, 72.52; H, 5.48. Found: C, 72.44; H, 5.46.

EXAMPLE 31

Preparation of
(E)-alpha-oxo-4-[(3-phenyl-2-propenyl)oxy]benzeneacetic acid

A mixture of (E)-alpha-oxo-4-[(3-phenyl-2-propenyl)oxy]benzeneacetic acid methyl ester 0.1 molar hydrate (0.7 g) in methanol and 0.5N sodium hydroxide (8 mL) was treated as in Example 19. Extraction provided solids which were crystallized from diethyl etherhexane to give 0.55 g of colorless (E)-alpha-oxo-4-[(3-phenyl-2-propenyl)oxy]benzeneacetic acid, mp 111°-112° C.

Analysis Calculated for $C_{17}H_{14}O_4$: C, 72.33; H, 5.00. Found: C, 72.16; H, 5.12.

EXAMPLE 32

Preparation of
(Z)-alpha-oxo-4-[(3-phenyl-2-propenyl)oxy]benzeneacetic acid methyl ester A stirred mixture of 4-hydroxy-alpha-oxobenzeneacetic acid methyl ester (1.79 g) in dimethylformamide (30 mL) under argon was treated with 55% sodium hydride (0.432 g), stirred for 15 minutes and treated with (Z)-(3-chloro-1-propenyl)benzene (1.9 g). The mixture was heated at 60° C. overnight and worked up as in Example 20. The crude dichloromethane extract was purified by HPLC (dichloromethane-hexane; 4:1 ) and the resulting 1.9 g of analytically pure (Z)-alpha-oxo-4-[(3-phenyl-2-propenyl)oxy]benzeneacetic acid methyl ester failed to crystallize.

Analysis Calculated for $C_{18}H_{16}O_4$: C, 72.96; H, 5.44. Found: C, 72.87; H, 5.47.

EXAMPLE 33

Preparation of
(Z)-alpha-oxo-4-[(3-phenyl-2-propenyl)oxy]benzeneacetic acid

A mixture of (Z)-alpha-oxo-4-[(3-phenyl-2-propenyl)oxy]benzeneacetic acid methyl ester (1 g) in methanol (15 mL) and 0.5N sodium hydroxide (10 mL) was treated as in Example 19. Extraction provided solids which were crystallized from diethyl ether-hexane to give 0.8 g of colorless (Z)-alpha-oxo-4-[(3-phenyl-2-propenyl)oxy]benzeneacetic acid, mp 103°-105° C.

Analysis Calculated for $C_{17}H_{14}O_4$: C, 72.33; H, 5.00. Found: C, 72.59; H, 4.88.

EXAMPLE 34

Preparation of
alpha-oxo-4-[(3-phenyl-2-propynyl)oxy]benzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (3-chloro-l-propynyl)benzene (0.754 g). The mixture was heated at 60° C. overnight and worked up as in Example 20. The crude dichloromethane extract was purified by HPLC (dichloromethane-hexane; 4: 1) and the resulting solids were crystallized from diethyl ether-hexane to give 0.8 g of alpha-oxo-4-[(3-phenyl-2-propynyl)oxy]benzeneacetic acid methyl ester mp 57°-59° C.

Analysis Calculated for $C_{18}H_{14}O_4$: C, 73.46; H, 4.79. Found: C, 73.13; H, 4.82.

EXAMPLE 35

Preparation of
alpha-oxo-4-[(3-phenyl=2=propynyl)oxy]benzeneacetic acid

A mixture of alpha-oxo-4-[(3-phenyl-2-propynyl)oxy]benzeneacetic acid methyl ester (0.7 g) in methanol (10 mL) and 0.SN sodium hydroxide (8 mL) was treated as in Example 19. Extraction provided solids which were crystallized from diethyl ether-hexane to give 0.55 g of colorless alpha-oxo-4-[(3-phenyl-2-propynyl)oxy]benzeneacetic acid, mp 97°-99° C.

Analysis Calculated for $C_{17}H_{12}O_4$: C, 72.85; H, 4.32. Found: C, 72.83; H, 4.41.

EXAMPLE 36

Preparation of
alpha-oxo-4-[[2-(phenoxy)ethyl]oxy]benzeneacetic acid methyl ester A stirred mixture of 4-hydroxy-alpha-oxobenzeneacetic acid methyl ester (1.81 g) in dimethylformamide (25 mL) under argon was treated with 55% sodium hydride (0.437 g), stirred for 15 minutes and treated with the mesylate of 2-phenoxyethanol (2.38 g). The mixture was heated at 60° C. overnight and worked up as in Example 20. The crude residue in dichloromethane was passed through a plug of silica gel (5 g) and evaporated and the resulting solids were crystallized from diethyl ether-hexane to give 1.85 g of alpha-oxo-4-[[2-(phenoxy)ethyl]oxy]benzeneacetic acid methyl ester mp 79°-81° C.

Analysis Calculated for $C_{17}H_{16}O_5$: C, 67.99; H, 5.37. Found: C, 67.84; H, 5.30.

EXAMPLE 37

Preparation of alpha-oxo-4-[[2-(phenoxy)ethyl]oxy]benzeneacetic acid

A mixture of alpha-oxo-4-(2-phenoxyethoxy)benzeneacetic acid methyl ester (1.6 g) in methanol (10 mL) and 0.5N sodium hydroxide (30 mL) was treated as in Example 19. Extraction provided solids which were crystallized from diethyl ether-hexane to give 1.4 g of colorless alpha-oxo-4-[[2-(phenoxy)ethyl]oxy]benzeneacetic acid, mp 102°–103° C.

Analysis Calculated for $C_{16}H_{14}O_5$: C, 67.13; H, 4.93. Found: C, 66.90; H, 4.90.

EXAMPLE 38

Preparation of 4-[[2-(2-fluorophenoxy)ethyl]oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(2-fiuorophenoxy)ethanol (1.17 g). The mixture was heated at 60° C. overnight and worked up as in Example 20. The dichloromethane extract was evaporated and the residue was purified by HPLC (dichloromethane-hexane; 4:1) and the resulting solids were crystallized from dichloromethane-diethyl ether to give 0.8 g of 4-[[2-(2-fiuorophenoxy)ethyl]oxy]-alpha-oxobenzeneacetic acid methyl ester, mp 112°–113° C.

Analysis Calculated for $C_{17}H_{15}FO_5$: C, 64.15; H, 4.75; F, 5.97. Found: C, 63.87; H, 4.84; F, 6.23.

EXAMPLE 39

Preparation of 4-[[2-(2-fluorophenoxy)ethyl]oxy]-alpha-oxobenzeneacetic acid A mixture of 4-[[2-(2-fiuorophenoxy)ethyl]oxy]-alpha-oxobenzeneacetic acid methyl ester (0.6 g) in methanol (20 mL) and 0.5N sodium hydroxide (8 mL) was treated as in Example 19. Extraction provided solids which were crystallized from diethyl ether-hexane to give 0.55 g of colorless 4-[[2-(2-fluorophenoxy)ethyl]oxy]-alpha-oxobenzeneacetic acid, mp 108°–110° C.

Analysis Calculated for $C_{16}H_{13}FO_5$: C, 63.16; H, 4.31; F, 6.24. Found: C, 63.07; H, 4.42; F, 6.20.

EXAMPLE 40

Preparation of 4-[[2-(3-fluorophenoxy)ethyl]oxy]-alpha-oxobenzeneacetic acid methyl ester A stirred mixture of 4-hydroxy-alpha-oxobenzeneacetic acid methyl ester (0.724 g) in dimethylforrnamide (10 mL) under argon was treated with 55% sodium hydride (0.175 g), stirred for 15 minutes and treated with the mesylate of 2-(3-fluorophenoxy)ethanol (1.17 g). The mixture was heated at 60° C. overnight and worked up as in Example 20. The dichloromethane extract was evaporated and the residue was purified by HPLC (dichloromethane-hexane; 4: 1) and the resulting solids were crystallized from diethyl etherhexane to give 0.84 g of 4-[[2-(3-fluorophenoxy)ethyl]oxy]-alpha-oxobenzeneacetic acid methyl ester, mp 68°–69° C.

Analysis Calculated for $C_{17}H_{15}FO_5$: C, 64.15; H, 4.75; F, 5.97. Found: C, 63.79; H, 4.76; F, 6.06.

EXAMPLE 41

Preparation of 4-[[2-(3-fiuorophenoxy)ethyl]oxy]-alpha-oxobenzeneacetic acid A mixture of 4-[[2-(3-fluorophenoxy)ethyl]oxy]-alpha-oxobenzeneacetic acid methyl ester (0.62 g) in methanol (5 mL) and 0.5N sodium hydroxide (6 mL) was treated as in Example 19. Extraction provided solids which were crystallized from diethyl ether-hexane to give 0.5 g of colorless 4-[[2-(3-fluorophenoxy)ethyl]oxy]-alpha-oxobenzeneacetic acid, mp 108°–109° C.

Analysis Calculated for $C_{16}H_{13}FO_5$: C, 63.16; H, 4.31; F, 6.24. Found: C, 62.90; H, 4.30; F, 6.22.

EXAMPLE 42

Preparation of 4-[[2=(4-fluorophenoxy)ethyl]oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of ethyleneglycol monoparafluorophenyl ether (1.4 g). The mixture was heated at 60° C. overnight and worked up as in Example 20. The material was purified by HPLC (dichloromethane-hexane-ethyl acetate; 25:25: 1) and crystallized from dichloromethane-hexane to provide 0.77 g of 4-[[2-(4-fiuorophenoxy)ethyl]oxy]-alpha-oxobenzeneacetic acid methyl ester, mp 77°–79° C.

Analysis Calculated for $C_{17}H_{15}FO_5$: C, 64.15; H, 4.75; F, 5.97. Found: C, 63.90; H, 4.77; F, 5.70.

EXAMPLE 43

Preparation of 4-[[2-(4-fluorophenoxy)ethyl]oxy]-alpha-oxobenzeneacetic acid A mixture of 4- [[2-(4-fluorophenoxy)ethyl]oxy]-alpha-oxobenzeneacetic acid methyl ester (0.65 g) in methanol and 0.5N sodium hydroxide (8 mL) was treated as in Example 19. Extraction with dichloromethane-diethyl ether provided solids which were crystallized from dichloromethane-hexane to give 0.53 g of colorless 4-[[2-(4-fluorophenoxy) ethyl]oxy]-alpha-oxobenzeneacetic acid, mp 97°–98° C.

Analysis Calculated for $C_{16}H_{13}FO_5$: C, 63.16; H, 4.31; F, 6.24. Found: C, 62.86; H, 4.24; F, 6.21.

EXAMPLE 44

Preparation of 4-[[2-(4-chlorophenoxy)ethyl]oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(4-chlorophenoxy)ethanol (1.25 g). The mixture was heated at 60° C. overnight and worked up as in Example 20. The material from dichloromethane extraction was purified by HPLC (dichloromethane-hexane; 4:1 ) and crystallized from dichloromethane-hexane to provide 0.815 g of 4-[[2-(4- chlorophenoxy) ethyl]oxy]-alpha-oxobenzeneacetic acid methyl ester, mp 103°–105° C.

Analysis Calculated for $C_{17}H_{15}ClO_5$: C, 61.00; H, 4.52; Cl, 10.59. Found: C, 60.65; H, 4.62; Cl, 10.32.

EXAMPLE 45

Preparation of 4-[[2-(4-chlorophenoxy)ethyl]oxy]-alpha-oxobenzeneacetic acid A mixture of 4-[[2-(4-chlorophenoxy)ethyl]-alpha-oxobenzeneacetic acid methyl ester (0.72 g) in methanol and 0.5N sodium hydroxide (8 mL) was treated as in Example 19. Extraction provided solids which were crystallized from diethyl ether-hexane to give 0.63 g of colorless 4-[[2-(4-chlorophenoxy)ethyl]oxy]-alpha-oxobenzeneacetic acid, mp 121°–122° C.

Analysis Calculated for $C_{16}H_{13}ClO_5$: C, 59.92; H, 4.09; Cl, 11.05. Found: C, 59.82; H, 4.18; Cl, 10.89.

EXAMPLE 46

Preparation of 4-[[2-(4-nitrophenoxy)ethyl]oxy]-alpha-oxobenzeneacetic acid methyl ester (4:1) molar hydrate A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(4-nitrophenoxy)ethanol (1.56 g). The mixture was heated at 60° C. overnight and worked up as in Example 20. The material was purified by HPLC (dichloromethane-hexane; 9:1) and crystallized from dichloromethane-hexane to provide 0.75 g of 4-[[2-(4-nitrophenoxy)ethyl]oxy]-alpha-oxobenzeneacetic acid methyl ester as a 4:1 molar hydrate, mp 122°–123° C.

Analysis Calculated for $C_{17}H_{15}NO_7$. 4:1 $H_2O$: C, 58.37; H, 4.47; N, 4.00. Found: C, 58.55; H, 4.43; N, 3.93.

EXAMPLE 47

Preparation of 4-[[2-(4-nitrophenoxy)ethyl]oxy]-alpha-oxobenzeneacetic acid

A mixture of 4-[[2-(4-nitrophenoxy)ethyl]oxy]-alpha-oxobenzeneacetic acid methyl ester (4:1) molar hydrate (0.65 g) in methanol and 0.5N sodium hydroxide (8 mL) was treated as in Example 19. Extraction provided 0.6 g of crude product which solidified and was crystallized from dichloromethane-hexane to give 0.55 g of colorless 4-[[2-(4nitrophenoxy)ethyl]oxy]-alpha-oxobenzeneacetic acid, mp 129°–130° C.

Analysis Calculated for $C_{16}H_{13}NO_7$: C, 58.01; H, 3.96; N, 4.23. Found: C, 58.19; H, 3.93; N, 4.18.

EXAMPLE 48

Preparation of 4-[[2-(4-methylphenoxy)ethyl]oxy]-alpha-oxobenzeneacetic acid methyl ester A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(4-methylphenoxy)ethanol (1.15 g). The mixture was heated at 60° C. overnight and worked up as in Example 20. The material was purified by HPLC (dichloromethane-hexane; 4:1) and crystallized from diethyl ether-hexane to provide 0.83 g of 4-[[2-(4-methylphenoxy)ethyl]oxy]-alpha-oxobenzeneacetic acid methyl ester, mp 105°–107° C.

Analysis Calculated for $C_{18}H_{18}O_5$: C, 68.78; H, 5.77. Found: C, 68.78; H, 5.89.

EXAMPLE 49

Preparation of 4-[[2-(4-methylphenoxy)ethyl]oxy]-alpha-oxobenzeneacetic acid A mixture of 4-[[2-(4-methylphenoxy)ethyl]oxy]-alpha-oxobenzeneacetic acid methyl ester (0.68 g) in methanol and 0.5N sodium hydroxide (8 mL) was treated as in Example 19. Extraction provided solids which were crystallized from diethyl ether-hexane to give 0.6 g of colorless 4-[[2-(4-methylphenoxy)ethyl]oxy]-alpha-oxobenzeneacetic acid, mp 135–136° C.

Analysis Calculated for $C_{17}H_{16}O_5$: C, 67.99; H, 5.37. Found: C, 67.79; H, 5.33.

EXAMPLE 50

PREPARATION OF ALPHA-OXO-4-[[2-(4-TRIFLUOROMETHYLPHENOXY)ETHYL]OXY]BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the tosylate of 2-(4-trifluoromethylphenoxy)ethanol (1.8 g). The mixture was heated at 60° C. overnight and worked up as in Example 20. The material was purified by HPLC (dichloromethane-hexane; 4:1 ) and crystallized from diethyl ether-hexane to provide 1 g of alpha-oxo-4-[[2-(4-trifluoromethylphenoxy)ethyl]oxy] benzeneacetic acid methyl ester, mp 96°–98° C.

Analysis Calculated for $C_{18}H_{15}F_3O_5$: C, 58.70; H, 4.11; F, 15.47. Found: C, 58.45; H, 4.17; F, 15.17.

EXAMPLE 51

PREPARATION OF ALPHA-OXO-4-[[2-(4-TRIFLUOROMETHYLPHENOXY)ETHYL]OXY]BENZENEACETIC ACID

A mixture of alpha-oxo-4-[[2-(4-trifluoromethylphenoxy)ethyl]oxy]benzeneacetic acid methyl ester (0.55 g) in methanol and 0.5N sodium hydroxide (8 mL) was treated as in Example 19. Extraction provided 0.5 g of material which solidified and was crystallized from diethyl ether-hexane to give 0.45 g of colorless alpha-oxo-4-[[2-(4-trifluoromethyl phenoxy)ethyl]oxy]benzeneacetic acid, mp 121°–123° C.

Analysis Calculated for $C_{17}H_{13}F_3O_5$: C, 57.63; H, 3.70; F, 16.09. Found: C, 57.53; H, 3.76; F, 16.00.

EXAMPLE 52

PREPARATION OF 4-[[2-[4-)AMINOSULFONYL)PHENOXY]ETHYL]OXY]-ALPHA-OXOBENZENEACETIC ACID METHYL ESTER

A stirred mixture of 4-hydroxy-alpha-oxobenzeneacetic acid methyl ester (0.905 g) in dimethylformamide (10 mL) under argon was treated with 55% sodium hydride (0.218 g), stirred for 15 minutes and treated with the tosylate of 2-(4-aminosulfonylphenoxy)ethanol (1.67 g). The mixture was heated at 60° C. overnight and worked up as in Example 20. The material from ethyl acetate extraction was purified by HPLC (dichloromethane-ethyl acetate; 4:1) and crystallized from dichloromethane-hexane to provide 0.9 g of 4-[[2-[4-(amino-sulfonyl)phenoxy]ethyl]oxy]-alpha-oxobenzeneacetic acid methyl ester, mp 136°-137° C.

Analysis Calculated for $C_{17}H_{17}NO_7S$: C, 53.82; H, 4.52; N, 3.69; S, 8.45. Found: C, 53.65; H, 4.63; N, 3.66; S, 8.26.

EXAMPLE 53

PREPARATION OF 4-[[2-[4-(AMINOSULFONYL)PHENOXY]ETHYL]OXY]-ALPHA-OXOBENZENEACETIC ACID (4:1) MOLAR HYDRATE

A mixture of 4-[[2-[4-(aminosulfonyl)phenoxy]ethyl]oxy]-alpha-oxobenzeneacetic acid methyl ester (0.3 g) and 0.5N sodium hydroxide (6 mL) was warmed on the steam bath for 5 minutes and allowed to cool over 10 minutes. The clear solution was acidified with 1N hydrochloric acid (4 mL) and the resulting mixture chilled, filtered, and the solids washed with water. The solids were dried over phosphorus pentoxide at 70° C. and 0.1 mm to give 0.27 g of colorless 4-[[2-[4-(aminosulfonyl)phenoxy]ethyl]oxy]-alpha-oxobenzeneacetic acid as a 4:1 molar hydrate, mp 178°-179° C. with decomposition.

Analysis Calculated for $C_{16}H_{15}NO_7S$. 0.25 $H_2O$: C, 51.96; H, 4.22; N, 3.79; S, 8.67; $H_2O$, 1.22 Found: C, 51.62; H, 4.01; N, 3.72; S, 8.73; $H_2O$, 1.37.

EXAMPLE 54

PREPARATION OF 4,4'-[1,2-ETHANEDIYLBIS(OXY)BIS(ALPHA-OXOBENZENEACETIC ACID) DIMETHYL ESTER (4:1) MOLAR HYDRATE

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with ethylene glycol di-p-tosylate (0.74 g). The mixture was heated at 60° C. overnight and worked up as in Example 20. Extraction with dichloromethane and crystallization from dichloromethane-hexane provided 0.46 g of 4,4'-[1,2-ethanediylbis(oxy)bis(alpha-oxobenzeneacetic acid) dimethyl ester as an 0.25 molar hydrate, mp 144°-145° C.

Analysis Calculated for $C_{20}H_{18}O_8$. 4:1 $H_2O$: C, 61.45; H, 4.77. Found: C, 61.66; H, 4.78.

EXAMPLE 55

PREPARATION OF 4,4'-[1,2-ETHANEDIYLBIS(OXY)BIS(ALPHA-OXOBENZENEACETIC ACID) ACID (4:1) MOLAR HYDRATE

A mixture of 4,4'-[1,2-ethanediylbis(oxy)bis(alpha-oxobenzeneacetic acid) dimethyl ester (4:1) molar hydrate (0.385 g) in methanol and 0.5N sodium hydroxide (8 mL) was treated as in Example 19. Extraction with tetrahydrofuran provided solids where were crystallized from acetonitrile to give 0.315 g of colorless 4,4'-[1,2-ethanediylbis(oxy) bis(alpha-oxobenzene-acetic acid) acid as an 0.25 molar hydrate, mp 212°-213° C.

Analysis Calculated for $C_{18}H_{14}O_8$. 0.25 $H_2O$: C, 59.59; H, 4.03. Found: C, 59.42; H, 4.09.

EXAMPLE 56

PREPARATION OF 4-[[2-[4-(1,1'-BIPHENYL)OXY]ETHYL]OXY]-ALPHA-OXOBENZENEACETIC ACID METHYL ESTER (4:1) MOLAR HYDRATE

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(4-phenylphenoxy)ethanol (1.4 g). The mixture was heated at 60° C. overnight and worked up as in Example 20. The crude dichloromethane extract was purified by HPLC (dichloromethane-hexane; 4:1) and the resulting solids were crystallized from dichloromethane-diethyl ether to provide 0.45 g of 4-[[2-[4-(1,1'-biphenyl)oxy]ethyl]oxy]-alpha-oxobenzeneacetic acid methyl ester as an 0.25 molar hydrate, mp 143°-145° C.

Analysis Calculated for $C_{23}H_{20}O_5$. 0.25 $H_2O$: C, 72.52; H, 5.42. Found: C, 72.84; H, 5.46.

EXAMPLE 57

PREPARATION OF 4-[[2-[4-(1,1'-BIPHENYL)OXY]ETHYL]OXY]-ALPHA-OXOBENZENEACETIC ACID (b 4:1) MOLAR HYDRATE

A mixture of 4-[[2-[4-(1,1'-biphenyl)oxy]ethyl]oxy]-alpha-oxobenzeneacetic acid methyl ester (4:1) molar hydrate (0.35 g) in methanol and 0.5N sodium hydroxide (8 mL) was treated as in Example 19. Dichloromethane extraction provided 0.3 g of the acid which solidified and was crystallized from dichloromethane-diethyl ether to give 0.25 g of colorless 4-[[2-[4-(1,1'-biphenyl)oxy]ethyl]oxy]-alpha-oxobenzeneacetic acid as an 0.25 molar hydrate, mp 179°-180° C.

Analysis Calculated for $C_{22}H_{18}O_5$. 0.25 $H_2O$: C, 72.02; H, 5.08. Found: C, 72.25; H, 5.20.

EXAMPLE 58

PREPARATION OF ALPHA-OXO-4-[[2-(4-PHENOXYPHENOXY)ETHYL]OXY]-BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(4-phenoxyphenoxy)ethanol (1.5 g). The mixture was heated at 60° C. overnight and worked up as in Example 20. The material from dichloromethane extraction was purified by HPLC (dichloromethane-hexane; 4:1) and crystallized from diethyl ether-hexane to provide 1.1 g of alpha-oxo-4-[[2-(4-phenoxy-phenoxy)ethyl]oxy]benzeneacetic acid methyl ester, mp 97°-98° C.

Analysis Calculated for $C_{23}H_{20}O_6$: C, 70.40; H, 5.14. Found: C, 70.02; H, 5.30.

EXAMPLE 59

PREPARATION OF ALPHA-OXO-4-[[2-(4-PHENOXYPHENOXY)ETHYL]OXY]BENZENEACETIC ACID

A mixture of 4-[[2-[4-(1,1'-biphenyl)oxy]ethyl]oxy]-alpha-oxobenzeneacetic acid methyl ester (0.8 g) in methanol (20 mL) and 0.5N sodium hydroxide (8 mL)

was treated as in Example 19. Extraction provided solids which were crystallized from diethyl etherhexane to give 0.55 g of colorless alpha-oxo-4-[[2-(4-phenoxyphenoxy)ethyl]oxy]benzeneacetic acid, mp 124°–126° C.

Analysis Calculated for $C_{22}H_{18}O_6$: C, 69.84; H, 4.79. Found: C, 69.83; H, 4.93.

EXAMPLE 60

PREPARATION OF 4-[[2-(4-METHOXYPHENOXY]ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of ethyleneglycol monoparamethoxyphenyl ether (1.5 g). The mixture was heated at 60° C. overnight and worked up as in Example 20. The material from dichloromethane extraction was purified by HPLC (dichloromethane-ethyl acetate; 50:1) and crystallized from dichloromethane-hexane to provide 0.875 g of 4-[[2-(4-methoxyphenoxy)ethyl]oxy]-alpha-oxobenzeneacetic acid methyl ester, mp 114°–115° C.

Analysis Calculated for $C_{18}H_{18}O_6$: C, 65.45; H, 5.49. Found: C, 65.84; H, 5.56.

EXAMPLE 61

PREPARATION OF 4-[[2-(4-METHOXYPHENOXY)ETHYL]OXY]-ALPHA-OXOBENZENEACETIC ACID

A mixture of 4-[[2-(4-methoxyphenoxy)ethyl]oxy]-alpha-oxobenzeneacetic acid methyl ester (0.77 g) in methanol and 0.5N sodium hydroxide (8 mL) was treated as in Example 19. Extraction with dichloromethane provided material which solidified and was crystallized from diethyl ether-hexane to give 0.65 g of colorless 4-[[2-(4-methoxyphenoxy)ethyl]oxy]-alpha-oxobenzeneacetic acid, mp 138°–139° C.

Analysis Calculated for $C_{17}H_{16}O_6$: C, 64.55; H, 5.10. Found: C, 64.45; H, 5.04.

EXAMPLE 62

PREPARATION OF 4-[[2-(3,4-DIMETHOXYPHENOXY)ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(3,4-dimethoxyphenoxy)ethanol (1.65 g). The mixture was heated at 60° C. overnight and worked up as in Example 20. The material was purified by HPLC (dichloromethane-diethyl ether, 99:1) and crystallized from dichloromethane-hexane to provide 0.9 g of 4-[[2-(3,4-dimethoxyphenoxy)ethyl]oxy]-alpha-oxobenzeneacetic acid methyl ester, mp 93°–94° C.

Analysis Calculated for $C_{19}H_{20}O_7$: C, 63.33; H, 5.59. Found: C, 63.05; H, 5.51.

EXAMPLE 63

PREPARATION OF 4-[[2-(3,4-DIMETHOXYPHENOXY)ETHYL]OXY]-ALPHA-OXOBENZENEACETIC ACID

A mixture of 4-[[2-(3,4-dimethoxyphenoxy)ethyl]oxy]-alpha-oxobenzeneacetic acid methyl ester (0.7 g) in methanol and 0.5N sodium hydroxide (8 mL) was heated on the steam bath for 0.5 hours and cooled. 2N hydrochloric acid (5 mL) was added and the resulting solids were filtered and washed with water. The solids were dried by boiling in benzene (20 mL), filtered, hexane (5 mL) was added, and the resulting mixture was chilled to give 0.63 g of colorless 4-[[2-(3,4-dimethoxyphenoxy)ethyl]oxy]-alphaoxobenzeneacetic acid, mp 140°–141° C.

Analysis Calculated for $C_{18}H_{18}O_7$: C, 62.42; H, 5.24. Found: C, 62.70; H, 4.90.

EXAMPLE 64

PREPARATION OF 4-[[2-(3,4,5-TRIMETHOXYPHENOXY)ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(3,4,5-trimethoxyphenoxy)ethanol (1.8 g). The mixture was heated at 60° C. overnight and worked up as in Example 20. The material form dichloromethane extraction was purified by HPLC (dichloromethane-diethyl ether, 50:1) and crystallized from dichloromethane-hexane to provide 1 g of 4-[[2-(3,4,5-trimethoxyphenoxy)ethyl]oxy]-alpha-oxobenzeneacetic acid methyl ester, mp 82°–83° C. Analysis Calculated for $C_{20}H_{22}O_8$: C, 61.53; H, 5.68. Found: C, 60.82; H, 5.71.

EXAMPLE 65

PREPARATION OF 4-[[2-(3,4,5-TRIMETHOXYPHENOXY)ETHYL]OXY]-ALPHA-OXOBENZENEACETIC ACID

A mixture of 4-[[2-(3,4,5-trimethoxyphenoxy)ethyl]oxy]-alpha-oxobenzeneacetic acid methyl ester (0.9 g) in methanol and 0.5N sodium hydroxide (8 mL) was heated on the steam bath for 0.5 hours, chilled, and 2N hydrochloric acid (5 mL) added. The resulting solids were filtered, washed with water and then boiled in benzene to dry. Filtration, evaporation and crystallization from diethyl ether-hexane provided 0.625 g of colorless 4-[[2-(3,4,5-trimethoxyphenoxy)ethyl]oxy]-alpha-oxobenzeneacetic acid, mp 118°–119° C.

Analysis Calculated for $C_{19}H_{20}O_8$: C, 60.64; H, 5.36. Found: C, 60.53; H, 5.30.

EXAMPLE 66

PREPARATION OF ALPHA-OXO-4-[[(PHENOXY)METHYL]OXY]-BENZENEACETIC ACID METHYL ESTER

A stirred mixture of 4-hydroxy-alpha-oxobenzeneacetic acid methyl ester (1.0 g) in dimethylformamide (10 mL) under argon was treated with 55% sodium hydride (0.262 g), stirred for 15 minutes and treated with chloromethoxybenzene (1.1 g). The mixture was heated at 60° C. for 1.5 hours and worked up as in Example 20.

The material was crystallized from diethyl ether-hexane to provide 1 g of alpha-oxo-4-[[(phenoxy)methyl]oxy]-benzeneacetic acid methyl ester, mp 52°–54° C.

Analysis Calculated for $C_{16}H_{14}O_5$: C, 67.13; H, 4.93. Found: C, 67.20; H, 4.90.

EXAMPLE 67
PREPARATION OF ALPHA-OXO-4-[[(PHENOXY)METHYL]OXY]-BENZENEACETIC ACID (5:1) MOLAR HYDRATE

A mixture of alpha-oxo-4-[[(phenoxy)methyl]oxy]-benzeneacetic acid methyl ester (0.43 g) in methanol and 0.5N sodium hydroxide (4 mL) was treated as in Example 19. Extraction provided 0.415 g which solidified and was crystallized from benzene-hexane to give 0.32 g of colorless alpha-oxo-4-[[(phenoxy)methyl]oxy]-benzeneacetic acid as an 0.2 molar hydrate, mp 72°–74° C.

Analysis Calculated for $C_{15}H_{12}O_5$. 0.2 $H_2O$: C, 65.31; H, 4.53; $H_2O$, 1.31. Found: C, 65.28; H, 4.74; $H_2O$, 1.24.

EXAMPLE 68
PREPARATION OF ALPHA-OXO-4-[[(3-PHENOXY)PROPYL]OXY]-BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (3-bromopropoxy)benzene (1.3 g). The mixture was heated at 60° C. overnight and worked up as in Example 20. The material from dichloromethane extraction was purified by HPLC (dichloromethane-hexane; 3:1) and crystallized from dichloromethane-hexane to provide 0.7 g of alpha-oxo-4-[[(3-phenoxy) propyl]oxy]benzeneacetic acid methyl ester, mp 61°–62° C.

Analysis Calculated for $C_{18}H_{18}O_5$: C, 68.78; H, 5.77. Found: C, 68.83; H, 5.73.

EXAMPLE 69
PREPARATION OF ALPHA-OXO-4-[[(3-PHENOXY)PROPYL]OXY]-BENZENEACETIC ACID

A mixture of alpha-oxo-4-[[(3-phenoxy)propyl]oxy]-benzeneacetic acid methyl ester (0.63 g) in methanol and 0.5N sodium hydroxide (8 mL) was treated as in Example 19. Extraction with dichloromethane provided material which was crystallized from diethyl ether-hexane to give 0.34 g of colorless alpha-oxo-4-[[(3-phenoxy)propyl]oxy]benzeneacetic acid, mp 50°–52° C.

Analysis Calculated for $C_{17}H_{16}O_5$: C, 67.99; H, 5.37. Found: C, 67.92; H, 5.35.

EXAMPLE 70
PREPARATION OF ALPHA-OXO-4-[[(4-PHENOXY)BUTYL]OXY]-BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (4-bromobutoxy)benzene (1.37 g). The mixture was heated at 60° C. overnight and worked up as in Example 20. The material from dichloromethane extraction was purified by HPLC (dichloromethane-hexane; 3:1) and crystallized from dichloromethane-hexane to provide 0.85 g of alpha-oxo-4-[[(4phenoxy)butyl]oxy]benzeneacetic acid methyl ester, mp 57°–59°C.

Analysis Calculated for $C_{19}H_{20}O_5$: C, 69.50; H, 6.14. Found: C, 69.38; H, 6.00.

EXAMPLE 71
PREPARATION OF ALPHA-OXO-4-[[(4-PHENOXY)BUTYL]OXY]-BENZENEACETIC ACID

A mixture of alpha-oxo-4-[[(4-phenoxy)butyl]oxy]-benzeneacetic acid methyl ester (0.85 g) in methanol and 0.5N sodium hydroxide (8 mL) was treated as in Example 19. Extraction provided material which was crystallized from diethyl ether-hexane to give 0.7 g of colorless alpha-oxo-4-[[(4-phenoxy)butyl]oxy]benzeneacetic acid, mp 103°–105° C.

Analysis Calculated for $C_{18}H_{18}O_5$: C, 68.78; H, 5.77. Found: C, 68.95; H, 5.91.

EXAMPLE 72
PREPARATION OF ALPHA-OXO-4-[[(5-PHENOXY)PENTYL]OXY]-BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (5-bromopentoxy)benzene (1.4 g). The mixture was heated at 60° C. overnight and worked up as in Example 20. The material from dichloromethane extraction was purified by HPLC (dichloromethane-hexane; 4:1) to provide 0.9 g of analytically pure alpha-oxo-4-[[(5-phenoxy)pentyl]oxy]benzeneacetic acid methyl ester which failed to crystallize.

Analysis Calculated for $C_{20}H_{22}O_5$: C, 70.16; H, 6.48. Found: C, 70.01; H, 6.24.

EXAMPLE 73
PREPARATION OF ALPHA-OXO-4-[[(5-PHENOXY)PENTYL]OXY]-BENZENEACETIC ACID

A mixture of alpha-oxo-4-[[(5-phenoxy)pentyl]oxy]-benzeneacetic acid acid methyl ester (0.9 g) in methanol and 0.5N sodium hydroxide (10 mL) was treated as in Example 19. Extraction provided material which was crystallized from benzene-hexane to give 0.77 g of colorless alpha-oxo-4-[[(5-phenoxy)pentyl]oxy]benzeneacetic acid, mp 69°–70° C. Analysis Calculated for $C_{19}H_{20}O_5$: C, 69.50; H, 6.14. Found: C, 69.49; H, 6.12.

EXAMPLE 74
PREPARATION OF ALPHA-OXO-4-[[(6-PHENOXY)HEXYL]OXY]-BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with (6-bromohexyloxy)benzene (1.5 g). The mixture was heated at 60° C. overnight and worked up as in Example 20. The material from dichloromethane extraction was purified by HPLC (dichloromethane-hexane; 5:1) and crystallized from diethyl ether-hexane to provide 0.95 g of alpha-oxo-4-[[(6-phenoxy)hexyl]oxy]-benzeneacetic acid methyl ester, mp 50°–52° C.

Analysis Calculated for $C_{21}H_{24}O_5$: C, 70.77; H, 6.79. Found: C, 71.01; H, 6.62.

EXAMPLE 75

PREPARATION OF ALPHA-OXO-4-[[(6-PHENOXY)HEXYL]OXY]-BENZENEACETIC ACID

A mixture of alpha-oxo-4-[[(6-phenoxy)hexyl]oxy]-benzeneacetic acid methyl ester (0.75 g) in methanol and 0.5N sodium hydroxide (8 mL) was treated as in Example 19. Extraction provided solids which were crystallized from diethyl ether-hexane to give 0.5 g of colorless alpha-oxo-4-[[(6-phenoxy)hexyl]oxy]benzeneacetic acid, mp 121°–122° C.

Analysis Calculated for $C_{20}H_{22}O_5$: C, 70.16; H, 6.48. Found: C, 70.29; H, 6.43.

EXAMPLE 76

PREPARATION OF 4-[[2-[[2-(PHENOXY)ETHYL]OXY]ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of diethyleneglycol monophenyl ether (1.56 g). The mixture was heated at 60° C. overnight and worked up as in Example 20. The material was purified by HPLC (dichloromethane-ethyl acetate; 50:1) and crystallized from dichloromethane-hexane to provide 0.9 g of 4-[[2-[[2-(phenoxy)ethyl]oxy]ethyl]oxy]-alpha-oxobenzeneacetic acid methyl ester, mp 75°–76° C.

Analysis Calculated for $C_{19}H_{20}O_6$: C, 66.27; H, 5.85, Found: C, 66.09; H, 5.75.

EXAMPLE 77

PREPARATION OF 4-[[2-[[2-(PHENOXY)ETHYL]OXY]ETHYL]OXY]-ALPHA-OXOBENZENEACETIC ACID

A mixture of 4-[[2-[[2-(phenoxy)ethyl]oxy]ethyl]oxy]-alpha-oxobenzeneacetic acid methyl ester (0.7 g) in methanol and 0.5N sodium hydroxide (8 mL) was treated as in Example 19. Extraction provided solids which were crystallized from benzene-hexane to give 0.6 g of colorless 4-[[2-[[2-(phenoxy)ethyl]oxy]ethyl]oxy]-alpha-oxobenzeneacetic acid, mp 58°–59° C.

Analysis Calculated for $C_{18}H_{18}O_6$: C, 65.45; H, 5.49. Found: C, 65.32; H, 5.47.

EXAMPLE 78

PREPARATION OF 4,4'-[OXYBIS(2,1-ETHANEDIENYLOXY)]BIS(ALPHA-OXOBENZENEACETIC ACID)

A stirred mixture of 4-hydroxybenzoylformic acid sodium salt (1.13 g) in dimethylsulfoxide (10 mL) under argon was treated with 4N sodium hydroxide (1.5 mL), stirred for 15 minutes and treated with the bis-mesylate of diethyleneglycol (0.786 g). The mixture was heated at 60° C. overnight and poured into excess hydrochloric acid. The product was extracted with ethyl acetate, washed with water, dried ($Na_2SO_4$), filtered, and evaporated to give 1.1 g of crude solid. Crystallization from ethyl acetate-hexane and recrystallization from acetonitrile provided 0.2 g of 4,4'-[oxybis(2,1-ethanedienyloxy)]bis(alpha-oxobenzeneacetic acid) as a yellow solid, mp 158°–160° C.

Analysis Calculated for $C_{20}H_{18}O_9$: C, 59.70; H, 4.51. Found: C, 59.55; H, 4.59.

EXAMPLE 79

PREPARATION OF RAC.-4-8 [(2-HYDROXY-3-PHENOXY)PROPYL]OXY]-ALPHA-OXOBENZENEACETIC ACID METHYL ESTER

A stirred mixture of 4-hydroxy-alpha-oxobenzeneacetic acid methyl ester (2.71 g) in dimethylformamide (20 mL) under argon was treated with 55% sodium hydride (0.65 g), stirred for 15 minutes and treated with epichlorohydrin (12 mL). The mixture was heated at 60° C. for four hours and worked up as in Example 20. The material was purified by HPLC (dichloromethane-diethyl ether; 50:1) to provide 2.4 g of 4-(oxiranylmethoxy)alpha-oxobenzeneacetic acid methyl ester, as an oil.

Analysis Calculated for $C_{12}H_{12}O_5$: C, 61.02; H, 5.12. Found: C, 60.84; H, 5.29.

A mixture of 4-(oxiranylmethoxy)-alpha-oxobenzeneacetic acid methyl ester (0.944 g), phenol (0.94 g) and pyridine (1 drop) were heated at 100° C. under argon for 3 hours and cooled. The product was purified by HPLC (dichloromethane-diethyl ether, 20:1) to give 1 g of analytically pure rac.-4-[[(2-hydroxy-3-phenoxy)propyl]oxy]-alpha-oxobenzeneacetic acid methyl ester as an oil.

Analysis Calculated for $C_{18}H_{18}O_6$: C, 65.45; H, 5.49. Found: C, 65.19; H, 5.32.

EXAMPLE 80

PREPARATION OF RAC.-4-[[(2-HYDROXY-3-PHENOXY)PROPYL]OXY]-ALPHA-OXOBENZENEACETIC ACID

A mixture of rac.-4-[[(2-hydroxy-3-phenoxy)propyl]oxy]-alpha-oxobenzeneacetic acid methyl ester (0.8 g) in methanol and 0.5N sodium hydroxide (8 mL) was treated as in Example 19. Extraction with dichloromethane provided material which was boiled in benzene to dry and was crystallized from dichloromethane to give 0.52 g of colorless rac.-4-[[(2-hydroxy-3-phenoxy)propyl]oxy]-alpha-oxobenzeneacetic acid, mp 132°–133° C.

Analysis Calculated for $C_{17}H_{16}O_6$: C, 64.55; H, 5.10. Found: C, 63.84; H, 4.65.

EXAMPLE 81

PREPARATION OF ALPHA-OXO-4-[[2-(PHENYLTHIO)ETHYL]OXY]BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-phenylthioethanol (1.16 g). The mixture was heated at 60° C. for five hours and worked up as in Example 20. The material was purified by HPLC (dichloromethane-hexane; 4:1) and crystallized from diethyl etherhexane to provide 0.5 g of alpha-oxo-4-[[2-(phenylthio)ethyl]oxy]benzeneacetic acid methyl ester, mp 49°–51° C.

Analysis Calculated for $C_{17}H_{16}O_4S$: C, 64.54; H, 5.10; S, 10.13. Found: C, 64.58; H, 5.33; S, 9.99.

EXAMPLE 82

PREPARATION OF ALPHA-OXO-4-[[2-(PHENYLTHIO)ETHYL]OXY]BENZENEACETIC ACID

A mixture of alpha-oxo-4-[[2-(phenylthio)ethyl]oxy]benzeneacetic acid methyl ester (0.5 g) in methanol and 0.5N sodium hydroxide (6 mL) was treated as in Example 19. Extraction provided material which was crystallized from benzene-hexane to give 0.43 g of colorless alpha-oxo-4-[[2-(phenylthio)ethyl]oxy]benzeneacetic acid, mp 72°–73° C.

Analysis Calculated for $C_{16}H_{14}O_4S$: C, 63.56; H, 4.67; S, 10.60, Found: C, 63.39; H, 4.69; S, 10.50.

EXAMPLE 83

PREPARATION OF 4-[[2-(1-NAPTHALENYLOXY)ETHYL]OXY]ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(1-naphthyloxy)ethanol (1.37 g). The mixture was heated at 60° C. overnight and worked up as in Example 20. The material was purified by HPLC (dichloromethane-hexane; 4:1 ) and crystallized from diethyl etherhexane to provide 0.8 g of 4-[2-(1-naphthalenyloxy)ethyl]oxy]-alpha-oxobenzeneacetic acid methyl ester, mp 87°–91° C.

Analysis Calculated for $C_{21}H_{18}O_5$: C, 71.99; H, 5.18, Found: C, 72.05; H, 5.25.

EXAMPLE 84

PREPARATION OF 4-[[2-(1-NAPHTHALENYLOXY)ETHYL]OXY]ALPHA-OXOBENZENEACETIC ACID

A mixture of 4-[[2-(1-naphthalenyloxy)ethyl]oxy]-alpha-oxobenzeneacetic acid methyl ester (0.7 g) in methanol and 0.5N sodium hydroxide (6 mL) was treated as in Example 19. Extraction with dichloromethane provided material which was crystallized from dichloro-methane-diethyl ether to give 0.54 g of colorless 4-[[2-(1-naphthalenyloxy) ethyl]oxy]-alpha-oxobenzeneacetic acid, mp 124°–125° C. after drying over phosphorus pentoxide at 60° C. and 0.1 mm.

Analysis Calculated for $C_{20}H_{16}O_5$: C, 71.42; H, 4.79. Found: C, 71.45; H, 4.98.

EXAMPLE 85

PREPARATION OF 4-[[2-(2-NAPHTHALENYLOXY)ETHYL]OXY]-ALPHA-OXOBENZENEACETIC ACID METHYL ESTER

A stirred mixture of 4-hydroxy-alpha-oxobenzeneacetic acid methyl ester (3.62 g) in dimethylformamide (40 mL) under argon was treated with 55% sodium hydride (0.875 g), stirred for 15 minutes and treated with the mesylate of 2-(2-naphthyloxy)ethanol (5.48 g). The mixture was heated at 60° C. overnight and worked up as in Example 20. The material from dichloromethane extraction was crystallized from dichloromethane-hexane to provide 4.2 g of 4-[[2-(2-naphthalenyloxy)ethyl]oxy]-alpha-oxobenzeneacetic acid methyl ester, mp 155°–157° C.

Analysis Calculated for $C_{21}H_{18}O_5$: C, 71.99; H, 5.18. Found: C, 71.75; H, 5.32.

EXAMPLE 86

PREPARATION OF 4-[[2-(2-NAPHTHALENYLOXY)ETHYL]OXY]-ALPHA-OXOBENZENEACETIC ACID

A mixture of 4-[[2-(2-naphthalenyloxy)ethyl]oxy]-alpha-oxobenzeneacetic acid methyl ester (3.2 g) in 95% ethanol (700 mL) was heated at reflux and 1N sodium hydroxide (15 mL) was added dropwise. Heating was continued for five minutes and the resulting mixture was chilled in ice, filtered, washed with water and dried at 80° C. over phosphorus pentoxide at 0.1 mm to give 3.2 g of colorless 4-[[2-(2-naphthalenyloxy)ethyl]oxy]-alphaoxobenzeneacetic acid sodium salt, mp>295° C. with decomposition.

Analysis Calculated for $C_{20}H_{15}O_5Na$: C, 67.04; H, 4.22; Na, 6.42 Found: C, 66.76; H, 4.35; Na, 6.71.

A mixture of 4-[[2-(2-naphthalenyloxy)ethyl]oxy]-alpha-oxobenzeneacetic acid sodium salt (3.0 g), dichloromethane (500 mL), and 1N hydrochloric acid (25 mL) was stirred for one hour until all solids dissolved. The layers were separated, the water layer was extracted 2×100 mL of dichloromethane and the organic layers were washed in turn with water. The combined organic layers were dried ($Na_2SO_4$), filtered and evaporated to give 2.8 g of crude product. Crystallization from dichloromethane-hexane provided 2.6 g of 4[[2- (2-naphthalenyloxy)ethyl]oxy]-alpha-oxobenzeneacetic acid, mp 170°–171° C.

Analysis Calculated for $C_{20}H_{16}O_5$: C, 71.42; H, 4.79, Found: C, 71.08; H, 4.94.

Solid 4-[[2-(2-naphthalenyloxy)ethyl]oxy]-alphaoxobenzeneacetic acid (1.5 g) was added to a stirred solution of diethanolamine (0.53 g) in anhydrous ethanol (30 mL) and the mixture was heated until all solids dissolved. The resulting solution was chilled and the solids were filtered, washed with cold ethanol and dried to give 1.8 g of 4-[[2-(2-naphthalenyloxy)ethyl]oxy]-alpha-oxobenzeneacetic acid (1:1) 2,2'-iminobis(ethanol) salt, mp 144°–145° C. with decomposition.

Analysis Calculated for $C_{20}H_{16}O_5.1:1\ C_4H_{11}NO_2$: C, 65.29; H, 6.16; N, 3.17. Found: C, 64.99; H, 6.31; N, 3.11.

EXAMPLE 87

PREPARATION OF 4-[[4-(2-NAPHTHALENYLOXY)BUTYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with 2-(4-bromobutoxy)naphthlene (1.12 g). The mixture was stirred and heated under argon at 60° C. overnight and worked up as in Example 20. The material from dichloromethane extraction was crystallized from dichloromethane-diethyl ether to provide 1.1 g of 4-[[4-(2-naphthalenyloxy)butyl]oxy]-alpha-oxobenzeneacetic acid methyl ester, mp 93°–95° C.

Analysis Calculated for $C_{23}H_{22}O_5$: C, 73.00; H, 5.86. Found: C, 72.98; H, 5.94.

EXAMPLE 88

PREPARATION OF 4-[[4-(2-NAPHTHALENYLOXY)BUTYL]OXY]-ALPHA-OXOBENZENEACETIC ACID

A mixture of 4-[[4-(2-naphthalenyloxy)butyl]oxy]-alpha-oxobenzeneacetic acid methyl ester (0.9 g) in methanol (15 mL), acetone (5 mL), and 0.5N sodium hydroxide (10 mL) was treated as in Example 19. Extraction with dichloromethane provided material which was crystallized from diethyl ether-hexane to give 0.43 g of colorless 4-[[4-(2naphthalenyloxy) butyl]oxy]-alpha-oxobenzeneacetic acid, mp 133°–135°C.

Analysis Calculated for $C_{22}H_{20}O_5$: C, 72.51; H, 5.53. Found: C, 72.31; H, 5.52.

EXAMPLE 89

PREPARATION OF 4-[[2-(2-NAPHTHALENYLTHIO)ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(2-naphthylthio)ethanol (1.4 g). The mixture was heated at 60° C. overnight and worked up as in Example 20. The material from dichloromethane extraction was purified by HPLC (dichloromethane-hexane; 4:1) and crystallized from diethyl ether-hexane to provide 0.55 g of 4-[[2-(2-naphthalenylthio) ethyl]oxy]-alpha-oxobenzeneacetic acid methyl ester, mp 63°–65° C.

Analysis Calculated for $C_{21}H_{18}O_4S$: C, 68.83; H, 4.95; S, 8.75. Found: C, 68.66; H, 5.12; S, 8.88.

EXAMPLE 90

PREPARATION OF 4-[[2-(2-NAPHTHALENYLTHIO)ETHYL]OXY]-ALPHA-OXOBENZENEACETIC ACID

A mixture of 4-[[2-(2-naphthalenylthio)ethyl]oxy]-alpha-oxobenzeneacetic acid methyl ester (0.495 g) in methanol and 0.5N sodium hydroxide (5 mL) was treated as in Example 19. Extraction with dichloromethane provided material which was crystallized from diethyl ether-hexane to give 0.4 g of colorless 4-[[2-(2-naphthalenylthio)ethyl]oxy]-alpha-oxobenzeneacetic acid, mp 121°–123° C.

Analysis Calculated for $C_{20}H_{16}O_4S$: C, 68.17; H, 4.58; S, 9.10. Found: C, 67.87; H, 4.41; S, 9.36.

EXAMPLE 91

PREPARATION OF 4-[[4-(2-NAPHTHALENYLTHIO)BUTYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate prepared from 4-(2-naphthylthio)-butanol (1.55 g). The mixture was stirred and heated under argon at 60° C. overnight and worked up as in Example 20. The material from dichloromethane extraction was purified by HPLC (dichloromethane-hexane; 3:1) and crystallized from diethyl etherhexane to provide 0.625 g of 4-[[4-(2-naphthalenylthio)butyl]oxy]-alpha-oxobenzeneacetic acid methyl ester, mp 64°–65° C.

Analysis Calculated for $C_{23}H_{22}O_4S$: C, 70.03; H, 5.62; S, 8.13. Found: C, 69.77; H, 5.59; S, 8.04.

EXAMPLE 92

PREPARATION OF 4-[[4-(2-NAPHTHALENYLTHIO)BUTYL]OXY]-ALPHA-OXOBENZENEACETIC ACID

A mixture of 4-[[4-(2-naphthalenylthio)butyl]oxy]-alpha-oxobenzeneacetic acid methyl ester (0.53 g) in methanol (5 mL), acetone (2 mL), and 0.5N sodium hydroxide (4 mL) was treated as in Example 19. Extraction with dichloromethane provided material which was crystallized from diethyl ether-hexane to give 0.48 g of colorless 4-[[4-(2-naphthalenylthio) butyl]oxy]-alpha-oxobenzeneacetic acid, mp 113°–115° C.

Analysis Calculated for $C_{22}H_{20}O_4S$: C, 69.45; H, 5.30; S, 8.43. Found: C, 69.24; H, 5.24; S, 8.13.

EXAMPLE 93

PREPARATION OF 4-[[3-(2-NAPHTHALENYL)PROPYL]OXY]ALPHA-OXOBENZENEACETIC ACID METHYL ESTER

A stirred mixture of 4-hydroxy-alpha-oxobenzeneacetic acid methyl ester (1.01 g) in dimethylformamide (10 mL) under argon was treated with 55% sodium hydride (0.262 g), stirred for 15 minutes and treated with 2-(3-bromopropyl)naphthalene (1.7 g). The mixture was heated at 60° C. overnight and worked up as in Example 20. The material from dichloromethane extraction was purified by HPLC (dichloromethane-hexane; 4:1) and crystallized from diethyl ether-hexane to provide 0.4 g of 4-[[3-(2-naphthalenyl) propyl]oxy]-alpha-oxobenzeneacetic acid methyl ester, mp 97°–99° C.

Analysis Calculated for $C_{22}H_{20}O_4$: C, 75.84; H, 5.79. Found: C, 75.84; H, 5.80.

EXAMPLE 94

PREPARATION OF 4-[[3-(2-NAPHTHALENYL)PROPYL]OXY]-ALPHA-OXOBENZENEACETIC ACID

A mixture of 4-[[3-(2-naphthalenyl)propyl]oxy]-alpha-oxobenzeneacetic acid methyl ester (0.6 g) in methanol (10 mL) and 0.5N sodium hydroxide (4 mL) was treated as in Example 19. Extraction with dichloromethane provided material which was crystallized from dichloromethane-hexane to give 0.5 g of colorless 4-[[3-(2-naphthalenyl)propyl]oxy]-alpha-oxobenzeneacetic acid, mp 123°–124° C.

Analysis Calculated for $C_{21}H_{18}O_4$: C, 75.43; H, 5.43. Found: C, 75.43; H, 5.37.

EXAMPLE 95

PREPARATION OF (E)-4-[[3-(2-NAPTHALENYL)-2-PROPENYL]OXY]-ALPHA-OXOBENZENEACETIC ACID METHYL ESTER

A stirred mixture of 4-hydroxy-alpha-oxobenzeneacetic acid methyl ester (1.01 g) in dimethylformamide (10 mL) under argon was treated with 55% sodium hydride (0.262 g), stirred for 15 minutes and treated with 2-(3-bromo-1-propenyl)naphthalene (1.7 g). The mixture was heated at 60° C. overnight and worked up as in Example 20. The material from dichloromethane extraction was purified by HPLC (dichloromethane-hexane; 4:1) and crystallized from dichloromethane-diethyl ether to provide 0.95 g of (E)-4-[[3-(2-naphthalenyl)-2-propenyl]oxy]-alpha-oxobenzeneacetic acid methyl ester, mp 100°–102° C.

Analysis Calculated for $C_{22}H_{18}O_4$: C, 76.29; H, 5.24. Found: C, 76.24; H, 5.19.

EXAMPLE 96

PREPARATION OF (E)-4-[[3-(2-NAPHTHALENYL)-2-PROPENYL]OXY]-ALPHA-OXOBENZENEACETIC ACID METHYL ESTER

A mixture of (E)-4-[[3-(2-naphthalenyl)-2-propenyl]oxy]-alpha-oxobenzeneacetic acid methyl ester (0.85 g) in methanol (20 mL), acetone (5 mL), and 0.5N sodium hydroxide (6 mL) was treated as in Example 19. Extraction with dichloromethane provided material which was crystallized from dichloromethane-hexane to give 0.75 g of colorless (E)-4-[[3-(2-naphthalenyl)-2-propenyl]oxy]-alpha-oxobenzeneacetic acid, mp 142°–143° C.

Analysis Calculated for $C_{21}H_{16}O_4$: C, 75.89; H, 4.85. Found: C, 75.95; H, 4.89.

EXAMPLE 97

PREPARATION OF 4-[[2-(METHOXY)ETHYL]OXY]-ALPHA-OXOBENZENEACETIC ACID

A stirred mixture of 4-hydroxy-alpha-oxobenzeneacetic acid (0.498 g) in dimethylsulfoxide (5 mL) under argon was treated with 4N sodium hydroxide (1.5 mL), stirred for 5 minutes and treated with the mesylate prepared from 2-methoxyethanol (0.462 g). The mixture was heated at 60° C. for 3 hours and poured into excess 1N hydrochloric acid. The product was extracted into diethyl ether (3×50 mL) and the organic layers were washed in turn with water (2×25 mL). The combined organic layers were dried ($Na_2SO_4$), filtered, and evaporated to give 0.56 g of crude product as a solid. Crystallization from ethyl acetate-hexane provided 0.3 g of 4-[[2-(methoxy)ethyl]oxy]-alphaoxobenzeneacetic acid, mp 129°–130° C.

Analysis Calculated for $C_{11}H_{12}O_5$: C, 58.93; H, 5.39. Found: C, 58.69; H, 5.32.

EXAMPLE 98

PREPARATION OF 4-[[2-(CYCLOHEXYLOXY)ETHYL]OXY]-ALPHA-OXOBENZENEACETIC ACID METHYL ESTER

A stirred mixture of 4-hydroxy-alpha-oxobenzeneacetic acid methyl ester (0.724) in dimethylformamide (10 mL) under argon was treated with 55% sodium hydride (0.175 g), stirred for 15 minutes and treated with the tosylate prepared from 2-(cyclohexyloxy)ethanol (1.49 g). The mixture was heated at 60° C. overnight and worked up as in Example 20. The material from dichloromethane extraction was purified by HPLC (diethyl ether-hexane; 1:1) to provide 0.9 g of pure 4-[[2-(cyclohexyloxy)ethyl]oxy]-alpha-oxobenzeneacetic acid methyl ester as an oil.

Analysis Calculated for $C_{17}H_{22}O_5$: C, 66.65; H, 7.24. Found: C, 66.50; H, 6.93.

EXAMPLE 99

PREPARATION OF 4-[[2-(CYCLOHEXYLOXY)ETHYL]OXY]-ALPHA-OXOBENZENEACETIC ACID

A mixture of 4-[[2-(cyclohexyloxy)ethyl]oxy]-alpha-oxobenzeneacetic acid methyl ester (0.7 g) in methanol (10 mL) and 0.5N sodium hydroxide (7 mL) was treated as in Example 19. Extraction with diethyl ether provided material which was crystallized from diethyl ether-hexane to give 0.6 g of colorless 4-[[2-(cyclohexyloxy)ethyl]oxy]-alphaoxobenzeneacetic acid, mp 96°–98° C.

Analysis Calculated for $C_{16}H_{20}O_5$: C, 65.74; H, 6.90. Found: C, 65.83; H, 6.97.

EXAMPLE 100

PREPARATION OF 4-[[2-(CYCLOOCTYLOXY)ETHYL]OXY]-ALPHA-OXOBENZENEACETIC ACID METHYL ESTER

A stirred mixture of 4-hydroxy-alpha-oxobenzeneacetic acid methyl ester (1.27 g) in dimethylformamide (10 mL) under argon was treated with 55% sodium hydride (0.303 g), stirred for 15 minutes and treated with the tosylate prepared from 2-(cyclooctyloxy)ethanol (2.18 g). The mixture was heated at 60° C. overnight and worked up as in Example 20. The material from dichloromethane extraction was purified by HPLC (dichloromethane-hexane-ethyl acetate; 80:20:2) to provide 1.0 g of pure 4-[[2-(cyclooctyloxy)ethyl]oxy]-alpha-oxobenzeneacetic acid methyl ester as an oil.

Analysis Calculated for $C_{19}H_{26}O_5$: C, 68.24; H, 7.84. Found: C, 68.28; H, 7.86.

EXAMPLE 101

PREPARATION OF 4-[[2-(CYCLOOCTYLOXY)ETHYL]OXY]-ALPHA-OXOBENZENEACETIC ACID

A mixture of 4-[[2-(cyclooctyloxy)ethyl]oxy]-alpha-oxobenzeneacetic acid methyl ester (0.3 g) in methanol (10 mL) and 0.5N sodium hydroxide (4 mL) was treated as in Example 19. Extraction with dichloromethane provided material which was crystallized from diethyl ether-hexane to give 0.22 g of colorless 4-[[2-(cyclooctyloxy)ethyl]oxy]-alphaoxobenzeneacetic acid, mp 64°–65° C.

Analysis Calculated for $C_{18}H_{24}O_5$: C, 67.48; H, 7.55. Found: C, 67.30; H, 7.69.

EXAMPLE 102

PREPARATION OF ALPHA-OXO-4-[[2-[TRICYCLO(3.3.1.1-3,7)DEC-1-YLOXY]ETHYL]OXY]BENZENEACETIC ACID

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the tosylate prepared from 2-(1-adamantyloxy)ethanol (1.5 g). The mixture was heated at 60° C. overnight and worked up as in Example 20. The material from dichloromethane extraction was purified by HPLC (dichloromethane-hexane-ethyl acetate; 80:20:2) and crystallized from diethyl ether-hexane to provide 0.77 g of alpha-oxo-4-[[2-[tricyclo(3.3.1.1-3,7)dec-1-yloxy]ethyl]oxy]benzeneacetic acid, mp 107°–109° C.

Analysis Calculated for $C_{21}H_{26}O_5$: C, 70.37; H, 7.31. Found: C, 70.29; H, 7.31.

EXAMPLE 103

PREPARATION OF ALPHA-OXO-4-[[2-[TRICYCLO(3.3.1.1-3,7)DEC-1-YLOXY]ETHYL]OXY]BENZENEACETIC ACID

A mixture of alpha-oxo-4-[[2-[tricyclo(3.3.1.1-3,7)dec-1-yloxy]ethyl]oxy]benzeneacetic acid methyl ester (0.685 g) in methanol (10 mL) heated on the steam bath and added sufficient actone to dissolve the solids. Then 0.5N sodium hydroxide (8 mL) was added and the mixture was treated as in Example 19. Extraction with dichloromethane provided material which was crystallized from diethyl ether-hexane to give 0.524 g of colorless alpha-oxo-4-[[2-[tricyclo(3.3.1.1-3,7)dec-1-yloxy]ethyl]oxy]benzeneacetic acid, mp 155°–156° C.

Analysis Calculated for $C_{20}H_{24}O_5$: C, 69.75; H, 7.02. Found: C, 69.81; H, 7.12.

EXAMPLE 104

PREPARATION OF RAC.-4-[[2-(2-NAPHTHALENYLOXY)ETHYL]OXY]-ALPHA-OXOBENZENEACETIC ACID 2,3-DIHYDROXYPROPYL ESTER

The acid chloride, prepared from 4-[[2-(2-naphthalenyloxy)ethyl]oxy]-alpha-oxobenzene-acetic acid (0.5 g) as described in Example 6, was dissolved in dichloromethane (10 mL) and added dropwise to a stirred, cold (<−50° C.) mixture of glycerine (0.9 mL) in tetrahydrofuran (10 mL). The cooling bath was removed and the mixture stirred for 1 hour at room temperature. The mixture was diluted with dichloromethane and washed once with saturated aqueous sodium bicarbonate, once with water, and the organic solution was dried ($Na_2SO_4$), filtered, and evaporated to give crude product. The material was purified by HPLC (ethyl acetate) to provide, after crystallization from ethyl acetate-hexane, 0.25 g of rac.-4-[[2-(2-naphthalenyloxy)ethyl]oxy]-alpha-oxobenzeneacetic acid 2,3-dihydroxypropyl ester as a colorless solid, mp 124°–125° C.

Analysis Calculated for $C_{23}H_{22}O_7$: C, 67.31; H, 5.40. Found: C, 67.11; H, 5.36.

EXAMPLE 105

PREPARATION OF 4-[[2-(2-NAPHTHALENYLOXY)ETHYL]OXY]-ALPHA-OXOBENZENEACETIC ACID 2-[2-(2-HYDROXYETHOXY)ETHOXY]ETHYL ESTER

The acid chloride, prepared from 4-[[2-(2-naphthalenyloxy)ethyl]oxy]-alpha-oxobenzene-acetic acid (0.5 g) as described in Example 6, was dissolved in dichloromethane (10 mL) and added dropwise to a stirred, cold (<−50° C.) mixture of triethylene glycol (0.9 g) in dichloro-methane (10 mL). The cooling bath was removed and the mixture stirred for 1 hour at room temperature. The mixture was diluted with dichloromethane and washed once with saturated aqueous sodium bicarbonate, once with water, and the organic solution was dried ($Na_2SO_4$), filtered, and evaporated to give crude product. The material was purified by HPLC (dichloro-methane-ethyl acetate; 2:1) to provide, after crystallization from ethyl acetate-hexane, 0.36 g of 4-[[2-(2-naphthalenyloxy)ethyl]oxy]-alpha-oxobenzeneacetic acid 2-[2-(2-hydroxyethoxy)ethoxy]ethyl ester as a colorless solid, mp 70°–71° C.

Analysis Calculated for $C_{26}H_{28}O_8$: C, 66.66; H, 6.02. Found: C, 66.35; H, 6.01.

EXAMPLE 106

PREPARATION OF 4-[[2-(2-NAPHTHALENYLOXY)ETHYL]OXY]-ALPHA-OXOBENZENEACETIC ACID 2-(DIMETHYLAMINO)ETHYL ESTER

The acid chloride, prepared from 4-[[2-(2-naphthalenyloxy)ethyl]oxy]-alphaoxobenzeneacetic acid (0.5 g) as described in Example 6, was dissolved in dichloromethane (10 mL) and added dropwise to a stirred, cold (<−50° C.) mixture of 2-(dimethylamino)ethanol (0.178 g) in dichloromethane (10 mL). The cooling bath was removed and the mixture stirred for 1 hour at room temperature. The mixture was diluted with dichloromethane and washed once with saturated aqueous sodium bicarbonate, once with water, and the organic solution was dried ($Na_2SO_4$), filtered, and evaporated to give crude product. Crystallization from diethyl ether-hexane provided pure 4-[[2-(2-naphthalenyloxy)ethyl]oxy]-alpha-oxobenzeneacetic acid 2-(dimethylamino)ethyl ester as a colorless solid, mp 93°–94° C.

Analysis Calculated for $C_{24}H_{25}NO_5$: C, 70.75; H, 6.18; N, 3.44. Found: C, 70.91; H, 6.23; N, 3.45.

EXAMPLE 107

PREPARATION OF 4-[[2-(2-ANTHRACENYLOXY)ETHYL]OXY]-ALPHA-OXOBENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate of 2-(2-hydroxyethoxy)anthracene (1.26 g). The mixture was heated under argon at 60° C. overnight. The cooled mixture was treated with glacial acetic acid (2 drops) and the volatiles were removed under vacuum. The residue was mixed with water and the solids were filtered off, dissolved in dichloromethane, dried ($Na_2SO_4$), filtered, and evaporated to give crude product. Crystallization from dichloro-methane-diethyl ether provided 0.75 g of 4-[[2-(2anthracenyloxy)ethyl]oxy]-alpha-oxobenzeneacetic acid methyl ester as a yellow solid, mp 188°–189° C.

Analysis Calculated for $C_{25}H_{20}O_5$: C, 74.99; H, 5.03. Found: C, 74.68; H, 4.96.

EXAMPLE 108

PREPARATION OF 4-[[2-(2-ANTHRACENYLOXY)ETHYL]OXY]-ALPHA-OXOBENZENEACETIC ACID

A mixture of 4-[[2-(2-anthracenyloxy)ethyl]oxy]-alpha-oxobenzeneacetic acid methyl ester (0.615 g) in hot tetrahydrofuran (100 mL) was treated with 1N sodium hydroxide (4 mL) and diluted with water. The resulting solids were recovered by filtration and stirred in a mixture of dichloromethane and excess 2N hydrochloric acid until the solids dissolved. The organic layer was separated, dried ($Na_2SO_4$), filtered, and evaporated to give crude product. Crystallization from acetone-hexane gave 0.45 g of 4-[[2-(2-anthracenyloxy) ethyl]oxy]-alpha-oxobenzene-acetic acid as a colorless solid, mp 213°–214° C.

Analysis Calculated for $C_{24}H_{18}O_5$: C, 74.60; H, 4.70. Found: C, 74.25; H, 4.63.

EXAMPLE 109
PREPARATION OF ALPHA-OXO-4-[[2-(9-PHENANTHRENYLOXY)ETHYL]OXY]BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with 2-(9-phenanthrenyloxy)ethyl methanesulfonate (1.26 g). The mixture was heated under argon at 60° C. overnight. The cooled mixture was treated with glacial acetic acid (2 drops) and the volatiles were removed under vacuum. The residue was mixed with water and the solids were filtered off, dissolved in dichloromethane, dried ($Na_2SO_4$), filtered, and evaporated to give crude product. Crystallization from dichloro-methane-diethyl ether provided 0.8 g of alpha-oxo-4-[[2-(9-phenanthrenyloxy)ethyl]oxy]benzeneacetic acid methyl ester as a yellow solid, mp 147°–148° C.

Analysis Calculated for $C_{25}H_{20}O_5$: C, 74.99; H, 5.03. Found: C, 74.81; H, 5.00.

EXAMPLE 110
PREPARATION OF ALPHA-OXO-4-[[2-(9-PHENANTHRENYLOXY)ETHYL]OXY]BENZENEACETIC ACID

A mixture of alpha-oxo-4-[[2-(9-phenanthrenyloxy)ethyl]oxy]benzeneacetic acid methyl ester (0.685 g) in hot tetrahydrofuran (100 mL) was treated with 1N sodium hydroxide (4 mL) and diluted with water. The organic solvent was removed under vacuum and the aqueous solution was acidified with excess hydrochloric acid and extracted with dichloromethane. The organic layer was dried ($Na_2SO_4$), filtered, and evaporated to give crude product. Crystallization from acetone-hexane provided 0.45 g of alpha-oxo-4-[[2-(9-phenanthrenyloxy) ethyl]oxy]benzeneacetic acid as a colorless solid, mp 179°–180° C.

Analysis Calculated for $C_{24}H_{18}O_5$: C, 74.60; H, 4.70. Found: C, 74.46; H, 4.70.

EXAMPLE 111
PREPARATION OF ALPHA-OXO-4-[[2-(5,6,7,8-TETRAHYDRO-2-NAPHTHALENYLOXY)ETHYL]OXY]BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with 2-(5,6,7,8-tetrahydro-2-naphthalenyloxy)ethyl methanesulfonate (1.08 g). The mixture was heated under argon at 60° C. overnight. The cooled mixture was treated with glacial acetic acid (2 drops) and the volatiles were removed under vacuum. The residue was mixed with water and extracted with dichloromethane. The organic layers were dried ($Na_2SO_4$), filtered and evaporated to give crude product. The material was purified by HPLC (dichloromethane-hexane; 4:1) to provide, after crystallization from diethyl ether-hexane, 0.86 g of alpha-oxo-4-[[2-(5,6,7,8-tetrahydro-2-naphthalenyloxy) ethyl]oxy]benzeneacetic acid methyl ester as a colorless solid, mp 95°–99° C.

Analysis Calculated for $C_{21}H_{22}O_5$: C, 71.17; H, 6.26. Found: C, 71.15; H, 6.28.

EXAMPLE 112
PREPARATION OF ALPHA-OXO-4-[[2-(5,6,7,8-TETRAHYDRO-2-NAPHTHALENYLOXY)ETHYL]OXY]BENZENEACETIC ACID

A mixture of alpha-oxo-4-[[2-(5,6,7,8-tetrahydro-2-naphthalenyloxy)ethyl]oxy]benzeneacetic acid methyl ester (0.75 g) in hot methanol (10 mL) plus enough tetrahydrofuran to dissolve all solids, was treated with 1N sodium hydroxide (4 mL) and diluted with water. The organic solvent was removed under vacuum and the residue was mixed with water, acidified with excess hydrochloric acid, and extracted with dichloromethane. The organic layer was dried ($Na_2SO_4$), filtered, and evaporated to give crude product. Crystallization from diethyl ether-hexane provided 0.56 g of alpha-oxo-4-[[2-(5,6,7,8-tetrahydro-2-naphthalenyloxy)ethyl]oxy]benzeneacetic acid as a colorless solid, mp 144°–145° C.

Analysis Calculated for $C_{20}H_{20}O_5$: C, 70.58; H, 5.92. Found: C, 70.42; H, 5.92.

EXAMPLE 113
PREPARATION OF RAC.-ALPHA-OXO-4-[[2-(1,2,3,4-TETRAHYDRO-2-NAPHTHALENYLOXY)ETHYL]OXY]BENZENEACETIC ACID METHYL ESTER

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with rac.-2-(1,2,3,4-tetrahydro-2-naphthalenyloxy)ethyl methanesulfonate (1.08 g). The mixture was heated under argon at 60° C. overnight. The cooled mixture was treated with glacial acetic acid (2 drops) and the volatiles were removed under vacuum. The residue was mixed with water and extracted with dichloromethane. The organic layers were dried ($Na_2SO_4$), filtered and evaporated to give crude product. The material was purified by HPLC (dichloromethane-hexane; 1:1 plus 2% ethyl acetate) to provide, after crystallization from diethyl ether-hexane, 0.79 g of rac.-alpha-oxo-4-[[2-(1,2,3,4-tetrahydro-2-naphthalenyloxy)ethyl]oxy]benzeneacetic acid methyl ester as a colorless solid, mp 86°–87° C.

Analysis Calculated for $C_{21}H_{22}O_5$: C, 71.17; H, 6.26. Found: C, 71.11; H, 6.21.

EXAMPLE 114
PREPARATION OF RAC.-ALPHA-OXO-4-[[2-(1,2,3,4-TETRAHYDRO-2-NAPHTHALENYLOXY)ETHYL]OXY]BENZENEACETIC ACID

A mixture of rac.-alpha-oxo-4-[[2-( 1,2,3,4-tetrahydro-2-naphthalenyloxy)ethyl]oxy]benzeneacetic acid methyl ester (0.69 g) in hot methanol (10 mL) plus enough tetrahydrofuran to dissolve the solids, was treated with 1N sodium hydroxide (4 mL) and diluted with water. The organic solvent was removed under vacuum and the residue was mixed with water, acidified with excess hydrochloric acid, and extracted with dichloromethane. The organic layer was dried ($Na_2SO_4$), filtered, and evaporated to give crude product. Crystallization from diethyl ether-hexane provided 0.575 g of rac.-alpha-oxo-4-[[2-(1,2,3,4-tetrahydro-2-naphthalenyloxy)ethyl]oxy]benzeneacetic acid as a colorless solid, mp 119°–120° C.

Analysis Calculated for $C_{20}H_{20}O_5$: C, 70.58; H, 5.92. Found: C, 70.51; H, 5.90.

EXAMPLE 115

PREPARATION OF ALPHA-OXO-4-[[2-[3-(2-PHENOXYETHOXY)-2-NAPHTHALENYLOXY]ETHYL]OXY]BENZENEACETIC ACID METHYL ESTER (2:1) HYDRATE

A mixture of 2,3-dihydroxynaphthalene (5.6 g) and sodium bicarbonate powder (2.9 g) in dimethylformamide (50 mL) was stirred and heated at 135° C. for 1 hour. When the gas evolution ceased, the mixture was cooled to about 60° C. and beta-bromophenetole (7 g) was added. The mixture was stirred at 60° C. overnight, cooled, diluted with water and filtered. The solids were crystallized from dichloromethane-diethyl ether to give 3.9 g of 3-(2-phenoxyethoxy)-2-naphthol as a colorless solid, mp 141°–142° C.

A stirred mixture of 3-(2-phenoxyethoxy)-2-naphthol (3.9 g), ethylene carbonate (1.4 g) and tetraethylammonium bromide (0.8 g) was heated at 155°–160° C. for 2 hours. The cooled reaction was diluted with dichloromethane and washed with 1N sodium hydroxide and with water. The organic layer was dried ($Na_2SO_4$), filtered, and evaporated to give crude material which was purified by HPLC (dichloromethane-ethyl acetate; 20:1) and crystallized from dichloromethane-diethyl ether to give 3.3 g of 2-[[3-(2-phenoxyethoxy)2-naphthalenyl]oxy]ethanol as a colorless solid, mp 119°–120° C.

A stirred mixture of 4-hydroxy-alpha-oxobenzeneacetic acid methyl ester (0.724 g) in dimethylformamide (10 mL) under argon was treated with 55% sodium hydride (0.175 g), stirred for 15 minutes and treated with the mesylate (1.6 g) prepared from 2-[[3-(2-phenoxyethoxy)-2-naphthalenyloxy]ethanol. The mixture was heated under argon at 60° C. overnight. The cooled mixture was treated with glacial acetic acid (2 drops) and the volatiles were removed under vacuum. The residue was mixed with water and extracted with dichloromethane. The organic layer was washed with water, dried ($Na_2SO_4$), filtered, and evaporated to give crude product. The material was purified by HPLC (dichloromethane-hexane; 4:1 plus 2% ethyl acetate) to provide, after crystallization from dichloromethane-diethyl ether, 0.525 g of alpha-oxo-4-[[2-[3-(2-phenoxyethoxy)-2naphthalenyloxy]ethyl]oxy]benzeneacetic acid methyl ester (2:1) hydrate as a colorless solid, mp 146°–147° C.

Analysis Calculated for $C_{29}H_{26}O_7.2:1\ H_2O$: C, 70.29; H, 5.49. Found: C, 70.45; H, 5.24.

EXAMPLE 116

PREPARATION OF ALPHA-OXO-4-[[2-[3-(2-PHENOXYETHOXY)-2-NAPHTHALENYLOXY]ETHYL]OXY]BENZENEACETIC ACID

A mixture of alpha-oxo-4-[[2-[3-(2-phenoxyethoxy)-2-naphthalenyloxy]ethyl]oxy]benzeneacetic acid methyl ester (0.50 g) in hot methanol (10 mL) plus enough tetrahydrofuran to dissolve the solids, was treated with 1N sodium hydroxide (2 mL) and diluted with water. The organic solvent was removed under vacuum and the residue was mixed with water, acidified with excess 2N hydrochloric acid, and extracted with dichloromethane. The organic layer was dried ($Na_2SO_4$), filtered, and evaporated to give crude product. Crystallization from acetone-hexane provided 0.45 g of alpha-oxo-4-[[2-[3-(2-phenoxyethoxy)-2-naphthalenyloxy]ethyl]oxy]benzeneacetic acid as a colorless solid, mp 176°–177° C.

Analysis Calculated for $C_{28}H_{24}O_7$: C, 71.18; H, 5.12. Found: C, 71.27; H, 5.09.

EXAMPLE 117

PREPARATION OF 4-[[2-[3-(2-HYDROXYETHOXY)-2-NAPHTHALENYLOXY]ETHYL]OXY]-ALPHA-OXOBENZENEACETIC ACID METHYL ESTER

A stirred mixture of 2,3-dihydroxynaphthalene (4.8 g), ethylene carbonate (5.8 g) and tetraethylammonium bromide (2.1 g) was heated at 155°–160° C. for 2 hours. The cooled reaction was diluted with dichloromethane, filtered, and the crude material was crystallized from toluene to give 4.3 g of 2,2-[2,3-naphthalenebis(oxy)]bisethanol as a colorless solid, mp 143°–145° C.

A stirred mixture of 2,2-[2,3-naphthalenebis(oxy)]bisethanol (4.2 g) and pyridine (40 mL) was chilled in a dry ice/acetone bath to just above freezing and treated dropwise with methanesulfonyl chloride (1.3 mL). The mixture was stirred for 1 hour at 0° C. and then overnight at room temperature. The pyridine solution was diluted with ice and water and acidified with excess 2N hydrochloric acid. The mixture was extracted with dichloromethane, washed with water, dried ($Na_2SO_4$), filtered, and evaporated. The material was purified by HPLC (dichloromethane-ethyl acetate; 1:1) to provide, after crystallization from dichloromethane-diethyl ether, 2.6 g of 2-[3-(2-hydroxyethoxy)-2-naphthalenyloxy)]ethyl methanesulfonate as a colorless solid, mp 100°–102° C.

A stirred mixture of 4-hydroxy-alpha-oxobenzeneacetic acid methyl ester (1.27 g) in dimethylformamide (10 mL) under argon was treated with 55% sodium hydride (0.306 g), stirred for 15 minutes and treated with 2-[3-(2-hydroxyethoxy)-2-naphthalenyloxy)]ethyl methanesulfonate (2.3 g). The mixture was heated under argon at 60° C. overnight. The cooled mixture was treated with glacial acetic acid (2 drops) and the volatiles were removed under vacuum. The residue was mixed with water and extracted with dichloromethane. The organic layer was washed with water, dried ($Na_2SO_4$), filtered, and evaporated to give crude product. The material was purified by HPLC (dichloromethane-ethyl acetate; 9:1) to provide, after crystallization from dichloromethane-diethyl ether, 0.67 g of 4-[[2-[3-(2-hydroxyethoxy)-2-naphthalenyloxy]ethyl]oxy]-alpha-oxobenzeneacetic acid methyl ester as a colorless solid, mp 130°–135° C. which was used without further purification.

EXAMPLE 118

PREPARATION OF 4-[[2-[3-(2-HYDROXYETHOXY)-2-NAPHTHALENYLOXY]ETHYL]OXY]-ALPHA-OXOBENZENEACETIC ACID

A mixture of 4-[[2-[3-(2-hydroxyethoxy)-2-naphthalenyloxy]ethyl]oxy]-alphaoxobenzeneacetic acid methyl ester (0.6 g) in hot methanol (10 mL) plus enough tetrahydrofuran to dissolve the solids, was treated with 1N sodium hydroxide (4 mL) and diluted with water. The organic solvent was removed under vacuum and the residue was mixed with water, acidified with excess 2 N hydrochloric acid, and extracted with dichloromethane-tetrahydrofuran. The organic layer was dried ($Na_2SO_4$), filtered, and evaporated to give crude product. Crystallization from acetone-hexane provided 0.4 g of 4-[[2-[3-(2-hydroxyethoxy)-2-naphthalenyloxy]ethyl]oxy]-alpha-oxobenzeneacetic acid as a colorless solid, mp 176°–177° C.

Analysis Calculated for $C_{22}H_{20}O_7$: C, 66.66; H, 5.09. Found: C, 66.38; H, 4.99.

EXAMPLE 119

PREPARATION OF ALPHA-OXO-4-[[2-[3-(PHENYLMETHOXY)-2-NAPHTHALENYLOXY]ETHYL]OXY]BENZENEACETIC ACID METHYL ESTER

A stirred mixture of 3-(phenylmethoxy)-2-naphthalenol (5 g), ethylene carbonate (1.9 g) and tetraethylammonium bromide (1.5 g) was heated at 155°–160° C. for 2 hours. The cooled reaction was diluted with dichloromethane, washed with 1N sodium hydroxide, water, dried ($Na_2SO_4$), filtered, and evaporated. The material was purified by HPLC (dichloromethane-ethyl acetate; 20:1) to provide, after crystallization from dichloromethanediethyl ether, 3.9 g of 2-[3-(phenylmethoxy)-2-naphthalenyloxy]ethanol as a colorless solid, mp 95°–97° C.

A stirred mixture of 4-hydroxy-alpha-oxobenzeneacetic acid methyl ester (2.29 g) in dimethylformamide (30 mL) under argon was treated with 55% sodium hydride (0.552 g), stirred for 15 minutes and treated with the mesylate (4.3 g) prepared from 2-[3-(phenylmethoxy)-2-naphthalenyloxy]ethanol. The mixture was heated under argon at 60° C. overnight. The cooled mixture was treated with glacial acetic acid (2 drops) and the volatiles were removed under vacuum. The residue was mixed with water and extracted with dichloromethane. The organic layer was washed with water, dried ($Na_2SO_4$), filtered, and evaporated to give crude product. The material was purified by HPLC (dichloromethane-hexane; 3:1 plus 2% ethyl acetate) to provide, after crystallization from dichloromethane-methanol, 3.0 g of alpha-oxo-4-[[2-[3-(phenylmethoxy)-2-naphthalenyloxy]ethyl]oxy]benzeneacetic acid methyl ester as a colorless solid, mp 115°–117° C.

Analysis Calculated for $C_{28}H_{24}O_6$: C, 73.67; H, 5.30. Found: C, 73.32; H, 5.20.

EXAMPLE 120

PREPARATION OF 4-[[2-(3-HYDROXY-2-NAPHTHALENYLOXY)ETHYL]OXY]-ALPHA-OXOBENZENEACETIC ACID METHYL ESTER

A mixture of alpha-oxo-4-[[2-[3-(phenylmethoxy)-2-naphthalenyloxy]ethyl]oxy]benzeneacetic acid methyl ester (0.456 g) in tetrahydrofuran (3 mL) was added to a flask containing 10% palladium on carbon catalyst and 5 mL of tetrahydrofuran in a hydrogen atmosphere. The mixture was stirred until one equivalent of hydrogen was absorbed and the reaction was filtered and the organic solvent was removed by evaporation. Chromatography on silica gel and elution with dichloromethane-hexane mixtures provided purified product. Crystallization from dichloromethane-diethyl ether gave 0.067 g of pure 4-[[2-(3-hydroxy-2-naphthalenyloxy)ethyl]oxy]-alphaoxobenzeneacetic acid methyl ester as a colorless solid, mp 177°–178° C.

EXAMPLE 121

PREPARATION OF 4-[[2-(3-HYDROXY-2-NAPHTHALENYLOXY)ETHYL]OXY]-ALPHA-OXOBENZENEACETIC ACID

A mixture of 4-[[2-(3-hydroxy)-2-naphthalenyloxy)ethyl]oxy]-alpha-oxobenzeneacetic acid methyl ester (0.065 g) in hot methanol (2 mL) plus tetrahydrofuran (5 mL) was treated with 1N sodium hydroxide (0.5 mL) and diluted with water. The organic solvent was removed under vacuum and the residue was mixed with water, acidified with excess 2N hydrochloric acid, and extracted with dichloromethane. The organic layer was dried ($Na_2SO_4$), filtered, and evaporated to give crude product. Crystallization from dichloromethane-diethyl ether provided 0.055 g of 4-[[2-(3-hydroxy-2-naphthalenyloxy) ethyl]oxy]-alpha-oxobenzeneacetic acid as a colorless solid, mp 191°–192° C.

Analysis Calculated for $C_{20}H_{16}O_6$: C, 68.18; H, 4.58. Found: C, 67.78; H, 4.51.

EXAMPLE 122

Preparation of alpha-oxo-4-[4-(3-pyridinyl)butoxy]benzeneacetic acid methyl ester (4:1) molar hydrate A stirred mixture of 4-hydroxy-alpha-oxobenzeneacetic acid methyl ester (1.14 g), 3-pyridinebutanol (1.04 g), triphenylphosphine (2.07 g), and tetrahydrofuran (25 mL) was stirred at 0° C. while adding dropwise a solution of diethyl azodicarboxylate (1.37 g) in tetrahydrofuran (10 mL). The mixture was stirred for 2 hours at 0° C. and evaporated to dryness. The material was purified by HPLC (hexane-acetone; 2:1) to provide 1.4 g of alpha-oxo-4-[4-(3-pyridinyl)butoxy]benzeneacetic acid methyl ester (4:1) molar hydrate as a colorless oil.

Analysis Calculated for $C_{18}H_{19}NO_4.4:1H_2O$: C, 68.02; H, 6.18; N, 4.41. Found: C, 68.24; H, 6.19; N, 4.68.

EXAMPLE 123

Preparation of alpha-oxo-4-[4-(3-pyridinyl)butoxy]benzeneacetic acid

A mixture of alpha-oxo-4-[4-(3-pyridinyl)butoxy]benzeneacetic acid methyl ester (4:1) molar hydrate (1.1 g) in hot methanol (10 mL) was treated with 1N sodium hydroxide (5 mL) and diluted with water. The organic solvent was removed under vacuum and the residue in water was washed with diethyl ether. The aqueous layer was concentrated to about 25 mL and chilled in ice. Cold 2N hydrochloric acid (2.5 mL) was added dropwise and the product was allowed to crystallize and was filtered and air dried. Recrystallization from acetone provided 0.64 g of alpha-oxo-4-[4-(3-pyridinyl)butoxy]benzeneacetic acid as a colorless solid, mp 163°–165° C.

Analysis Calculated for $C_{17}H_{17}NO_4$: C, 68.22; H, 5.72; N, 4.68. Found: C, 67.83; H, 5.73; N, 5.02.

EXAMPLE 124

Preparation of alpha-oxo-4-[4-(4-pyridinyl)butoxy]benzeneacetic acid methyl ester A stirred mixture of 4-hydroxy-alpha-oxobenzeneacetic acid methyl ester (1.086 g) in dimethylformamide (10 mL) under argon was treated with 55% sodium hydride (0.261 g), stirred for 15 minutes and treated with the mesylate prepared from 0.906 g of 4-pyridinebutanol. The mixture was heated under argon at 60° C. for 4 hours. The cooled mixture was treated with glacial acetic acid (2 drops) and the volatiles were removed under vacuum. The residue was mixed with dichloromethane and dilute cold sodium bicarbonate solution. The dichloromethane extracts were dried ($Na_2SO_4$), filtered, and evaporated to give crude product. The material was purified by HPLC (hexane-acetone; 2: 1) to provide 0.58 g of alpha-oxo-4-[4-(4-pyridinyl)butoxy]benzeneacetic acid methyl ester as a colorless oil whose NMR was compatible with the desired product.

EXAMPLE 125

Preparation of alpha-oxo-4-[4-(4-pyridinyl)butoxy]benzeneacetic acid

A mixture of alpha-oxo-4-[4-(4-pyridinyl)butoxy]benzeneacetic acid methyl ester (0.58 g) in hot methanol (10 mL) was treated with 1N sodium hydroxide (3.0 mL) and diluted with water. The organic solvent was removed under vacuum and the residue in water was washed with diethyl ether. The aqueous layer was concentrated to about 25 mL and chilled in ice. Cold 2N hydrochloric acid (1.5 mL) was added dropwise and the product was allowed to crystallize and was filtered and air dried. Recrystallization from water provided 0.55 g of alpha-oxo-4-[4-(4-pyridinyl)butoxy]benzeneacetic acid as a colorless solid, mp 198°–199° C.

Analysis Calculated for $C_{17}H_{17}NO_4$:.C, 68.22; H, 5.72; N, 4.68. Found: C, 67.95; H, 5.68; N, 4.56

EXAMPLE 126

Preparation of alpha-oxo-4-[[2-(7-quinolyloxy)ethyl]oxy]benzeneacetic acid methyl ester A stirred mixture of 4-hydroxy-alpha-oxobenzeneacetic acid methyl ester (1.267 g) in dimethylformamide (10 mL) under argon was treated with 55% sodium hydride (0.305 g), stirred for 15 minutes and treated with the mesylate prepared from 1.135 g of 2-(7quinolyloxy)ethanol. The mixture was heated under argon at 60° C. for 5 hours. The cooled mixture was treated with glacial acetic acid (2 drops) and the volatiles were removed under vacuum. The residue was mixed with dichloromethane and dilute cold sodium bicarbonate solution. The dichloromethane extracts were washed with water, dried ($Na_2SO_4$), filtered, and evaporated to give crude product. The material was purified by HPLC (ethyl acetate) and crystallized from dichloromethane-hexane to provide 0.93 g of alpha-oxo-4-[[2-(7-quinolyloxy)ethyl]oxy]benzeneacetic acid methyl ester as a colorless solid, mp 92°–94° C.

Analysis Calculated for $C_{20}H_{17}NO_5$: C, 68.37; H, 4.88; N, 3.99. Found: C, 68.68; H, 4.86; N, 3.99.

EXAMPLE 127

Preparation of alpha-oxo-4-[[2-(7-quinolyloxy)ethyl]oxy]benzeneacetic acid monohydrate A mixture of alpha-oxo-4-[[2-(7-quinolyloxy)ethyl]oxy]benzeneacetic acid methyl ester (0.5 g) in hot methanol (5 mL) and tetrahydrofuran (5 mL) was treated with 1N sodium hydroxide (2.0 mL) and diluted with water. The organic solvent was removed under vacuum and the residue was dissolved in hot water. Cold 2N hydrochloric acid (1.0 mL) was added dropwise and the product was allowed to crystallize and was filtered, washed with water and dried to give 0.45 g of alpha-oxo-4-[[2-(7-quinolyloxy)ethyl]oxy]benzeneacetic acid monohydrate as a colorless solid, mp 229°–231° C.

Analysis Calculated for $C_{19}H_{15}NO_5.H_2O$: C, 64.22; H, 4.82; N, 3.94, Found: C, 64.30; H, 4.50; N, 3.94.

EXAMPLE 128

Preparation of 4-[[2=(7-isoquinolyloxy)ethyl]oxy]alpha-oxobenzeneacetic acid methyl ester A stirred mixture of 4-hydroxy-alpha-oxobenzeneacetic acid methyl ester (1.267 g) in dimethylformamide (10 mL) under argon was treated with 55% sodium hydride (0.305 g), stirred for 15 minutes and treated with the mesylate prepared from 1.135 g of 2-(7-isoquinolyloxy)ethanol. The mixture was heated under argon at 60° C. for 5 hours. The cooled mixture was treated with glacial acetic acid (2 drops) and the volatiles were removed under vacuum. The residue was partitioned between dichloromethane and dilute cold sodium bicarbonate solution. The dichloromethane layer was washed with water, dried ($Na_2SO_4$), filtered, and evaporated to give crude product. The material was purified by HPLC (ethyl acetate) and crystallized from dichloromethane-hexane to provide 0.83 g of 4-[[2-(7-isoquinolyloxy)ethyl]oxy]-alpha-oxobenzeneacetic acid methyl ester as a colorless solid, mp 144°–145° C.

Analysis Calculated for $C_{20}H_{17}NO_5$: C, 68.37; H, 4.88; N, 3.99. Found: C, 68.25; H, 4.82; N, 3.88.

EXAMPLE 129

Preparation of 4-[[2-(7-isoquinolyloxy)ethyl]oxy]-alpha-oxobenzeneacetic acid (5:2) molar hydrate A mixture of 4-[[2-(7-isoquinolyloxy)ethyl]oxy]-alpha-oxobenzeneacetic acid methyl ester (0.5 g) in hot methanol (5 mL) and tetrahydrofuran (5 mL) was treated with 1N sodium hydroxide (2.0 mL) and diluted with water. The organic solvent was removed under vacuum and the residue was dissolved in hot water. Cold 2N hydrochloric acid (1.0 mL) was added dropwise and the product was allowed to crystallize and was filtered, washed with water and dried to give 0.45 g of 4-[[2-(7-isoquinolyloxy)ethyl]oxy]-alpha-oxobenzeneacetic acid as a colorless solid, mp 260° C. with decomposition.

Analysis Calculated for $C_{19}H_{15}NO_5.5:2\ H_2O$: C, 66.23; H, 4.62; N, 4.06; $H_2O$, 2.09. Found: C, 66.04; H, 4.49; N, 4.03; H20, 1.79.

EXAMPLE 130

Preparation of alpha-oxo-4-[[2-(4-quinolyloxy)ethyl]oxy]benzeneacetic acid methyl ester A stirred mixture of 4-hydroxy-alpha-oxobenzeneacetic acid methyl ester (1.267 g) in dimethylformamide (10 mL) under argon was treated with 55% sodium hydride (0.305 g), stirred for 15 minutes and treated with the mesylate prepared from 1.135 g of 2-(4-quinolyloxy)ethanol. The mixture was heated under argon at 60° C. for 3 hours. The cooled mixture was treated with glacial acetic acid (2 drops) and the volatiles were removed under vacuum. The residue was mixed with dichloromethane and dilute cold sodium bicarbonate solution. The dichloromethane extracts were washed with water, dried ($Na_2SO_4$), filtered, and evaporated to give crude product. The material was purified by HPLC (ethyl acetate-methanol; 20: 1) and crystallized from dichloromethane-hexane to provide 1.2 g of alpha-oxo-4-[[2-(4-quinolyloxy)ethyl]oxy]benzeneacetic acid methyl ester as a colorless solid, mp 135°–136° C.

Analysis Calculated for $C_{20}H_{17}NO_5$: C, 68.37; H, 4.88; N, 3.99. Found: C, 68.35; H, 4.87; N, 4.01.

EXAMPLE 131

Preparation of alpha-oxo-4-[[2-(4-quinolyloxy)ethyl]oxy]benzeneacetic acid

A mixture of alpha-oxo-4-[[2-(4-quinolyloxy)ethyl]oxy]benzeneacetic acid methyl ester (0.50 g) in hot methanol (10 mL) was treated with 1N sodium hydroxide (4.0 mL) and diluted with water. The organic solvent was removed under vacuum and the residue was dissolved in water and chilled in ice. Cold 2N hydrochloric acid (2.0 mL) was added dropwise and the product was allowed to crystallize and was filtered, washed with water and dried to give 0.477 g of alpha-oxo-4-[[2-(4-quinolyloxy)ethyl]oxy]benzeneacetic acid as a colorless solid, mp 271° C. with decomposition.

Analysis Calculated for $C_{19}H_{15}NO_5$: C, 67.65; H, 4.48; N, 4.15. Found: C, 67.25; H, 4.80; N, 3.90.

EXAMPLE 132

Preparation of alpha-oxo-4-[[(trifluoromethyl)sulfonyl]oxy]benzeneacetic acid methyl ester A solution of alpha-oxo-4-hydroxybenzeneacetic acid methyl ester (2 g) and phenyl-bis-[(trifluoromethyl)sulfonyl]amine (4.2 g) in dichloromethane (30 mL) was cooled in an ice bath and triethylamine (1.65 mL) was added dropwise. The mixture was held at 0° C. for 1 hour and was allowed to warm to room temperature over 2 hours. It was diluted to 100 mL with diethyl ether and washed with successive 25 mL portions of water (twice), 0.5N sodium hydroxide, 0.5N hydrochloric acid, and saturated brine. Concentration of the dried ($MgSO_4$) extract gave a mixture of an oil and a solid from which the oil was decanted to give 2.77 g of alpha-oxo-4-[[(trifluoromethyl)sulfonyl]oxy]benzeneacetic acid methyl ester suitable for use in the next step. The analytical sample was obtained as a colorless oil by chromatography of a portion over silica gel, eluting with ethyl acetate-hexane (9:1).

Analysis Calculated for $C_{10}H_7F_3O_6S$: C, 38.47; H, 2.26; S, 10.27; F, 18.25. Found: C, 38.75; H, 2.29; S, 9.98; F, 18.55.

EXAMPLE 133

Preparation of 4-[[2-[8-(2,2-dimethyl-1-oxobutoxy)-2-naphthalenyloxy]ethyl]oxy]alpha-oxobenzeneacetic acid methyl ester To a stirred suspension of sodium hydride (55% dispersion in mineral oil, 0.105 g) in dimethylformamide (5 mL) was added dropwise a solution of 4-hydroxy-alpha-oxobenzene acetic acid methyl ester (0.432 g) in dimethylformamide (5 mL) under argon. The mixture was then treated dropwise with a solution of 2-[8-(2,2-dimethyl-1-oxobutoxy)-2naphthalenyloxy]ethyl methanesulfonate (0.76 g) in dimethylformamide (5 mL). The reaction was heated for 18 hours at 60° C., diluted with brine, and extracted with ethyl acetate. After evaporation of volatiles, the residue was purified by chromatography over silica gel (hexane-ethyl acetate; 10: 1) to yield 0.375 g of 4-[[2-[8-(2,2-dimethyl-1-oxobutoxy)-2-naphthalenyloxy]ethyl]oxy]-alpha-oxobenzeneacetic acid methyl ester as a white solid, mp 119°–120° C.

Analysis Calculated for $C_{27}H_{28}O_7$: C, 69.80; H, 6.07. Found: C, 68.48; H, 5.90.

EXAMPLE 134

Preparation of 4-[[2-[8-(2,2-dimethyl-1-oxobutoxy)-2-naphthalenyloxy]ethyl]oxy]alpha-oxobenzeneacetic acid To a solution of 4-[[2-[8-(2,2-dimethyl-1 -oxobutoxy)-2-naphthalenyloxy]ethyl]oxy]-alpha-oxobenzeneacetic acid methyl ester (0.3 g) in methanol (7 mL) was added aqueous 1N sodium hydroxide (1.35 mL). After 15 minutes, the reaction was acidified with 1N hydrochloric acid (2 mL) and extracted with dichloromethane. The organic layer was washed with brine and evaporated to provide 4-[[2-[8-(2,2-dimethyl-1-oxobutoxy)-2naphthalenyloxy]ethyl]oxy]-alpha-oxobenzeneacetic acid as a white solid, mp 167°–168° C.

Analysis Calculated for $C_{26}H_{26}O_7$: C, 69.32; H, 5.82. Found: C, 69.17; H, 5.89.

EXAMPLE 135

Preparation of 4-[[2-[2-[(2,2-dimethyl-1-oxobutoxy)methyl]-6-methylphenoxy]ethyl]oxy]-alpha-oxobenzeneacetic acid methyl ester To a stirred suspension of sodium hydride (55% dispersion in mineral oil; 0.218 g) in dimethylformamide (5 mL) was added dropwise 4-hydroxy-alpha-oxobenzeneacetic acid methyl ester (0.9 g) in dimethylformamide (5 mL) under argon. The resulting mixture was then treated dropwise with a solution of 2-[2-[(2,2-dimethyl-1 -oxobutoxy)methyl]-6-methyl-phenoxy]ethyl 4-methylphenylsulfonate (1.4 g) in dimethylformamide (5 mL). The reaction was heated for 18 hours at 60° C., then was diluted with brine, and extracted with ethyl acetate. After evaporation of the extracts, the residue was purified by chromatography over silica gel (hexane-ethyl acetate; 10:1) to yield 0.606 g of 4-[[2-[2-[(2,2-dimethyl-1-6-methylphenoxy]ethyl]oxy]-alpha-oxobenzeneacetic acid methyl ester as a clear oil.

Analysis Calculated for $C_{25}H_{30}O_7$: C, 67.86; H, 6.83. Found: C, 67.42; H, 6.18.

EXAMPLE 136

Preparation of 4-[[2-[2-[(2,2-dimethyl-1-oxobuyloxy)methyl]-6-methylphenoxy]ethyl]oxy]-alpha-oxobenzeneacetic acid (2:1) hydrate To a solution of 4-[[2-[2-[(2,2-dimethyl-1-oxobuyloxy)methyl]-6-methylphenoxy]ethyl]oxy]-alpha-oxobenzeneacetic acid methyl ester (0.554 g) in methanol (10 mL) was added aqueous 1N sodium hydroxide (2.5 mL). After 30 minutes at 50° C., the reaction was acidified with 1N hydrochloric acid (2 mL) and extracted with dichloromethane. The organic phase was washed with brine and evaporated to provide 0.47 g of 4-[[2-[2-[(2,2-dimethyl-1-oxobuyloxy) methyl]-6-methylphenoxy]ethyl]oxy]-alpha-oxobenzeneacetic acid (2:1) hydrate as a clear oil.

Analysis Calculated for $C_{24}H_{28}O_7.2:1\ H_2O$: C, 65.83; H, 6.40. Found: C, 65.64; H, 6.53.

EXAMPLE 137

Preparation of 4-[[2-[2-(hydroxymethyl)-6-methyl phenoxy]ethyl]oxy]-alpha-oxobenzeneacetic acid To a solution of 4-[[2-[2-[(2,2-dimethyl-1-oxobuyloxy)methyl]-6-methylphenoxy]ethyl]oxy]-alpha-oxobenzeneacetic acid [2:1]hydrate (0.032 g) in methanol (10 mL) was added aqueous 1N sodium hydroxide (1.0 mL). After 18 hours at 40° C., the reaction was acidified with 1N hydrochloric acid (2 mL), then concentrated in vacuo to ~2 mL and extracted with dichloromethane. The organic extract was evaporated to provide 0.014 g of 4-[[2-[2-(hydroxymethyl)-6-methylphenoxy]ethyl]oxy]-alpha-oxobenzeneacetic acid as a white solid.

Analysis by (+)-FAB Calculated for $[C_{18}H_{18}O_6-H]+$: 331.1182 Found: 331.1186. Calculated for $[C_{18}H_{18}O_6-H]+$: 329.1025 Found: 329.1002.

EXAMPLE 138

Preparation of 4-[[2-[6-(acetyioxy)-2-naphthalenyloxy]ethyl]oxy]-alpha-oxobenzeneacetic acid methyl ester To a stirred suspension of sodium hydride (55% dispersion in mineral oil; 0.393 g) in dimethylformamide (20 mL) was added dropwise 4-hydroxy-alpha-oxobenzeneacetic acid methyl ester (1.6 g) in dimethylformamide (15 mL) under argon. The resulting mixture was then treated dropwise with a solution of 2-[6-(acetyloxy)-2-naphthalenyloxy]ethyl methanesulfonate (2.23 g) in dimethylformamide (15 mL). The reaction was heated for 18 hours at 65° C., diluted with brine and extracted with ethyl acetate. After evaporation of the extracts, the residue was purified by chromatography over silica gel (hexane-diethyl ether; 1:1, increasing to 1:2) to yield 1.0 g of 4-[[2-[6-(acetyloxy)-2-naphthalenyloxy]ethyl]oxy-alpha-oxobenzeneacetic acid methyl ester as a white .solid, mp 120°–122° C.

Analysis Calculated for $C_{23}H_{20}O_7$: C, 67.64; H, 4.94. Found: C, 67.32; H, 4.84.

EXAMPLE 139

Preparation of 4-[[3-(2-naphthoylamino)propyl]oxy]-alpha-oxobenzeneacetic acid methyl ester A stirred mixture of 4-hydroxy-alpha-oxobenzeneacetic acid methyl ester (1.27 g) in dimethylformamide (10 mL) under argon was treated with 55% sodium hydride (0.306 g), stirred for 10 minutes and treated with N-(3-bromopropyl)-2-naphthylenecarboxamide (1.7 g). The mixture was heated under argon at 60° C. for 5 hours. The cooled mixture was treated with glacial acetic acid (2 drops) and the volatiles were removed under vacuum. The residue was mixed with water and extracted with dichloromethane. The organic extracts were washed with water, dried ($Na_2SO_4$), filtered, and evaporated to give crude product. The material was purified by HPLC (dichloromethane-ethyl acetate; 9:1) and crystallized from dichloromethane-ethyl ether to provide 0.9 g of 4-[[3-(2-naphthoylamino)propyl]oxy]-alpha-oxobenzeneacetic acid methyl ester as a colorless solid, mp 143°–144° C.

Analysis Calculated for $C_{23}H_{21}NO_5$: C, 70.58; H, 5.41; N, 3.58. Found: C, 70.24; H, 5.55; N, 3.49.

EXAMPLE 140

Preparation of 4-[[3-(2-naphthoylamino)propyl]oxy]-alpha-oxobenzeneacetic acid

A mixture of 4-[[3-(2-naphthoylamino)propyl]oxy]-alpha-oxobenzeneacetic acid methyl ester (0.76 g) in hot methanol (10 mL) and sufficient tetrahydrofuran to dissolve the solids was treated with 1N sodium hydroxide (4.0 mL) and diluted with water. The organic solvent was removed under vacuum and the residue was mixed with water, acidified with excess 2N hydrochloric acid, and extracted with dichloromethane. The organic layer was dried ($Na_2SO_4$), filtered, and evaporated to give crude product. Crystallization from acetone-hexane provided 0.43 g of 4-[[3-(2-naphthoylamino) propyl]oxy]-alpha-oxobenzeneacetic acid as a colorless solid, mp 169°–170° C.

Analysis Calculated for $C_{22}H_{19}NO_5$: C, 70.05; H, 5.07; N, 3.71. Found: C, 69.89; H, 5.16; N, 3.60.

EXAMPLE 141

Preparation of 4-[[2-benzofuranyl)methoxy]-alpha-oxobenzeneacetic acid

A stirred mixture of 4-hydroxy-alpha-oxobenzeneacetic acid methyl ester (1.52 g) in dimethylformamide (10 mL) under argon was treated with 55% sodium hydride (0.405 g), stirred for 10 minutes and treated with 2-chloromethylbenzofuran (1.4 g). The mixture was stirred at room temperature under argon for 3 hours, diluted with water, and extracted with ethyl acetate. Evaporation of the organic extracts provided crude methyl ester as a liquid. Treatment of a portion of this ester (1.02 g) with potassium hydroxide (0.18 g) in a methanol-water mixture, followed by acidification of the mixture with hydrochloric acid and filtration provided 4-[[2-benzofuranyl)methoxy]-alpha-oxobenzeneacetic acid as a white solid, mp 120° C.

Analysis Calculated for $C_{17}H_{12}O_5$: C, 68.92; H, 4.05. Found: C, 68.64; H, 4.26.

EXAMPLE 142

Preparation of 4-[3-(2-naphthalenyloxy)-1-propynyl]-alpha-oxobenzeneacetic acid

Argon was bubbled through a solution of 2-(2-propynyl)oxynaphthalene (0.36 g), alpha-oxo-4-[[(trifluoromethyl)sulfonyl]oxy]benzeneacetic acid methyl ester (0.51 g), triethylamine (2.0 mL) and lithium chloride (0.2 g) in dimethylformamide (5 mL) for 15 minutes and bis(triphenylphosphine)palladium dichloride (0.06 g) was added. The bath temperature was raised to 90° C. for 2 hours. The mixture was cooled, diluted with diethyl ether-ethyl acetate (1:1; 50 mL) and extracted with water (2×50 mL). Addition of saturated sodium chloride solution to the combined aqueous layers gave a precipitate which was collected, dissolved in tetrahydrofuran (25 mL) and acidified by the addition of excess 6N hydrochloric acid plus saturated brine. The layers were separated and the organic phase was dried (MgSO4), evaporated and the residue crystallized from dichloromethane-hexane to afford 0.216 g of 4-[3-(2-naphthalenyloxy)-1-propynyl]-alpha-oxobenzeneacetic acid, mp 120°-124° C. (dec).

Analysis Calculated for $C_{21}H_{14}O_4$: C, 76.36; H, 4.27. Found: C, 76.07; H, 4.18.

EXAMPLE 143

Preparation of 4-[3-(2-naphthalenyloxy)propyl]-alpha-oxobenzeneacetic acid

A suspension of 4-[3-(2-naphthalenyloxy)-1-propynyl]-alpha-oxobenzeneacetic acid (0.13 g) in dichloromethane (19 mL) was hydrogenated over 10 % palladium on carbon (0.016 g) at atmospheric pressure. The resulting mixture was filtered twice through a pad of celite to remove insoluble materials, then the tiltrate was evaporated and the residue was crystallized from ethyl acetate-hexane to afford 0.083 g of 4-[3-(2-naphthalenyloxy) propyl]-alpha-oxobenzeneacetic acid, mp 151°-154° C.

Analysis Calculated for $C_{21}H_{18}O_4$: C, 75.43; H, 5.43. Found: C, 74.92; H, 5.35.

EXAMPLE 144

Preparation of N-(2- propynyl )-2-naphthalenecarboxamide

Propargylamine (0.80 mL) and triethylamine (1.67 mL) were added simultaneously to a solution of 2-naphthoyl chloride (2.22 g) in dichloromethane (25 mL) cooled in an ice bath. The mixture was held at 0° C. for 1 hour and allowed to warm to room temperature over 3 hours. The solution was diluted with ethyl acetate, washed in turn with water, 1N hydrochloric acid, 1N sodium hydroxide, and saturated brine. Evaporation of the dried ($K_2CO_3$) organic layer gave a residue which was crystallized from dichloromethanehexane to give 2.06 g of N-(2-propynyl)-2-naphthalenecarboxamide, mp 163°-165° C.

Analysis Calculated for $C_{14}H_{11}NO$: C, 80.36; H, 5.30; N, 6.69. Found: C, 80.09; H, 5.27; N, 6.65.

EXAMPLE 145

Preparation of 4-[3-[[(2-naphthalenyl)carbonyl]amino]-1-propynyl]-alpha-oxobenzeneacetic acid methyl ester Argon was bubbled through a solution of N-(2-propynyl)-2-naphthalenecarboxamide (0.335 g), alpha-oxo-4-[[(trifluoromethyl)sulfonyl]oxy]benzeneacetic acid methyl ester (0.5 g), triethylamine (0.44 mL) and lithium chloride (0.1 g) in dimethylformamide (4 mL) for 15 minutes and then bis(triphenylphosphine)palladium dichloride (0.07 g) was added. The mixture was allowed to stir over night at room temperature, diluted with 50 mL of dichloro-methane and washed with water (2×50 mL) and brine (25 mL). The dried (MgSO4) organic phase was concentrated to give a residue which was chromatographed over 50 g of silica gel (dichloromethane-ethyl acetate; 9:1) to afford 0.33 g of a yellow powder. Crystallization from ethyl acetate-hexane gave 0.25 g of 4-[3-[[(2-naphthalenyl) carbonyl]amino]-1-propynyl]-alpha-oxobenzeneacetic acid methyl ester, mp 113°-114° C.

Analysis Calculated for $C_{23}H_{17}NO_4$: C, 74.38; H, 4.61; N, 3.77. Found: C, 74.20; H, 4.56; N, 3.82.

EXAMPLE 146

Preparation of 4-[3-[[(2-naphthalenyl)carbonyl]amino]-1-propynyl]-alpha-oxobenzeneacetic acid A solution of 4-[3-[[(2-naphthalenyl)carbonyl]amino]-1-propynyl]-alpha-oxobenzeneacetic acid methyl ester (0.225 g) in tetrahydrofuran (2 mL) and methanol (1 mL) was treated with 1N sodium hydroxide (1 mL). After five minutes, the reaction mixture was concentrated and the resulting white suspension partitioned between dichloromethane (10 mL) and 1N hydrochloric acid (2 mL). The aqueous layer was diluted with saturated sodium chloride and was extracted with tetrahydrofuran (2×10 mL). The combined extracts were dried (MgSO4) and concentrated to give 0.2 g of a white solid, mp 153°-155° C. Crystallization from dichloromethane-ethyl acetate-hexane gave 0.15 g of 4-[[(2-naphthalenyl)carbonyl]amino]-1-propynyl]-alpha-oxobenzeneacetic acid, mp 156-°158° C.

Analysis Calculated for $C_{22}H_{15}NO_4$: C, 73.94; H, 4.23; N, 3.92, Found: C, 73.76; H, 4.21; N, 3.80.

EXAMPLE 147

Preparation of 4-[3 -[[(2-naphthalenyl)carbonyl]amino]propyl]-alpha-oxobenzeneacetic acid A solution of 4-[3-[[(2-naphthalenyl)carbonyl]amino]-1-propynyl]-alpha-oxobenzeneacetic acid (0.1 g) in dichloromethane (5 mL) was hydrogenated over 10% palladium on carbon (0.021 g) at atmospheric pressure for 4 hours. The mixture was filtered through a pad of celite and concentrated to give 0.106 g of a solid. Crystallization from ethyl acetate-hexane gave 0.056 g of 4-[3-[[(2-naphthalenyl)carbonyl]amino]propyl]-alpha-oxobenzeneacetic acid, mp 126°-128° C.

Analysis Calculated for $C_{22}H_{19}NO_4$: C, 72.67; H, 5.39; N, 3.78. Found: C, 72.41; H, 5.41; N, 3.79.

EXAMPLE 148

Preparation of 4-[[2-(2-naphthalenyloxy)ethyl]thio]-alpha-oxobenzeneacetic acid methyl ester A stirred mixture of 1-(4-mercaptophenyl)ethanone (1.2 g) in dimethylformamide (10 mL) under argon was treated with 55% sodium hydride (0.350 g), stirred for 15 minutes and treated with the mesylate of 2-(2-naphthyloxy)ethanol (2.2 g). The mixture was heated at 60° C. for 2 hours and diluted with water and filtered. The solids were dissolve in dichloromethane, washed once with water, dried (Na2SO4), filtered and evaporated. Crystallization from dichloromethane-hexane provided 2.0 g of 1-[4-[[2-(2naphthalenyloxy)ethyl]thio]phenyl]ethanone, mp 151°-152° C.

Analysis Calculated for $C_{20}H_{18}O_2S$: C, 74.51; H, 5.63; S, 9.94. Found: C, 74.73; H, 5.64; S, 9.70.

A solution of 1-[4-[[2-(2-naphthalenyloxy)ethyl]thio]-phenyl]ethanone (1.9 g) in pyridine (10 mL) was treated with selenium dioxide (0.732 g) and heated at 100° C. overnight. The solution was filtered, acidified with 6N hydrochloric acid and the solids collected by filtration. The solids were dissolved in dichloromethane, washed with water, dried (Na$_2$S$_2$O$_4$), filtered and evaporated. The crude 4-[[2-(2-naphthalenyloxy)ethyl]thio]-alpha-oxobenzeneacetic acid was purified by preparation of the methyl ester.

A solution of crude 4-[[2-(2-naphthalenyloxy)ethyl]thio]-alpha-oxobenzeneacetic acid (1.6 g) in dichloromethane (500 mL) and triethylamine (1 mL) was treated with methyl chloroformate (0.58 mL) and stirred at room temperature for 1 hour. The mixture was diluted with water, extracted with dichloromethane, dried (Na$_2$SO$_4$), filtered and evaporated. The material from dichloromethane extraction was purified by HPLC (dichloromethane-hexane; 2:1) and crystallized from dichloromethane-diethyl ether to provide 0.85 g of 4-[[2-(2-naphthalenyloxy)ethyl]thio]-alpha-oxobenzeneacetic acid methyl ester, mp 124°-125° C.

Analysis Calculated for C$_{21}$H$_{18}$O$_4$S: C, 68.83; H, 4.95; S, 8.75. Found: C, 69.02; H, 5.08; S, 8.50.

EXAMPLE 149

Preparation of
4-[[2-(2-naphthalenyloxy)ethyl]thio]-alpha-oxobenzeneacetic acid

A mixture of 4-[[2-(2-naphthalenyloxy)ethyl]thio]-alpha-oxobenzeneacetic acid methyl ester (0.72 g) in hot methanol (10 mL) and sufficient tetrahydrofuran to dissolve the solids was treated with 1N sodium hydroxide (4.0 mL) and diluted with water. The organic solvent was removed under vacuum and the residue was mixed with water, acidified with excess 2N hydrochloric acid, and extracted with dichloromethane. The organic layer was dried (Na$_2$SO$_4$), filtered, and evaporated to give crude product. Crystallization from acetone-hexane provided 0.6 g of 4-[[2-(2-naphthalenyloxy)ethyl]thio]-alpha-oxobenzeneacetic acid as a colorless solid, mp 161°-162° C.

Analysis Calculated for C$_{20}$H$_{16}$O$_4$S: C, 68.17; H, 4.58; S, 9.10. Found: C, 68.14; H, 4.47; S, 8.91.

EXAMPLE 150

Preparation of
rac.-4-[[2-(2-naphthalenyloxy)ethyl]sulfinyl]-alpha-oxobenzeneacetic acid methyl ester A solution of 4-[[2-(2-naphthalenyloxy)ethyl]thio]-alpha-oxobenzeneacetic acid methyl ester (2.56 g) in dichloromethane (75 mL) was chilled in ice and 85 % metachloroperbenzoic acid (1.42 g) was added. The mixture was stirred cold for 1 hour, diluted with saturated sodium bicarbonate solution, and extracted with dichloromethane. The dried (Na$_2$SO$_4$) was filtered, evaporated and the residue was crystallized from dichloromethane-hexane to give 2.2 g of rac.-4-[[2-(2-naphthalenyloxy)ethyl]sulfinyl]-alpha-oxobenzeneacetic acid methyl ester, mp 129°-130° C.

Analysis Calculated for C$_{21}$H$_{18}$O$_5$S: C, 65.95; H, 4.74; S, 8.38. Found: C, 65.90; H, 4.75; S, 8.28.

EXAMPLE 151

Preparation of
rac.-4-[[2-(2-naphthalenyloxy)ethyl]sulfinyl]-alpha-oxobenzeneacetic acid A mixture of rac.-4-[[2-(2-naphthalenyloxy)ethyl]sulfinyl]-alpha-oxobenzeneacetic acid methyl ester (0.5 g) in hot methanol (5 mL) and sufficient tetrahydrofuran to dissolve the solids was treated with 1N sodium hydroxide (2.0 mL) and diluted with water. The organic solvent was removed under vacuum and the residue was mixed with water, acidified with excess 2N hydrochloric acid, and extracted with dichloromethane. The organic layer was dried (Na$_2$SO$_4$), filtered, and evaporated to give crude product. Crystallization from acetone-hexane provided 0.35 g of rac.-4-[[2-(2-naphthalenyloxy)ethyl]sulfinyl]-alpha-oxobenzeneacetic acid as a yellow solid, mp 157°-158° C.

Analysis Calculated for C$_{20}$H$_{16}$O$_5$S: C, 65.21; H, 4.38; S, 8.70. Found: C, 65.06 H, 4.27; S, 8.99.

EXAMPLE 152

Preparation of
4-[[2-(2-naphthalenyloxy)acetyl]amino]-alpha-oxobenzeneacetic acid methyl ester A stirred mixture of para-aminobenzophenone (6.75 g) in dichloromethane (75 mL) and triethylamine (20 mL) was chilled to −78° C. and treated with the acid chloride prepared from 2-naphthoxyacetic acid (10.1 g). The mixture was stirred for 30 minutes at −78° C. and for 1 hour at room temperature. The mixture was diluted with water and sodium bicarbonate solution and the solids were recovered by filtration and washed with water and dichloromethane to give 13.3 g of N-(4-acetylphenyl)-2-naphthoxyacetamide, 208°-210° C.

A mixture of N-(4-acetylphenyl)-2-naphthoxyacetamide (3.0 g) in pyridine (50 mL) was treated with selenium dioxide (1.66 g) and heated at 90° C. overnight under argon. The mixture was filtered, diluted with 6N hydrochloric acid and the solids were recoved by filtration to give 3.0 g of crude 4-[[2-(2-naphthalenyloxy)acetyl]amino]-alpha-oxobenzeneacetic acid.

A mixture of 4-[[2-(2-naphthalenyloxy)acetyl]amino]-alpha-oxobenzeneacetic acid (3.0 g) in dichloromethane (50 mL) and triethylamine (2.1 g ) was stirred at 0° C. and treated with methyl chloroformate (1.16 mL). The mixture was stirred for one hour and diluted with water, extracted with dichloromethane, dried (Na$_2$SO$_4$), filtered and evaporated. The residue was crystallized from dichloromethane-hexane to give 2.2 g of 4-[[2-(2-naphthalenyloxy) acetyl]amino]-alpha-oxobenzeneacetic acid methyl ester, mp 175°-176° C.

Analysis Calculated for C$_{21}$H$_{17}$NO$_5$: C, 69.41; H, 4.72; N, 3.85. Found: C, 69.10 H, 4.71; N, 3.85.

EXAMPLE 153

Preparation of
4-[[2-(2-naphthalenyloxy)acetyl]amino]-alpha-oxobenzeneacetic acid A mixture of 4-[[2-(2-naphthalenyloxy)acetyl]amino]-alpha-oxobenzeneacetic acid methyl ester (0.7 g) in hot methanol (10 mL) and sufficient tetrahydrofuran to dissolve the solids was treated with 1N sodium hydroxide (2.5 mL) and diluted with water. The organic solvent was removed under vacuum and the residue was mixed with water, acidified with excess 2N hydrochloric acid, and extracted with dichloromethane. The organic layer was dried (Na$_2$SO$_4$), faltered, and evaporated to give the crude product. Crystallization from acetone-hexane provided 0.61 g of 4-[[2-(2-naphthalenyloxy)acetyl]amino]-alpha-oxobenzeneacetic acid as a colorless solid, mp 215°-216° C.

Analysis Calculated for C$_{20}$H$_{15}$NO$_5$: C, 68.76; H, 4.33; N, 4.01, Found: C, 68.68; H, 4.35; N, 3.91.

EXAMPLE 154

Preparation of
4=[(2-naphthalenyl)methoxy]-alpha-oxobenzeneacetic acid methyl ester A solution of 4-hydroxy-alpha-oxobenzeneacetic acid methyl ester (0.50 g in 5 mL of dimethylformamide was treated with 60% sodium hydride (0.112 g) and after 15 minutes, 2-bromomethylnaphthalene (0.61 g) was added. The reaction mixture was stirred 45 minutes at room temperature, was quenched with 0.1 mL of acetic acid and was diluted with diethyl ether-ethyl acetate (10: 1, 50 mL). The mixture was washed with water (2×10 mL) and brine (1×10 mL), dried (1MgSO$_4$) and chromatographed over 100 g of silica gel eluting with dichloromethane-hexane (1:1) to give 0.61 g of 4-[(2-naphthalenyl)methoxy]alpha-oxobenzeneacetic acid methyl ester, mp 101°–102° C.

Analysis Calculated for $C_{20}H_{16}O_4$: C, 74.99; H, 5.03. Found: C, 74.59; H, 5.10.

EXAMPLE 155

Preparation of
4-[(2-naphthalenyl)methoxy]-alpha-oxobenzeneacetic acid

A solution of 4-[(2-naphthalenyl)methoxy]-alpha-oxobenzeneacetic acid methyl ester (0.58 g) in methanol (3 mL) and tetrahydrofuran (8 mL) was treated with 1N sodium hydroxide (2.0 mL) and a white precipitate formed immediately. After 5 minutes, the reaction mixture was concentrated, the residue was acidified with excess hydrochloric acid and partitioned between dichloromethane (100 mL) and water (10 mL). The organic layer was dried (MgSO$_4$) and concentrated. The resulting residue was crystallized from dichloromethane-hexane-tetrahydrofuran to give 0.315 g of 4-[(2-naphthalenyl)methoxy]-alpha-oxobenzeneacetic acid, mp 145°–146° C.

Analysis Calculated for $C_{19}H_{14}O_4$: C, 74.50; H, 4.61. Found: C, 74.31; H, 4.50.

EXAMPLE 156

Preparation of
4-[2-(2=naphthalenyl)-2-oxoethoxy]-alpha-oxobenzeneacetic acid methyl ester A solution of 4-hydroxy-alpha-oxobenzeneacetic acid methyl ester (0.50 g) in 5 mL of dimethylformamide was treated with 60% sodium hydride (0.112 g) and after 20 minutes, bromomethyl 2-naphthyl ketone (0.70 g) was added. The reaction mixture was stirred 3 hours at room temperature, was quenched with 0.1 mL of acetic acid and was diluted with ethyl acetate (75 mL). The mixture was washed with water (1 x 25 mL) and brine (1×25 mL), dried (MgSO$_4$) and chromatographed over 100 g of silica gel, eluting with dichloromethane-ethyl acetate (50:1) to give 0.62 g of 4-[2-(2-naphthalenyl)-2-oxoethoxy]-alpha-oxobenzeneacetic acid methyl ester, mp 120°–121° C.

Analysis Calculated for $C_{21}H_{16}O_5.0.33\ H_2O$: C, 71.19; H, 4.73. Found: C, 71.18; H, 4.65.

EXAMPLE 157

Preparation of
4-[2=(2-naphthalenyl)-2-oxoethoxy]-alpha-oxobenzeneacetic acid

A solution of 4-[2-(2-naphthalenyl)-2-oxoethoxy]-alpha-oxobenzeneacetic acid methyl ester (0.57 g) in methanol (3 mL) and tetrahydrofuran (8 mL) was treated with 1N sodium hydroxide (1.7 mL) and a white precipitate formed after 1 minutes. After 5 minutes, the reaction mixture was concentrated, the residue was acidified with excess hydrochloric acid and partitioned between dichloromethane (100 mL) and water (10 mL). The organic layer was dried (MgSO$_4$) and concentrated. The resulting residue was crystallized from ethyl acetate-hexane-tetrahydrofuran to give 0.343 of 4-[2-(2-naphthalenyl)-2-oxoethoxy]-alpha-oxobenzeneacetic acid, mp 167°–170° C.

Analysis Calculated for $C_{20}H_{14}O_5$: C, 71.85; H, 4.22. Found: C, 71.52; H, 4.20.

EXAMPLE 158

Preparation of
4-[(2-quinolinyl)methoxy]-alpha-oxobenzeneacetic acid methyl ester A solution of 4-hydroxy-alpha-oxobenzeneacetic acid methyl ester (0.50 g) and 2-chloromethylquinoline hydrochloride (0.60 g) were suspended in 6 mL of dimethylformamide and 60% sodium hydride (0.224 g) was added. When gas evolution ceased, the bath temperature was raised to 50° C. for 2 hours. The reaction mixture was quenched with 0.1 mL of acetic acid and was diluted with ethyl acetate (75 mL). The mixture was washed with water (2×25 mL) and brine (1×25 mL), dried (MgSO$_4$) and chromatographed over 100 g of silica gel, eluting with dichoromethane-ethyl acetate (50: 1) to give 0.39 g of 4-[(2-quinolinyl)methoxy]-alpha-oxobenzeneacetic acid methyl ester, mp 109°–110° C.

Analysis Calculated for $C_{19}H_{15}NO_4.0.05\ CH_2Cl_2$: C, 70.27; H, 4.67; N, 4.30. Found: C, 70.24; H, 4.57; N, 4.32.

EXAMPLE 159

Preparation of
4-[(2-quinolinyl)methoxy]-alpha-oxo-benzeneacetic acid

A solution of 4-[(2-quinolinyl)methoxy]-alpha-oxobenzeneacetic acid methyl ester (0.34 g) in methanol (2 mL) and tetrahydrofuran (8 mL) was treated with 1N sodium hydroxide (1.1 mL) and a white precipitate formed. After 5 minutes, the reaction mixture was concentrated and the residue was acidified with excess hydrochloric acid. The residue was triturated with water (25 mL) and dichloromethane-tetrahydrofuran (150 mL, 9:1) and the solids were crystallized twice from dimethylsulfoxide-acetonitrile-water to give 0.142 g of 4-[(2-quinolinyl)methoxy]-alpha-oxo-benzeneacetic acid, mp 225°–228° C.

Analysis Calculated for $C_{18}H_{13}NO_4.0.1\ H_2O$: C, 69.92; H, 4.27; N, 4.53. Found: C, 69.75; H, 4.17; N, 4.52.

EXAMPLE 160

Preparation of
4-[[2-(2-naphthalenyloxy)ethyl]oxy]-alpha-oxobenzeneacetamide

A solution of 4-[[2-(2-naphthalenyloxy)ethyl]oxy]-alpha-oxobenzeneacetic acid methyl ester (0.5 g) in methanol (40 mL) and tetrahydrofuran (40 mL) was chilled in an ice bath and saturated with ammonia gas. The cooling bath was removed and the mixture was stirred at room temperature for 4 hours and the solution was evaporated to dryness. Crystallization from tetrahydrofuran-ethyl alcohol provided 0.4 g of 4-[[2-(2- naphthalenyloxy)ethyl]oxy]-alpha-oxobenzeneacetamide as a colorless solid, mp 194°–196° C.

Analysis Calculated for $C_{20}H_{17}NO_4$: C, 71.63; H, 5.11; N, 4.18. Found: C, 71.60; H, 5.14; N, 4.14.

EXAMPLE 161

Preparation of N,N-dimethyl-4-[[2-(2-naphthalenyloxy)ethyl]oxy]-alpha-oxobenzeneacetamide A solution of 4-[[2-(2-naphthalenyloxy)ethyl]oxy]-alpha-oxobenzeneacetic acid methyl ester (0.5 g) in methanol (40 mL) and tetrahydrofuran (40 mL,) was chilled in an ice bath and excess anhydrous gaseous dimethylamine was bubbled into the solution. The cooling bath was removed and the mixture was stirred at room temperature for 6 hours and the mixture was evaporated to dryness. Crystallization from tetrahydrofuran-ethyl alcohol provided 0.5 g of N,N-dimethyl-4-[[2-(2-naphthalenyloxy)ethyl]oxy]-alpha-oxobenzeneacetamide as a colorless solid, mp 170°–172° C.

Analysis Calculated for $C_{22}H_{21}NO_4$: C, 72.71; H, 5.82; N, 3.85. Found: C, 72.67; H, 5.88; N, 3.78.

EXAMPLE 162

Preparation of N-(2-hydroxyethyl)-4-[[2-(2-naphthalenyloxy)ethyl]oxy]-alpha-oxobenzeneacetamide A solution of 4-[[2-(2-naphthalenyloxy)ethyl]oxy]-alpha-oxobenzeneacetic acid methyl ester (0.5 g) in methanol (40 mL) and tetrahydrofuran (10 mL) was treated with ethanolamine (0.094 g) and the mixture was refluxed for 48 hours. The solvents were removed by evaporation and the residue was purified by HPLC (ethyl acetate-methanoltriethylamine; 95:5:2) followed by crystallization from tetrahydrofuran-ethyl alcohol to give 0.29 g of N-(2-hydroxyethyl)-4-[[2-(2-naphthalenyloxy)ethyl]oxy]-alpha-oxobenzeneacetamide as a colorless solid, mp 138°–140° C.

Analysis Calculated for $C_{22}H_{21}NO_5$: C, 69.65; H, 5.58; N, 3.69. Found: C, 69.36; H, 5.52; N, 3.54.

EXAMPLE 163

Preparation of N,N-bis(2-hydroxyethyl)-4-[[2-(2-naphthalenyloxy)ethyl]oxy]-alpha-oxobenzeneacetamide A solution of 4-[[2-(2-naphthalenyloxy)ethyl]oxy]-alpha-oxobenzeneacetic acid methyl ester (0.5 g) in methanol (40 mL) and tetrahydrofuran (10 mL) was treated with diethanolamine (0. 162 g) and the mixture was refluxed for 18 hours. The solvents were removed by evaporation and the residue was crystallized from acetone to give 0.185 g of N,N-bis(2-hydroxyethyl)-4-[[2-(2-naphthalenyloxy)ethyl]oxy]-alpha-oxobenzeneacetamide as a colorless solid, mp 128°–133° C.

Analysis Calculated for $C_{24}H_{25}NO_6$: C, 68.07; H, 5.95; N, 3.31. Found: C, 68.10; H, 5.87; N, 3.28.

EXAMPLE 164

Preparation of N-[2-(dimethylamino)ethyl]-4-[[2-(2-naphthalenyloxy)ethyl]oxy]-alpha-oxobenzeneacetamide A solution of 4-[[2-(2-naphthalenyloxy)ethyl]oxy]-alpha-oxobenzeneacetic acid methyl ester (0.5 g) in methanol (75 mL) was treated with N,N-dimethylethylenediamine (0.2 mL) and the mixture was refluxed for 18 hours. The solvents were removed by evaporation and the residue was purified by HPLC (ethyl acetate-methanol-triethylamine; 95:5:2) followed by crystallization from ethyl acetate-hexane to give 0.28 g of N-[2-(dimethylamino)ethyl]-4-[[2-(2-naphthalenyloxy)ethyl]oxy]-alpha-oxobenzeneacetamide as a colorless solid, mp 102°–104° C.

Analysis Calculated for $C_{24}H_{26}N_2O_4$: C, 70.92; H, 6.45; N, 6.89. Found: C, 71.00; H, 6.45; N, 6.94.

EXAMPLE 165

Preparation of 4-[N-[2-(2-naphthalenyloxy)ethyl]formamido]-alpha-oxobenzeneacetic acid methyl ester A stirred mixture of N-(4-acetylphenyl)formamide (4.9 g) in dimethylformamide (50 mL) under argon was treated with 55% sodium hydride (1.31 g), stireed for 15 minutes and treated with 2-(2-naphthalenyloxy)ethyl methanesulfonate (7.6 g). The mixture was heated at 60° C. overnight and worked upas in Example 20. The material from dichloromethane extraction was purified by HPLC (dichloromethane-ethyl acetate; 20:1 ) and crystallized from dichloromethane-hexane to provide 5.9 g of N-(4-acetylphenyl)-N[2-(2-naphthalenyloxy)ethyl]formamide as a colorless solid, mp 115°–116° C.

Analysis Calculated for $C_{21}H_{19}NO_3$: C, 75.66; H, 5.74; N, 4.20. Found: C, 75.38; H, 5.72; N, 4.16.

A solution of N-(4-acetylphenyl)-N-[2-(2-naphthalenyloxy)ethyl]formamide (1.2 g) in pyridine (10 mL) was treated with selenium dioxide (0.61 g) and heated at 100° C. for five hours. The solution was cooled, diluted with dichloromethane (40 mL), and filtered through celite. The filtrate was chilled in an ice bath and treated with methyl chloroformate (2 mL) and stirred for 15 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-ethyl acetate; 50:1 ) and crystallized from dichloromethane-hexane to provide 0.92 g of 4-[N-[2-(2-naphthalenyloxy)ethyl]formamido]-alpha-oxobenzeneacetic acid methyl ester as a colorless solid, mp 103°–104° C.

Analysis Calculated for $C_{22}H_{19}NO_5$: C, 70.02; H, 5.07; N, 3.71. Found: C, 69.81; H, 4.89; N, 3.50

EXAMPLE 166

Preparation of 4-[N-[2-(2-naphthalenyloxy)ethyl]formamido]-alpha-oxobenzeneacetic acid A solution of 4-[N-[2-(2-naphthalenyloxy)ethyl]formamido]-alpha-oxobenzeneacetic acid methyl ester (0.5 g) in warm methanol (5 mL) and tetrahydrofuran (5 mL) was treated with 1N sodium hydroxide (2 mL) and the mixture was concentrated to remove the organic solvents. The residue was acidified with excess hydrochloric acid and extracted with dichloromethane. The organic layer was washed with water, dried ($Na_2SO_4$), filtered and evaporated. The residue was crystallized acetone-hexane to give 0.32 g of 4-[N-[2-(2-naphthalenyloxy)ethyl]formamido]-alpha-oxobenzeneacetic acid, mp 155°–156° C. as a yellow solid.

Analysis Calculated for $C_{21}H_{17}NO_5$: C, 69.41; H, 4.72; N, 3.85. Found: C, 69.25; H, 4.61; N, 3.80.

EXAMPLE 167

Preparation of
4-[[2-(2-naphthalenyloxy)ethyl]amino]-alpha-oxobenzeneacetic acid methyl ester A solution of 4-[N-[2-(2-naphthalenyloxy)ethyl]formamido]-alpha-oxobenzeneacetic acid methyl ester (1.13 g) in tetrahydrofuran (30 mL) and 1N hydrochloric acid (9 mL) was refluxed for four hours and cooled. The mixture was diluted with dichloromethane (100 mL), washed with saturated aqueous sodium bicarbonate solution and water, dried ($Na_2SO_4$), filtered and evaporated to give 1 g of crude product. Crystallization from acetone provided 0.8 g of purified 4-[N-[2-(2-naphthalenyloxy)ethyl]formamido]-alpha-oxobenzeneacetic acid methyl ester, mp 177°–179° C., as a yellow solid.

Analysis Calculated for $C_{21}H_{19}NO_4$: C, 72.19; H, 5.48; N, 4.01. Found: C, 71.95; H, 5.32; N, 3.90.

EXAMPLE 168

Preparation of
4-[[2-(2-naphthalenyloxy)ethyl]amino]-alpha-oxobenzeneacetic acid A solution of 4-[N-[2-(2-naphthalenyloxy)ethyl]formamido]-alpha-oxobenzeneacetic acid methyl ester (0.5 g) in hot methanol (5 mL) and tetrahydrofuran (10 mL) was treated with 1N sodium hydroxide (3.0 mL) and the mixture was concentrated to remove the organic solvents. The residue, in water, was treated with 2N hydrochloric acid and the mixture was chilled, filtered, and washed with water. The solids were dissolved in a mixture of tetrahydrofuran and dichloromethane, dried ($Na_2SO_4$), filtered, and evaporated to give crude product. Crystallization from acetone-hexane provided 0.4 g of purified 4-[N-[2-(2-naphthalenyloxy)ethyl]formamido]-alpha-oxobenzeneacetic acid as a yellow solid, mp 172° C. with decomposition.

Analysis Calculated for $C_{20}H_{17}NO_4$: C, 71.63; H, 5.11; N, 4.18. Found: C, 71.50; H, 4.98; N, 4.17.

EXAMPLE 169

Preparation of
rac.-4-[[2-(2-naphthalenyloxy)ethyl]oxy]-alpha-oxobenzeneacetic acid (2,2-dimethyl-1,3-dioxolan-4-yl)methyl ester Oxalyl chloride (1 mL) was added dropwise with stirring to a chilled (0° C.) solution of 2-[[2-(2-naphthalenyloxy)ethyl]oxy]-alpha-oxobenzeneacetic acid (1 g) in dichloromethane (20 mL) containing a catalytic amount of dimethylformamide. After the addition was complete, the cooling bath was removed and the mixture was stirred at room temperature for 1 hour. The solvent was then removed in vacuo to give the crude acid chloride.

A solution of the above acid chloride in dichloromethane (15 mL) was added dropwise with stirring to a chilled (0° C.) solution of solketal (0.529g) and triethylamine (0.7 mL) in dichloromethane (20 mL) and the reaction was stirred cold for one hour. The mixture was washed with water, dried ($Na_2SO_4$), filtered and evaporated to give crude product. The material was purified by HPLC (dichloromethane-hexane-ethyl acetate; 10:10:1) and the resulting solid was crystallized from dichloromethane-hexane to yield 1 g of colorless rac.-4-[[2-(2-naphthalenyloxy)ethyl]oxy]-alpha-oxobenzeneacetic acid (2,2-dimethyl-1,3-dioxolan-4-yl)methyl ester, mp 128°–129° C.

Analysis Calculated for $C_{26}H_{26}O_7$: C, 69.32; H, 5.82. Found: C, 69.03; H, 5.73.

EXAMPLE 170

Preparation of
4-[[2-(2-naphthalenyloxy)ethyl]sulfonyl]-alpha-oxobenzeneacetic acid methyl ester A solution of rac.-4-[[2-(2-naphthalenyloxy)ethyl]sulfinyl]-alpha-oxobenzeneacetic acid methyl ester (1 g) in dichloromethane (50 mL) was treated with 85% metachloroperbenzoic acid (0.81 g) and stirred at room temperature for one hour. The mixture was washed with saturated sodium bicarbonate solution, dried ($Na_2SO_4$), filtered, passed through silica gel (5 g) and the product eluted with dichloromethane. Crysallization from dichloromethane-hexane gave 0.61 g of 4-[[2-(2-naphthalenyloxy)ethyl]sulfonyl]-alpha-oxobenzeneacetic acid methyl ester, mp 110°–111° C.

Analysis Calculated for $C_{21}H_{18}O_6S$: C, 63.31; H, 4.55; S, 8.05, Found: C, 63.10; H, 4.44; S, 8.11.

EXAMPLE 171

Preparation of
4-[[2-(2-naphthalenyloxy)ethyl]sulfonyl]-alpha-oxobenzeneacetic acid A solution of 4-[[2-(2-naphthalenyloxy)ethyl]sulfonyl]-alpha-oxobenzeneacetic acid methyl ester (0.76 g) in warm methanol (5 mL) and tetrahydrofuran (5 mL) was treated with 1N sodium hydroxide (2.1 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from diethyl ether-hexane provided 0.39 g of purified 4-[[2-(2-naphthalenyloxy)ethyl]sulfonyl]-alpha-oxobenzeneacetic acid as a colorless solid, mp 135°–136° C.

Analysis Calculated for $C_{20}H_{16}O_6S$: C, 62.49; H, 4.20; S, 8.34. Found: C, 62.18; H, 4.25; S, 8.26.

EXAMPLE 172

Preparation of
4-[[2-(cyclooctyloxy)ethyl]thio]-alpha-oxobenzeneacetic acid methyl ester.

A stirred mixture of 1-(4-mercaptophenyl)ethanone (0.76 g) in dimethylformamide (10 mL) under argon was treated with 55% sodium hydride (0.218 g), stirred for 20 minutes and treated with 2-(cyclooctyloxy)ethyl methanesulfonate (1.25 g). The mixture was heated at 60° C. overnight, cooled, diluted with water, extracted twice with dichloromethane, and the organic layers were washed with water. The combined organic layers were dried ($Na_2SO_4$), filtered, and evaporated to give crude material which was purified by HPLC (dichloromethane-hexane-ethyl acetate; 48:48:4) to provide 1.08 g of 1-[4-[[2-(cyclooctyloxy)ethyl]thio]phenyl]ethanone as a colorless oil.

A mixture of 1-[4-[[2-(cyclooctyloxy)ethyl]thio]phenyl]ethanone (1.08 g) in pyridine (10 mL) was treated with selenium dioxide (0.78 g) and heated at 100° C. overnight under argon. The mixture was cooled, diluted with dichloromethane (50 mL), and filtered through celite. The filtrate was chilled in an ice bath and treated with methyl chloroformate (3 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane) to provide 1.04 g of 4-[[2-(cyclooctyloxy)ethyl]thio]-alpha-oxobenzeneacetic acid methyl ester as a pale yellow oil.

Analysis Calculated for $C_{19}H_{26}O_4S$: C, 65.11; H, 7.48; S, 9.15. Found: C, 65.01; H, 7.48; S, 8.91.

EXAMPLE 173

Preparation of 4-[[2-(cyclooctyloxy)ethyl]thio]-alpha-oxobenzeneacetic acid

A solution of 4-[[2-(cyclooctyloxy)ethyl]thio]-alpha-oxobenzeneacetic acid methyl ester (0.96 g) in warm methanol (10 mL) and tetrahydrofuran (10 mL) was treated with 1N sodium hydroxide (3.5 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from diethyl ether-hexane provided 0.86 g of purified 4-[[2-(cyclooctyloxy)ethyl]thio]-alpha-oxobenzeneacetic acid as a yellow solid, mp 84°-85° C.

Analysis Calculated for $C_{18}H_{24}O_4S$: C, 64.26; H, 7.19; S, 9.53, Found: C, 64.30; H, 7.23; S, 9.41.

EXAMPLE 174

Preparation of 4-[[2-[2-[(2,2-dimethyl-1-oxobutoxy)methyl]-6methylphenoxy]ethyl]thio]-alpha-oxobenzeneacetic acid methyl ester A stirred mixture of 1-(4-mercaptophenyl)ethanone (0.9 g) in dimethylformamide (10 mL) under argon was treated with 55% sodium hydride (0.262 g), stirred for 10 minutes and treated with 2-[[6-methyl-2-(2,2-dimethyl-1-oxobutoxy)methyl]phenoxy]ethyl methanesulfonate (2.15 g). The mixture was heated at 60° C. for one hour, cooled, acidified with 3 drops of glacial acetic acid and the volatiles removed by evaporation. The residue was diluted with water, extracted twice with dichloromethane, and the organic layers were washed with water. The combined organic layers were dried ($Na_2SO_4$), filtered, and evaporated to give crude material which was purified by HPLC (dichloromethane-hexane-diethyl ether); 48:48:4) to provide 1.97 g of 2,2-dimethylbutanoic acid [2-[2-[(4-acetylphenyl)thio]ethoxy]-3-methylphenyl]methyl ester as a yellow oil.

Analysis Calculated for $C_{24}H_{30}O_4S$: C, 69.54; H, 7.29; S, 7.73. Found: C, 69.42; H, 7.36; S, 7.86.

A mixture of 2,2-dimethylbutanoic acid [2-[2-[(4-acetylphenyl)thio]ethoxy]-3methylphenyl]methyl ester (1.97 g) in pyridine (10 mL) was treated with selenium dioxide (1.05 g) and heated at 100° C. overnight under argon. The mixture was cooled, diluted with dichloromethane (50 mL), and filtered through celite. The filtrate was chilled in an ice bath and treated with methyl chloroformate (3 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane-diethyl ether, 49:49:2) to provide 2.07 g of 4-[[2-[2-[(2,2-dimethyl-1-oxobutoxy)methyl]-6-methylphenoxy]ethyl]thio]-alpha-oxobenzeneacetic acid methyl ester as a pale yellow oil.

Analysis Calculated for $C_{25}H_{30}O_6S$: C, 65.48; H, 6.59; S, 6.99, Found: C, 65.75; H, 6.68; S, 7.13.

EXAMPLE 175

Preparation of 4-[[2-[2-[(2,2-dimethyl-1-oxobutoxy)methyl]-6-methylphenoxy]ethyl]thio]-alpha-oxobenzeneacetic acid.

A solution of 4-[[2-[2-[(2,2-dimethyl-1-oxobutoxy)methyl]-6-methylphenoxy]ethyl]thio]-alpha-oxobenzeneacetic acid methyl ester (1.9 g) in warm methanol (10 mL) and tetrahydrofuran (5 mL) was treated with 1N sodium hydroxide (5 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Purification was accomplished by chromatography on 60 g of silica gel using dichloromethane-diethyl ether-formic acid (50:50:1) to elute impurities followed by elution with diethyl ether-formic acid (99:1) to recover 1.1 g of pure 4-[[2-[2-[(2,2-dimethyl-1-oxobutoxy) methyl]-6-methylphenoxy]ethyl]thio]-alpha-oxobenzeneacetic acid as a yellow oil.

Analysis Calculated for $C_{24}H_{28}O_6S$: C, 64.84; H, 6.35; S, 7.21. Found: C, 64.83; H, 6.34; S, 7.28.

EXAMPLE 176

Preparation of 4-[[[2-(2-naphthalenyloxy)ethyl]amino]carbonyl]-alpha-oxobenzeneacetic acid methyl ester A stirred mixture of 2-(2-naphthalenyloxy)ethanamine (4.9 g) in dichloromethane (25 mL) and triethylamine (5 mL) was chilled to 0° C. and treated with the acid chloride prepared from 4-acetyl benzoic acid (4.3 g) and then the mixture was stirred at room temperature for 10 minutes. The mixture was diluted with water and acidified with excess 2N hydrochloric acid, extracted with dichloromethane and the organic layer was washed in turn with sodium bicarbonate solution and saturated sodium chloride solution. The organic layer was dried ($Na_2SO_4$), filtered, and evaporated to give crude material which was purified by HPLC (ethyl acetate-dichloromethane; 1:9) and crystallized from ethyl acetate to provide 4.7 g of 4-acetyl-N-[2-(2-naphthalenyloxy)ethyl]benzamide as a colorless solid, mp 131°-132° C.

Analysis Calculated for $C_{21}H_{19}NO_3$: C, 75.66; H, 5.74; N, 4.20. Found: C, 75.41; H, 5.75; N, 4.09.

A mixture of 4-acetyl-N-[2-(2-naphthalenyloxy)ethyl]benzamide (1.2 g) in pyridine (10 mL) was treated with selenium dioxide (0.61 g) and heated at 100° C. for 5 hours under argon. The mixture was cooled, diluted with dichloromethane (30 ml), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried (Na$_2$SO$_4$), filtered and evaporated. The crude material was purified by HPLC (dichloromethane-ethyl acetate; 20:1) and crystallized from dichloromethane-hexane to provide 0.815 g of 4-[[[2-(2naphthalenyloxy)ethyl]amino]carbonyl]-alpha-oxobenzeneacetic acid methyl ester as a colorless solid, mp 114°–115° C.

Analysis Calculated for C$_{22}$H$_{19}$NO$_5$: C, 70.02; H, 5.07; N, 3.71. Found: C, 70.09; H, 4.98; N, 3.51.

EXAMPLE 177

Preparation of 4-[[[2-(2-naphthalenyloxy)ethyl]amino]carbonyl]-alpha-oxobenzeneacetic acid.

A solution of 4-[[[2-(2-naphthalenyloxy)ethyl]amino]carbonyl]-alpha-oxobenzeneacetic acid methyl ester (0.35 g) in methanol (5 mL) and tetrahydrofuran (5 mL) was treated with 1N sodium hydroxide (1 mL) and after 5 minutes the mixture was concentrated to remove the organic solvents. The residue was acidified with excess hydrochloric acid and extracted with dichloromethane containing a little tetrahydrofuran. The organic layer was washed with water, dried (Na$_2$SO$_4$), filtered and evaporated to give crude product. Crystallization from acetone-hexane provided 0.275 g of purified 4-[[[2-(2-naphthalenyloxy)ethyl]amino]carbonyl]-alpha-oxobenzeneacetic acid as a colorless solid, mp 173°–175° C.

Analysis Calculated for C$_{21}$H$_{17}$NO$_5$: C, 69.41; H, 4.72; N, 3.85. Found: C, 69.35; H, 4.56; N, 3.64.

EXAMPLE 178

Preparation of 4-[2-(2-naphthalenyloxy)ethoxy]-3-nitro-alpha-oxobenzeneacetic acid methyl ester A stirred mixture of 4-hydroxy-3-nitroacetophonone (2 g) in dimethylformamide (30 mL) under argon was treated with 55% sodium hydride (0.48 g), stirred for 30 minutes and treated with 2-(2-naphthalenyloxy)ethyl methanesulfonate (2.75 g). The mixture was heated at 60° C. for 72 hours and the dimethylformamide evaporated. The residue was mixed with water and excess sodium hydroxide solution, the product was extracted twice with dichloromethane, and the organic layers were washed with water. The combined organic layers were dried (Na$_2$SO$_4$), filtered, and evaporated to give crude material which was purified by HPLC (dichloromethane-hexane; 9:1) and crystallized from dichloromethane-diethyl ether to provide 0.9 g of 1-[4-[2-(2-naphthalenyloxy)ethoxy]-3-nitrophenyl]ethanone as a yellow solid, mp 158°–160° C.

Analysis Calculated for C$_{20}$H$_{17}$NO$_5$: C, 68.37; H, 4.88; N, 3.99. Found: C, 68.40; H, 4.90; N, 4.21.

A mixture of 1-[4-[2-(2-naphthalenyloxy)ethoxy]-3-nitrophenyl]ethanone (0.875 g) in pyridine (20 mL) was treated with selenium dioxide (0.416 g) and heated at 100° C. overnight under argon. The mixture was cooled, diluted with dichloromethane (50 mL), and filtered through celite. The tiltrate was chilled in an ice bath and treated with methyl chloroformate (2 mL) and stirred for 10 minutes. The resulting mixture was washed with successive portions of 1N hydrochloric acid (twice) and saturated aqueous sodium chloride solution. The organic extracts were dried (Na$_2$SO$_4$), filtered and evaporated. The crude material was purified by HPLC (dichloromethane-hexane; 9:1) and crystallized from dichloromethane-hexane to provide 0.65 g of 4-[2-(2naphthalenyloxy)ethoxy]-3-nitro-alpha-oxobenzeneacetic acid methyl ester as a yellow solid, mp 127°–129° C.

Analysis Calculated for C$_{21}$H$_{17}$NO$_7$: C, 63.80; H, 4.33; N, 3.54. Found: C, 63.53; H, 4.30; N, 3.43.

EXAMPLE 179

Preparation of 4-[2-(2=naphthalenyloxy)ethoxy]-3-nitro-alpha-oxobenzeneacetic acid.

A solution of 4-[2-(2-naphthalenyloxy)ethoxy]-3-nitro-alpha-oxobenzeneacetic acid methyl ester (0.55 g) in warm methanol (10 mL) and tetrahydrofuran (10 mL) was treated with 1N sodium hydroxide (2 mL) and after 5 minutes the mixture was diluted with water and concentrated to remove the organic solvents. The residue was acidified with excess hydrochloric acid and extracted with dichloromethane containing a little tetrahydrofuran. The organic layer was washed with water, dried (Na$_2$SO$_4$), filtered and evaporated to give crude product. Crystallization from acetone-hexane provided 0.42 g of purified 4-[2-(2-naphthalenyloxy)ethoxy]-3-nitro-alpha-oxobenzeneacetic acid as a yellow solid, mp 164° C. with decomposition.

Analysis Calculated for C$_{20}$H$_{15}$NO$_7$: C, 62.99; H, 3.96; N, 3.67. Found: C, 62.94; H, 4.06; N, 3.46.

EXAMPLE 180

Preparation of 3-methyl-4-[2-(2-naphthalenyloxy)ethoxy]-alpha-oxobenzeneacetic acid methyl ester A stirred mixture of 4-hydroxy-3-methylacetophonone (2 g) in dimethylformamide (30 mL) under argon was treated with 55% sodium hydride (0.58 g), stirred for 30 minutes and treated with 2-(2-naphthalenyloxy)ethyl methanesulfonate (3.65 g). The mixture was heated at 60° C. for 2 hours, cooled, diluted with water and filtered. The damp solids were mixed with water and excess sodium hydroxide solution, the product was extracted twice with dichloromethane, and the organic layers were washed with water. The combined organic layers were dried (Na$_2$SO$_4$), filtered, and evaporated to give crude material which was purified by HPLC (dichloromethane-hexane; 9:1) and crystallized from dichloromethane-diethyl ether to provide 3.2 g of 1-[3-methyl-4-[2(2-naphthalenyloxy)ethoxy]phenyl]ethanone as a colorless solid, mp 129°–131° C.

Analysis Calculated for C$_{21}$H$_{20}$O$_3$: C, 78.73; H, 6.29. Found: C, 78.91; H, 6.16.

A mixture of 1-[3-methyl-4-[2-(2-naphthalenyloxy)ethoxy]phenyl]ethanone (1 g) in pyridine (20 mL) was treated with selenium dioxide (0.522 g) and heated at 100° C. overnight under argon. The mixture was cooled, diluted with dichloromethane (50 mL), and filtered through celite. The tiltrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried (Na$_2$SO$_4$), filtered and evaporated. The crude material was purified by HPLC (dichloromethane-hexane; 9:1) and crystallized from dichloromethane-hexane to provide 0.8 g of 3-methyl-4-[2-(2naphthalenyloxy)ethoxy]-alpha-oxobenzeneacetic acid methyl ester as a colorless solid, mp 118°–119° C.

Analysis Calculated for C$_{22}$H$_{20}$O$_5$: C, 72.51; H, 5.53. Found: C, 72.56; H, 5.44.

EXAMPLE 181

Preparation of
3-methyl-4-[2-(2-naphthalenyloxy)ethoxy]-alpha-oxobenzeneacetic acid A solution of 3-methyl-4-[2-(2-naphthalenyloxy)ethoxy]-alpha-oxobenzeneacetic acid methyl ester (0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from acetone-hexane provided 0.5 g of purified 3-methyl-4-[2-(2-naphthalenyloxy)ethoxy]-alpha-oxobenzeneacetic acid as a colorless solid, mp 167°–169° C.

Analysis Calculated for $C_{21}H_{18}O_5$: C, 71.99; H, 5.18. Found: C, 72.04; H, 5.21.

EXAMPLE 182

Preparation of
2-methyl-4-[2=(2-naphthalenyloxy)ethoxy]-alpha-oxobenzeneacetic acid methyl ester A stirred mixture of 4-hydroxy-2-methylacetophenone (2 g) in dimethylformamide (30 mL) under argon was treated with 55% sodium hydride (0.58 g), stirred for 30 minutes and treated with 2-(2-naphthalenyloxy)ethyl methanesulfonate (3.65 g). The mixture was heated at 60° C. for 2 hours, cooled, diluted with water and filtered. The damp solids were mixed with water and excess sodium hydroxide solution, the product was extracted twice with dichloromethane, and the organic layers were washed with water. The combined organic layers were dried ($Na_2SO_4$), filtered, and evaporated to give crude material which was crystallized from dichloromethane-diethyl ether to provide 3.5 g of 1-[2-methyl-4-[2-(2-naphthalenyloxy)ethoxy]phenyl]ethanone as a colorless solid, mp 128°–130° C.

Analysis Calculated for $C_{21}H_2O_3$: C, 78.73; H, 6.29. Found: C, 78.81; H, 6.25.

A mixture of 1-[2-methyl-4-[2-(2-naphthalenyloxy)ethoxy]phenyl]ethanone (1 g) in pyridine (20 mL) was treated with selenium dioxide (0.522 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 9:1) and crystallized from dichloromethane-hexane to provide 0.8 g of 2-methyl-4-[2-(2-naphthalenyloxy)ethoxy]-alpha-oxobenzeneacetic acid methyl ester as a colorless solid, mp 118°–120° C.

Analysis Calculated for $C_{22}H_{20}O_5$: C, 72.51; H, 5.53. Found: C, 72.72; H, 5.57.

EXAMPLE 183

Preparation of
2-methyl-4-[2-(2-naphthalenyloxy)ethoxy]-alpha-oxobenzeneacetic acid (4:1) hydrate A solution of 2-methyl-4-[2-(2-naphthalenyloxy)ethoxy]-alpha-oxobenzeneacetic acid methyl ester (0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.52 g of purified 2-methyl-4-[2-(2-naphthalenyloxy)ethoxy]-alpha-oxobenzeneacetic acid (4:1) hydrate as a colorless solid, mp 129°–131° C.

Analysis Calculated for $C_{21}H_{18}O_5.4:1\ H_2O$: C, 71.08; H, 5.25; H20, 1.27. Found: C, 71,17; H, 5.21; H20, 1.15.

EXAMPLE 184

Preparation of
3=chloro-4-[2-(2-naphthalenyloxy)ethoxy]-alpha-oxobenzeneacetic acid methyl ester.

A stirred mixture of 3-chloro-4-hydroxyacetophenone (2 g) in dimethylformamide (30 mL) under argon was treated with 55% sodium hydride (0.524 g), stirred for 30 minutes and treated with 2-(2-naphthalenyloxy)ethyl methanesulfonate (3 g). The mixture was heated at 60° C. overnight, cooled, diluted with water and filtered. The damp solids were mixed with water and excess sodium hydroxide solution, the product was extracted twice with dichloromethane, and the organic layers were washed with water. The combined organic layers were dried ($Na_2SO_4$), filtered, and evaporated to give crude material which was crystallized from dichloromethane-diethyl ether to provide 2.9 g of 1-[3-chloro-4-[2-(2-naphthalenyloxy)ethoxy]phenyl]ethanone as a colorless solid, mp 164°–166° C.

Analysis Calculated for $C_{20}H_{17}ClO_3$: C, 70.49; H, 5.03; $ClO_{10.40}$. Found: C, 70.43; H, 5.04; Cl, 10.64.

A mixture of 1-[3-chloro-4-[2-(2-naphthalenyloxy)ethoxy]phenyl]ethanone (1 g) in pyridine (20 mL) was treated with selenium dioxide (0.488 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 9:1) and crystallized from dichloromethane-hexane to provide 0.75 g of 3-chloro-4-[2-(2-naphthalenyloxy)ethoxy]-alpha-oxobenzeneacetic acid methyl ester as a colorless solid, mp 133°–134° C.

Analysis Calculated for $C_{21}H_{17}ClO_5$: C, 65.55; H, 4.45; Cl, 9.21.
Found: C, 65.42; H, 4.39; Cl, 9.05.

EXAMPLE 185

Preparation of 3-chloro-4-[2-(2-naphthalenyloxy)ethoxy]-alpha-oxobenzeneacetic acid A solution of 3-chloro-4-[2-(2-naphthalenyloxy)ethoxy]-alpha-oxobenzeneacetic acid methyl ester (0.7 g) in warm methanol (10 mL) and tetrahydrofuran (10 mL) was treated with 1N sodium hydroxide (2.5 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from acetone-hexane provided 0.63 g of purified 3-chloro-4-[2-(2-naphthalenyloxy)ethoxy]-alpha-oxobenzeneacetic acid as a colorless solid, mp 167°–168° C.

Analysis Calculated for $C_{20}H_{15}ClO_5$: C, 64.79; H, 4.08; Cl, 9.56.

Found: C, 64.78; H, 3.98; Cl, 9.79.

EXAMPLE 186

Preparation of 2-chloro-4-[2-(2-naphthalenyloxy)ethoxy]-alpha-oxobenzeneacetic acid methyl ester A stirred mixture of 2-chloro-4-hydroxyacetophonone (2 g) in dimethylformamide (30 mL) under argon was treated with 55% sodium hydride (0.524 g), stirred for 30 minutes and treated with 2-(2-naphthalenyloxy)ethyl methanesulfonate (3 g). The mixture was heated at 60° C. overnight, cooled, diluted with water and filtered. The damp solids were mixed with water and excess sodium hydroxide solution, the product was extracted twice with dichloromethane, and the organic layers were washed with water. The combined organic layers were dried ($Na_2SO_4$), filtered, and evaporated to give crude material which was crystallized from dichloromethane-diethyl ether to provide 3.2 g of 1-[2-chloro-4-[2-(2-naphthalenyloxy)ethoxy]phenyl]ethanone as a colorless solid, mp 119°–120° C.

Analysis Calculated for $C_{20}H_{17}ClO_3$: C, 70.49; H, 5.03; Cl, 10.40.

Found: C, 70.28; H, 5.02; Cl, 10.45.

A mixture of 1-[2-chloro-4-[2-(2-naphthalenyloxy)ethoxy]phenyl]ethanone (1 g) in pyridine (20 mL) was treated with selenium dioxide (0.482 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 9:1) and crystallized from dichloromethane-hexane to provide 0.7 g of 2-chloro-4-[2-(2-naphthalenyloxy)ethoxy]-alpha-oxobenzeneacetic acid methyl ester as a colorless solid, mp 123°–125° C.

Analysis Calculated for $C_{21}H_{17}ClO_5$: C, 65.55; H, 4.45; Cl, 9.21.

Found: C, 65.48; H, 4.45; Cl, 9.51.

EXAMPLE 187

Preparation of 2-chloro-4-[2-(2-naphthalenyloxy)ethoxy]-alpha-oxobenzeneacetic acid A solution of 2-chloro-4-[2-(2-naphthalenyloxy)ethoxy]-alpha-oxobenzeneacetic acid methyl ester (0.56 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from acetone-hexane provided 0.435 g of purified 2-chloro-4-[2-(2-naphthalenyloxy)ethoxy]-alpha-oxobenzeneacetic acid as a colorless solid, mp 152°–153° C.

Analysis Calculated for $C_{20}H_{15}ClO_5$: C, 64.79; H, 4.08; Cl, 9.56.

Found: C, 64.53; H, 4.04; Cl, 9.86.

EXAMPLE 188

Preparation of 3,5-dichloro-4-[2-(2-naphthalenyloxy)ethoxy]-alpha-oxobenzeneacetic acid methyl ester A stirred mixture of 3,5-dichloro-4-hydroxyacetophonone (1.7 g) in dimethylformamide (30 mL) under argon was treated with 55% sodium hydride (0.362 g), stirred for 30 minutes and treated with 2-(2-naphthalenyloxy)ethyl methanesulfonate (2 g). The mixture was heated at 75° C. for 48 hours and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated to give crude material which was purified by HPLC (dichloromethane-hexane; 3:1) and crystallized from dichloromethane-diethyl ether to provide 2.4 g of 1-[3,5-dichloro-4-[2-(2-naphthalenyloxy)ethoxy]phenyl]ethanone as a colorless solid, mp 110°–111° C.

Analysis Calculated for $C_{20}H_{16}Cl_2O_3$: C, 64.02; H, 4.30; Cl, 18.90.

Found: C, 63.77; H, 4.32; Cl, 18.63.

A mixture of 1-[3,5-dichloro-4-[2-(2-naphthalenyloxy)ethoxy]phenyl]ethanone (1.5 g) in pyridine (25 mL) was treated with selenium dioxide (0.665 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 3:1) and crystallized from dichloromethane-hexane to provide 0.9 g of 3,5-dichloro-4-[2-(2-naphthalenyloxy)ethoxy]-alpha-oxobenzeneacetic acid methyl ester as a colorless solid, mp 120°–121° C.

Analysis Calculated for $C_{21}H_{16}Cl_2O_5$: C, 60.16; H, 3.85; Cl, 16.91.

Found: C, 60.45; H, 3.81; Cl, 17.18.

EXAMPLE 189

Preparation of
3,5-dichloro-4-[2-(2-naphthalenyloxy)ethoxy]-alpha-oxobenzeneacetic acid (6:1) molar benzene solvate A solution of 3,5-dichloro-4-[2-(2-naphthalenyloxy)ethoxy]-alpha-oxobenzeneacetic acid methyl ester (0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from benzene-hexane provided 0.575 g of purified 3,5-dichloro-4-[2-(2-naphthalenyloxy)ethoxy]-alpha-oxobenzeneacetic acid (6:1) molar benzene solvate as a colorless solid, mp 108°–110° C.

Analysis Calculated for $C_{20}H_{14}Cl_2O_5 \cdot 6{:}1\ C_6H_6$: C, 60.31; H, 3.61; Cl, 16.95.

Found: C, 60.62; H, 3.49; Cl, 17.25.

EXAMPLE 190

Preparation of
2,6-dichloro-4-[2-(2-naphthalenyloxy)ethoxy]-alpha-oxobenzeneacetic acid methyl ester A stirred mixture of 4-bromo-3,5-dichlorophenol (1.9 g) in dimethylformamide (20 mL) under argon was treated with 55% sodium hydride (0.345 g), stirred for 30 minutes and treated with 2-(2-naphthalenyloxy)ethyl methanesulfonate (2.1 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, evaporated and crystallized from dichloromethane-diethyl ether to provide 3.3 g of 2-[2-(4-bromo-3,5-dichlorophenoxy)ethoxy]naphthalene as a colorless solid, mp 140°–142° C.

Analysis Calculated for $C_{18}H_{13}BrCl_2O_2$: C, 52.46; H, 3.18; Br, 19.39; Cl, 17.21.

Found: C, 52.40; H, 3.08; Br, 19.09; Cl, 16.95.

A mixture of 2-[2-(4-bromo-3,5-dichlorophenoxy)ethoxy]naphthalene (3.28 g) in dimethylformamide (10 mL) and cuprous cyanide (0.833 g) was heated under argon at 155° C. for four hours. The cooled mixture was diluted with aqueous 10% sodium cyanide solution (100 mL) and extracted twice with dichloromethane. The organic solutions were washed in turn with aqueous 10% sodium cyanide solution and water, dried ($Na_2SO_4$), filtered and evaporated to give 2.2 g of crude 2,6-dichloro-4-[2-(2-naphthalenyloxy)ethoxy]benzonitrile. A portion crystallized from dichloromethanediethyl ether provide pure colorless material, mp 156°–158° C.

Analysis Calculated for $C_{19}H_{13}Cl_2NO_2$: C, 63.71; H, 3.66; N, 3.91; Cl, 19.79.

Found: C, 63.46; H, 3.71; N, 3.88; Cl, 19.61.

Methyl magnesium bromide was prepared in the usual way from magnesium metal (0.634 g) and methyl iodide (1.6 mL) in diethyl ether. Most of the diethyl ether was removed by distillation prior to the addition of a solution of 2,6-dichloro-4-[2-(2-naphthalenyloxy)ethoxy]benzonitrile (3.1 g) in benzene (25 mL). Distillation was continued to remove all of the diethyl ether and the resulting mixture was refluxed at 80° C. for 5 hours and allowed to stand overnight at room temperature. An aqueous solution of 2N hydrochloric acid (20 mL,) was added and the benzene was removed by distillation and the aqueous mixture was boiled at 100° C. for 30 minutes, cooled and diluted with water. The crude product was extracted with dichloromethane (twice), washed in turn with dilute hydrochloric acid, dilute aqueous sodium bicarbonate solution, dried ($Na_2SO_4$), filtered and evaporated. The crude material was purified by HPLC (dichloromethane-diethyl ether; 20:1) and crystallized from dichloromethanediethyl ether to give 1.85 g of 1-[2,6-dichloro-4-[2-(2-naphthalenyloxy)ethoxy]phenyl]ethanone as a colorless solid, mp 127°–129° C.

Analysis Calculated for $C_{20}H_{16}Cl_2O_3$: C, 64.02; H, 4.30; Cl, 18.90.

Found: C, 63.72; H, 4.38; Cl, 18.82.

A mixture of 1-[2,6-dichloro-4-[2-(2-naphthalenyloxy)ethoxy]phenyl]ethanone (1.5 g) in pyridine (25 mL) was treated with selenium dioxide (0.665 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 3:1) and crystallized from dichloromethane-hexane to provide 1 g of 2,6-dichloro-4-[2-(2-naphthalenyloxy)ethoxy]-alpha-oxobenzeneacetic acid methyl ester as a colorless solid, mp 142°–144° C.

Analysis Calculated for $C_{21}H_{16}Cl_2O_5$: C, 60.16; H, 3.85; Cl, 16.91.

Found: C, 59.99; H, 3.81; Cl, 16.73.

EXAMPLE 191

Preparation of
2,6-dichloro-4-[2-(2-naphthalenyloxy)ethoxy]-alpha-oxobenzeneacetic acid A solution of 2,6-dichloro-4-[2-(2-naphthalenyloxy)ethoxy]-alpha-oxobenzeneacetic acid methyl ester(0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from acetone-hexane provided 0.53 g of purified 2,6-dichloro-4-[2-(2-naphthalenyloxy)ethoxy]-alpha-oxobenzeneacetic acid as a colorless solid, mp 155°–156° C.

Analysis Calculated for $C_{20}H_{14}Cl_2O_5$: C, 59.28; H, 3.48; Cl, 17.50.

Found: C, 59.94; H, 3.41; Cl, 17.22.

EXAMPLE 192

Preparation of
3,5-dimethoxy-4-[2-(2-naphthalenyloxy)ethoxy]-alpha-oxobenzeneacetic acid methyl ester A stirred mixture of 3,5-dimethoxy-4-hydroxyacetophonone (2 g) in dimethylformamide (30 mL) under argon was treated with 55% sodium hydride (0.445 g), stirred for 30 minutes and treated with 2-(2-naphthalenyloxy)ethyl methanesulfonate (2.7 g). The mixture was heated at 80° C. for 48 hours and evaporated to dryness. The residue was mixed with water and excess sodium hydroxide solution, the product was extracted twice with dichloromethane, and the organic layers were washed with water. The combined organic layers were dried (Na$_2$SO$_4$), filtered, and evaporated to give crude material which was purified by HPLC (dichloromethane-diethyl ether; 49:1) and crystallized from dichloromethane-diethyl ether to provide 2.1 g of 1-[3,5-dimethoxy-4-[2-(2-naphthalenyloxy)ethoxy]phenyl]ethanone as a colorless solid, mp 76°–77° C.

Analysis Calculated for C$_{22}$H$_{22}$O$_5$: C, 72.12; H, 6.05. Found: C, 72.09; H, 6.10.

A mixture of 1-[3,5-dimethoxy-4-[2-(2-naphthalenyloxy)ethoxy]phenyl]ethanone (1.5 g) in pyridine (25 mL) was treated with selenium dioxide (0.682 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried (Na$_2$SO$_4$), filtered and evaporated. The crude material was purified by HPLC (dichloromethane-hexane-diethyl ether, 75:25:2) and crystallized from diethyl ether to provide 1 g of 3,5-dimethoxy-4-[2-(2-naphthalenyloxy)ethoxy]-alpha-oxobenzeneacetic acid methyl ester as a pale yellow solid, mp 69°–71° C.

Analysis Calculated for C$_{23}$H$_{22}$O$_7$: C, 67.31; H, 5.40. Found: C, 67.17; H, 5.45.

EXAMPLE 193

Preparation of
3,5-dimethoxy-4-[2-(2-naphthalenyloxy)ethoxy]-alpha-oxobenzeneacetic acid A solution of 3,5-dimethoxy-4-[2-(2-naphthalenyloxy)ethoxy]-alpha-oxobenzeneacetic acid methyl ester (0.5 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried (Na$_2$SO$_4$), filtered and evaporated to give crude product. Crystallization from diethyl ether-hexane provided 0.45 g of purified 3,5-dimethoxy-4-[2-(2-naphthalenyloxy)ethoxy]-alpha-oxobenzeneacetic acid as a yellow solid, mp 114°–116° C.

Analysis Calculated for C$_{22}$H$_{20}$O$_7$: C, 66.66; H, 5.09. Found: C, 66.42; H, 5.09.

EXAMPLE 194

Preparation of
2,6-dimethoxy-4-[2-(2-naphthalenyloxy)ethoxy]-alpha-oxobenzeneacetic acid methyl ester A stirred mixture of impure 2,6-dimethoxy-4-hydroxyacetophonone (3.6 g) in dimethylformamide (30 mL) under argon was treated with 55% sodium hydride (0.803 g), stirred for 30 minutes and treated with 2-(2-naphthalenyloxy)ethyl methanesulfonate (4.9 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried (Na$_2$SO$_4$), filtered, and evaporated to give crude material which was purified by HPLC (dichloromethane-hexane-diethyl ether; 50:50:3) and crystallized from dichloromethane-diethyl ether to provide 1.8 g of 1-[2,6-dimethoxy-4-[2-(2-naphthalenyloxy)ethoxy]phenyl]ethanone as a colorless solid, mp 97°–98° C.

Analysis Calculated for C$_{22}$H$_{22}$O$_5$: C, 72.12; H, 6.05. Found: C, 72.08; H, 6.04.

A mixture of 1-[2,6-dimethoxy-4-[2-(2-naphthalenyloxy)ethoxy]phenyl]ethanone (1.5 g) in pyridine (25 mL) was treated with selenium dioxide (0.682 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried (Na$_2$SO$_4$), filtered and evaporated. The crude material was purified by HPLC (dichloromethane-diethyl ether; 49:1) and crystallized from dichloromethane-diethyl ether to provide 1.1 g of 2,6-dimethoxy-4-[2-(2-naphthalenyloxy)ethoxy]-alpha-oxobenzeneacetic acid methyl ester as a pale yellow solid, mp 161°–162° C.

Analysis Calculated for C$_{23}$H$_{22}$O$_7$: C, 67.31; H, 5.40. Found: C, 67.00; H, 5.53.

EXAMPLE 195

Preparation of
2,6-dimethoxy-4-[2-(2-naphthalenyloxy)ethoxy]-alpha-oxobenzeneacetic acid A solution of 2,6-dimethoxy-4-[2-(2-naphthalenyloxy)ethoxy]-alpha-oxobenzeneacetic acid methyl ester (0.5 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried (Na$_2$SO$_4$), filtered and evaporated to give crude product. Crystallization from dichloromethane-hexane provided 0.45 g of purified 2,6-dimethoxy-4-[2-(2-naphthalenyloxy)ethoxy]-alpha-oxobenzeneacetic acid as a yellow solid, mp 154° C. with decomposition. Analysis Calculated for C$_{22}$H$_{20}$O$_7$: C, 66.66; H, 5.09. Found: C, 66.39; H, 5.17.

EXAMPLE 196

Preparation of
2-fluoro-4-[2-(2-naphthalenyloxy)ethoxy]-alpha-oxobenzeneacetic acid methyl ester A stirred mixture of impure 2-fluoro-4-hydroxyacetophonone (1.85 g) in dimethylformamide (30 mL) under argon was treated with 55% sodium hydride (0.524 g), stirred for 30 minutes and treated with 2-(2-naphthalenyloxy)ethyl methanesulfonate (2.9 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated to give crude material which was crystallized from dichloromethane-diethyl ether to provide 3.0 g of 1-[2-fluoro-4-[2-(2-naphthalenyloxy)ethoxy]phenyl]ethanone as a colorless solid, mp 144°–146° C.

Analysis Calculated for $C_{20}H_{17}FO_3$: C, 74.06; H, 5.28; F, 5.86.

Found: C, 74.11; H, 5.34; F, 6.03.

A mixture of 1-[2-fluoro-4-[2-(2-naphthalenyloxy)ethoxy]phenyl]ethanone (1 g) in pyridine (20 mL) was treated with selenium dioxide (0.5 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethane-hexane; 9:1) and crystallized from dichloromethane-hexane to provide 0.55 g of 2-fluoro-4-[2-(2-naphthalenyloxy)ethoxy]-alpha-oxobenzeneacetic acid methyl ester as a colorless solid, mp 135°–136° C.

Analysis Calculated for $C_{21}H_{17}FO_5$: C, 68.47; H, 4.65; F, 5.16.

Found: C, 68.39; H, 4.63; F, 5.06.

EXAMPLE 197

Preparation of 2-fluoro-4-[2-(2-naphthalenyloxy)ethoxy]-alpha-oxobenzeneacetic acid A solution of 2-fluoro-4-[2-(2-naphthalenyloxy)ethoxy]-alpha-oxobenzeneacetic acid methyl ester (0.5 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.425 g of purified 2-fluoro-4-[2-(2-naphthalenyloxy)ethoxy]-alpha-oxobenzeneacetic acid as a yellow solid, mp 155°–156° C.

Analysis Calculated for $C_{20}H_{15}FO_5$: C, 67.79; H, 4.27; F, 5.36.

Found: C, 67.52; H, 4.41; F, 5.20.

EXAMPLE 198

Preparation of 3-fluoro-4-[2-(2-naphthalenyloxy)ethoxy]-alpha-oxobenzeneacetic acid methyl ester A stirred mixture of impure 2-fluoro-4-hydroxyacetophonone (1.85 g) in dimethylformamide (30 mL) under argon was treated with 55% sodium hydride (0.524 g), stirred for 30 minutes and treated with 2-(2-naphthalenyloxy)ethyl methanesulfonate (2.9 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated to give crude material which was crystallized from dichloromethane-diethyl ether to provide 2.8 g of 1-[3-fluoro-4-[2-(2-naphthalenyloxy)ethoxy]phenyl]ethanone as a colorless solid, mp 171°–173° C.

Analysis Calculated for $C_{20}H_{17}FO_3$: C, 74.06; H, 5.28; F, 5.86.

Found: C, 74.01; H, 5.28; F, 5.58.

A mixture of 1-[3-fluoro-4-[2-(2-naphthalenyloxy)ethoxy]phenyl]ethanone (1 g) in pyridine (20 mL) was treated with selenium dioxide (0.5 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. After the organic extracts were dried ($Na_2SO_4$), filtered and evaporated, the crude material was purified by HPLC (dichloromethane-hexane; 9:1) and crystallized from dichloromethane-hexane to provide 0.75 g of 3-fluoro-4-[2-(2-naphthalenyloxy)ethoxy]-alpha-oxobenzeneacetic acid methyl ester as a colorless solid, mp 136°–138° C.

Analysis Calculated for $C_{21}H_{17}FO_5$: C, 68.47; H, 4.65; F, 5.16.

Found: C, 68.44; H, 4.60; F, 4.94.

EXAMPLE 199

Preparation of 3-fluoro-4-[2-(2-naphthalenyloxy)ethoxy]-alpha-oxobenzeneacetic acid A solution of 3-fluoro-4-[2-(2-naphthalenyloxy)ethoxy]-alpha-oxobenzeneacetic acid methyl ester (0.5 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from acetone-hexane provided 0.42 g of purified 3-fluoro-4-[2-(2-naphthalenyloxy)ethoxy]-alpha-oxobenzeneacetic acid as a yellow solid, mp 168°–169° C.

Analysis Calculated for $C_{20}H_{15}FO_5$: C, 67.79; H, 4.27; F, 5.36.

Found: C, 67.86; H, 4.29; F, 5.44.

EXAMPLE 200

Preparation of 2,6-difluoro-4-[2-(2-naphthalenyloxy)ethoxy]-alpha-oxobenzeneacetic acid methyl ester A stirred mixture of 2,6-difluoro-4-hydroxybenzonitrile (3 g) in dimethylformamide (30 mL) under argon was treated with 55% sodium hydride (0.842 g), stirred for 30 minutes and treated with 2-(2-naphthalenyloxy)ethyl methanesulfonate (5.1 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated. The crude material was purified by HPLC (dichloromethane-hexane 2:1) and crystallized from dichloromethane-hexane to provide 4.3 g of 2,6-difluoro-4-[2-(2-naphthalenyloxy) ethoxy]benzonitrile as a colorless solid, mp 148°–149° C.

Analysis Calculated for $C_{19}H_{13}F_2NO_2$: C, 70.15; H, 4.03; N, 4.31; F, 11.68.

Found: C, 69.99; H, 3.92; N, 4.19; F, 11.56.

Methyl magnesium bromide was prepared in the usual way from magnesium metal (0.94 g) and methyl iodide (2.4 mL) in diethyl ether. Most of the diethyl ether was removed by distillation prior to the addition of a solution of 2,6-difluoro-4-[2-(2-naphthalenyloxy)ethoxy]benzonitrile (4.2 g) in tetrahydrofuran (35 mL). Distillation was continued to remove all of the diethyl ether and the resulting mixture was refluxed at 60° C. for 2 hours and chilled in ice. An aqueous solution of 2N hydrochloric acid (30 mL) was added and the tetrahydrofuran was removed by distillation and the aqueous mixture was boiled at 100° C. for 45 minutes, cooled and diluted with water. The crude product was extracted with dichloromethane (twice), washed in turn with dilute hydrochloric acid, dilute aqueous sodium bicarbonate solution, dried ($Na_2SO_4$), filtered and evaporated. The residue was purified by HPLC (dichloromethane-hexane; 3:1) and crystallized from dichloromethane-diethyl ether to give 2.5 g of 1-[2,6-difluoro-4-[2-(2-naphthalenyloxy)ethoxy]phenyl]ethanone as a colorless solid, mp 119°–120° C.

Analysis Calculated for $C_{20}H_{16}F_2O_3$: C, 70.17; H, 4.71; F, 11.10.

Found: C, 70.06; H, 4.71; F, 11.43.

A mixture of 1-[2,6-difluoro-4-[2-(2-naphthalenyloxy)ethoxy]phenyl]ethanone (2.5 g) in pyridine (30 mL) was treated with selenium dioxide (1.2 g) and heated at 100° C. overnight under argon. The mixture was cooled, diluted with dichloromethane (75 mL), and filtered through celite. The filtrate was chilled in an ice bath and treated with methyl chloroformate (2.5 mL) and stirred for 10 minutes. The resulting mixture was washed with successive portions of 1N hydrochloric acid (twice) and saturated aqueous sodium bicarbonate solution. After the organic extracts were dried ($Na_2SO_4$), filtered and evaporated, the crude residue was purified by HPLC (dichloromethane-hexane; 9:1) and crystallized from dichloromethane-methanol to provide 1.4 g of 2,6-difluoro-4-[2-(2-naphthalenyloxy)ethoxy]-alpha-oxobenzeneacetic acid methyl ester as a colorless solid, mp 130°–131° C.

Analysis Calculated for $C_{21}H_{16}F_2O_5$: C, 65.29; H, 4.17; F, 9.83.

Found: C, 65.39; H, 3.92; F, 9.53.

EXAMPLE 201

Preparation of 2,6-difluoro-4-[2-(2-naphthalenyloxy ethoxy]-alpha-oxobenzeneacetic acid A solution of 2,6-difluoro-4-[2-(2-naphthalenyloxy)ethoxy]-alpha-oxobenzeneacetic acid methyl ester (0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.51 g of 2,6-difluoro-4-[2-(2-naphthalenylox-y)ethoxy]-alpha-oxobenzeneacetic acid as a yellow solid, mp 157°–158° C.

Analysis Calculated for $C_{20}H_{14}F_2O_5$: C, 64.52; H, 3.79; F, 10.21.

Found: C, 64.42; H, 3.70; F, 10.44.

EXAMPLE 202

Preparation of 3,5-difluoro-4-[2-(2-naphthalenyloxy)ethoxy]-alpha-oxobenzeneacetic acid methyl ester A stirred mixture of 3,5-difluoro-4-hydroxybenzonitrile (2.07 g) in dimethylformamide (30 mL) under argon was treated with 55% sodium hydride (0.524 g), stirred for 30 minutes and treated with 2-(2-naphthalenyloxy)ethyl methanesulfonate (2.9 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated. The crude material was first purified by HPLC (dichloromethane-hexane 3:1) and then crystallized from dichloromethane-hexane to provide 2.8 g of 1-[3,5-difluoro-4-[2-(2-naphthalenyloxy)ethoxy]phenyl]ethanone as a colorless solid, mp 108°–110° C.

Analysis Calculated for $C_{20}H_{16}F_2O_3$: C, 70.17; H, 4.71; F, 11.10.

Found: C, 70.20; H, 4.53; F, 11.28.

A mixture of 1-[3,5-difluoro-4-[2-(2-naphthalenyloxy)ethoxy]phenyl]ethanone (1.5 g) in pyridine (25 mL) was treated with selenium dioxide (0.732 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution, then the organic layer was dried ($Na_2SO_4$), filtered and evaporated. The isolated material was purified by HPLC (dichloromethane-hexane; 3:1) and crystallized from dichloromethane-hexane to provide 1.1 g of 3,5-difluoro-4-[2-(2-naphthalenyloxy)ethoxy]-alpha-oxobenzeneacetic acid methyl ester as a colorless solid, mp 114°–115° C.

Analysis Calculated for $C_{21}H_{16}F_2O_5$: C, 65.29; H, 4.17; F, 9.83.

Found: C, 65.51; H, 3.90; F, 9.71.

EXAMPLE 203

Preparation of 3,5-difluoro-4-[2-(2-naphthalenyloxy)ethoxy]-alpha-oxobenzeneacetic acid.

A solution of 3,5-difluoro-4-[2-(2-naphthalenyloxy)ethoxy]-alpha-oxobenzeneacetic acid methyl ester (0.6 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated. Crystallization of the residue from dichloromethane-hexane provided 0.525 g of purified 3,5-difluoro-4-[2-(2-naphthalenyloxy)ethoxy]-alpha-oxobenzeneacetic acid as a yellow solid, mp 129°–130 ° C.

Analysis Calculated for $C_{20}H_{14}F_2O_5$: C, 64.52; H, 3.79; F, 10.21.

Found: C, 64.19; H, 3.82; F, 10.23.

EXAMPLE 204

Preparation of 2,3,5,6-tetrafluoro-4-[2-(2-naphthalenyloxy)ethoxy]-alpha-oxobenzeneacetic acid methyl ester A stirred chilled mixture of aluminum chloride (40 g) and carbon disulfide (40 mL) was maintained below 5° C. during the sequential dropwise addition of a solution composed of 2,3,5,6-tetrafluorophenol (24.9 g) in carbon disulfide (15 mL) followed by acetyl chloride (21.3 mL). The resulting mixture was refluxed for 4 days and poured onto a mixture of ice and hydrochloric acid. The organic material was extracted with diethyl ether (3 times), washed in turn with water, combined and evaporated. The wet residue was mixed with a little methanol and 4N aqueous sodium hydroxide (100 mL), heated at 100° C. for 30 minutes, diluted with water, cooled and acidified with hydrochloric acid. The mixture was extracted with diethyl ether (3 times), washed with water, dried ($Na_2SO_4$), filtered and evaporated. Crystallization of the isolated material from diethyl ether-hexane provided 3.4 g of 1-[(4-hydroxy-2,3,5,6-tetrafluoro)phenyl]ethanone, mp 109°–111° C.

A stirred mixture of 1-[(4-hydroxy-2,3,5,6-tetrafluoro)phenyl]ethanone (2.1 g) in dimethylformamide (20 mL) under argon was treated with 55% sodium hydride (0.436 g), stirred for 30 minutes and treated with 2-(2-naphthalenyloxy)ethyl methanesulfonate (2.7 g). The mixture was heated at 60° C. overnight and evaporated to dryness. The residue was mixed with water and excess sodium hydroxide solution, the product was extracted twice with dichloromethane, and the organic layers were washed with water. The combined organic layers were dried ($Na_2SO_4$), filtered, and evaporated. The crude material was purified by HPLC (dichloromethane-hexane 2:1) and crystallized from dichloromethane-diethyl ether to provide 2.25 g of 1-[2,3,5,6-tetrafluoro-4-[2-(2-naphthalenyloxy)ethoxy]-phenyl]ethanone as a colorless solid, mp 114°–115° C.

Analysis Calculated for $C_{20}H_{14}F_4O_3$: C, 63.50; H, 3.73; F, 20.09.

Found: C, 63.70; H, 3.69; F, 20.27.

A mixture of 1-[2,3,5,6-tetrafluoro-4-[2-(2-naphthalenyloxy)ethoxy]phenyl]ethanone (2.1 g) in pyridine (25 mL) was treated with selenium dioxide (0.932 g) and heated at 100° C. overnight under argon. The mixture was cooled, diluted with dichloromethane (50 mL), and filtered through celite. The filtrate was chilled in an ice bath and treated with methyl chloroformate (2 mL) and stirred for 10 minutes. The resulting mixture was washed with successive portions of 1N hydrochloric acid (twice) and saturated aqueous sodium bicarbonate solution. The organic extracts were dried ($Na_2SO_4$), filtered and evaporated. The crude material was purified by HPLC (dichloromethanehexane; 9:1) and crystallized from diethyl ether-hexane to provide 0.95 g of 2,3,5,6-tetrafluoro-4-[2-(2-naphthalenyloxy)ethoxy]-alpha-oxobenzeneacetic acid methyl ester as a colorless solid, mp 69°–71° C.

Analysis Calculated for $C_{21}H_{14}F_4O_5$: C, 59.72; H, 3.34; F, 17.99.

Found: C, 59.75; H, 3.25; F, 18.27.

EXAMPLE 205

Preparation of 2,3,5,6-tetrafluoro-4-[2-(2-naphthalenyloxy)ethoxy]-alpha-oxobenzeneacetic acid A solution of 2,3,5,6-tetrafluoro-4-[2-(2-naphthalenyloxy)ethoxy]-alpha-oxobenzeneacetic acid methyl ester (0.5 g) in warm methanol (10 mL) and tetrahydrofuran (10 mL) was treated with 1N sodium hydroxide (2 mL) and after 10 minutes the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.185 g of purified 2,3,5,6-tetrafluoro-4-[2-(2-naphthalenyloxy)ethoxy]-alpha-oxobenzeneacetic acid as a yellow solid, mp 146°–148° C.

Analysis Calculated for $C_{20}H_{12}F_4O_5$: C, 58.83; H, 2.96; F, 18.61.

Found: C, 58.87; H, 2.97; F, 18.82.

EXAMPLE 206

Preparation of 3-methyl-2-(trifluoromethylsulfonyloxy)benzoic acid methyl ester In an inert atmosphere, a stirred solution of 3-methylsalicylic acid methyl ester (9.96 g) in dichloromethane (150 mL) cooled in an ice bath, was treated portionwise with 55% sodium hydride dispersion in mineral oil (3.0 g). The mixture was stirred at 0° C. for 15 minutes, then trifluoromethyl sulfonic acid (18.65 mL) was added dropwise over 20 minutes. The cooling bath was removed and the reaction was allowed to proceed for an additional hour. Water (75 mL) was added and the phases were separated. The organic layer was washed in turn with 10% potassium carbonate (75 mL) and with brine. The dried ($Na_2SO_4$) organic layer was evaporated and the resulting amber oil was purified by HPLC (diethyl ether-hexane; 1:4) to yield 14.3 g of 3-methyl-2-(trifluoromethylsulfonyloxy)benzoic acid methyl ester as an oil.

Analysis Calculated for $C_{10}H_9F_3O_5S$: C, 40.27; H, 3.04; F, 19.11; S, 10.75.

Found: C, 40.48; H, 3.20; F, 19.35; S, 11.10.

EXAMPLE 207

Preparation of rac-3-methyl-2-[3-(2-tetrahydropyranyloxy)-1-propynyl]benzoic acid methyl ester Argon was bubbled for 30 minutes through a solution of 3-methyl-2-(trifluoromethylsulfonyloxy)benzoic acid methyl ester (18.7 g), rac-tetrahydro-2-(2-propynyloxy)-2H-pyran (13.2 g) and triethylamine (60 mL) in dry dimethylformamide (200 mL), then bis(triphenylphosphine)palladium (II) chloride (1.32 g) was added and the mixture was stirred at 85°–90° C. for 3 hours. The reaction was cooled and the solvents were removed in vacuo to give a dark oil which was purified by HPLC to give 3-methylsalicylic acid methyl ester (3.04 g) as a non-polar impurity as well as 8.15 g of the desired rac-3-methyl-2-[3-(2-tetrahydropyranyloxy)-1-propynyl]benzoic acid methyl ester as a straw colored oil.

Analysis Calculated for $C_{17}H_{20}O_4$: C, 70.81; H, 6.99.

Found: C, 70.81; H, 7.01.

EXAMPLE 208

Preparation of rac-3-methyl-2-[3-[2-(tetrahydropyranyloxy)-1-propynyl]benzene methanol A solution of diisobutylaluminum hydride (1.5M in hexane; 39.3 mL) was added over 15 minutes to a solution of rac-3-methyl-2-[3-[2-(2-tetrahydropyranyloxy)-1-propynyl] benzoic acid methyl ester (7.52 g) in toluene (200 mL) maintained at −40° C. by using a dry ice-acetonitrile bath. After 20 minutes, water (25 mL) was added and the cooling bath was removed. When the mixture had warmed to 15° C., it was diluted with a saturated sodium potassium tartrate solution (150 mL) and toluene (100 mL). After the phases were separated, the aqueous layer was washed with toluene (2×100 mL), then the organic extracts were washed in turn with sodium potassium tartrate solution (100 mL) and brine, dried (Na$_2$SO$_4$), filtered and evaporated to give 6.75 g of rac-3-methyl-2-[3-[2-(tetrahydropyranyloxy)-1-propynyl]benzenemethanol as a colorless oil. A small portion (0.1 g) was purified for analysis by chromatography over silica gel (2 g; diethyl ether-hexane).

Analysis Calculated for C$_{16}$H$_{20}$O$_3$: C, 73.82; H, 7.74. Found: C, 74.19; H, 8.12.

EXAMPLE 209

Preparation of 2,2-dimethylbutanoic acid [3-methyl-2-[3-(2-tetrahydropyranyloxy)-1-propynyl]-phenyl]methyl ester 2,2-Dimethylbutyryl chloride (4.2 g) was added dropwise to a solution of rac-3-methyl-2-[3-[2-(tetrahydropyranyloxy)-1-propynyl]benzenemethanol (6.65 g), triethylamine (9 mL) and N,N-dimethylaminopyridine (0.002 g) in dichloromethane (100 mL). After stirring for 22 hours at room temperature, the reaction mixture was diluted with dichloromethane (50 mL) and then was washed in turn with sodium bicarbonate solution and with brine. Evaporation of the dried (Na$_2$SO$_4$) organic layer furnished 9 g of an oil which was purified by HPLC (diethyl ether-hexane; 1:9) to provide 7.6 g of rac-2,2-dimethylbutanoic acid [3-methyl-2-[3-(2-tetrahydropyranyloxy)-1-propynyl]phenyl]methyl ester as a colorless oil.

Analysis Calculated for C$_{22}$H$_{30}$O$_4$: C, 73.71; H, 8.44. Found: C, 73.91; H, 8.56.

EXAMPLE 210

Preparation of 2,2-dimethylbutanoic acid [2-(3-hydroxy-1-propynyl)-3-methylphenyl]methyl ester A solution of rac-2,2-dimethylbutanoic acid [3-methyl-2-[3-(2-tetrahydropyranyloxy)-1-propynyl]phenyl]methyl ester (2 g) and pyridinium p-toluenesulfonate in ethanol (30 mL) was stirred and heated in an oil bath maintained at 55° C. for 3.5 hours then the solvent was evaporated and the residue triturated with diethyl ether. After a small amount of pyridinium p-toluenesulfonate was Filtered off, the filtrate was evaporated and the residual oil was purified by HPLC (diethyl ether-hexane; 1:3) to furnish 1.38 g of 2,2-dimethylbutanoic acid [2-(3-hydroxy-1-propynyl)-3-methylphenyl]methyl ester as a colorless oil.

Analysis Calculated for C$_{17}$H$_{22}$O$_3$: C, 74.42; H, 8.08. Found: C, 74.16; H, 8.23.

EXAMPLE 211

Preparation of 4-[3-[2-[(2,2-dimethyl-1-oxobutoxy)methyl]-6-methyl phenyl]-2-propynyloxy]-alpha-oxobenzeneacetic acid methyl ester A stirred solution of 2,2-dimethylbutanoic acid [2-(3-hydroxy-1-propynyl)-3-methylphenyl]methyl ester (1.05 g), 4-hydroxyphenylglyoxylic acid methyl ester (0.693 g) and triphenylphosphine (1.26 g) in tetrahydrofuran (30 mL) was cooled to 0° C., and a solution of diethyl azodicarboxylate (0.76 mL) in tetrahydrofuran (5 mL) was added over 5 minutes. The reaction mixture was stirred at 0° C. for 1 hour then at room temperature overnight. The solvent was evaporated and the residue triturated with diethyl ether to remove most of the triphenylphosphine oxide. The filtrate was concentrated in vacuo and the resulting oil was chromatographed over silica gel (10 g; diethyl ether-hexane; 1:19) to furnish 1.4 g of 4-[3-[2-[(2,2-dimethyl-1-oxobutoxy)methyl]-6-methylphenyl]-2-propynyloxy]-alpha-oxobenzeneacetic acid methyl ester as a colorless oil.

Analysis Calculated for C$_{26}$H$_{28}$O$_6$: C, 71.54; H, 6.47. Found: C, 71.53; H, 6.43.

EXAMPLE 212

Preparation of 4-[3-[2-[(2,2-dimethyl-1-oxobutoxy)methyl]-6-methyl-phenyl]-2-propynyloxy]-alpha-oxobenzeneacetic acid (1:1) morpholine salt A solution of 4-[3-[2-[(2,2-dimethyl-1-oxobutoxy)methyl]-6-methylphenyl]-2-propynyloxy]-alpha-oxobenzeneacetic acid methyl ester (1.25 g) in methanol (5 mL) was treated with 3N sodium hydroxide solution (1.25 mL) and the mixture was stirred for 5 minutes at room temperature. Most of the methanol was removed under reduced pressure, and the concentrate was partitioned between diethyl ether (25 mL,) and water (25 mL). The separated aqueous layer was acidified with 1N hydrochloric acid (5 mL) and extracted with diethyl ether (2×50 mL). The combined organic phases were washed with brine, dried (Na$_2$SO$_4$) and evaporated in vacuo to give 1.13 g of 4-[3-[2-[(2,2-dimethyl-1-oxobutoxy)methyl]-6-methylphenyl]-2-propynyloxy]-alphaoxobenzeneacetic acid as a colorless oil.

Morpholine (0.2 mL) was added to a solution of the crude acid (0.97 g) in diethyl ether (25 mL) and the mixture was stirred at room temperature until a crystalline solid began to form, then was chilled at 0° C. for 1 hour. The solids were filtered off and recrystallized from ethyl acetate to provide 0.89 g of 4-[3-[2-(2,2-dimethyl-1-oxobutoxy)methyl]-6-methylphenyl]-2-propynyloxy]-alpha-oxobenzeneacetic acid (1:1) morpholine salt, mp 111°-112° C.

Analysis Calculated for C$_{25}$H$_{26}$O$_6$.(1:1)C$_4$H$_9$NO: C, 68.35; H, 6.92; N 2.75.

Found: C, 68.45; H, 6.75; N 2.79.

EXAMPLE 213

Preparation of (Z)-2,2-dimethylbutanoic acid [2-(3-hydroxy-1-propenyl)-3-methylphenyl]methyl ester A solution of rac-dimethylbutanoic acid [3-methyl-2-[3-(2-tetrahydropyranyloxy)-1-propynyl]phenyl]methyl ester (2 g) in methanol (50 mL) was hydrogenated over 10% palladium on carbon (0.2 g) at room temperature and ambient pressure. The reaction essentially stopped within 1 hour with the absorption of 145 mL of hydrogen. After the catalyst was removed by filtration through Celite, the methanol was removed in vacuo to give 1.6 g of an oil. Examination of the product by NMR indicated that the THP protecting group had been unexpectedly hydrolyzed, and that the oil was predominantly the cis-propenol, (Z)-2,2-dimethylbutanoic acid 2-(3-hydroxy-1-propenyl)-3-methylphenyl] methyl ester. A small potion was chromatographed over silica gel to obtain the analytically pure material.

Analysis Calculated for $C_{17}H_{24}O_3$: C, 73.88; H, 8.75. Found: C, 73.63; H, 8.87.

EXAMPLE 214

Preparation of (Z)-4-[3-[2-[(2,2-dimethyl-1-oxobutoxy)methyl]-6-methylphenyl]-2-propenyloxy]-alpha-oxobenzeneacetic acid methyl ester As in Example 15, (Z)-2,2-dimethylbutanoic acid [2-(3-hydroxy-1-propenyl)-3-methylphenyl]methyl ester (0.649 g) was reacted with 4-hydroxyphenylglyoxylic acid methyl ester (0.430 g) in the presence of diethyl azodicarboxylate (0.47 g) and triphenylphosphine (0.776 g) in tetrahydrofuran (20 mL). After the usual work up, the crude product was purified by chromatography over silica gel (10 g; diethyl etherhexane; 1:9) to furnish 0.823 g of (Z)-4-[3-[2-[(2,2-dimethyl-1-oxobutoxy)methyl]-6-methylphenyl]-2-propenyloxy]-alpha-oxobenzeneacetic acid methyl ester as a oil.

Analysis Calculated for $C_{26}H_{30}O_6$: C, 71.21; H, 6.90. Found: C, 70.91; H, 7.05.

EXAMPLE 215

Preparation of 4-[3-[2-[(2,2-dimethyl-1-oxobutoxy)methyl]-6-methylphenyl]-2-propenyloxy]-alpha-oxobenzeneacetic acid (1:1) morpholine salt As in Example 19, (Z)-4-[3-[2-[(2,2-dimethyl-1-oxobutoxy)methyl]-6-methylphenyl]-2-propenyloxy]-alpha-oxobenzeneacetic acid methyl ester (0.718 g) in methanol (5 mL) was treated with 1N sodium hydroxide (1.8 mL). The usual work up gave 0.695 g 4-[3-[2-[(2,2-dimethyl-1-oxobutoxy)methyl]-6-methylphenyl]-2-propenyloxy]-alpha-oxobenzeneacetic acid as an oil.

As described before in Example 212, morpholine (0.145 mL) was added to a solution of the acid (0.655 g) in diethyl ether (25 mL). The mixture was stirred chilled in a ice bath to initiate crystallization, then resulting solids (0.775 g) were recovered by filtration and recrystallized from diethyl ether to yield 0.65 g of (Z)-4-[3-[2-(2,2-dimethyl-1-oxobutoxy)methyl]-6-methylphenyl]-2-propenyloxy]-alpha-oxobenzeneacetic acid (1:1) morpholine salt, mp 77°–79° C.

Analysis Calculated for $C_{25}H_{28}O_6.(1:1)C_4H_9NO$: C, 68.08; H, 7.29; N 2.74. Found: C, 68.18; H, 7.34; N 2.59.

EXAMPLE 216

Preparation of (Z)-2,2-dimethylbutanoic acid [2-(2-formylethenyl)-3-methylphenyl]methyl ester A mixture of (Z)-2,2-dimethylbutanoic acid [2-(3-hydroxy-1-propenyl)-3-methylphenyl]methyl ester (0.81 g) and activated manganese dioxide in dichloromethane (50 mL) was stirred vigorously for 1 hour. The solids were filtered off, washed with water and the combined filtrates were evaporated to yield 0.775 g of (Z)-2,2-dimethylbutanoic acid [2-(2-formylethenyl)-3-methylphenyl]methyl ester as a colorless oil.

Analysis Calculated for $C_{17}H_{22}O_3$: C, 74.42; H, 8.08. Found: C, 74.94; H, 8.46.

EXAMPLE 217

Preparation of (E)-2,2-dimethylbutanoic acid [2-(2-formylethenyl)-3-methylphenyl]methyl ester A solution of (Z)-2,2-dimethylbutanoic acid [2-(2-formylethenyl)-3-methylphenyl]methyl ester (0.77 g) in chloroform (40 mL) in a 200 mL round bottomed pyrex flask was placed in direct sunlight for 50 hours. The photoisomerization was followed by NMR and the reaction attained equilibrium within 6 hours with an E/Z ratio of 2.7:1. The solvent was evaporated and the isomers were separated by flash chromatography over 75 g of silica gel (diethyl ether-hexane; 1:9) to furnish 0.22 g of the starting (Z)-2,2-dimethylbutanoic acid [2-(2-formylethenyl)-3 -methylphenyl]methyl ester and 0.395 g of the isomeric (E)-2,2-dimethylbutanoic acid [2-(2-formylethenyl)-3-methylphenyl]methyl ester as a colorless oil.

Analysis Calculated for $C_{17}H_{22}O_3$: C, 74.42; H, 8.08. Found: C, 74.33; H, 8.12.

EXAMPLE 218

Preparation of (E)-2,2-dimethylbutanoic acid [2-(3-hydroxy-1-propenyl)-3-methylphenyl]methyl ester A solution of (E)-2,2-dimethylbutanoic acid [2-(2-formylethenyl)-3-methylphenyl]methyl ester (0.271 g) in methanol (5 mL) was treated with sodium borohydride (0.06 g) and the mixture was stirred at room temperature for 10 minutes. After the solvent was removed under reduced pressure, the residual material was partitioned between dichloromethane and water, then the dried organic phase (MgSO$_4$) was evaporated to afford 0.24 g of (E)-2,2-dimethylbutanoic acid [2-(3-hydroxy-1-propenyl)-3-methylphenyl]methyl ester as a colorless oil.

Analysis Calculated for $C_{17}H_{24}O_3$: C, 73.88; H, 8.75. Found: C, 74.01; H, 8.78.

EXAMPLE 219

Preparation of (E)-4-[3-[2-[(2,2-dimethyl-1-oxobutoxy)methyl]-6-methylphenyl]-2-propenyloxy]-alpha-oxobenzeneacetic acid methyl ester As described in Example 15, (E)-2,2-dimethylbutanoic acid [2-(3-hydroxy-1-propenyl)-3-methylphenyl]methyl ester (0.24 g) was reacted with 4-hydroxyphenylglyoxylic acid methyl ester (0.16 g) in the presence of diethyl azodicarboxylate (0.192 g) and triphenylphosphine (0.287 g) in tetrahydrofuran (15 mL). After the previously described work up, the crude ester was purified by chromatography over silica gel (5 g; diethyl ether-hexane; 1:9) to afford 0.241 g of (E)-4-[3-[2-[(2,2-dimethyl-1-oxobutoxy)methyl]-6-methylphenyl]-2-propenyloxy]-alpha-oxobenzeneacetic acid methyl ester as a oil.

Analysis Calculated for $C_{26}H_{30}O_6$: C, 71.21; H, 6.90. Found: C, 71.05; H, 6.83.

EXAMPLE 220

Preparation of
(E)-4-[3-[2-[(2,2-dimethyl-1-oxobutoxy)methyl]-6-methylphenyl]-2-propenyl]oxy]-alpha-oxobenzeneacetic acid (1:1) morpholine salt As in Example 19, (E)-4-[3-[2-[(2,2-dimethyl-1-oxobutoxy)methyl]-6-methylphenyl] -2-propenyloxy]-alpha-oxobenzeneacetic acid methyl ester (0.201 g) in methanol (1 mL) was treated with 1N sodium hydroxide (0.5 mL). The usual work up gave 0.187 g of (E)-4-[3-[2-[(2,2-dimethyl-1-oxobutoxy)methyl]-6-methylphenyl]-2-propenyloxy]-alpha-oxobenzeneacetic acid as an oil.

As in Example 212, morpholine (0.04 mL) was added to a solution of the acid (0.187 g) in diethyl ether (5 mL). The mixture was stirred chilled in a ice bath to initiate crystallization, then the resulting solids were recovered by filtration and recrystallized from diethyl ether to yield 0.205 g of (E)-4-[3-[2-(2,2-dimethyl-1-oxobutoxy)methyl]-6-methylphenyl]-2-propenyloxy]-alpha-oxobenzeneacetic acid (1:1) morpholine salt, mp 71°–73° C.

Analysis Calculated for $C_{25}H_{28}O_6 \cdot (1:1)C_4H_9NO$: C, 68.08; H, 7.29; N 2.74.
Found: C, 68.01; H, 7.41; N 2.73.

EXAMPLE 221

Preparation of 2,2-dimethylbutanoic acid [2-(3-hydroxypropyl)-3-methylphenyl]methyl ester A solution of rac-2,2-dimethylbutanoic acid[3-methyl-2-[3-(2-tetrahydropyranyloxy)-1-propynyl]phenyl]methyl ester (1.2 g) in methanol (50 mL) was hydrogenated over 10% palladium on carbon (0.2 g) at room temperature and ambient pressure for 90 minutes. After the catalyst was removed by filtration through Celite, the methanol was removed in vacuo to give 1.2 g of rac-2,2-dimethylbutanoic acid [2-[3-(2-tetrahydropyranyloxy)-1-propyl]-3-methylphenyl]methyl ester as an oil. A solution of the oil (1.2 g) and pyridinium p-toluenesulfonate (0.1 g) in ethanol (25 mL) was stirred and heated in an oil bath maintained at 55° C. After 6 hours, the solvent was evaporated and the residue was partitioned between diethyl ether and water. The aqueous phase was extracted with diethyl ether, then the combined organic extracts were dried ($Na_2SO_4$) and evaporated to furnish 1 g of an oil. The material was purified by HPLC (diethyl ether-hexane; 1:9) to give 0.72 g of 2,2-dimethylbutanoic acid [2-(3-hydroxy-1-propyl)-3-methylphenyl]methyl ester.

Analysis Calculated for $C_{17}H_{26}O_3$: C, 73.35; H, 9.41.
Found: C, 72.90; H, 9.38.

EXAMPLE 222

Preparation of
4-[3-[2-[(2,2-dimethyl-1-oxobutoxy)methyl]-6-methylphenyl]propoxy]-alpha-oxobenzeneacetic acid methyl ester As in Example 15, 2,2-dimethylbutanoic acid 2-(3-hydroxy-1-propyl)-3-methylphenyl]methyl ester (0.659 g) was reacted with 4-hydroxyphenylglyoxylic acid methyl ester (0.43 g) in the presence of diethyl azodicarboxylate (0.47 g) and triphenylphosphine (0.776 g) in tetrahydrofuran (20 mL). After the previously described work up, the crude ester was purified by chromatography over silica gel (10 g; diethyl ether-hexane; 1:9) to furnish 0.95 g of 4-[3-[2-[(2,2-dimethyl-1-oxobutoxy)methyl]-6-methylphenyl]propoxy]-alpha-oxobenzeneacetic acid methyl ester as a oil.

Analysis Calculated for $C_{26}H_{32}O_6$: C, 70.89; H, 7.35.
Found: C, 71.35; H, 7.52.

EXAMPLE 223

Preparation of
4-[3-[2-[(2,2-dimethyl-1-oxobutoxy)methyl]-6-methylphenyl]-2-propoxy]-alpha-oxobenzeneacetic acid (1:1) morpholine salt As in Example 19, 4-[3-[2-[(2,2-dimethyl-1-oxobutoxy)methyl]-6-methylphenyl]propoxy]-alpha-oxobenzeneacetic acid methyl ester (0.854 g) in methanol (4 mL) was treated with 1N sodium hydroxide (2.2 mL). The usual work up gave 0.685 g of 4-[3-[2-[(2,2-dimethyl-1-oxobutoxy)methyl]-6-methylphenyl]propoxy]-alpha-oxobenzeneacetic acid as an oil.

As described before in Example 212, morpholine (0.134 mL) was added to a solution of the acid (0.655 g) in diethyl ether (20 mL). The mixture was stirred chilled in a dry ice-acetone bath to induce crystallization, then the bath was removed and the mixture was stirred at room temperature for 1 hour. The solids were filtered off and recrystallized from diethyl ether to yield 0.415 g of 4-[3-[2-(2,2-dimethyl-1-oxobutoxy)methyl]-6-methylphenyl]propoxy]-alpha-oxobenzeneacetic acid (1:1) morpholine salt, mp 78°–80° C.

Analysis Calculated for $C_{25}H_{28}O_6 \cdot (1:1)C_4H_9NO$: C, 68.08; H, 7.29; N 2.74.
Found: C, 68.18; H, 7.34; N 2.59.

EXAMPLE 224

Preparation of
2-[4'-fluoro-3-(1-methylethyl)[1,1'-biphenyl]-2-yl]-4,5-dihydro-3,4,4-trimethyloxazolinium iodide (4:1) molar hydrate A solution of 4-fluorobromobenzene (9.7 g) in dry tetrahydrofuran (20 mL) was added dropwise to a stirred mixture of magnesium (1.38 g) in dry tetrahydrofuran (5 mL) and after the addition was completed, the reaction was stirred at 70° C. for 2 hours. The resulting solution was cooled and then was added over 10 minutes to a solution of 2-(2,6-dimethoxyphenyl)-4,5-dihydro-4,4-dimethyloxazoline (10.92 g) in dry tetrahydrofuran (50 mL). The mixture was stirred at 70° C. for 40 hours, then after the reaction mixture temperature was lowered to 45° C., a solution of isopropyl magnesium bromide in diethyl ether (2M; 34.8 mL) was added and the stirred reaction was maintained at 45° C. for another 16 hours. The mixture was cooled in an ice bath and was treated with a saturated solution of ammonium chloride (100 mL). The separated aqueous layer was extracted with ethyl acetate (3×100 mL), then the organic phase and extracts were combined and washed in turn with water, 1N hydrochloric acid, water and brine. The dried ($Na_2SO_4$) organic layer was evaporated, and the residual oil (11.93 g) was purified by HPLC (ethyl acetate-hexane; 1:13) to provide 5.2 g of 2-[4'-fluoro-3-(1-methylethyl)[1,1'-biphenyl]-2-yl]-4,5-dihydro-4,4-dimethyloxazoline as an oil.

A solution of the above material (5.17 g) and methyl iodide (9.6 mL) in nitromethane (200 mL) was heated at 70° C. for 90 minutes, then the solvent was removed under reduced pressure. The residue was stirred with diethyl ether and the resulting orange solid was filtered off, washed with diethyl ether and dried to yield 6.5 g of 2-[4'-fluoro-3-(1-methylethyl)[1,1'-biphenyl]-2-yl]-4,5- dihydro-3,4,4-trimethyloxazolinium iodide as its (4:1) molar hydrate, mp 188°–189° C. Crystallization from propanol furnished the analytical sample, mp 194°–196° C.

Analysis Calculated for $C_{21}H_{25}FINO \cdot (4.1)H_2O$: C, 55.09; H, 5.61; F, 4.15; N, 3.06; $H_2O$, 1.02 Found: C, 54.88; H, 5.96; F, 3.77; N, 2.94; $H_2O$, 1.05.

EXAMPLE 225

Preparation of 4'-fluoro-3-(1-methylethyl)[1,1'-biphenyl]-2-carboxaldehyde

Sodium borohydride (0.76 g) was added portionwise to a stirred solution of 2-[4'-fluoro-3-(1-methylethyl)[1,1'-biphenyl]-2-yl]-4,5-dihydro-3,4,4-trimethyloxazolinium iodide (4:1) molar hydrate (6.4 g) in tetrahydrofuran (110 mL) containing ethanol (50 mL) cooled in an ice bath. After the mixture was stirred 0° C. for 30 minutes and then at room temperature for 3 hours, it was rechilled in an ice bath and 3N hydrochloric acid (60 mL) was added dropwise. The reaction was heated for 16 hours at 70° C., then was cooled and concentrated to about half volume in vacuo. After water (100 mL) and dichloromethane (100 mL) were added, the phases were separated and the aqueous layer was extracted with dichloromethane (2×100 mL). The combined organic layers, washed in turn with brine, saturated sodium bisulfite solution, and brine, dried (MgSO$_4$) and evaporated to give 4.4 of the crude aldehyde as an oil. The material was purified by bulb to bulb distillation (130°–140° C.; 0.05 mm) to give 3.35 of 4'-fluoro-3-(1-methylethyl)[1,1'-biphenyl]-2-carboxaldehyde.

Analysis Calculated for $C_{16}H_{15}FO$: C, 79.31; H, 6.24; F, 7.84.

Found: C, 79.28; H, 6.45: F, 7.59.

EXAMPLE 226

Preparation of (E)-3-[4'-fluoro-3-(1-methylethyl)[1,1'-biphenyl]-2-yl]-2-propenoic acid methyl ester A solution of (carbomethoxymethylene)triphenylphosphorane (3.18 g) and 4'-fluoro-3-(1-methylethyl)[1,1'-biphenyl]-2-carboxaldehyde (2.27 g) in methanol (18 mL) was stirred at room temperature for 2 hours then the solvent was removed in vacuo. The residue was taken up in diethyl ether (50 mL) and after the mixture was stirred at ambient temperature for 20 minutes, the precipitated triphenylphosphine oxide was filtered off. Evaporation of the filtrate afforded 3.9 g of crude ester which, after purification by HPLC (ethyl acetate-hexane; 1:19) was crystallized from ethanol to provide 1.1 g of (E)-3-[4'-fluoro-3-(1-methylethyl)[1,1'-biphenyl]-2-yl]-2-propenoic acid methyl ester as a colorless solid, mp 87°–89° C.

Analysis Calculated for C19H19FO2: C, 76.49; H, 6.42; F, 6.37.

Found: C, 76.85; H, 6.51; F, 6.36.

EXAMPLE 227

Preparation of (E)-3-[4'-fluoro-3-(1-methylethyl)[1,1'-biphenyl]-2-yl]-2-propen-1-ol A solution of (E)-3-[4'-fluoro-3-(1-methylethyl)[1,1'-biphenyl]-2-yl]-2-propenoic acid methyl ester (1.37 g) in dry dichloromethane (30 mL) was chilled to −60° C. and a solution of diisobutylaluminum hydride in toluene (1.5M; 7.3 mL) was added dropwise with stirring over 5 minutes. The reaction mixture was maintained at −60° C. for 3 hours, then a saturated sodium sulfate solution (20 mL) was slowly added over several minutes. The formed solids were removed by filtration and washed with dichloromethane. The organic phase of the filtrate was separated, then washed in turn with water and brine, dried (MgSO$_4$) and evaporated. The crude product was purified by flash chromatography over silica gel (ethyl acetate-hexane; 3:7) to give an oil (0.86 g) that was crystallized from hexane to yield 0.62 of (E)-3-[4'-fluoro-3-(1-methylethyl)[1,1'-biphenyl]-2-yl]-2-propen-1-ol as a colorless solid, mp 71°–72° C.

Analysis Calculated for $C_{18}H_{19}FO$: C, 79.97; H, 7.08; F, 7.03.

Found: C, 80.03; H, 7.11; F, 6.95.

EXAMPLE 228

Preparation of (E)-4-[3-[4'-fluoro-3-(1-methylethyl)[1,1'-biphenyl]-2-yl]-2-propenyloxy]-alpha-oxobenzeneacetic acid methyl ester As in Example 15, (E)-3-[4'-fluoro-3-(1-methylethyl)[1,1'-biphenyl]-2-yl]-2-propen-1-ol (0.58 g) was reacted with 4-hydroxyphenylglyoxylic acid methyl ester (0.387 g) in the presence of diethyl azodicarboxylate (0.448 g) and triphenylphosphine (0.68 g) in tetrahydrofuran (25 mL). The usual work up afforded 1.3 g of a crude mixture that was purified by flash chromatography over silica gel (130 g; ethyl acetate-hexane; 3:7) to furnish 0.55 g of (E)-4-[3-[4'-fluoro-3-(1-methylethyl)[1,1'-biphenyl]-2-yl]-2-propenyloxy]-alpha-oxobenzeneacetic acid methyl ester as a oil.

EXAMPLE 229

Preparation of (E)-4-[3-[4'-fluoro-3-(1-methylethyl)[1,1'-biphenyl]-2-yl]-2-propenyloxy]-alpha-oxobenzeneacetic acid As in Example 19, (E)-4-[3-[4'-fluoro-3-(1-methylethyl)[1,1'-biphenyl]-2-yl]-2-propenyloxy]-alpha-oxobenzeneacetic acid methyl ester (0.5 g) in a mixture of methanol (4 mL) and tetrahydrofuran (2 mL) was treated with 1N potassium hydroxide (1.4 mL). The usual work up gave 0.4 g of a solid, which after crystallization from diethyl ether-hexane provided 0.3 g of (E)-4-[3-[4'-fluoro-3-(1-methylethyl)[1,1'-biphenyl]-2-yl]-2-propenyloxy]-alpha-oxobenzeneacetic acid as a colorless solid, mp 142°–143° C.

Analysis Calculated for $C_{26}H_{23}FO_4$: C, 74.63; H, 5.54; F, 4.54.

Found: C, 74.63; H, 5.50; F, 4.63.

EXAMPLE 230

Preparation of 4'-fluoro-3-(1-methylethyl)[1,1'-biphenyl]-2-ol formate

3-Chloroperbenzoic acid (4.73 g) was added to a solution of 4'-fluoro-3-(1-methylethyl)[1,1'-biphenyl]-2-carboxaldehyde (3.55 g) in dichloromethane (100 mL) and the reaction mixture was stirred at room temperature overnight. The precipitated solids were removed by filtration and the filtrate was washed in turn with water, saturated sodium bisulfite solution, sodium bicarbonate solution and brine. After the dried (MgSO$_4$) organic layer was evaporated, the crude product was purified by HPLC (ethyl acetate-hexane; 1:49) to afford 2.5 g of 4'-fluoro-3-(1-methylethyl)[1,1'biphenyl]-2-ol formate as a oil.

Analysis Calculated for $C_{16}H_{15}FO_2$: C, 74.40; H, 5.85; F, 7.36.

Found: C, 74.36; H, 5.83; F, 7.38.

EXAMPLE 231

Preparation of 4'-fluoro-3-(1-methylethyl)[1,1'-biphenyl]-2-ol.

To a solution of 4'-fluoro-3-(1-methylethyl)[1,1'-biphenyl]-2-ol formate (2 g) in ethanol (5 mL) was added a 10% solution of potassium hydroxide in ethanol (10 mL) and the reaction mixture was stirred at room temperature for 1 hour. The reaction was concentrated in vacuo, and the residue was partitioned between dichloromethane (20 mL) and 1N hydrochloric acid (20 mL). The separated aqueous layer was extracted with dichloromethane (2×20 mL), then the combined organic layers were washed with water, dried (MgSO₄) and evaporated to furnish 1.9 g of 4'-fluoro-3-(1-methylethyl) [1,1'-biphenyl]-2-ol as a oil which solidified on standing. A small sample was sublimed to give the analytical specimen, mp 41°–43° C.

Analysis Calculated for $C_{15}H_{15}FO$: C, 78.24; H, 6.57; F, 8.25.

Found: C, 78.11; H, 6.56; F, 8.17.

EXAMPLE 232

Preparation of 2-[4'-fluoro-3-(1-methylethyl)[1,1'-biphenyl]-2-yloxy]ethanol

A mixture of 4'-fluoro-3-(1-methylethyl)[1,1'-biphenyl]-2-ol (1.84 g), ethylene carbonate (0.78 g) and tetraethylammonium iodide (0.68 g) was heated in an oil bath at 155° C. for 2 hours, then was cooled and taken up in dichloromethane. The solution was washed in turn with water, 1N sodium hydroxide, 1N hydrochloric acid and brine, then was dried (MgSO₄) and evaporated. The residual material was chromatographed over 70 g of silica gel (ethyl acetate-hexane; 3:7) to provide 0.57 g of 2-[4'-fluoro-3-(1-methylethyl)[1,1'-biphenyl]-2-yloxy]ethanol. The compound was crystallized from hexane to give the analytical sample, mp 77°–78° C.

Analysis Calculated for $C_{17}H_{19}FO_2$: C, 74.43; H, 6.98; F, 6.98.

Found: C, 74.49; H, 6.94; F, 6.94.

EXAMPLE 233

Preparation of 4-[2-[4'-fluoro-3-(1-methylethyl)[1,1'-biphenyl]-2-yloxy]ethoxy]-alpha-oxobenzeneacetic acid methyl ester As in Example 15, (2-[4'-fluoro-3-(1-methylethyl)[1,1'-biphenyl]-2-yloxy]ethanol (0.393 g) was treated with 4-hydroxyphenylglyoxylic acid methyl ester (0.258 g) in the presence of diethyl azodicarboxylate (0.298 g) and triphenylphosphine (0.449 g) in tetrahydrofuran (25 mL). The usual work up afforded 0.6 g of crude product which was purified by flash chromatography over silica gel (60 g; ethyl acetate-hexane; 3:7) to furnish 0.3 g of 4-[2-[4'-fluoro-3-(1-methylethyl)[1,1'-biphenyl]-2-yloxy]ethoxy]-alpha-oxobenzeneacetic acid methyl ester. Crystallization of the ester from ethyl acetatehexane yielded the analytical specimen, mp 77°–79° C.

Analysis Calculated for $C_{26}H_{25}FO_5$: C, 71.55; H, 5.77; F, 4.35.

Found: C, 71.51; H, 5.74; F, 4.53.

EXAMPLE 234

Preparation of 4-[2-[4'-fluoro-3-(1-methylethyl)[1,1'-biphenyl]-2-yloxy]ethoxy]-alpha-oxobenzeneacetic acid As in Example 19, 4-[2-[4'-fluoro-3-(1-methylethyl)[1,1'-biphenyl]-2-yloxy]ethoxy]-alpha-oxobenzeneacetic acid methyl ester (0.186 g) in a mixture of methanol (2 mL) and tetrahydrofuran (1 mL) was treated with 1N potassium hydroxide (0.52 mL). The usual work up gave 0.17 g of a solid, which after crystallization from diethyl ether-hexane afforded 0.12 g of 4-[2-[4'-fluoro-3-(1-methylethyl)[1,1'-biphenyl]-2-yloxy]ethoxy]-alpha-oxobenzeneacetic acid, mp 123°–125° C.

Analysis Calculated for $C_{25}H_{23}FO_5$: C, 71.08; H, 5.49.

Found: C, 71.06; H, 5.56.

EXAMPLE 235

Preparation of (E)-4-[3-[4-(4-fluorophenyl)-2-(1-methylethyl)-3-quinolinyl]-2-propenyloxy]-alpha-oxobenzeneacetic acid methyl ester As in Example 15, (E)-3-[4-(4-fluorophenyl)-2-(1-methylethyl)-3-quinolinyl]-2-propen-1-ol (1.0 g) was coupled with 4-hydroxyphenylglyoxylic acid methyl ester (0.565 g) in the presence of diethyl azodicarboxylate (0.683 g) and triphenylphosphine (1.02 g) in tetrahydrofuran (30 mL). The usual work up, followed by purification of the crude product by flash chromatography over silica gel (50 g; diethyl ether-hexane; 1:4) and crystallization from diethyl ether to provide 0.94 g of (E)-4-[3-[4-(4-fluorophenyl)-2-(1-methylethyl)-3-quinolinyl]-2-propenyloxy]-alpha-oxobenzeneacetic acid methyl ester, mp 109°–111° C.

Analysis Calculated for $C_{30}H_{26}FNO_4$: C, 74.52; H, 5.42; F, 3.93; N, 2.90.

Found: C, 74.33; H, 5.35; F, 3.75; N, 2.82.

EXAMPLE 236

Preparation of (E)-4-[3-[4-(4-fluorophenyl)-2-(1-methylethyl)-3-quinolinyl]-2-propenyloxy]-alpha-oxobenzeneacetic acid As in Example 19, (E)-4-[3-[4-(4-fluorophenyl)-2-(1-methylethyl)-3-quinolinyl]-2propenyloxy]-alpha-oxobenzeneacetic acid methyl ester (0.84 g) in a mixture of methanol (10 mL) and tetrahydrofuran (1.5 mL) was treated with 1N sodium hydroxide (1.9 mL). The usual work up furnished 0.82 g of a solid, which was crystallized from ethyl acetate to yield 0.63 g of (E)-4-[3-[4-(4-fluorophenyl)-2-(1-methylethyl)-3-quinolin]-2-propenyloxy]-alpha-oxobenzeneacetic acid, mp 232°–234° C.

Analysis Calculated for $C_{29}H_{24}FNO_4$: C, 74.19; H, 5.15; F, 4.03; N, 2.98.

Found: C, 73.87; H, 5.21: F, 3.87; N, 2.95.

EXAMPLE 237

Preparation of 3-(4-fluorophenyl)-1-(1-methylethyl)-1H-indole-2-carboxaldehyde

Phosphoryl oxychloride (6.7 mL) was added dropwise to dimethylformamide (20 mL) at such a rate that the temperature did not exceed 10° C., then the mixture was heated to 80° C. as a solution of 3-(4-fluorophenyl)-1-(1-methylethyl)-1H-indole (15.6 g) in dimethylformamide (20 mL) was added, and then was stirred at that temperature for 21 hours. The reaction mixture was cooled (10° C.) during the addition of 4N sodium hydroxide (85 mL), it was stirred at 40 ° C. for 30 minutes then was allowed to equilibrate to room temperature. The resulting gummy solid was filtered off, dissolved in dichloromethane (150 mL), then washed with water, dried (MgSO$_4$) and evaporated. The residual solid was chromatographed over a short column of silica gel. The initial fractions, eluted with diether-hexane (1:9), gave 3.0 g of a mixture of starting indole and the desired aldehyde (3:1). Crystallization of this material from aqueous ethanol afforded 1.55 g of recovered starting material and the mother liquor was combined with later fractions that had been eluted from the column with diethyl ether-hexane (1:4) to give a total of 11.3 g of impure 3-(4-fluorophenyl)-1-(1-methylethyl)-1H-indole-2-carboxaldehyde contaminated with the starting indole (4:1). The bulk of this material was used in subsequent reactions without further purification, but a portion was flash chromatographed over silica gel, and then crystallized from ethanol to provide the analytically pure aldehyde, mp 95°–96 ° C.

Analysis Calculated for C$_{18}$H$_{16}$FNO: C, 76.85; H, 5.73; F, 6.75; N, 4.98.

Found: C, 76.68; H, 5.76; F, 6.69; N, 4.74.

EXAMPLE 238

Preparation of (E)-3-[3-(4-fluorophenyl)-1-(1-methylethyl)-1H-indol-2-yl]-2-propenoic acid methyl ester As in Example 226, the impure 3-(4-fluorophenyl)-1-(1-methylethyl)-1H-indole-2-carboxaldehyde (5.56 g) from the previous example was reacted in methanol (75 mL) with (carbomethoxymethylene)triphenylphosphorane (6.2 g) was stirred at room temperature for 1 hour. The pale yellow solids that formed were filtered and washed with cold methanol to furnish 4.58 g of (E)-3-[3-(4-fluorophenyl)-1-(1-methylethyl)-1H-indol-2-yl]-2-propenoic acid methyl ester. A sample was crystallized from dichloromethane-hexane to yield the analytical specimen, mp 155°–157° C.

Analysis Calculated for C$_{21}$H$_{20}$FNO$_2$: C, 74.76; H, 5.98; F, 5.63; N, 4.15.

Found: C, 74.47; H, 6.01; F, 5.82; N, 4.82.

EXAMPLE 239

Preparation of (E)-3-[3-(4-fluorophenyl)-1-(1-methylethyl)-1H-indol-2-yl]-2-propen-1-ol As in Example 227, (E)-3-[3-(4-fluorophenyl)-1-(1-methylethyl)-1H-indol-2-yl]-2-propenoic acid methyl ester (4.43 g) in dry dichloromethane (60 mL) was treated with diisobutylaluminum hydride in toluene (1.5M; 30 mL) at −65° C. for 1 hour, then was worked up as previously described to give 4.15 g of (E)-3-[3-(4-fluorophenyl)-1-(1-methylethyl)-1H-indol-2-yl]-2-propen-1-ol as a yellow oil. A portion (0.2 g) was purified by chromatography over silica gel (diethyl ether-hexane; 1:19) to furnish 0.175 g of the analytically pure alcohol as an oil.

Analysis Calculated for C$_{20}$H$_{20}$FNO: C, 77.64; H, 6.52; F, 6.14; N, 4.53.

Found: C, 77.42; H, 6.69; F, 6.42; N, 4.35.

EXAMPLE 240

Preparation of (E)-4-[3-[3-(4-fluorophenyl)-1-(1-methylethyl)-1H-indol-2-yl]-2-propenyloxy]-alpha-oxobenzeneacetic acid methyl ester As in Example 15, (E)-3-[3-(4-fluorophenyl)-1-(1-methylethyl)- 1H-indol-2-yl]-2-propen-1-ol (1.0 g) was reacted with 4-hydroxyphenylglyoxylic acid methyl ester (0.585 g) in the presence of diethyl azodicarboxylate (0.71 g) and triphenylphosphine (1.06 g) in tetrahydrofuran (30 mL). The crude reaction product, isolated in the usual manner, was purified by flash chromatography over silica gel (130 g; ethyl acetate-hexane; 1:4) to furnish 0.61 g of (E)-4-[3-[3-(4-fluorophenyl)-1-(1-methylethyl)-1H-indol-2-yl]-2-yl]-2-propenyloxy]-alpha-oxobenzeneacetic acid methyl ester as a yellow oil. A portion (0.2 g) was rechromatographed over silica gel (diethyl ether-hexane; 1:19) to furnish 0.225 g of the analytically pure ester as an oil.

Analysis Calculated for C$_{29}$H$_{26}$FNO$_4$: C, 73.87; H, 5.56; F, 4.03; N, 2.97.

Found: C, 73.49; H, 5.93; F, 3.78; N, 2.88.

EXAMPLE 241

Preparation of (E)-4-[3-[3-(4-fluorophenyl)- 1-(1-methylethyl)-1H-indol-2-yl]-2-propenyloxy]alpha-oxobenzeneacetic acid (1:1) morpholine salt As in Example 19, (E)-4-[3-[3-(4-fluorophenyl)-1-(1-methylethyl)-1H-indol-2-yl]-2-propenyloxy]-alpha-oxobenzeneacetic acid methyl ester (0.354 g) in methanol (5 mL) was treated with 1N sodium hydroxide (0.9 mL). The usual work up gave 0.4 g of a oil, which was dissolved in diethyl ether and morpholine (0.07 g) was added. Crystallization was induced and the recovered solid was recrystallized from dichloromethane-ethyl acetate to provide 0.26 g of (E)-4-[3-[3-(4-fluorophenyl)-1-(1-methylethyl)-1H-indole-2-yl]-2-propenyloxy]-alpha-oxobenzeneacetic acid (1:1) morpholine salt as a colorless solid, mp 151°–152° C.

Analysis Calculated for C$_{28}$H$_{24}$FNO$_4$·C$_4$H$_9$NO: C, 70.57; H, 6.11; F, 3.49; N, 5.14. Found: C, 69.88; H, 6.22; F, 3.79; N, 4.90.

EXAMPLE 242

Preparation of (E)-4-[3-[1-(4-fluorophenyl)-4-(1-methylethyl)-2-phenyl-1H-imidazol-5-yl]-2-propenyloxy]-alpha-oxobenzeneacetic acid methyl ester As in Example 15, (E)-3-[1-(4-fluorophenyl)-4-(1-methylethyl)-2-phenyl-1H-imidazol-5-yl]-2-propen-1-ol (0.773 g) was reacted with 4-hydroxyphenylglyoxylic acid methyl ester (0.378 g) in the presence of diethyl azodicarboxylate (0.418 g) and triphenylphosphine (0.63 g) in tetrahydrofuran (20 mL). The crude reaction product, isolated in the usual manner, was purified by flash chromatography over silica gel (90 g; ethyl acetate-hexane; 1:3) to give 0.65 g of (E)-4-[3-[1-(4-fluorophenyl)-1-(1-methylethyl)-1H-indol-2-yl]-2-propenyloxy]-alpha-oxobenzeneacetic acid methyl ester as a pale yellow solid. A portion was crystallized from diethyl ether-hexane to provide the analytical specimen, mp 132°–133° C.

Analysis Calculated for C$_{30}$H$_{27}$FN$_2$O$_4$: C, 72.28; H, 5.46; F, 3.81; N, 5.62. Found: C, 71.97; H, 5.44; F, 3.75; N, 5.36.

EXAMPLE 243

Preparation of (E)-4-[3-[1-(4-fluorophenyl)-4-(1-methylethyl)-2-phenyl-1H-imidazol-5-yl]-2-propenyloxy]-alpha-oxobenzeneacetic acid methyl ester monohydrate and its (1:1) morpholine salt As in Example 19, (E)-4-[3-[1-(4-fluorophenyl)-4-(1-methylethyl)-2-phenyl-1H-imidazol-5-yl]-2-propenyloxy]-alpha-oxobenzeneacetic acid methyl ester (0.5 g) in methanol (5 mL) was treated with 1N sodium hydroxide (1.1 mL). The usual work up provided 0.5 g of a solid that was crystallized from acetone-hexane to furnish 0.42 g of (E)-4-[3-[1-(4-fluorophenyl)-4-(1-methylethyl)-2-phenyl-1H-imidazol-5-yl]-2-propenyloxy]-alpha-oxobenzeneacetic acid mono hydrate as a colorless solid, mp 183°–185° C.

Analysis Calculated for $C_{29}H_{25}FN_2O_4 \cdot H_2O$: C, 69.31; H, 5.42; F, 3.78; N, 5.57. Found: C, 69.63; H, 5.10; F, 3.36; N, 5.36.

A portion was converted as in Example 212 to its morpholine salt, which was crystallized from ethyl acetate-cyclohexane to give the analytical sample, mp 122°–124° C.

Analysis Calculated for $C_{29}H_{25}FN_2O_4 \cdot C_4H_9NO$: C, 69.34; H, 6.00; F, 3.32; N, 7.35 Found: C, 69.52; H, 6.31; F, 3.13; N, 6.86.

EXAMPLE 244

Preparation of alpha-oxo-4-[2-oxo-2-(4-pheny;-1-piperidinyl)ethoxy]-benzeneacetic acid methyl ester A mixture of 4-hydroxy-alpha-oxobenzeneacetic acid methyl ester (0.611 g) in dimethylformamide (6 mL) under argon was treated with 55% sodium hydride (0.148 g), stirred for 30 minutes in a ice-water bath and then 1-(bromoacetyl)-4-phenyl-piperidine (0.8 g) in dimethylformamide (5 mL) was added. The solution was stirred at room temperature for 18 hours and worked up as in Example 20. The crude product was purified by flash chromatography (ethyl acetate-hexane; 3:7 increasing to 2:5) to provide 0.9 g of 4-[2-oxo-2-(4-phenyl-1-piperidinyl)ethoxy]-alpha-oxobenzeneacetic acid methyl ester as an oil.

Analysis Calculated for $C_{22}H_{23}NO_5$: C, 69.28; H, 6.08; N, 3.67, Found: C, 68.75; H, 5.99; N, 3.75.

EXAMPLE 245

Preparation of alpha-oxo-4-[2-oxo-2-(4-phenyl-1-piperidinyl)ethoxy]-benzeneacetic acid 4-[2-Oxo-2-(4-phenyl-1-piperidinyl)ethoxy]-alpha-oxobenzeneacetic acid ethyl ester (0.9 g) in methanol (80 mL) was treated with 1N sodium hydroxide solution (2.6 mL), and the mixture was stirred at room temperature for 25 minutes. After the methanol was evaporated under reduced pressure, water (25 mL) was added and the solution was acidified with 3N hydrochloric acid, then the aqueous layer was extracted with a dichloromethane-tetrahydrofuran mixture (35 mL; 5:2). The organic layer was dried (MgSO4), evaporated and the resulting solid was crystallized from dichloromethane-tetrahydrofuran-hexane and then from dichloromethane-tetrahydrofuran to furnish 0.25 g of 4-[2-oxo-2-(4-phenyl-1-piperidinyl)ethoxy]-alpha-oxobenzeneacetic acid, mp 209°–210° C. An additional 0.16 g of the acid was recovered from the mother liquor.

Analysis Calculated for $C_{21}H_{21}NO_5$: C, 68.65; H, 5.76; N, 3.81. Found: C, 68.26; H, 5.69; N, 3.70.

EXAMPLE 246

Preparation of 4-[2-(cyclooctylamino)-2-oxoethoxy]-alpha-oxobenzeneacetic acid methyl ester Bromoacetyl chloride (0.25 mL) was added slowly to a chilled (ice-water-bath) solution of cyclooctylamine (0.763g) in dichloromethane (15 mL) and the mixture was stirred with cooling for 45 minutes, then at room temperature overnight. After water (20 mL) was added, the layers were separated and the dried organic layer (MgSO4) was evaporated to provide 0.7 g of N-cyclooctyl-bromoacetamide. A solution of 4-hydroxy-alpha-oxobenzeneacetic acid methyl ester (0.605 g) in dimethylformamide (8 mL) under argon was treated with 55% sodium hydride (0.147 g), stirred for 30 minutes and then N-cyclooctyl-bromoacetamide (0.7 g) in dimethylformamide (5 mL) was added. The solution was stirred at room temperature for 18 hours and worked up as in Example 20. The crude material was purified by flash chromatography (ethyl acetate-hexane; 3:7) to yield 0.4 g of 4-[2-(cyclooctylamino)-2-oxoethoxy]-alpha-oxobenzeneacetic acid methyl ester as an oil.

Analysis Calculated for $C_{19}H_{25}NO_5$: C, 65.69; H, 7.25; N, 4.03. Found: C, 65.54; H, 7.29; N, 3.98.

EXAMPLE 247

Preparation of 4-[2-(cyclooctylamino)-2-oxoethoxy]-alpha-oxobenzeneacetic acid

A solution of 4-[2-(cyclooctylamino)-2-oxoethoxy]-alpha-oxobenzeneacetic acid methyl ester (0.4 g) in methanol (40 mL) was treated with 1N sodium hydroxide solution (1.3 mL), and the mixture was stirred at room temperature for 15 minutes. After the solvents were evaporated under reduced pressure, water (20 mL) was added and the solution was acidified with 3N hydrochloric acid, then the aqueous layer was extracted with a mixture of dichloromethane-tetrahydrofuran (30 mL; 2:1). The organic layer was dried (MgSO4), evaporated and the resulting oil was crystallized from diethyl ether-hexane to yield 0.084 g of 4-[2-(cyclooctylamino)-2-oxoethoxy]-alpha-oxobenzeneacetic acid, mp 139°–140 ° C.

Analysis Calculated for $C_{18}H_{23}NO_5$: C, 64.85; H, 6.95; N, 4.20. Found: C, 64.63; H, 6.84; N, 4.02.

EXAMPLE 248

Preparation of 4-[2-oxo-2-(4-phenyl-1-piperazinyl)ethoxy]-alpha-oxobenzeneacetic acid ethyl ester A mixture of 4-hydroxy-alpha-oxobenzeneacetic acid ethyl ester (0.582 g) in dimethylformamide (8 mL) under argon was treated with 55% sodium hydride (0.131 g), stirred for 30 minutes in a ice-water bath and then 1-(bromoacetyl)-4-phenyl-piperazine (1.0 g) in dimethylformamide (5 mL) was added. The solution was stirred at room temperature for 18 hours and worked up as in Example 20. The crude product was purified by HPLC (ethyl acetate-hexane; 1:1) to yield 0.8 g of 4-[2-oxo-2-(4-phenyl-1-piperazinyl)ethoxy]-alpha-oxobenzeneacetic acid ethyl ester as an oil.

Analysis Calculated for $C_{22}H_{24}N_2O_5$: C, 66.65; H, 6.10; N, 7.07. Found: C, 66.71; H, 6.34; N, 7.09.

EXAMPLE 249

Preparation of
4-[2-oxo-2-(4-phenyl-1-piperazinyl)ethoxy]-alpha-oxobenzeneacetic acid 4-[2-Oxo-2-(4-phenyl-1-piperazinyl)ethoxy]-alpha-oxobenzeneacetic acid ethyl ester (0.7 g) in methanol (40 mL) was treated with sodium carbonate (0.24 g) in water (6 mL), and the mixture was stirred at room temperature for 1.25 hours. After the methanol was evaporated under reduced pressure, water was added and the solution was acidified with 3N hydrochloric acid, then the aqueous layer was extracted with a dichloromethane-tetrahydrofuran mixture (1:1). The organic layer was dried (MgSO₄), evaporated, and the residue was crystallized from acetone to furnish 0.3 g of 4-[2-oxo-2-(4-phenyl-1-piperazinyl)ethoxy]-alpha-oxobenzeneacetic acid, mp 188°–192 ° C.

Analysis Calculated for $C_{20}H_{20}N_2O_5$: C, 65.21; H, 5.47; N, 7.60. Found: C, 65.08; H, 5.39; N, 7.41.

EXAMPLE 250

Preparation of
4-[2-oxo-2-(1,2,3,4-tetrahydro-2-isoquinolinyl)ethoxy]-alpha-oxobenzeneacetic acid ethyl ester Bromoacetyl chloride (0.25 mL) was added slowly to a cold (5° C.) solution of 1,2,3,4-tetrahydroisoquinoline (0.8 g) in dichloromethane (25 mL) and the mixture was stirred in an ice bath for 45 minutes, then at room temperature overnight. Water (20 mL) was added, the layers were separated and the organic layer was washed in turn with 0.5N hydrochloric acid and sodium bicarbonate solution. The dried extract (MgSO₄) was evaporated to provide 0.762 g of 2-(2-bromo-1-oxoethyl)-1,2,3,4-tetrahydroisoquinoline.

A mixture of 4-hydroxy-alpha-oxobenzeneacetic acid ethyl ester (0.582 g) in dimethylformamide (8 mL) under argon was treated with 55% sodium hydride (0.141 g), stirred for 30 minutes and then 2-(2-bromo-1-oxoethyl)-1,2,3,4-tetrahydroisoquinoline (0.762 g) in dimethylformamide (6 mL) was added. The solution was stirred at room temperature for 20 hours and worked up as in Example 20. The crude product was purified by HPLC (ethyl acetate-hexane; 2:3) to yield 0.3 g of 4-[2-oxo-2-(1,2,3,4-tetrahydro-2-isoquinolinyl)ethoxy]-alpha-oxobenzeneacetic acid ethyl ester as an oil.

Analysis Calculated for $C_{21}H_{21}NO_5$: C, 68.65; H, 5.76; N, 3.81. Found: C, 67.93; H, 5.70; N, 4.03.

EXAMPLE 251

Preparation of
4-[2-oxo-2-(1,2,3,4-tetrahydro-2-isoquinolinyl)ethoxy]-alpha-oxobenzeneacetic acid 4-[2-Oxo-2-(1,2,3,4-tetrahydro-2-isoquinolinyl)ethoxy]-alpha-oxobenzeneacetic acid ethyl ester (0.3 g) in methanol (10 mL) was treated with sodium carbonate (0.113 g) in water (3 mL), and the mixture was stirred at room temperature for 20 minutes. After the solvents were removed in vacuo, water (10 mL) was added and the solution acidified with 3N hydrochloric acid, then the aqueous layer was extracted with dichloromethane-tetrahydrofuran (1:1). The organic layer was dried (MgSO₄), evaporated and the residual solid was crystallized from acetone-tetrahydrofuran-hexane to yield 0.078 g of 4-[2-oxo-2-(1,2,3,4-tetrahydro-2-isoquinolinyl)ethoxy]-alpha-oxobenzeneacetic acid, mp 218°–220° C.

Analysis Calculated for $C_{19}H_{17}NO_5$: C, 67.25; H, 5.05; N, 4.13. Found: C, 67.45; H, 4.92; N, 4.02.

EXAMPLE 252

Preparation of
alpha-oxo-4-[2-oxo-2-[4-[2-[2-(trifluoromethyl)phenyl]ethyl]-1-piperazinyl]ethoxy]-bezeneacetic acid ethyl ester Bromoacetyl chloride (0.125 mL) was added slowly to a chilled (5 ° C.) solution of 1-[2-[2-(trifluoromethyl)phenyl]ethyl]piperazine (0.774 g) in dichloromethane (20 mL) and the mixture was stirred in an ice bath for 45 minutes, then at room temperature for 18 hours. After the addition of water (20 mL), the organic layer was separated and washed in turn with 0.5N hydrochloric acid and sodium bicarbonate solution. The dried (MgSO₄) extract was evaporated to give 0.5 g of 1-(2-bromo-1-oxoethyl)-4-[2-[2-(trifluoromethyl)phenyl]ethyl]piperazine.

A mixture of 4-hydroxy-alpha-oxobenzeneacetic acid ethyl ester (0.256 g) in dimethylformamide (4 mL) under argon was treated with 55% sodium hydride (0.06 g), stirred for 15 minutes and then the above 1-(2-bromo-1-oxoethyl)-4-[2-[2-(trifluoromethyl)phenyl]ethyl]piperazine (0.5 g) in dimethylformamide (2 mL) was added. The mixture was stirred at room temperature for 23 hours and worked up as in Example 20. The crude product was purified by flash chromatography over silica gel (ethyl acetate-toluene; 1:1 increasing to 4:1) to afford 0.21 g of alpha-oxo-4-[2-oxo-2-[4-[2-[2-(trifiuoromethyl)phenyl]ethyl]-1-piperazinyl]ethoxy]-benzeneacetic acid ethyl ester as an oil.

EXAMPLE 253

Preparation of
alpha-oxo-4-[2-oxo-2-[4-[2-[2-(trifluoromethyl)phenyl]ethyl]-1-piperazinyl]ethoxy]benzeneacetic acid (1:1) hydrochloride A solution of alpha-oxo-4-[2-oxo-2-[4-[2-[2-(trifluoromethyl)phenyl]ethyl]-1-piperazinyl]ethoxy]benzeneacetic acid ethyl ester (0.21 g) in methanol (10 mL) was treated with sodium carbonate (0.059 g) in water (3 mL), and the mixture was stirred at room temperature for 20 minutes. After the solvents were removed in vacuo, water (10 mL) were added and the solution was acidified with 3N hydrochloric acid. The resulting solids were filtered off, dried and crystallized from tetrahydrofuran-dichloromethane-hexane to yield 0.1 g of alpha-oxo-4-[2-oxo-2-[4-[2-[2 -(trifluoromethyl)phenyl]ethyl]-1-piperazinyl]ethoxy]benzeneacetic acid hydrochloride salt, mp 196°–199° C.

Analysis Calculated for $C_{23}H_{23}F_3N_2O_5 \cdot HCl$: C, 55.14; H, 4.83; F, 11.38; N, 5.59. Found: C, 55.76; H, 4.83; F, 12.00; N, 5.60.

EXAMPLE 254

Preparation of
4-[2-(4-morpholinyl)-2-oxoethoxy]-alpha-oxobenzeneacetic acid ethyl ester A mixture of 4-hydroxy-alpha-oxobenzeneacetic acid ethyl ester (0.71 g) in dimethylformamide (7 mL) under argon was treated with 55% sodium hydride (0.16 g), stirred for 15 minutes and then 4-(bromoacetyl)morpholine (0.76 g) in dimethylformamide (5 mL) was added. The mixture was stirred at room temperature for 18 hours and worked up as in Example 20. The crude product was purified by HPLC (toluene-hexane; 3:1) and then crystallized twice from ethyl acetate-hexane to provide 0.76 g of 4-[2-(4-morpholinyl)-2-oxoethoxy]-alpha-oxobenzeneacetic acid ethyl ester, mp 103°–106° C.

Analysis Calculated for $C_{16}H_{19}NO_6$: C, 59.81; H, 5.96; N, 4.36. Found: C, 59.59; H, 6.00; N, 4.23.

EXAMPLE 255

Preparation of 4-[2-(4-morpholinyl)-2-oxoethoxy]-alpha-oxobenzeneacetic acid

4-[2-(4-Morpholinyl)-2-oxoethoxy]-alpha-oxobenzeneacetic acid ethyl ester (0.4 g) in methanol (70 mL) was treated with sodium carbonate (0.158 g) in water (2 mL), and the mixture was stirred at room temperature for 1.5 hours. After the solvents were removed in vacuo, dichloromethane (40 mL) and water (40 mL) were added and the mixture was acidified with 3N hydrochloric acid. Tetrahydrofuran was added to dissolve the solids, then the separated aqueous layer was extracted twice with dichloromethane-tetrahydrofuran (1:1). The combined organic layers were dried (MgSO4), evaporated, and the residual solid was crystallized from dichloromethane-tetrahydrofuran-hexane to yield 0.36 g of 4-[2-(4-morpholinyl)-2-oxoethoxy]-alpha-oxobenzeneacetic acid, mp 182°–184° C.

Analysis Calculated for $C_{14}H_{15}NO_6$: C, 57.34; H, 5.16; N, 4.78. Found: C, 56.96; H, 5.06; N, 4.63.

EXAMPLE 256

Preparation of 4-[3-(4-acetyl-3-hydroxy-2-propylphenoxy)propoxy]-alpha-oxobenzeneacetic acid ethyl ester A mixture of 4-hydroxy-alpha-oxobenzeneacetic acid ethyl ester (0.776 g) in dimethylformamide (10 mL) under argon was treated with 55% sodium hydride (0.175 g), stirred for 15 minutes and then 1-[4-(3-bromopropoxy)-2-hydroxy-3-propylphenyl] ethanone (1.26 g) was added and rinsed in with a little dimethylformamide. The mixture was heated at 50° C. for 6 hours and worked up as in Example 20. The crude material was purified by HPLC (ethyl acetate-hexane; 1:4) to furnish 0.7 g of 4-[3-(4-acetyl-3-hydroxy-2-propylphenoxy)propoxy]-alpha-oxobenzeneacetic acid ethyl ester as an oil.

Analysis Calculated for $C_{24}H_{28}O_7$: C, 67.28; H, 6.59. Found: C, 66.95; H, 6.57.

EXAMPLE 257

Preparation of 4-[3-(4-acetyl-3-hydroxy-2-propylphenoxy)propoxy]-alpha-oxobenzeneacetic acid A solution of 4-[3-(4-acetyl-3-hydroxy-2-propylphenoxy)propoxy]-alpha-oxobenzeneacetic acid ethyl ester (0.7 g) in methanol (50 mL) was treated with sodium carbonate (0.38 g) in water (2.5 mL), and the reaction was stirred at room temperature for 2 hours. After the solvents were removed in vacuo, dichloromethane (40 mL) and water (40 mL) were added and the mixture was acidified with 3N hydrochloric acid. The dried (Na2SO4) organic layer was evaporated, and the residue was crystallized from dichloromethane-hexane to yield in two crops, 0.435 g of 4-[3-(4-acetyl-3-hydroxy-2-propylphenoxy)propoxy]-alpha-oxobenzeneacetic acid, mp 129°–130° C.

Analysis Calculated for $C_{22}H_{24}O_7$: C, 65.99; H, 6.04. Found: C, 66.14; H, 6.10.

EXAMPLE 258

Preparation of 4-[6-[2,3-bis-(phenylmethoxy)phenyl]hexyloxy]-alpha-oxobenzeneacetic acid ethyl ester A solution of 4-hydroxy-alpha-oxobenzeneacetic acid ethyl ester (0.97 g) in dimethylformamide (12 mL) was treated with 55% sodium hydride (0.22 g), stirred for 15 minutes and then 1,2-bis-(phenylmethoxy)-3-(6-bromohexyl)benzene (2.27 g) was added and rinsed in with dimethylformamide (3 mL). The mixture was stirred overnight at room temperature and worked up as in Example 20. The residual oil was purified by HPLC (ethyl acetate-hexane; 1:9) and crystallized from diethyl ether-hexane to provide 1.7 g of 4-[6-[2,3-bis-(phenylmethoxy)phenyl]hexyloxy]-alpha-oxobenzeneacetic acid ethyl ester, mp 39°–42° C.

Analysis Calculated for $C_{36}H_{38}O_6$: C, 76.30; H, 6.76. Found: C, 76.53; H, 6.72.

EXAMPLE 259

Preparation of 4-[6-[2,3-bis-(phenylmethoxy)phenyl]hexyloxy]-aipha-oxobenzeneacetic acid 4-[6-[2,3-bis-(Phenylmethoxy)phenyl]hexyloxy]-alpha-oxobenzeneacetic acid ethyl ester (0.5 g) in methanol (50 mL) was treated with sodium carbonate (0.121 g) in water (2 mL), and the reaction was stirred at room temperature for 3 hours. After the solvents were removed in vacuo, dichloromethane and water were added and the mixture was acidified with 3N hydrochloric acid. The dried (Na2SO4) organic layer was evaporated to yield 0.4 g of 4-[6-[2,3-bis-(phenylmethoxy)phenyl]hexyloxy]-alpha-oxobenzeneacetic acid as an oil.

Analysis Calculated for $C_{34}H_{34}O_6$: C, 75.82; H, 6.36. Found: C, 75.30; H, 6.47.

EXAMPLE 260

Preparation of 4-[6-(2,3-dihydroxyphenyl)hexyloxy]-alpha-oxobenzeneacetic acid

A mixture of 4-[6-[2,3-bis-(phenylmethoxy)phenyl]-hexyloxy]-alpha-oxobenzeneacetic acid (0.3 g) in acetic acid (20 mL) containing concentrated hydrochloric acid (5 mL) was stirred at 80° C. for 2.5 hours. The cooled solution was diluted with water (100 mL) and extracted with three portions of ethyl acetate, then the combined extracts were dried (Na2SO4), and evaporated in vacuo. The residual oil was triturated in turn with cyclohexane and carbon tetrachloride to remove non polar impurities, then was crystallized from dichloromethane and recrystallized from dichloromethane-carbon tetrachloride to give 4-[6-(2,3-dihydroxyphenyl)hexyloxy]-alpha-oxobenzeneacetic acid as a colorless solid, mp 127°–130° C.

Analysis Calculated for $C_{20}H_{22}O_7$: C, 67.03; H, 6.19. Found: C, 66.38; H, 6.27.

EXAMPLE 261

Preparation of
4-[3-(5,6-dihydro-6-oxo-5-phenanthridinyl)propoxy]-alpha-oxobenzeneacetic acid ethyl ester A solution of 4-hydroxy-alpha-oxobenzeneacetic acid ethyl ester (0.376 g) in dimethylformamide (5 mL) was treated with 55% sodium hydride (0.085 g), stirred for 15 minutes and then 5-(3-bromopropyl)-5,6-dihydro-6-oxophenanthridine (0.613 g) in dimethylformamide (5 mL) was added. The mixture was stirred at room temperature for 22 hours and worked up as in Example 20. The residual oil was purified by HPLC (ethyl acetate-hexane; 7:13), and crystallization of the resulting solid from ethyl acetate-tetrahydrofuran gave 0.4 g of 4-[3-(5,6-dihydro-6-oxo-5-phenanthridinyl)propoxy]-alpha-oxobenzeneacetic acid ethyl ester, mp 95°–97° C. A second crop of the title compound (0.16 g, mp 95°–97° C.) was recovered from the mother liquor.

Analysis Calculated for $C_{26}H_{23}NO_5$: C, 72.71; H, 5.40; N, 3.26. Found: C, 72.37; H, 5.41; N, 3.13.

EXAMPLE 262

Preparation of
4-[3-(5,6-dihydro-6-oxo-5-phenanthridinyl)propoxy]-alpha-oxobenzeneacetic acid A solution of 4-[3-(5,6-dihydro-6-oxo-5-phenanthridinyl)propoxy]-alpha-oxobenzeneacetic acid ethyl ester (0.4 g) in hot methanol (80 mL) was treated with sodium carbonate (0.118 g) in water (1.5 mL), and the reaction was stirred at room temperature for 4 hours. After the methanol was removed in vacuo, dichloromethane and water were added and the mixture was acidified with 3N hydrochloric acid. The resulting solid was filtered off, dried and crystallized from ethyl acetate-tetrahydrofuran to yield 0.321 g of 4-[3-(5,6-dihydro-6-oxo-5-phenanthridinyl)propoxy]-alpha-oxobenzeneacetic acid in two crops, mp 202°–204° C.

Analysis Calculated for $C_{24}H_{19}NO_5$: C, 71.81; H, 4.77; N, 3.49. Found: C, 71.36; H, 4.64; N, 3.25.

EXAMPLE 263

Preparation of
4-[3-(1,2-dihydro-2-oxo-1-quinolinyl)propoxy]-alpha-oxobenzeneacetic acid ethyl ester A solution of 4-hydroxy-alpha-oxobenzeneacetic acid ethyl ester (0.73 g) in dimethylformamide (10 mL) was treated with 55% sodium hydride (0.164 g), stirred for 15 minutes and then 1-(3-bromopropyl)-1,2-dihydro-2-oxoquinoline (1 g) was added and rinsed in with dimethylformamide (4 mL). The mixture was stirred at room temperature for 22 hours and worked up as in Example 20. The residual solid was purified by flash chromatography over silica gel (ethyl acetate-hexane; 1:4). Crystallization of the resulting solid furnished 1.0.g of 4-[3-(1,2-dihydro-2-oxo-1-quinolinyl)propoxy]-alpha-oxobenzeneacetic acid ethyl ester, mp 108°–109° C.

Analysis Calculated for $C_{22}H_{21}NO_5$: C, 69.69; H, 5.58; N, 3.69. Found: C, 69.78; H, 5.54; N, 3.63.

EXAMPLE 264

Preparation of
4-[3-(1,2-dihydro-2-oxo-1-quinolinyl)propoxy]-alpha-oxobenzeneacetic acid A solution of 4-[3-(1,2-dihydro-2-oxo-1-quinolinyl)propoxy]-alpha-oxobenzeneacetic acid ethyl ester (0.5 g) in hot methanol (50 mL) was treated with sodium carbonate (0.14 g) in water (1.5 mL), and the reaction was stirred at room temperature for 5 hours. After the methanol was removed in vacuo, dichloromethane and water were added and the mixmre was acidified with 3N hydrochloric acid. The precipitated solid was faltered off, dried and then crystallized from ethyl acetate-tetrahydrofuran to afford 0.337 g of 4-[3-(1,2-dihydro-2-oxo-1-quinolinyl)propoxy]-alpha-oxobenzeneacetic acid, mp 183°–186° C.

Analysis Calculated for $C_{20}H_{17}NO_5$: C, 68.37; H, 4.88; N, 3.39. Found: C, 68.11; H, 4.88; N, 3.74.

EXAMPLE 265

Preparation of
4-[5-[3,5-bis(1,1-dimethylethyl)-4-hydroxyphenyl]-5-oxopentyloxy]-alpha-oxobenzeneacetic acid ethyl ester 4-Hydroxy-alpha-oxobenzeneacetic acid ethyl ester (1.44 g) and 55% sodium hydride (0.36 g) in dimethylformamide (30 mL) was stirred for 20 minutes and then treated with 5-bromo-1-[3,5-bis(1,1-dimethylethyl)-4-[(2-methoxyethoxy) methoxy]phenyl]pentanone (3.4 g) in dimethylformamide (6 mL). The mixture was stirred at room temperature for 20 hours and then after an additional 4 hours at 50° C., it was worked up as in Example 20. The residual oil was purified by HPLC (ethyl acetate-toluene; 1:17) to give 2.7 g of 4-[5-[3,5-bis(1,1-dimethylethyl)-4-[(2-methoxyethoxy) methoxy]phenyl]-5-oxopentyloxy]-alpha-oxobenzeneacetic acid ethyl ester as an oil. A solution of the above 4-[5-[3,5-bis(1,1-dimethylethyl)-4-[(2-methoxyethoxy) methoxy]phenyl]-5-oxopentyloxy]-alpha-oxobenzeneacetic acid ethyl ester (2.1 g) was dissolved in dichloromethane (20 mL) containing trifluoroacetic acid (1.1 mL) was stirred at room temperature for 31 hours, then saturated sodium bicarbonate solution was added (25 mL). The separated organic layer was dried (MgSO$_4$) and evaporated and the crude product was purified by HPLC (ethyl acetate-hexane; 4:21). Trituration of the resulting material with hexane afforded 1.4 g of 4-[5-[3,5-bis(1,1-dimethylethyl) -4-hydroxyphenyl]-5-oxopentyloxy]-alpha-oxobenzeneacetic acid ethyl ester, mp 95°–96° C.

Analysis Calculated for $C_{29}H_{38}O_6$: C, 72.17; H, 7.94. Found: C, 72.01; H, 8.05.

EXAMPLE 266

Preparation of
4-[5-[3,5-bis(1,1-dimethylethyl)-4-hydroxyphenyl]-5-oxopentyloxy]-alpha-oxobenzeneacetic acid As in example 10, a solution of 4-[5-[3,5-bis(1,1-dimethylethyl)-4-hydroxyphenyl]-5-oxopentyloxy]-alpha-oxobenzeneacetic acid ethyl ester (0.8 g) in hot methanol (80 mL) was treated with 2N sodium hydroxide (1.75 mL) was stirred at room temperature for 75 minutes. The methanol was removed in vacuo, then the mixture was acidified with 3N hydrochloric acid and extracted with dichloromethane-tetrahydrofuran (2:1). The dried (MgSO$_4$) extracts were evaporated and the solid residue was triturated from hexane, and then crystallized from acetone-hexane to provide 0.7 g of 4-[5-[3,5-bis(1,1-dimethylethyl)-4-hydroxyphenyl]-5-oxopentyloxy]-alpha-oxobenzeneacetic acid, mp 144°–145° C.

Analysis Calculated for $C_{27}H_{34}O_6$: C, 71.34; H, 7.54. Found: C, 71.56; H, 7.61.

EXAMPLE 267

Preparation of 4-[3-[3-hydroxy-4-(methoxycarbonyl)-2-propylphenoxy)propoxy]-alpha-oxobenzeneacetic acid ethyl ester A mixture of 4-hydroxy-alpha-oxobenzeneacetic acid ethyl ester (0.47 g) and 55% sodium hydride (0.116 g) in dimethylformamide (10 mL) was stirred for 15 minutes and then treated with 4-(3-bromopropoxy)-2-hydroxy-3-propylbenzoic acid methyl ester (0.8 g) in dimethylformamide (5 mL). The mixture was heated at 50° C. for 20 hours and worked up as in Example 20. The residual oil was purified by flash chromatography over silica gel (ethyl acetate-hexane; 3:17) and then was crystallized from hexane to give 0.6 g of 4-[3-[3-hydroxy-4-(methoxycarbonyl)-2-propylphenoxy) propoxy]-alpha-oxobenzeneacetic acid ethyl ester, mp 62°–64° C.

Analysis Calculated for $C_{24}H_{28}O_8$: C, 64.85; H, 6.35. Found: C, 64.90; H, 6.10.

EXAMPLE 268

Preparation of 4-[3-[3-hydroxy-4-(methoxycarbonyl)-2-propylphenoxy)propyl]-alpha-oxobenzeneacetic acid As in Example 19, a solution of 4-[3-[3-hydroxy-4-(methoxycarbonyl)-2-propylphenoxy)propoxy]-alpha-oxobenzeneacetic acid ethyl ester (0.3 g) in methanol (30 mL) was treated with 4N sodium hydroxide (0.53 mL) and then was stirred at room temperature for 1 hour. Most of the solvents were removed in vacuo, then the mixture was acidified with 3N hydrochloric acid and extracted with ethyl acetate. The dried (MgSO$_4$) extracts were evaporated and the crude oil was crystallized from a carbon tetrachloride-hexane mixture containing a small amount of dichloromethane to yield 0.164 g of 4-[3-[3-hydroxy-4-(methoxycarbonyl)-2-propylphenoxy)propoxy]-alpha-oxobenzeneacetic acid, as a colorless solid, mp 86°–87° C.

Analysis Calculated for $C_{22}H_{24}O_8$: C, 63.45; H, 5.81. Found: C, 63.45; H, 5.68.

EXAMPLE 269

Preparation of 4-[3-[4-carboxy-3-hydroxy-2-propylphenoxy)propoxy]-alpha-oxobenzeneacetic acid A solution of 4-[3-[3-hydroxy-4-(methoxycarbonyl)-2-propylphenoxy)propoxy]-alphaoxobenzeneacetic acid (0.3 g) in methanol (30 mL) was treated with 4N sodium hydroxide (0.58 mL) was stirred at reflux for 46 hours. The methanol was removed in vacuo, then the mixture was acidified with 3N hydrochloric acid and extracted with dichloromethane-tetrahydrofuran (1:1). The dried (MgSO$_4$) extracts were evaporated and the solid residue was crystallized from dichloromethane-hexane, and then from acetone-hexane to afford 4-[3-[4-carboxy-3-hydroxy-2-propylphenoxy)propoxy]-alpha-oxobenzeneacetic acid, mp 182°–185° C.

Analysis Calculated for $C_{21}H_{22}O_8$: C, 62.68; H, 5.51. Found: C, 62.46; H, 5.27.

EXAMPLE 270

Preparation of 4-[3-[4-acetyl-3-methoxy-2-propylphenoxy)propoxy]-alpha-oxobenzeneacetic acid ethyl ester A solution of 4-hydroxy-alpha-oxobenzeneacetic acid ethyl ester (0.471 g) in dimethylformamide (10 mL) was treated with 55% sodium hydride (0.117 g), stirred for 15 minutes and then a solution of with 1-[4-(3-bromopropoxy)-2-methoxy-3propylphenyl]ethanone (0.8 g) in dimethylformamide (5 mL) was added. The mixture was heated at 50° C. for 17 hours and worked up as in Example 20. The residual oil was purified by HPLC (ethyl acetate-hexane; 1:4), followed by flash chromatography over silica gel (ethyl acetate-toluene; 1:19) to yield 0.4 g of 4-[3-[4-acetyl-3-methoxy-2-propylphenoxy)propoxy]-alpha-oxobenzeneacetic acid ethyl ester as an oil.

Analysis Calculated for $C_{25}H_{30}O_7$: C, 67.86; H, 6.83. Found: C, 67.81; H, 7.00.

EXAMPLE 271

Preparation of 4-[3-[4-acetyl-3-methoxy-2-propylphenoxy)propoxy]-alpha-oxobenzeneacetic acid As in example 10, a solution of 4-[3-[4-acetyl-3-methoxy-2-propylphenoxy)propoxy]-alpha-oxobenzeneacetic acid ethyl ester (0.4 g) in methanol (30 mL) was treated with 2N sodium hydroxide (0.25 mL) was stirred at room temperature for 4 hours. Most of the solvents were removed in vacuo, water was added, then the mixture was acidified with 3N hydrochloric acid and extracted with dichloromethane-tetrahydrofuran (1:1). The dried (MgSO$_4$) extracts were evaporated and the crude oil was purified by flash chromatography over silica gel (toluene-ethyl acetate-acetic acid; 75:25:0.5 increasing to 74:25:1) and crystallized from diethyl ether-hexane to provide 0.13 g of 4-[3-[4-acetyl-3-methoxy-2-propylphenoxy)propoxy]-alpha-oxobenzeneacetic acid, mp 94°–96° C.

Analysis Calculated for $C_{23}H_{26}O_7$: C, 66.65; H, 6.32. Found: C, 66.45; H, 6.42.

EXAMPLE 272

Preparation of 4-[3-(4-acetyl-3-hydroxyphenoxy)propoxy]-alpha-oxobenzeneacetic acid ethyl ester 4-Hydroxy-alpha-oxobenzeneacetic acid ethyl ester (1.2 g) in dimethylformamide (20 mL) under argon was stirred with 55% sodium hydride (0.299 g) for 15 minutes and then was treated with 1-[4-(3-bromopropoxy)-2-hydroxyphenyl]ethanone (1.7 g) in dimethylformamide (4 mL). The mixture was heated at 50° C. for 5 hours and worked up as in Example 20. The material was purified by HPLC (ethyl acetate-hexane; 1:39) to provide 0.8 g of an oil that was triturated with hexane to give 0.7 g of 4-[3-(4-acetyl-3-hydroxyphenoxy)propoxy]-alpha-oxobenzeneacetic acid ethyl ester as a colorless solid, mp 63°–65° C.

Analysis Calculated for $C_{21}H_{22}O_7$: C, 65.28; H, 5.74. Found: C, 65.23; H, 5.68.

EXAMPLE 273

Preparation of 4-[3-(4-acetyl-3-hydroxyphenoxy)propoxy]-alpha-oxobenzeneacetic acid As in example 10, 4-[3-(4-acetyl-3-hydroxyphenoxy)propoxy]-alpha-oxobenzeneacetic acid ethyl ester (0.7 g) in methanol (70 mL) was treated with a solution of sodium carbonate (0.42 g) in water and brought just to reflux temperature, then was allowed to cool to room temperature. After 1 hour, most of the methanol was removed in vacuo, then the mixture was diluted with water, acidified with 3N hydrochloric acid and extracted twice with dichloromethane-tetrahydrofuran (1:1). Evaporation of the dried (MgSO4) extracts and crystallization of the solid residue from dichloromethane-hexane afforded 0.58 g of 4-[3-(4-acetyl-3-hydroxyphenoxy)propoxy]-alpha-oxobenzeneacetic acid, mp 133°-135° C.

Analysis Calculated for $C_{19}H_{18}O_7$: C, 63.68; H, 5.06. Found: C, 63.11; H, 5.03.

EXAMPLE 274

Preparation of 4-[3-[[3,5-bis(1,1-dimethylethyl)-4-hydroxyphenyl]thio]propoxy]-alpha-oxobenzeneacetic acid ethyl ester A mixture of 4-hydroxy-alpha-oxobenzeneacetic acid ethyl ester (0.33 g) in dimethylformamide (6 mL) under argon was treated with 55% sodium hydride (0.082 g), stirred for 15 minutes then 3,5-bis(1,1-dimethylethyl)-4-[(3-bromopropyl)thio]phenol (0.61 g) was added. The mixture was heated at 50° C. for 20 hours and worked up as in Example 20. The residual oil was purified by flash chromatography over silica gel (ethyl acetate-hexane; 1:19) to provide 0.8 g of an oil that was triturated with hexane to give 0.331 g of 4-[3-[[3,5-bis(1,1-dimethylethyl)-4-hydroxyphenyl]thio]propoxy]-alpha-oxobenzeneacetic acid ethyl ester.

EXAMPLE 275

Preparation of 4-[3-[[3,5-bis(1,1-dimethylethyl)-4-hydroxyphenyl]thio]propoxy]-alpha-oxobenzeneacetic acid As in Example 19, a solution of 4-[3-[[3,5-bis(1,1-dimethylethyl)-4-hydroxyphenyl] thio]propoxy]-alpha-oxobenzeneacetic acid ethyl ester (0.32 g) in methanol (15 mL) was treated with 2N sodium hydroxide (0.75 mL) was stirred at room temperature. After 3 hours, most of the methanol was removed in vacuo, then the mixture was acidified with 3N hydrochloric acid and extracted with dichloromethane-tetrahydrofuran (1:1). The dried (MgSO4) extracts were evaporated and the crude product was purified by flash chromatography over silica gel (toluene-ethyl acetate-acetic acid; 80:20:0.25 increasing to 74:25:1) to give 4-[3-[[3,5-bis(1,1-dimethylethyl)-4-hydroxyphenyl]thio]propoxy]-alpha-oxobenzeneacetic acid as an oil.

Analysis Calculated for $C_{25}H_{32}O_5S$: C, 67.54; H, 7.25; S, 7.21. Found: C, 67.32; H, 7.09; S, 7.31.

EXAMPLE 276

Preparation of rac-delta-hydroxy-2-naphthalenebutanol

A solution of diborane in tetrahydrofuran (1M; 120 mL) was added dropwise with stirring to a cooled (−10° C.) solution of gamma-oxo-2-naphthalenebutanoic acid (10 g) in dry tetrahydrofuran (120 mL). The stirred mixture was maintained at ice bath temperature for 3 hours before the slow addition of a 10% solution of acetic acid in ethyl acetate (100 mL). The solvents were removed in vacuo and the residue partitioned between ethyl acetate (150 mL) and 1N hydrochloric acid (100 mL). The separated aqueous layer was extracted with ethyl acetate (50 mL), then the organic layers were washed in turn with 1N hydrochloric acid (2×100 mL) and brine. Evaporation of the combined, dried (MgSO4) extracts gave 7.3 g of crude diol that was first purified by HPLC (ethyl acetate-hexane; 4:1) and then crystallized from ethyl acetate-hexane to provide 4.11 g of rac-delta-hydroxy-2-naphthalenebutanol as a colorless solid.

EXAMPLE 277

Preparation of rac-alpha-(3-mesyloxypropyl)-2-naphthalenemethanol

Methanesulfonyl chloride (0.77 g was added slowly with stirring to a cooled (−40° C.) solution of rac-delta-hydroxy-2-naphthalenebutanol (1.45 g) in dry pyridine (6 mL). The mixture was stirred at −40° C. for 5 hours, then was poured into water (20 mL) and extracted with ethyl acetate (3×10 mL). The combined organic layers were washed in turn with water (2×10 mL), saturated magnesium sulfate solution (3×15 mL) and brine, then were dried (MgSO4) and evaporated. The resulting oil was purified by HPLC (ethyl acetate-hexane; 2:3) to provide 1.25 g of rac-alpha-(3-mesyloxypropyl)-2-naphthalenemethanol as an oil.

EXAMPLE 278

Preparation of rac-4-[4-[[(1,1-dimethylethyl)dimethylsilyl]oxy]-4-(2-naphthalenyl)butoxy]-alpha-oxobenzeneacetic acid methyl ester A mixture of rac-alpha-(3-mesyloxypropyl)-2-naphthalenemethanol (1.25 g), t-butyldimethylsilyl chloride (0.768 g) and imidazole (0.723 g) in dry dimethylformamide (14 mL) was stirred overnight at room temperature. The solvents were evaporated off and the residue was taken up in water (30 mL) and extracted with diethyl ether (3×8 mL). The combined organic layers were washed with brine (1×5 mL), then were dried (MgSO4) and evaporated to give 1.5 g of crude product. Purification of the material by HPLC (ethyl acetate-hexane; 3:17) furnished 1.25 g of rac-alpha-(3-mesyloxypropyl)-2-naphthalenemethanol protected as its t-butyldimethylsilyl ether derivative.

4-Hydroxy-alpha-oxobenzeneacetic acid methyl ester (0.611 g) in dimethylformamide (10 mL) under argon was treated with 55% sodium hydride (0.149 g), stirred for 30 minutes and then the above t-butyldimethylsilyl ether derivative (1.25 g) in dimethylformamide (5 mL). The mixture was stirred at 60° C. overnight and worked up as in Example 20 and the isolated material (1.25 g) was purified by flash chromatography over silica gel (ethyl acetate-hexane; 1:9) to provide of 1.11 g of rac-4-[4-[[(1,1-dimethylethyl)dimethylsilyl]oxy]-4-(2-naphthalenyl)butoxy]-alpha-oxobenzeneacetic acid methyl ester as an oil.

Analysis Calculated for $C_{29}H_{36}O_5Si$: C, 70.70; H, 7.37. Found: C, 70.69; H, 7.23.

EXAMPLE 279

Preparation of rac-4-[4-hydroxy-4-(2-naphthalenyl)butoxy]-alpha-oxobenzeneacetic acid methyl ester A solution of rac-4-[4-[[(1,1 -dimethylethyl)dimethylsilyl]oxy]-4-(2-naphthalenyl) butoxy]-alpha-oxobenzeneacetic acid methyl ester (1.0 g) in acetonitrile (22.5 mL) containing 48% aqueous hydrofluoric acid solution (2.5 mL) was stirred at room temperature for 1 hour. The reaction mixture was poured into saturated sodium bicarbonate solution and extracted with ethyl acetate (3×10 mL). The combined organic extracts were dried (MgSO4) and evaporated to provide 0.76 g of crude product that was purified by flash chromatography over silica gel (ethyl acetate-hexane; 7:13) to yield 0.554 g of rac-4-[4-hydroxy-4-(2-naphthalenyl)-butoxy]-alpha-oxobenzeneacetic acid methyl ester as an oil.

Analysis Calculated for $C_{23}H_{22}O_5$: C, 73.00; H, 5.86. Found: C, 72.89; H, 5.70.

EXAMPLE 280

Preparation of rac-4-[4-hydroxy-4-(2-naphthalenyl)butoxy]-alpha-oxobenzeneacetic acid As in Example 19, a stirred solution of rac-4-[4-hydroxy-4-(2-naphthalenyl)butoxy]-alpha-oxobenzeneacetic acid methyl ester (0.172 g) in warm methanol (2.5 mL) was treated with 1N sodium hydroxide (1 mL) and then water (25 mL) was added. After the methanol was removed in vacuo, the mixture was acidified with 1N hydrochloric acid (1.2 mL) and extracted with dichloromethane (1×50 mL, 1×10 mL). The dried (MgSO$_4$) extracts were concentrated and the residual gummy solid (~0.17 g) was crystallized from acetone-hexane to give 0.06 g of rac-4-[4-hydroxy-4-(2-naphthalenyl) butoxy]-alpha-oxobenzeneacetic acid as a colorless solid, mp 108°–110° C.

Analysis Calculated for $C_{22}H_{20}O_5$: C, 72.51; H, 5.53. Found: C, 73.21; H, 6.09.

EXAMPLE 281

Preparation of 4-[[4-(2-naphthalenyl)-4-oxobutyl]oxy]-alpha-oxobenzeneacetic acid methyl ester A solution of dimethylsulfoxide (0.079 g) in dichloromethane (2 mL) was added over 20 minutes to a stirred solution of oxalyl chloride (0.123 g) in dry dichloromethane (4 mL) maintained throughout at 178° C. by using an acetone-dry ice bath. After 30 minutes at −78° C., a solution of rac-4-[4-hydroxy-4-(2-naphthalenyl)-butoxy]-alpha-oxobenzeneacetic acid methyl ester (0.356 g) in dichloromethane (3 mL) was added over 30 minutes and the reaction mixture was stirred for 30 minutes in the acetone-dry ice bath, then triethylamine (0.144 mL) was added. The cooling bath was removed and the reaction was allowed to equilibrate to room temperature, then water was added and the phases were separated. After the aqueous layer was extracted with dichlormethane (2×7 mL), the combined organic layers were washed with brine, then were dried (MgSO$_4$) and evaporated. The residue was purified by flash chromatography over silica gel (ethyl acetate-hexane; 1:3) and then crystallized from ethyl acetate-hexane to furnish in two crops, 0.299 g of 4-[[4-(2-naphthalenyl)-4-oxobutyl]oxy]-alpha-oxobenzeneacetic acid methyl ester, mp 86°–87° C.

Analysis Calculated for $C_{23}H_{22}O_5$:C, 73.39; H, 5.36. Found: C, 73.49; H, 5.33.

EXAMPLE 282

Preparation of 4-[[4-(2-naphthalenyl)-4-oxobutyl]oxy]-alpha-oxobenzeneacetic acid As in Example 19, a stirred solution of 4-[[4-(2-naphthalenyl)-4-oxobutyl]oxy]-alpha-oxobenzeneacetic acid methyl ester (0.299 g) in hot methanol (2.5 mL) was treated with 1N sodium hydroxide (1.75 mL) and then water (25 mL) was added. After the methanol was removed in vacuo, the mixture was acidified with 1N hydrochloric acid (2.1 mL) and extracted with dichloromethane (1×40 mL, 1×20 mL). The dried (Na$_2$SO$_4$) extracts were evaporated and the residue was crystallized from acetone-hexane to give 0. 179 g of 4-[[4-(2-naphthalenyl)-4-oxobutyl]oxy]-alpha-oxobenzeneacetic acid as a colorless solid, mp 133°–135° C.

Analysis Calculated for $C_{22}H_{20}O_5$: C, 72.92; H, 5.01. Found: C, 73.95; H, 6.05.

EXAMPLE 283

Preparation of 4-[2-(1-naphthalenyl)-2-oxoethoxy]-alpha-oxobenzeneacetic acid methyl ester (4:1) molar hydrate Sodium hydride (55%; 0.238 g) and 4-hydroxy-alpha-oxobenzeneacetic acid methyl ester (0.978 g) in dimethylformamide (12 mL) were stirred at room temperature for 30 minutes and then 2-chloro-1-(1-naphthalenyl)ethanone (1 g) in dimethylformamide (6 mL) was added. The reaction mixture was stirred at 60° C. overnight and worked up as in Example 20. The crude product (1.7 g) was purified by flash chromatography over silica gel (ethyl acetate-hexane-dichloromethane; 2.5:37.5:60) to afford of 0.277 g of 4-[2-(1 -naphthalenyl)-2-oxoethoxy]-alpha-oxobenzeneacetic acid methyl ester. Crystallization of the ester from ethyl acetate-hexane gave the analytical specimen, mp 99°–100.5° C.

Analysis Calculated for $C_{21}H_{16}O_5.4{:}1H_2O$: C, 71.48; H, 4.71. Found: C, 71.49; H, 4.74.

EXAMPLE 284

Preparation of 4-[2-(1-naphthalenyl)-2-oxoethoxy]-alpha-oxobenzeneacetic acid methyl ester To a hot solution of 4-[2-(1-naphthalenyl)-2-oxoethoxy]-alpha-oxobenzeneacetic acid methyl ester (0.128 g) in methanol (3 mL) and tetrahydrofuran (0.5 mL) was added 1N sodium hydroxide (0.8 mL) followed by water (15 mL). The solvents were removed under reduced pressure, then the solution was acidified with 1N hydrochloric acid (1 mL) and extracted with dichloromethane (1×20 mL, 1×10 mL). The combined organic layers were washed with water, dried (MgSO$_4$) and evaporated and the resulting yellow solid (0.107 g) was crystallized from ethyl acetate-hexane to provide 0.063 g of 4-[2-(1-naphthalenyl)-2-oxoethoxy]-alpha-oxobenzeneacetic acid, mp 141°–143° C.

Analysis Calculated for $C_{20}H_{14}O_5$: C, 71.85; H, 4.22. Found: C, 72.01; H, 4.30.

EXAMPLE 285

Preparation of 4-[2-[4-(1,1-dimethylethyl)phenyl-2-oxoethoxy]-alpha-oxobenzeneacetic acid methyl ester A mixture of sodium hydride (55%; 0.224 g) and 4-hydroxy-alpha-oxobenzeneacetic acid methyl ester (0.918 g) in dimethylformamide (12 mL) were stirred at room temperature for 30 minutes and then 2-chloro-1-[4-(1,1-dimethylethyl)phenyl]ethanone (1 g) in dimethylformamide (6 mL) was added. The reaction mixture was stirred at 60° C. overnight and worked up as in Example 20. The crude product (1.97 g) was purified initially by HPLC (ethyl acetate-hexane; 1:3) to give 0.79 g of material that was further purified by flash chromatography over silica gel (ethyl acetate-hexane-dichloromethane; 3:37:60) to afford of 0.535 g of 4-[2-[4-(1,1-dimethylethyl)phenyl-2-oxoethoxy]-alpha-oxobenzeneacetic acid methyl ester as an oil.

EXAMPLE 286

Preparation of
4-[2-[4-(1,1-dimethylethyl)phenyl-2-oxoethoxy]-alpha-oxobenzeneacetic acid A solution of 4-[2-[4-(1,1-dimethylethyl)phenyl-2-oxoethoxy]-alpha-oxobenzeneacetic acid methyl ester (0.354 g) in hot methanol (10 mL) was treated with 1N sodium hydroxide (2.2 mL) and then diluted with water (30 mL). After the methanol was removed in vacuo, the solution was acidified with 1N hydrochloric acid (2.7 mL) and extracted with dichloromethane (1×70 mL, 1×15 mL). The combined organic layers were washed with water, dried (MgSO₄) and evaporated and the residual material (0.296 g) was crystallized from ethyl acetate-hexane to furnish 0.217 g of 4-[2-[4-(1,1-dimethylethyl)phenyl-2-oxoethoxy]-alpha-oxobenzeneacetic acid, mp 132°–134° C.

Analysis Calculated for $C_{20}H_{20}O_5$: C, 70.58; H, 5.92. Found: C, 71.12; H, 5.92.

EXAMPLE 287

Preparation of
4-[2-[[1,1'-biphenyl]-2-yl]-2-oxoethoxy]-alpha-oxobenzeneacetic acid methyl ester 4-Hydroxy-alpha-oxobenzeneacetic acid methyl ester (0.721 g) in dimethylformamide (8 mL) under argon was treated with 55% sodium hydride (0.175 g), stirred for 30 minutes and then 1-[1,1'-biphenyl]-2-yl-2-bromoethanone (1.1 g) in dimethylformamide (4 mL). The mixture was stirred at room temperature overnight and worked up as in Example 20. The residual oil (1.5 g) was purified by flash chromatography over silica gel (dichloromethane) to afford of 0.62 g of 4-[2-[[1,1'-biphenyl]-2-yl]-2-oxoethoxy]-alpha-oxobenzeneacetic acid methyl ester as an oil.

Analysis Calculated for $C_{23}H_{18}O_5$: C, 73.79; H, 4.85. Found: C, 74.04; H, 4.82.

EXAMPLE 288

Preparation of
4-[2-[[1,1'-biphenyl]-2-yl]-2-oxoethoxy]-alpha-oxobenzeneacetic acid A solution of 4-[-2-[[1,1'-biphenyl]-2-yl]-2-oxoethoxy]-alpha-oxobenzeneacetic acid methyl ester (0.563 g) in warm methanol (5 mL) was treated with 1N sodium hydroxide (3.3 mL). Within 5 minutes water (30 mL) was added, then after the methanol was removed in vacuo, the mixture was acidified with 1N hydrochloric acid (4.1 mL) and extracted with dichloromethane (1×60 mL, 2×10 mL). The combined organic layers were washed with water, then dried (MgSO₄) and evaporated. The resulting yellow foam was taken up in diethyl ether, and after the the mixture was filtered to remove some insoluble material, the fillrate was evaporated and the residue was lyophilized from benzene to furnish 0.36 g of 4-[2-[[1,1'-biphenyl]-2-yl]-2-oxoethoxy]-alpha-oxobenzeneacetic acid.

Analysis Calculated for $C_{22}H_{16}O_5$: C, 73.33; H, 4.48. Found: C, 73.54; H, 4.53.

EXAMPLE 289

Preparation of
4-(2-cyclooctyl-2-oxoethoxy)-alpha-oxobenzeneacetic acid ethyl ester 55% Sodium hydride (0.14 g) was stirred with 4-hydroxy-alpha-oxobenzeneacetic acid ethyl ester (0.622 g) in dimethylformamide (8 mL) under argon for 30 minutes and then the solution was treated with 2-chloro-1-cyclooctylethanone (0.53 g) in dimethylformamide (3 mL). The mixture, stirred at room temperature overnight and the at 60° C. for 1 hour, was worked up as in Example 20. The residual oil was purified by flash chromatography over silica gel (3% ethyl acetate in dichloromethane-hexane 1:1 ) to provide of 0.399 g of 4-(2-cyclooctyl-2-oxoethoxy)-alpha-oxobenzeneacetic acid ethyl ester as an oil.

Analysis Calculated for $C_{20}H_{26}O_5$: C, 69.34; H, 7.57. Found: C, 69.02.; H, 7.60.

EXAMPLE 290

Preparation of
4-[2-(cyclooctyl)-2-oxoethoxy]-alpha-oxobenzeneacetic acid

As in example 19, a stirred solution of 4-(2-cyclooctyl-2-oxoethoxy)-alpha-oxobenzeneacetic acid ethyl ester (0.318 g) in warm methanol (5 mL) was treated with 1N sodium hydroxide (2 mL). Within 5 minutes water (20 mL) was added, then after the methanol was removed in vacuo, the mixture was acidified with 1N hydrochloric acid (2.5 mL) and extracted with dichloromethane (1×40 mL, 1×10 mL). The dried (MgSO₄) extracts were evaporated and the resulting solid (0.255 g) was crystallized from diethyl ether-hexane to give 0.178 g of 4-[2-(cyclooctyl)-2-oxoethoxy]-alpha-oxobenzeneacetic acid as a colorless solid, mp 109°–110° C.

Analysis Calculated for $C_{18}H_{22}O_5$: C, 67.91; H, 6.97. Found: C, 67.75; H, 6.97.

EXAMPLE 291

Preparation of
4-[2-oxo-2-(2,4,6-trimethylphenyl]ethoxy]-alpha-oxobenzeneacetic acid ethyl ester 4-Hydroxy-alpha-oxobenzencacetic acid ethyl ester (0.583 g) in dimethylformamide (6 mL) under argon was treated with 55% sodium hydride (0.131 g), stirred for 30 minutes and then 2-bromo-(2,4,6-triphenyl)ethanone (0.723 g) in dimethylformamide (2 mL) was added. The reaction mixture was stirred at room temperature overnight and worked up as in Example 20. The isolated material (1.15 g) was purified by flash chromatography over silica gel (dichloromethane) to yield of 0.468 g of 4-[2-oxo-2-(2,4,6-trimethylphenyl]ethoxy]-alpha-oxobenzeneacetic acid ethyl ester as an oil which solidified on standing, mp 68.5°–70° C.

Analysis Calculated for $C_{21}H_{22}O_5$: C, 71.17; H, 6.26. Found: C, 70.88; H, 6.17.

EXAMPLE 292

Preparation of
4-[2-oxo-2-(2,4,6-trimethylphenyl]ethoxy]-alpha-oxobenzeneacetic acid A solution of 4-[2-oxo-2-(2,4,6-trimethylphenyl]ethoxy]-alpha-oxobenzeneacetic acid ethyl ester (0.357 g) in hot methanol (5 mL) was treated with 1N sodium hydroxide (2 mL). Water (20 mL) was added, then after the methanol was removed in vacuo, the solution was acidified with 1N hydrochloric acid (2.5 mL) and extracted with dichloromethane methane (1×40 mL, 1×7 mL). The combined organic layers were washed with brine, then dried (MgSO4) and evaporated. The resulting residue was crystallized from diethyl ether-hexane to furnish 0.242 g of 4-[2-oxo-2-(2,4,6-trimethylphenyl)ethoxy]-alpha-oxobenzeneacetic acid, mp 144°–145° C.

Analysis Calculated for $C_{19}H_{18}O_5$: C, 69.93; H, 5.56. Found: C, 70.01; H, 5.66.

EXAMPLE 293

Preparation of 4-[3-[4-(2-chlorophenyl)-9-methyl-6H-thieno[3,2-f][1,2,4]triazolo[4,3-a][1,4]=diazepin-2-yl]-2-propynyloxy]-alpha-oxobenzeneacetic acid ethyl ester (4:1) hydrate As in Example 15, 4-(-2-chlorophenyl)-2-(3-hydroxy-1-propynyl)-9-methyl-6H-thieno[3,2-f][1,2,4]triazolo[4,3-a][1,4]diazepine (0.369 g) was reacted with 4-hydroxyphenylglyoxylic acid ethyl ester (0.195 g) in the presence of diethyl azodicarboxylate (0.175 g) and triphenylphosphine (0.263 g) in dichloromethane (30 mL). The crude reaction product, isolated in the usual manner, was purified by flash chromatography over silica gel (120 g; ethanol-dichloromethane; 3.5:96.5) to furnish 0.398 g of 4-[3-[4-(2-chlorophenyl)-9-methyl-6H-thieno[3,2-f][1,2,4]triazolo[4,3-a][1,4]diazepin-2-yl]-2-propynyloxy]-alpha-oxobenzeneacetic acid ethyl ester (4:1 ) hydrate as a white foam.

Analysis Calculated for $C_{28}H_{21}ClN_4O_4S.4:1H_2O$: C, 61.20; H, 3.94; Cl, 6.45; N, 10.20; S, 5.83. Found: C, 61.13; H, 3.94; Cl, 6.66; N, 10.24; S, 5.65.

EXAMPLE 294

Preparation of 4-[3-[4-(2-chlorophenyl)-9-methyl-6H-thieno[3,2-f][1,2,4]triazolo[4,3-a][1,4]diazepin-2-yl]-2-propynyloxy]-alpha-oxobenzeneacetic acid (20:9) dichioromethane solvate A solution of 4-[3-[4-(2-chlorophenyl)-9-methyl-6H-thieno[3,2-f][1,2,4]triazolo[4,3-a][1,4]diazepin-2-yl]-2-propynyloxy]-alpha-oxobenzeneacetic acid ethyl ester (4:1) hydrate (0.306 g) in hot methanol (4 mL) was treated with 1N sodium hydroxide (1.8 mL) and then diluted with water (18 mL). After the methanol was removed in vacuo, the solution was acidified with 1N hydrochloric acid (2.2 mL) and extracted with dichloromethane (1×40 mL, 1×10 mL). The combined organic layers were washed with brine, dried (MgSO4) and evaporated to furnish 0.276 g of 4-[3-[4-(2-chlorophenyl)-9-methyl-6H-thieno[3,2-f][1,2,4]triazolo[4,3-a][1,4]diazepin-2-yl]-2-propynoloxy]-alpha-oxobenzeneacetic acid (20:9) dichloromethane solvate as a light yellow powder.

Analysis Calculated for $C_{26}H_{17}ClN_4O_4S.20:9CH_2Cl_2$: C, 57.22; H, 3.43; Cl, 12.13; N, 10.09; S, 5.77. Found: C, 56.97; H, 3.37; Cl, 11.84; N, 9.95; S, 5.24.

EXAMPLE 295

Preparation of 4-[3-[4-(2-chlorophenyl)-9-methyl-6H-thieno[3,2-f][1,2,4]triazolo[4,3-a][1,4]diazepin-2-yl]propoxy]-alpha-oxobenzeneacetic acid ethyl ester As in Example 15, 4-(-2-chlorophenyl)-2-(3-hydroxy-1-propyl)-9-methyl-6H-thieno[3,2-f][1,2,4]triazolo[4,3-a][1,4]diazepine (0.322 g) was treated with 4-hydroxyphenylglyoxylic acid ethyl ester (0.168 g) in the presence of diethyl azodicarboxylate (0.155 g) and triphenylphosphine (0.227 g) in dichloromethane (23 mL). The crude ester, isolated in the usual manner, was purified by flash chromatography over silica gel (150 g; ethanol-dichloromethane; 3.5:96.5) to furnish 0.354 g of 4-[3-[4-(2-chlorophenyl)-9-methyl-6H-thieno[3,2-f][1,2,4]triazolo[4,3-a][1,4]diazepin-2-yl] propoxy]-alpha-oxobenzcneacetic acid ethyl ester as a white foam.

Analysis Calculated for $C_{28}H_{25}ClN_4O_4S$: C, 61.25; H, 4.59; Cl, 6.46; N, 10.20; S, 5.84. Found: C, 61.04; H, 4.63; Cl, 6.18; N, 10.01; S, 5.63.

EXAMPLE 296

Preparation of 4-[3-[4-(2-chlorophenyl)-9-met hyl -6H-thieno[3,2-f][1,2,4]triazolo[4,3-a][1,4]diazepin-2-yl]-2-propoxy]-alpha-oxobenzeneacetic acid (10:7) hydrate(25:2) dichloromethane solvate A solution of 4-[3-[4-(2-chlorophenyl)-9-methyl-6H-thieno[3,2-f][1,2,4]triazolo[4,3-a][1,4]diazepin-2-yl]propoxy]-alpha-oxobenzeneacetic acid ethyl ester (0.3 g) in hot methanol (3 mL) was treated with 1N sodium hydroxide (1.1 mL) and then diluted with water (30 mL). After the methanol was removed in vacuo, the solution was acidified with 1N hydrochloric acid (1.2 mL) and extracted with dichlorormthane (3×15 mL). The combined organic layers were washed with brine, dried (MgSO4) and evaporated to yield 0.2 g 4-[3-[4-(2-chlorophenyl)-9-methyl-6H-thieno[3,2-f][1,2,4]triazolo[4,3-a][1,4]diazepin-2-yl]-2-propoxy]-alpha-oxobenzeneacetic acid (10:7) hydrate (25:2) dichloromethane solvale as a light yellow powder.

Analysis Calculated for $C_{26}H_{21}ClN_4O_4S.4:1H_2O.25:2CH_2Cl_2$: C, 57.97; H, 4.21;Cl, 7.61; N, 10.37; S, 5.93. Found: C, 57.76; H, 4.17; Cl, 7.81; N, 10.13; S, 5.83.

EXAMPLE 297

Preparation of (S)-alpha-[[(1,1-dimethyethoxy)carbonyl] amino]-4-[2-[2-[(2,2 dimethyl-1-oxobutoxy)methyl]-6-methylphenoxy]ethoxy]benzeneacetic acid benzyl ester As described in Example 15, a solution of diethyl azodicarboxylate (1.79 g) in dry tetrahydrofuran (15 mL) was added to a chilled (0°–5° C.) solution of (S)-alpha-amino-N-[[(1,1-dimethyethyl)oxy]carbonyl]-4-hydroxybenzeneacetic acid benzyl ester (2.93 g), 2-[2-[(2,2-dimethyl-1-oxobutoxy)methyl]-6-methylphenoxy]ethanol (2.3 g) and triphenylphosphine (2.69 g) in dry tetrahydrofuran (50 mL). After the reaction mixture was stirred at 0°–5° C. for 4 hours then at room temperature overnight, the reaction was worked up as previously described. Purification of the crude product by using HPLC (ethyl acetate-hexane; 3:17) furnished 3.56 g of (S)-alpha-[[(1,1-dimethyethoxy) carbonyl]amino]-4-[2-[2-[(2,2-dimethyl-1-oxobutoxy)methyl]-6-methylphenoxy] ethoxy]benzeneacetic acid benzyl ester as a colorless oil, $[\alpha]_D +31.52°$ (c, 1.21, methanol).

EXAMPLE 298

Preparation of
(S)-alpha-amino-4-[2-[2-[(2,2-dimethyl-1-oxobutoxy)-methyl]-6-methylphenoxy]ethoxy]benzeneacetic acid As in Example 17, a solution of (S)-alpha-[[(1,1-dimethyethoxy)carbonyl]amino]-4-[2-[2-[(2,2-dimethyl-1-oxobutoxy)methyl]-6-methylphenoxy]ethoxy]benzeneacetic acid benzyl ester (2.59 g) in dichloromethane (8 mL) containing trifluoroacetic acid (8 mL) was stirred at room temperature for 45 minutes. The crude product was isolated in the previously described manner, was purified by HPLC (ethyl acetate-hexane; 1:1) to furnish 1.97 g of (S)-alpha-amino-4-[2-[2-[(2,2-dimethyl-1-oxobutoxy)methyl]-6-methylphenoxy]ethoxy]benzeneacetic acid benzyl ester as an oil.

A solution of the benzyl ester (1.48 g) in methanol (50 mL) containing one drop of acetic acid was hydrogenated over 10% Palladium on carbon (0.15 g) at ambient temperature and pressure for 1 hour. The reaction was diluted with methanol (100 mL) to dissolve the precipitated solids, then the catalyst was filtered off through a bed of Celite. The tiltrates were evaporated and the resulting off-white solid was slurried with several portions of diethyl ether, then filtered and dried in vacuo to provide 0.9 g of (S)-alpha-amino-4-[2-[2-[(2,2-dimethyl-1-oxobutoxy)methyl]-6-methylphenoxy]ethoxy]benzeneacetic acid as a white solid, mp 170°–172° C., $[\alpha]_D +36.26°$ (c, 0.95, methanol).

Analysis Calculated for $C_{24}H_{31}NO_6$: C, 67.11; H, 7.27; N, 3.26. Found: C, 66.86; H, 7.22; N, 3.18.

EXAMPLE 299

Preparation of
N-hydroxy-N-methyl-4-[2-(2-naphthalenyloxy)ethoxy]-alpha-oxobenzeneacetamide A solution of 4-[2-(2-naphthalenyloxy)ethoxy]-alpha-oxobenzeneacetyl chloride, derived from 4-[2-(2-naphthalenyloxy)ethoxy]-alpha-oxobenzeneacetic acid (0.312 g) in the previously described manner (Example 6), in dichloromethane was treated with a solution of N-methylhydroxylamine hydrochloride (0.094 g) in pyridine (1.5 mL). After the reaction solution was stirred at room temperature for 18 hours, it was concentated in vacuo and then diluted with water. The resulting fine yellow precipitate was filtered off, dried and crystallized from methanol-water to afford 0.129 g of N-hydroxy-N-methyl-4-[2-(2-naphthalenyloxy)ethoxy]-alpha-oxobenzeneacetamide, mp 161°–165° C.

Analysis Calculated for $C_{21}H_{19}NO_5$: C, 69.03; H, 5.24; N, 3.83, Found: C, 69.26; H, 5.14; N, 3.62.

EXAMPLE 300

Preparation of
N-hydroxy-5-[2-(2-naphthalenyloxy)ethoxy]-alpha-oxo-2-thiopheneacetamide A solution of (E)-5-[2-(2-naphthalenyloxy)ethoxy]-alpha-oxo-2-thiopheneacetic acid ethyl ester (1.48 g) in a mixture of ethanol (20 mL) and tetrahydrofuran (10 mL) was treated in turn with hydroxylamine hydrochloride (0.77 g) and triethylamine (1.825 mL). After the reaction solution was stirred 50° C. for 18 hours, it was concentated in vacuo and was then taken up in dichloromethane (100 mL) and 0.1N hydrochloric acid (120 mL). The resulting dense precipitate was filtered off, then was washed in turn with dichloromethane and water to yield 1.1 g N-hydroxy-5-[2-(2-naphthalenyloxy) ethoxy]-alpha-oxo-2-thiopheneacetamide as an off-white solid. A portion (0.1 g) was crystallized from tetrahydrofuran-2-propanol to give the analytical specimen, mp 165°–167° C.

Analysis Calculated for $C_{18}H_{15}NO_5S$: C, 60.49; H, 4.23; N, 3.92; S, 8.97. Found: C, 60.59; H, 4.53; N, 3.74; S, 8.38.

EXAMPLE 301

Preparation of
(Z)-alpha-(hydroxyimino)-4-[2-(2-naphthalenyloxy)ethoxy]benzeneacetic acid A solution of hydroxylamine hydrochloride (0.089 g) in 1N sodium hydroxide solution (1.3 mL) was added to a solution of 4-[2-(2-naphthalenyloxy)ethoxy]-alpha-oxobenzeneacetic acid (0.291 g) in dimethylformamide and the mixture was heated on a steam bath till all the solids dissolved. The reactants were maintained in solution by intermittent heating over 2 hours, then the mixture was stirred at room temperature overnight. The formed precipitate was filtered off, then the filtrate was diluted with water and adjusted to pH 2 by the addition of dilute hydrochloric acid solution. The resulting solid was recovered by filtration and dried in vacuo to furnish 0.164 g of (Z)-alpha-(hydroxyimino-4-[2-(2-naphthalenyloxy)ethoxy]benzeneacetic acid, mp 178°–179° C.

Analysis Calculated for $C_{20}H_{17}NO_5$: C, 68.37; H, 4.88; N, 3.99. Found: C, 68.09; H, 4.85; N, 3.95.

EXAMPLE 302

Preparation of
(Z)-alpha-(hydroxyimino)-5-[2-(2-naphthalenyloxy)ethoxy]-2-thiopheneacetic acid A solution of (E)-5-[2-(2-naphthalenyloxy)ethoxy]-alpha-oxo-2-thiopheneacetic acid (0.637 g) in dimethylformamide (10 mL) was treated in turn with hydroxylamine hydrochloride (0.17 g) and triethylamine (0.675 mL). After the reaction solution was stirred at room temperature for 18 hours, a second portion of hydroxylamine hydrochloride (0.17 g) and triethylamine (0.675 mL) were added and the reaction was allowed to proceed at ambient temperature. After 22 hours, the solvent was removed in vacuo and the residual material was taken up in dichloromethane (50 mL) and 0.25N hydrochloric acid (25 mL). The separated aqueous layer was extracted with dichloromethane (3×50 mL), then the dichloromethane phase and extracts were backwashed in turn with brine (25 mL). Concentration of the combined, dried (MgSO₄) organic layers furnished 0.625 g of a dark oil that was crystallized two times from chloroform to give (Z)-alpha-(hydroxyimino)-5-[2-(2-naphthalenyloxy)ethoxy]-2-thiopheneacetic acid as an off white solid, mp 138°–140° C.; MS($C_{18}H_{15}NO_5S$), m/z 358 (M+1).

EXAMPLE 303

Preparation of
(Z)-4-[2-[2-[(2,2-dimethyl-1-oxobutoxy)methyl-]-6-methylphenyloxy]ethoxy]-alpha-methoxyiminobenzeneacetic acid methyl ester As described in Example 15, (E)-2,2-dimethylbutanoic acid [2-(2-hydroxyethoxy)-3-methylphenyl]-methyl ester (0.56 g) was reacted with 4-hydroxy-alpha-methoxyiminobenzeneacetic acid methyl ester (0.42 g) in the presence of diethyl azodicarboxylate (0.44 g) and triphenylphosphine (0.655 g) in tetrahydrofuran (20 mL). After the previously described work up, the methoxime was purified by chromatography over silica gel (75 g; diethyl ether-hexane; 1:4) to afford 0.405 g of (Z)-4-[2-[2-[(2,2-dimethyl-1-oxobutoxy)methyl]-6-methylphenyloxy]ethoxy]-alpha-methoxyiminobenzeneacetic acid methyl ester as a oil.

Analysis Calculated for $C_{26}H_{33}NO_7$: C, 66.62; H, 7.05; N, 2.97. Found: C, 66.30; H, 7.04: N, 2.79.

EXAMPLE 204

Preparation of
(Z)-4-[2-[2-[(2,2-Dimethyl-1-oxobutoxy)methyl]-6methylphenyloxy]ethoxy]-alpha-methoxyiminobenzeneacetic acid As in Example 19, (Z)-4-[2-[2-[(2,2-dimethyl-1-oxobutoxy)methyl]-6-methylphenyloxy]ethoxy]-alpha-methoxyiminobenzeneacetic acid methyl ester (0.231 g) in methanol (5 mL) was treated with 1N sodium hydroxide (0.54 mL) and the mixture was stirred overnight at room temperature. The usual work up gave 0.188 g of an oil which was purified by flash chromatography over silica gel (formic acid-diethyl ether 1:49) to yield 0.07 g of recovered starting ester along with 0.055 g of (Z)-4-[2-[2-[(2,2-dimethyl-1 -oxobutoxy)methyl]-6-methylphenyloxy]ethoxy]-alpha-methoxyiminobenzene acetic acid as an oil.

Analysis Calculated for $C_{25}H_{31}NO_7$: C, 65.63; H, 6.83; N 3.06. Found: C, 65.89; H, 7.12; N 2.82.

EXAMPLE 305

Preparation of
(E)-alpha-(methoxyimino)-5-[2-(2-naphthalenyloxy)ethoxy]-2-thiopheneacetic acid ethyl ester and
(Z)-alpha-(methoxyimino)-5-[2-(2-naphthalenyloxy)ethoxy]-2-thiopheneacetic acid ethyl ester 5-[2-(2-naphthalenyloxy)ethoxy]-alpha-oxo-2-thiopheneacetic acid (0.741 g) was combined with methoxylamine hydrochloride (0.2 g) in pyridine (10 mL) and stirred for 48 hours at room temperature, whereupon another 0.2 g of methoxylamine hydrochloride was added and the mixture was stirred for an additional 72 hours. After the solvent was removed under reduced pressure, the residue was partitioned between dichloromethane and water and the separated aqueous phase was extracted with dichloromethane. The combined organic layers were washed with water, dried ($MgSO_4$) and evaporated to yield 0.7 g of a yellow solid. Flash chromatography of the solid over silica gel (75 g: dichloromethane-hexane; 4:1) resulted in the isolation of two isomeric compounds.

The less polar isomer was crystallized from dichloromethane-hexane to give 0.265 g of (Z)-alpha-(methoxyimino)-5-[2-(2-naphthalenyloxy)ethoxy]-2-thiopheneacetic acid ethyl ester as pale yellow crystals, mp 152°-153.5° C.

Analysis Calculated for $C_{21}H_{21}NO_5S$: C, 63.14; H, 5.30; N, 3.51; S, 8.03. Found: C, 62.91; H, 5.36; N, 3.48; S, 7.89.

The more polar compound (0.3 g) was crystallized from dichloromethane-hexane to give 0.248 g (E)-alpha-(methoxyimino)-5-[2-(2-naphthalenyloxy)ethoxy]-2-thiopheneacetic acid ethyl ester as yellow crystals, mp 132°-133.5° C. Analysis Calculated for $C_{21}H_{21}NO_5S$: C, 63.14; H, 5.30; N, 3.51; S, 8.03. Found: C, 62.92; H, 5.24; N, 3.31; S, 8.06.

EXAMPLE 306

Preparation of
(Z)-alpha-(methoxyimino)-5-[2-(2-naphthalenyloxy)ethoxy]-2-thiopheneacetic acid (2:1) hydrate (Z)-alpha-(methoxyimino)-5-[2-(2-naphthalenyloxy)ethoxy]-2-thiopheneacetic acid ethyl ester (0.2 g) in methanol (2 mL) and tetrahydrofuran (2 mL) was treated with 3N sodium hydroxide (0.5 mL) and the stirred mixture was heated at 50° C. for 30 minutes. After the solvents were removed in vacuo, the concentrate was diluted with water (10 mL), acidified with 1N hydrochloric acid (3 mL) and extracted with dichloromethane (2×10 mL). The combined organic layers were washed with brine, dried ($MgSO_4$) and evaporated. The resulting solid was crystallized from dichloromethane-hexane to provide 0.157 g of (Z)-alpha-(methoxyimino)-5-[2-(2-naphthalenyloxy)ethoxy]-2-thiopheneacetic acid as its hernihydrate, mp 118°-120° C.

Analysis Calculated for $C_{19}H_{17}NO_5S.H_2O$: C, 59.99; H, 4.77; N, 3.68; S, 8.43. Found: C, 60.18; H, 4.57; N, 3.50; S, 8.52.

EXAMPLE 307

Preparation of
(E)-alpha-(methoxyimino)-5-[2-(2-naphthalenyloxy)ethoxy]-2-thiopheneacetic acid As in Example 306, a solution of (E)-alpha-(methoxyimino)-5-[2-(2-naphthalenyloxy) ethoxy]-2-thiopheneacetic acid ethyl ester (0.2 g) in methanol (2 mL) and tetrahydrofuran (1 mL) was treated with 3N sodium hydroxide (0.5 mL) and the stirred mixture was heated at 53° C. for 30 minutes. After the normal work up, the product was crystallized from dichloromethane-hexane to furnish 0.142 g of (E)-alpha-(methoxyimino)-5-[2-(2-naphthalenyloxy)ethoxy]-2-thiopheneacetic acid, mp 118°-120° C.

Analysis Calculated for $C_{19}H_{17}NO_5S$: C, 61.44; H, 4.61; N, 3.77; S, 8.63. Found: C, 61.17; H, 4.56; N, 3.62; S, 8.41.

EXAMPLE 308

Preparation of
(E)-alpha-(ethoxyimino)-5-[2-(2-naphthalenyloxy)ethoxy]-2-thiopheneacetic acid ethyl ester and
(Z)-alpha-(ethoxyimino)-5-[2-(2-naphthalenyloxy)ethoxy]-2-thiopheneacetic acid ethyl ester As described in example 305, 5-[2-(2-naphthalenyloxy)ethoxy]-alpha-oxo-2-thiopheneacetic acid (0.34 g) was combined with ethoxylamine hydrochloride (0.130 g) in pyridine (5 mL) and stirred for 10 days at room temperature. The rnixmre of isomers, obtained after work up of the reaction in the usual manner, were separated by flash chromatography over silica gel (70 g: dichlorornethane-hexane; 4:1 ). Fractions containing the less polar isomer were evaporated to give 0.151 g of (Z)-alpha-(ethoxyimino)-5-[2-(2-naphthalenyloxy)ethoxy]-2-thiopheneacetic acid ethyl ester, mp 114°-115.5° C.

Analysis Calculated for $C_{22}H_{23}NO_5S$: C, 63.91; H, 5.61; N, 3.39; S, 7.75. Found: C, 63.81; H, 5.30; N, 3.37; S, 7.82.

Fractions containing the more polar isomer were evaporated to give 0.158 g of (E)-alpha-(ethoxyimino)-5-[2-(2-naphthalenyloxy)ethoxy]-2-thiopheneacetic acid ethyl ester, mp 102.5°-104° C.

Analysis Calculated for $C_{22}H_{23}NO_5S$: C, 63.91; H, 5.61; N, 3.39; S, 7.75, Found: C, 63.66; H, 5.29; N, 3.12; S, 7.79.

EXAMPLE 309

Preparation of (Z)-alpha-(ethoxyimino)-5-[2-(2-naphthalenyloxy)ethoxy]-2-thiopheneacetic acid As in Example 306, a solution of (Z)-alpha-(ethoxyimino)-5-[2-(2-naphthalenyloxy) ethoxy]-2-thiopheneacetic acid ethyl ester (0. 141 g) in methanol (2 mL) and tetrahydrofuran (1 mL) was treated with 4N sodium hydroxide (0.5 mL) and the stirred mixture was heated at 55° C. for 30 minutes. After the normal work up, the product was crystallized from ethyl acetate-hexane to furnish 0.07 g of (Z-alpha-(ethoxyimino)-5-[2-(2-naphthalenyloxy)ethoxy]-2-thiopheneacetic acid, mp 114° C. (dec.).

Analysis Calculated for $C_{20}H_{19}NO_5S$: C, 62.32; H, 4.97; N, 3.65; S, 8.32. Found: C, 62.05; H, 4.82; N, 3.45; S, 8.25.

EXAMPLE 310

Preparation of (E)-alpha-(ethoxyimino)-5-[2-(2-naphthalenyloxy)ethoxy]-2-thiopheneacetic acid As in Example 306, a solution of (E)-alpha-(ethoxyimino)-5-[2-(2-naphthalenyloxy) ethoxy]-2-thiopheneacetic acid ethyl ester (0.131 g) in methanol (2 mL) and tetrahydrofuran (2 mL) was treated with 4N sodium hydroxide (0.5 mL) and the stirred mixture was heated at 55° C. for 45 minutes. After the usual work up, the isolated product was crystallized from ethyl acetate-hexane to afford 0.062 g of (E)-alpha-(ethoxyimino)-5-[2-(2-naphthalenyloxy)ethoxy]-2-thiopheneacetic acid, mp 17°–108° C. (dec.).

Analysis Calculated for $C_{20}H_{19}NO_5S$: C, 62.32; H, 4.97; N, 3.65; S, 8.32. Found: C, 63.23; H, 4.39; N, 3.62; S, 8.55.

EXAMPLE 311

Preparation of (E)-5-[2-(2-naphthalenyloxy)ethoxy]-alpha-[(2-propenyloxy)imino]-2-thiopheneacetic acid ethyl ester and (Z)-5-[2-(2-naphthalenyloxy)ethoxy]-alpha-[(2-propenyloxy)imino]-2-thiopheneacetic acid ethyl ester As described in Example 305, 5-[2-(2-naphthalenyloxy)ethoxy]-alpha-oxo-2-thiopheneacetic acid (0.34 g) was combined with 0-(2-propenyl)hydroxylamine hydrochloride (0.145 g) in pyridine (5 mL) and stirred for 72 hours at room temperature. The mixture of isomers, obtained after work up of the reaction were separated by flash chromatography over silica gel (70 g: dichloromethane-hexane; 4:1). Fractions containing the less polar isomer were evaporated to give 0.114 g of (Z)-5-[2-(2-naphthalenyloxy)ethoxy]-alpha-[(2-propenyloxy)imino]-2-thiopheneacetic acid ethyl ester, mp 104°–105° C.

Analysis Calculated for $C_{23}H_{23}NO_5S$: C, 64.92; H, 5.45; N, 3.29; S, 7.53. Found: C, 65.79; H, 5.67; N, 2.99; S, 7.00.

Fractions containing the more polar isomer were evaporated to give 0.075 g of (E)-5-[2-(2-naphthalenyloxy)ethoxy]-alpha-[(2-propenyloxy)imino]-2-thiopheneacetic acid ethyl ester, mp 75°–77° C.

Analysis Calculated for $C_{23}H_{23}NO_5S$: C, 64.92; H, 5.45; N, 3.29; S, 7.53. Found: C, 64.78; H, 5.42; N, 3.54; S, 7.37.

EXAMPLE 312

Preparation of (Z)-5-[2-(2-naphthalenyloxy)ethoxy]-alpha-[(2-propenyloxy)imino]-2-thiopheneacetic acid As in Example 306, a solution of (Z)-5-[2-(2-naphthalenyloxy)ethoxy]-alpha-[(2propenyloxy)imino]-2-thiopheneacetic acid ethyl ester (0.102 g) in methanol (2 mL) and tetrahydrofuran (1 mL) was treated with 4N sodium hydroxide (0.5 mL) and the stirred mixture was heated at 50° C. for 30 minutes. After the normal work up, the product was crystallized from ethyl acetate-hexane to furnish 0.057 g of (Z)-5-[2-(2-naphthalenyloxy)ethoxy]-alpha-[(2-propenyloxy)imino]-2-thiopheneacetic acid, mp 114°–115° C.

Analysis Calculated for $C_{21}H_{19}NO_5S$: C, 63.46; H, 4.82; N, 3.52; S, 8.07. Found: C, 63.26; H, 4.65; N, 3.43; S, 7.76.

EXAMPLE 313

Preparation of (E)-5-[2-(2-naphthalenyloxy)ethoxy]-alpha-[(2-propenyloxy)imino]-2-thiopheneacetic acid As in Example 306 a solution of (E)-5-[2-(2-naphthalenyloxy)ethoxy]-alpha-[(2propenyloxy)imino]-2-thiopheneacetic acid ethyl ester (0.064 g) in methanol (2 mL) and tetrahydrofuran (2 mL) was treated with 4N sodium hydroxide (0.5 mL) and the stirred mixture was heated at 55° C. for 45 minutes. After the normal work up, the product was crystallized from ethyl acetate-hexane to furnish 0.038 g of (E)-5-[2-(2-naphthalenyloxy)ethoxy]-alpha-[(2-propenyloxy)imino]-2-thiopheneacetic acid, mp 106°–108° C.

Analysis Calculated for $C_{21}H_{19}NO_5S$: C, 63.46; H, 4.82; N, 3.52; S, 8.07. Found: C, 63.72; H, 4.64; N, 3.49; S, 8.13.

EXAMPLE 314

Preparation of (E)-5-[2-(2-naphthalenyloxy)ethoxy]-alpha-[(phenylmethoxy)imino]-2-thiopheneacetic acid ethyl ester and (Z)-5-[2-(2-naphthalenyloxy)ethoxy]-alpha-[(phenylmethoxy)imino]-2-thiopheneacetic acid ethyl ester.

As described in example 305, 5-[2-(2-naphthalenyloxy)ethoxy]-alpha-oxo-2-thiopheneacetic acid (0.34 g) was combined with 0-benzylhydroxylamine hydrochloride (0.214 g) in pyridine (5 mL) and stirred for 72 hours at room temperature. The mixture of isomers, obtained from the usual work up, were separated by flash chromatography over silica gel (75 g: dichloromethane-hexane; 4:1). Fractions containing the less polar isomer were evaporated to give 0.197 g of (Z)-5-[2-(2-naphthalenyloxy)ethoxy]-alpha-[(phenylmethoxy)imino]-2-thiopheneacetic acid ethyl ester, mp 140°–141.5° C.

Analysis Calculated for $C_{27}H_{25}NO_5S$: C, 68.18; H, 5.30; N, 2.95; S, 6.74. Found: C, 67.07; H, 5.03; N, 2.78; S, 6.70.

Fractions containing the more polar isomer were evaporated to give 0.152 g of (E)-5-[2-(2-naphthalenyloxy)ethoxy]-alpha-[(phenylmethoxy)imino]-2-thiopheneacetic acid ethyl ester, mp 111°–112° C.

Analysis Calculated for $C_{27}H_{25}NO_5S$: C, 68.18; H, 5.30; N, 2.95; S, 6.74. Found: C, 67.35; H, 5.22; N, 2.81; S, 6.71.

EXAMPLE 315

Preparation of (Z)-5-[2-(2-naphthalenyloxy)ethoxy]-alpha-[(phenylmethoxy)imino]-2-thiopheneacetic acid As in Example 306, a solution of (Z)-5-[2-(2-naphthalenyloxy)ethoxy]-alpha-(phenylmethoxy)imino]-2-thiopheneacetic acid ethyl ester (0.163 g) in methanol (2 mL) and tetrahydrofuran (1 mL) was treated with 4N sodium hydroxide (0.5 mL) and the stirred mixture was heated at 50° C. for 30 minutes. After the normal work up, the product was crystallized from diethyl ether to provide 0.11 g of (Z)-5-[2-(2-naphthalenyloxy)ethoxy]-alpha-[(phenylmethoxy)imino]-2-thiopheneacetic acid, mp 117°–118° C.

Analysis Calculated for $C_{25}H_{21}NO_5S$: C, 67.10; H, 4.73; N, 3.13; S, 7.16. Found: C, 67.03; H, 4.46; N, 3.28; S, 7.33.

EXAMPLE 316

Preparation of (E)-5-[2-(2-naphthalenyloxy)ethoxy]-alpha-[(phenylmethoxy)imino]-2-thiopheneacetic acid As in Example 306, a solution of (E)-5-[2-(2-naphthalenyloxy)ethoxy]-alpha-(phenylmethoxy)imino]-2-thiopheneacetic acid ethyl ester (0.102 g) in methanol (2 mL) and tetrahydrofuran (2 mL) was treated with 4N sodium hydroxide (0.5 mL) and the stirred mixture was heated at 55° C. for 45 minutes. After the normal work up, the product was crystallized from diethyl ether-hexane to furnish 0.063 g of (E)-5-[2-(2-naphthalenyloxy)ethoxy]-alpha-[(phenylmethoxy)imino]-2-thiopheneacetic acid, mp 103°–104° C.

Analysis Calculated for $C_{25}H_{21}NO_5S$: C, 67.10; H, 4.73; N, 3.13; S, 7.16. Found: C, 67.01; H, 4.59; N, 3.17; S, 7.32.

EXAMPLE 317

Preparation of (E)-alpha-[(aminocarbonyl)hydrazono]-4-[2-(2-naphthalenyloxy)ethoxy]benzeneacetic acid methyl ester and (Z)-alpha-[(aminocarbonyl)hydrazono]-4-[2-(2-naphthalenyloxy)ethoxy]benzeneacetic acid methyl ester A mixture of 4-[2-(2-naphthalenyloxy)ethoxy]-alpha-oxobenzeneacetic acid methyl ester (1.75 g) in pyridine (25 mL) was warmed to dissolve and added semicarbazide hydrochloride (0.7 g). The stirred mixture was heated at 50° C. for 4 hours, cooled, acidified with hydrochloric acid and extracted twice with dichloromethane. The organic layers were washed with dilute hydrochloric acid, combined, dried ($Na_2SO_4$), filtered and evaporated to provide a crude mixture of (E) and (Z) isomers. The crude mixture was separated by HPLC (dichloromethane-tetrahydrofuran; 9:1) and the more polar component was crystallized from dichloromethane-methanol to provide 0.6 g of (E)-alpha-[(aminocarbonyl)hydrazono]-4-[2-(2-naphthalenyloxy)ethoxy]benzeneacetic acid methyl ester as a colorless solid, mp 180°–181° C.

Analysis Calculated for $C_{22}H_{21}N_3O_5$: C, 64.86; H, 5.20; N, 10.31. Found: C, 64.72; H, 5.21; N, 10.20.

The less polar component was crystallized from dichloromethane-methanol to provide 0.75 g of (Z)-alpha-[(aminocarbonyl)hydrazono]-4-[2-(2-naphthalenyloxy)ethoxy]benzeneacetic acid methyl ester as a colorless solid, mp 132°–134° C.

Analysis Calculated for $C_{22}H_{21}N_3O_5$: C, 64.86; H, 5.20; N, 10.31. Found: C, 64.60; H, 5.14; N, 10.13.

EXAMPLE 318

Preparation of (E)-alpha-[(aminocarbonyl)hydrazono]-4-[2-(2-naphthalenyloxy)ethoxy]benzeneacetic acid A mixture of (E)-alpha-[(aminocarbonyl)hydrazono]-4-[2-(2-naphthalenyloxy) ethoxy]benzeneacetic acid methyl ester (0.45 g) in warm methanol (3 mL) and tetrahydrofuran (10 mL) was treated with 1N sodium hydroxide (1.25 mL) and after 30 minutes the mixture was diluted with water and concentrated to remove the organic solvents. The residue was acidified with excess hydrochloric acid and extracted with a dichloromethane-tetrahydrofuran mixture. The organic layer was washed with water, dried ($Na_2SO_4$), filtered and evaporated to give crude product. Trituration from dichloromethane provided 0.242 g of pure (E)-alpha-[(aminocarbonyl)hydrazono]- 4-[2-(2-naphthalenyloxy)ethoxy]benzeneacetic acid as a colorless solid, mp 204° C. with decomposition.

Analysis Calculated for $C_{21}H_{19}N_3O_5$: C, 64.12; H, 4.87; N, 10.68. Found: C, 64.11; H, 4.80; N, 10.67.

EXAMPLE 319

Preparation of (E)-alpha-(dimethylhydrazono)-4-[2-(2-naphthalenyloxy)ethoxy]benzeneacetic acid methyl ester and (Z)-alpha-(dimethylhydrazono)-4-[2-(2-naphthalenyloxy)ethoxy]benzeneacetic acid methyl ester A mixture of 4-[2-(2-naphthalenyloxy)ethoxy]-alpha-oxobenzeneacetic acid methyl ester (3.5 g), 1,1-dimethylhydrazine (2.28 mL) in methanol (40 mL), tetrahydrofuran (20 mL) and one drop of glacial acetic acid was refluxed for 48 hours and evaporated to dryness. The crude mixture was separated by HPLC (dichloromethane-ether, 49:1) and the more polar component was crystallized from dichloromethane-methanol to provide 0.9 g of (E)-alpha-(dimethylhydrazono)-4-[2-(2-naphthalenyloxy)ethoxy]benzeneacetic acid methyl ester as a colorless solid, mp 137°–138° C.

Analysis Calculated for $C_{23}H_{24}N_2O_4$: C, 70.39; H, 6.16; N, 7.14. Found: C, 70.27; H, 6.16; N, 7.19.

The less polar component was crystallized from dichloromethane-methanol to provide 0.75 g of (Z)-alpha-(dimethylhydrazono)-4-[2-(2-naphthalenyloxy)ethoxy]benzeneacetic acid methyl ester as a yellow solid, mp 109°–111° C.

Analysis Calculated for $C_{23}H_{24}N_2O_4$: C, 70.39; H, 6.16; N, 7.14. Found: C, 70.27; H, 6.17; N, 7.18.

EXAMPLE 320

Preparation of (E)-alpha-(dimethylhydrazono)-4-[2-(2-naphthalenyloxy)ethoxy]benzeneacetic acid A mixture of (E)-alpha-(dimethylhydrazono)-4-[2-(2-naphthalenyloxy)ethoxy]benzeneacetic acid methyl ester (0.45 g) in warm methanol (3 mL) and tetrahydrofuran (10 mL) was treated with 1N sodium hydroxide (2 mL), heated on the steam bath for one hour, and the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.38 g of pure (E)-alpha-(dimethylhydrazono)-4-[2-(2-naphthalenyloxy)ethoxy]benzeneacetic acid as a colorless solid, mp 135° C. with decomposition.

Analysis Calculated for $C_{22}H_{22}N_2O_4$: C, 69.83; H, 5.86; N, 7.40. Found: C, 69.55; H, 5.90; N, 7.35.

EXAMPLE 321

Preparation of
(Z)-alpha-(dimethylhydrazono)-4-[2-(2-naphthalenyloxy)ethoxy]benzeneacetic acid A mix of (Z)-alpha-(dimethylhydrazono)-4-[2-(2-naphthalenyloxy)ethoxy]benzeneacetic acid methyl ester (0.45 g) in warm methanol (3 mL) and tetrahydrofuran (10 mL) was treated with 1N sodium hydroxide (2 mL), heated on the steam bath for 2 hours, and the mixture was diluted with water and concentrated to remove the organic solvents. The residue was acidified with excess hydrochloric acid and extracted with dichloromethane containing a little tetrahydrofuran. The organic layer was washed with water, dried ($Na_2SO_4$), filtered and evaporated to give crude product. Crystallization from dichloromethane-hexane provided 0.3 g of pure (Z)-alpha-(dimethylhydrazono)-4-[2-(2-naphthalenyloxy)ethoxy]benzeneacetic acid as a colorless solid, mp 136° C. with decomposition.

Analysis Calculated for $C_{22}H_{22}N_2O_4$: C, 69.83; H, 5.86; N, 7.40. Found: C, 69.84; H, 5.74; N, 7.13.

EXAMPLE 322

| Item | TABLET FORMULATION (Wet Granulation) Ingredient | 25 mg | 100 mg | 500 mg | 1000 mg |
|---|---|---|---|---|---|
| 1. | 4-[2-(2-Naphthyloxy)ethoxy]-alpha-oxo-benzeneacetic acid | 25.0 | 100 | 500 | 1000 |
| 2. | Lactose | 143.0 | 132 | — | — |
| 3. | Pregelatinized Starch | 10 | 16 | 30 | 50 |
| 4. | Modified Starch | 20 | 30 | 40 | 50 |
| 5. | Magnesium Stearate | 2 | 2 | 6 | 8 |
|   | Total | 200 | 280 | 576 | 1108 |

Manufacturing Procedure:
1. Mix Items 1, 2, 3 and 4 and granulate with water.
2. Dry the granulation at 50° C.
3. Pass the granulation through suitable milling equipment.
4. Add Item 5 and mix for three minutes; compress on a suitable press.

EXAMPLE 323

| Item | CAPSULE FORMULATION Ingredient | mg/capsule | | | |
|---|---|---|---|---|---|
| 1. | 4-[2-(2-Naphthyloxy)ethoxy]-alpha-oxo-benzeneacetic acid | 25 | 50 | 100 | 500 |
| 2. | Lactose Hydrous | 143 | 168 | 148 | — |
| 3. | Corn Starch | 20 | 20 | 40 | 70 |
| 4. | Talc | 10 | 10 | 10 | 25 |
| 5. | Magnesium Stearate | 2 | 2 | 2 | 5 |
|   | Total | 200 | 250 | 300 | 600 |

Manufacturing Procedure:
1. Mix Items 1, 2 and 3 in a suitable mixer for 30 minutes.
2. Add Items 4 and 5 and mix for 3 minutes.
3. Fill into suitable capsules.

We claim:
1. A compound of the formula

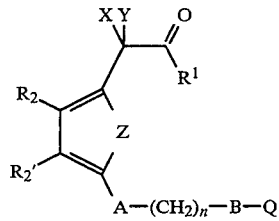

wherein
$R_1$ hydroxy;
$R_2$ and $R_2'$, independently, are hydrogen, alkyl, aryl, alkoxy, hydroxy, halogen, alkanoyl, aroyl or nitro;
A is a bond,

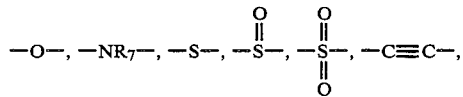

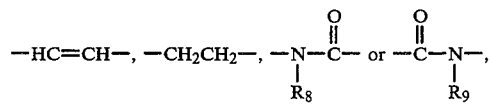

wherein
$R_7$ is hydrogen, lower alkyl or acyl and $R_8$ and $R_9$ are, independently, hydrogen or lower alkyl;
B is a bond;

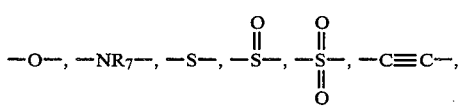

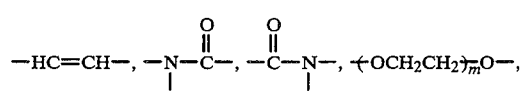

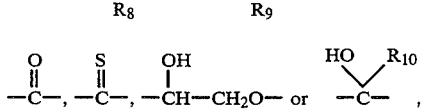

wherein
m is an integer from 1 to 4 and $R_7$, $R_8$, $R_9$ are as described above and $R_{10}$ is hydrogen;
n is an integer from 1 to 6, with the proviso that when A and B are, independently, a bond, $$-O-, -NR_7-, -S-, -\overset{O}{\underset{O}{\overset{\|}{S}}}-, -\overset{O}{\overset{\|}{N-C}}-, -\overset{O}{\overset{\|}{C-N}}-,$$
$$\phantom{-O-, -NR_7-, -S-, -\overset{O}{\underset{O}{\overset{\|}{S}}}-,} \underset{R_8}{} \phantom{-} \underset{R_9}{}$$

then n is an integer from 2 to 6;

Z is —S—, —CR$_2$≡CR$_2$—;

X and Y taken together are O=, or when one of X or Y is amino the other is hydrogen;

Q is phenyl, cyclohexyl, cyclooctyl, pyridinyl, adamantyl, 1,'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups, lower alkyl, alkoxy, acyloxy, halogen, acyloxyalkyl, alkoxyalkyl, aryloxyalkoxy, hytdroxy, hydroxyalkyl, hydroxyalkoxy, phenyl, trihaloalkyl, sulfamoyl, carboxycarbonyl or alkoxaylyl; or when a basic or acidic group is present, its pharmaceutically acceptable salt, and, when appropriate, its enantiometer, racemate, diastereomer or mixture thereof or geometric isomer or mixture thereof, or a pharmaceutically acceptable salt thereof.

2. A compound in accordance with claim 1, wherein R$_1$ is as previously described;

R$_2$ and R$_2'$, independently, are hydrogen, alkyl, alkoxy, hydroxy or halogen;

A is a bond, $$-O-, -NR_7-, -S-, -\overset{O}{\overset{\|}{S}}-, -\overset{O}{\underset{O}{\overset{\|}{S}}}-, -C\equiv C-,$$

$$-HC=CH-, -CH_2CH_2-, -\overset{O}{\underset{R_8}{\overset{\|}{N-C}}}- \text{ or } -\overset{O}{\underset{R_9}{\overset{\|}{C-N}}}-,$$

wherein R$_7$ is hydrogen or lower alkyl and R$_8$ and R$_9$ are hydrogen;

B is a bond, $$-O-, -S-, -C\equiv C-, -HC=CH-, -\overset{O}{\underset{R_8}{\overset{\|}{N-C}}}-,$$

$$\text{(OCH}_2\text{CH}_2\text{)}_{\overline{m}} \text{ or } -\overset{O}{\overset{\|}{C}}-,$$

wherein m is a 1 or 2 and R$_8$ is hydrogen;

n is an integer from 1 to 6, with the proviso that when A and B are, independently, a bond $$-O-, -NR_7-, -S-, -\overset{O}{\overset{\|}{S}}-, -\overset{O}{\underset{O}{\overset{\|}{S}}}-,$$

-continued
$$-\overset{O}{\underset{R_8}{\overset{\|}{N-C}}}- \text{ or } -\overset{O}{\underset{R_9}{\overset{\|}{C-N}}}-,$$

then n is an integer from 2 to 6;

Z is —S—, or —CR$_2$=CR$_2'$—;

X and Y taken together are O=, or when one of X or Y is amino, the other is hydrogen; Q is phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups, lower alkyl, alkoxy, acyloxy, halogen, acyloxyalkyl, alkoxyalkyl, aryloxyalkoxy, hydroxyl, hydroxyalkyl, hydroxyalkoxy, phenyl, trihaloalkyl, sulfamoyl, carboxycarbonyl or alkoxyalyl.

3. A compound in accordance with claim 1, wherein R$_1$ is hydrogen

R$_2$ is hydrogen;

A is —O—, —NR$_7$= or —S—, wherein R$_7$ is hydrogen;

B is a bond, $$-O-, -S-, -C\equiv C-, -HC=CH-, -\overset{O}{\underset{R_8}{\overset{\|}{N-C}}}- \text{ or } -\overset{O}{\overset{\|}{C}}-,$$

wherein R$_8$ is hydrogen;

n is an integer from 1 to 4, with the proviso that when B is a bond, $$-O-, -S-, \text{ or } -\overset{O}{\underset{R_8}{\overset{\|}{N-C}}}-,$$

then n is an integer from 2 to 4;

Z is —S—, or —CR$_2$=CR$_2'$—;

X and Y taken together are O=, or when one of X or Y is amino, the other is hydrogen;

Q is phenyl, cyclohexyl, cyclooctyl, adamantyl, anthracenyl, phenanthrenyl, naphthalenyl, 5,6,7,8-tetrahydro-1-naphthalenyl, 5,7,8-tetrahydro-2-naphthalenyl, 1,2,3,4-tetrahydro-1-naphthalenyl, 1,2,3,4-tetrahydro-2-naphthalenyl, quinolyl, isoquinolyl, of which phenyl or naphthalenyl can be substituted by one or more of the groups lower alkyl, phenyl, acyloxy, acyloxyalkyl or hydroxyalkyl.

4. A compound, in accordance with claim 1, (S)-alpha-amino-4-[[2-(cyclooctyloxy)ethyl]oxy]benzeneacetic acid hydrochloride.

5. A compound, in accordance with claim 1, 3-fluoro-4-[2-(2-naphthalenyloxy)ethoxy]-alpha-oxobenzeneacetic acid.

6. A compound, in accordance with claim 1, 4-[2-(1-naphthalenyl)-2-oxoethoxy]-alpha-oxobenzeneacetiac acid.

7. A compound, in accordance with claim 1 (E)-4-[3-[2-[(2,2-dimethyl-1-oxobutoxy)methyl]-6-methylphenyl]-2-propenyloxy]-alpha-oxobenzeneacetic acid (1:1) morpholine salt.

8. A compound, in accordance with claim 1, 4-[[2-(2-naphthalenyloxy)ethyl]oxy]-alpha-oxobenzeneacetic acid.

9. A compound, in accordance with claim 2, 4-[[2-(2-(2-naphthalenyloxy)ethyl]thio]-alpha-oxobenzeneacetic acid.

10. A compound, in accordance with claim 1, 4-[[2-(2-naphthalenylthio)ethyl]oxy]-alpha-oxobenzeneacetic acid.

11. A compound, in accordance with claim 1, 4-[[2-cyclooctyloxy)ethyl]oxy]-alpha-oxobenzeneacetic acid.

12. A compound, in accordance with claim 1, 4-[3-(4-acetyl-3-hydroxy-2-propylphenoxy)proproxy]-alpha-oxobenzeneacetic acid.

13. A compound, in accordance with claim 1, 5-[[2-(2-naphthalenyloxy)ethyl]oxo]-alpha-oxo-2-thiopheneacetic acid.

14. A compound, in accordance with claim 1, alpha-oxo-4-[[2-(phenoxy)ethyl]oxyl]benzeneacetic acid.

15. A compound, in accordance with claim 1, rac.-5-[[2-(2-naphthalenyloxy)ethyl]oxy]-alpha-oxo-2-thiopheneacetic acid 2,3-dihydroxypropyl ester.

16. A compound, in accordance with claim 1, (S)-alpha-amino-4-[2-[2-[(2,2-dimethyl-1-oxobutoxy)methyl]-6-methylphenoxy]-ethoxy]benzeneacetic acid.

17. A compound, in accordance with claim 1, (E)-4-[[3-(2-naphthalenyl)-2-propenyl]oxy]-alpha-oxobenzeneacetic acid.

18. A compound, in accordance with claim 1, 4-[[-2-[2-[(2,2-dimethyl-1-oxobutoxy)methyl]-6-methylphenoxy]ethyl]oxy]-alpha-oxobenzeneacetiac acid (2:1) hydrate.

19. A compound, in accordance with claim 1, 4-[[4-(2-naphthalenyloxy)butyl]oxy]-alpha-oxobenzeneacetic acid.

20. A pharmaceutical composition comprising a therapeutically effective amount of a compound of the formula

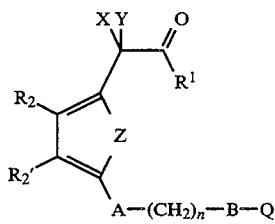

I wherein
R<sub>1</sub> is hydroxy;
R<sub>2</sub> and R<sub>2</sub>', independently, are hydrogen, alkyl, aryl, alkoxy, hydroxy, halogen, alkanoxyl, aroyl or nitro;
A is a bond,

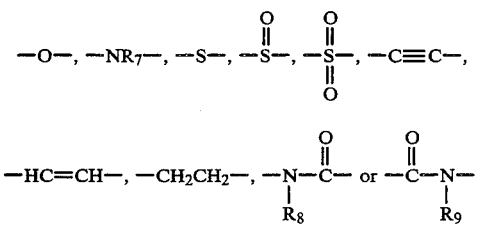

wherein
R<sub>7</sub> is hydrogen, lower alkyl or acyl and R<sub>8</sub> and R<sub>9</sub> are, independently, hydrogen or lower alkyl;
B is a bond;

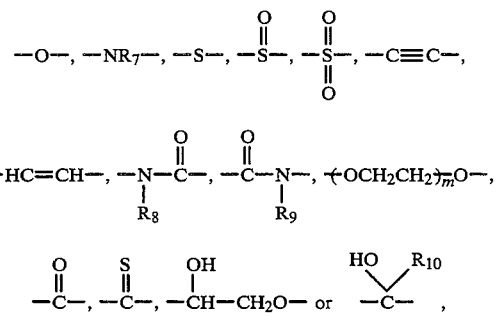

wherein m is an integer from 1 to 4 and R$_7$, R$_8$, R$_9$ are as described above and R$_{10}$ is hydrogen;
n is an integer from 1 to 6, with the proviso that when A and B are, independently, a bond,

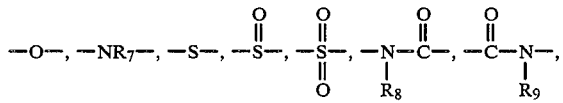

then n is an integer from 2 to 6;
Z is —S—, —CR$_2$=CR$_2$—;
X and Y taken together are O=, or when one of X or Y is amino, the other is hydrogen;
Q is phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups, lower alkyl, alkoxy, acyloxy, halogen, acyloxyalkyl, alkoxyalkyl, aryloxyalkoxy, hydroxy, hydroxyalkyl, hydroxyalkoxy, phenyl, trihaloalkyl, sulfamoyl, carboxycarbonyl or alkoxyalyl; or
when a basic or acidic group is present, its pharmaceutically acceptable salt, and, when appropriate, its enantiomer, racemate, diastereomer or mixture thereof or geometric isomer or mixture thereof, or a pharmaceutically acceptable salt thereof.

21. A pharmaceutical composition in accordance with claim 20, wherein
R$_1$ is as previously described;
R$_2$ and R$_2$', independently, are hydrogen, alkyl, alkoxy, hydroxy or halogen;
A is a bond;

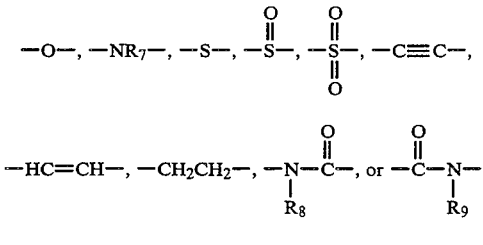

wherein R$_7$ is hydrogen or lower alkyl and R$_8$ and R$_9$ are hydrogen;
B is a bond,

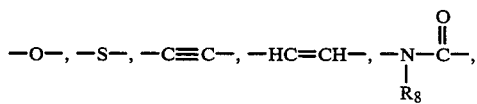

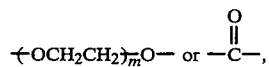

wherein m is 1 or 2 and $R_8$ is hydrogen;
n is an integer from 1 to 6, with the proviso that when A and B are, independently a bond,

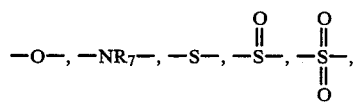

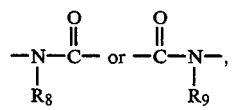

then n is an integer from 2 to 6;
Z is —S—, or —$CR_2$=$CR_2'$—; X and Y taken together is O=, or when one of X or Y is amino, the other is hydrogen; Q is phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups, lower alkyl, alkoxy, acyloxy, halogen, acyloxyalkyl, alkoxyalkyl, aryloxyalkoxy, hydroxy, hydroxyalkyl, hydroxyalkoxy, phenyl, trihaloalkyl, sulfamoyl, carboxycarbonyl or alkoxalyl.

22. A pharmaceutical composition in accordance with claim 20, wherein
$R_1$ is hydroxy
$R_2$ is hydrogen; A is

wherein $R_7$ is hydrogen; B is a bond,

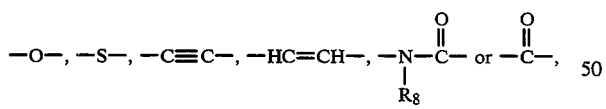

wherein $R_8$ is hydrogen;
n is an integer from 1 to 4, with proviso that when B is a bond,

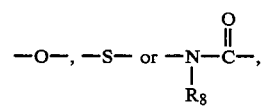

then n is an integer from 2 to 4;
Z is —S—, or —$CR_2$=$CR_2'$—;
X and Y taken together are O=, or when one of X or Y is amino, the other is hydrogen; Q is phenyl, cyclohexyl, cyclooctyl, adamantyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, of which phenyl or naphthalenyl can be substituted by one or more of the groups lower alkyl, phenyl, acyloxy, acyloxyalkyl or hydroxyalkyl.

23. A pharmaceutical composition in accordance with claim 20, (S)-alpha-amino-4-[[2-(cyclooctyloxy)ethyl]oxy]benzeneacetic acid hydrochloride.

24. A pharmaceutical composition in accordance with claim 20, 4-[[2-(2-naphthalenyloxy)ethyl]oxy]-alpha-oxobenzeneacetic acid.

25. A pharmaceutical composition in accordance with claim 20, 4-[2-(1-naphthalenyl)-2-oxoethoxy]-alpha-oxobenzeneacetic acid.

26. A pharmaceutical composition in accordance with claim 20, 4-[[2-(2-naphthalenyloxy)ethyl]thio]-alpha-oxobenzeneacetic acid.

27. A pharmaceutical composition in accordance with claim 20, 4-[[2-[2-[2,2-dimethyl-1-oxobutoxy)methyl]-6-methylphenoxy]ethyl]oxy]-alpha-oxobenzeneacetic acid (2:1) hydrate.

28. A pharmaceutical composition in accordance with claim 20, 4-[[5-(2-naphthalenyloxy)ethyl]oxy]-alpha-oxo-2-thiophenacetic acid.

29. A method of inhibiting carnitine acryltransferase in a host which comprises administering to such a host an effective amount of a compound of the formula

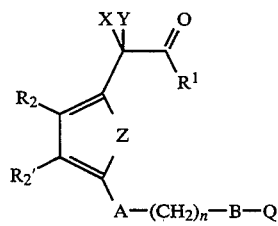

wherein $R_1$ is hydroxy,
$R_2$ and $R_2'$, independently, are is hydrogen, lower alkyl, aryl, aryl-lower alkyl, lower alkoxy, hydroxy, amino, lower alkylamino, di-lower alkylamino, cyano, halogen, mercapto, lower alkylthio, lower alkylsulfinyl, lower alkylsulfonyl, trihalo-lower alkyl, acyl or nitro;
A is a bond,

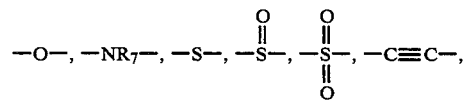

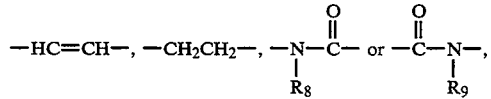

'wherein $R_7$ is hydrogen, lower alkyl or acyl and $R_8$ and $R_9$ are, independently, hydrogen or lower alkyl; n is an integer from 0 to 10;
B is a bond,

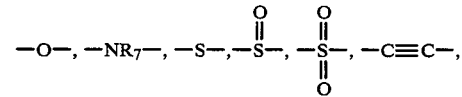

-continued

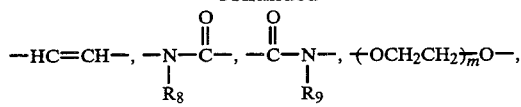

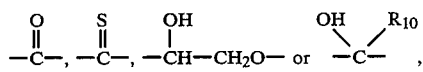

wherein m is an integer from 1 to 4 and $R_7$, $R_8$, $R_9$ are as described above and $R_{10}$ is hydrogen or lower alkyl;

Z is

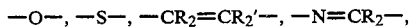

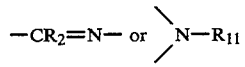

wherein $R_{11}$ is hydrogen or lower alkyl;

X and Y taken together are O=, S=, or when one of X or Y is amino, lower-alkylamino or di-lower alkylamino, the other is hydrogen, lower alkyl or aryl-lower alkyl; Q is a cycloalkyl, aryl or heterocyclic radical; provided that, when A is oxygen (O) and B is a bond, sulfur (S) or oxygen (O), then n is 2–10; or, when a basic or acidic group is present, its pharmaceutically acceptable salt, and when appropriate, its enantiomer, racemate, diastereomer or mixture thereof or geometric isomer or mixture thereof, or a pharmaceutically acceptable salt thereof.

30. A method in accordance with claim 29, wherein $R_2$ and $R_2'$, independently, are hydrogen, alkyl, aryl, alkoxy, hydroxy, halogen, alkanoyl, aroyl or nitro;

A is a bond,

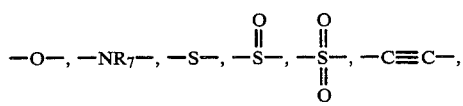

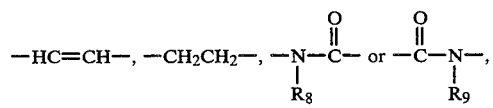

wherein $R_7$ is hydrogen, lower alkyl or acyl and $R_8$ and $R_9$ are independently hydrogen or lower alkyl;

B is a bond,

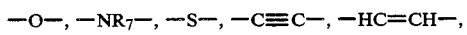

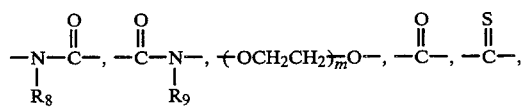

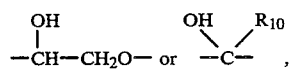

$R_{10}$ is hydrogen;

n is an integer from 1 to 6, with the proviso that when A and B are, independently a bond,

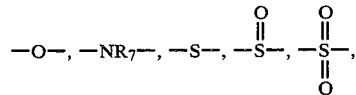

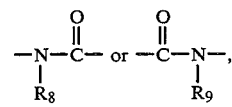

then n is an integer from 2 to 6;

Z is —S—, —$CR_2$=$CR_2'$—;

X and Y taken together are O=, or when one of X or Y is amino, the other is hydrogen; Q is phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-tetrahydro-2-naphthalenyl, quinolyl, isoquinolyl, which radical can be substituted by one or more of the following groups, lower alkyl, alkoxy, acyloxy, halogen, acyloxyalkyl, alkoxyalkyl, aryloxyalkoxy, hydroxy, hydroxyalkyl, hydroxyalkoxy, phenyl, trihaloalkyl, sulfamoyl, carboxycarbonyl or alkoxalyl.

31. A method in accordance with claim 29, wherein $R_1$ is as previously described, $R_2$ and $R_2'$, independently are, hydrogen, alkyl, alkoxy, hydroxy or halogen;

A is a bond,

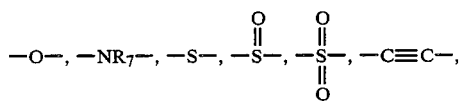

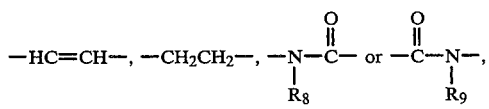

wherein $R_7$ is hydrogen or lower alkyl and $R_8$ and $R_9$ are, independently, hydrogen;

B is a bond,

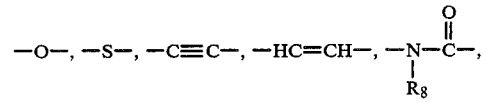

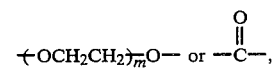

wherein m is 1 or 2 and $R_8$ is hydrogen;
n is a integer from 1 to 6, with the proviso that when A and B are, independently a bond,

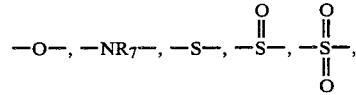

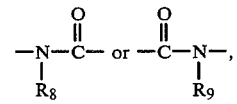

then n is an integer from 2 to 6;

Z is —S—, or —CR$_2$=CR$_2'$—;

X and Y taken together are O=, or when one of X or Y is amino, the other is hydrogen; Q is phenyl, cyclohexyl, cyclooctyl, pyridinyl, adamantyl, 1,1'-biphenyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, which radical can be substituted by one or more of the following groups, lower alkyl, alkoxy acyloxy, halogen, acyloxyalkyl, alkoxyalkyl, aryloxyalkoxy, hydroxy, hydroxyalkyl, hydroxyalkoxy, phenyl, trihaloalkyl, sulfamoyl, carboxycarbonyl or alkoxalyl.

32. A method in accordance with claim 29, wherein R$_1$ is hydroxy;

R$_2$ is hydrogen; A is —O—, —NR$_7$—, —S—, wherein R$_7$ is hydrogen;

B is a bond,

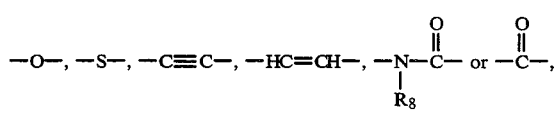

wherein R$_8$ is hydrogen;

n is an integer from 1 to 4, with the proviso that when B is a bond,

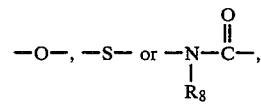

then n is an integer from 2 to 4;

Z is —S—, or —CR$_2$=CR$_2'$—;

X and Y taken together are O=, or when one of X or Y is amino, the other is hydrogen; Q is phenyl, cyclohexyl, cyclooctyl, adamantyl, anthracenyl, phenanthrenyl, naphthalenyl, 5,6,7,8-tetrahydro-1-naphthalenyl, 5,6,7,8-tetrahydro-2-naphthalenyl, 1,2,3,4-tetrahydro-1-naphthalenyl, 1,2,3,4-tetrahydro-2-naphthalenyl, quinolyl, isoquinolyl, of which phenyl or naphthalenyl can be substituted by one or more of the groups lower alkyl, phenyl, acyloxyalkyl or hydroxyalkyl.

33. A method in accordance with claim 29, (S)-alpha-amino-4-[[2-(cyclooctyloxy)ethyl]oxy]benzeneacetic acid hydrochloride.

34. A method in accordance with claim 29, 4-[[2-(2-naphthalenyloxy)ethyl]oxy]-alpha-oxobenzeneacetic acid.

35. A method in accordance with claim 29, 4-[2-(1-naphthalenyl)-2-oxoethoxy]-alpha-oxobenzeneacetic acid.

36. A method in accordance with claim 29, 4-[[-2-(2-naphthalenyloxy)ethyl]thio]-alpha-oxobenzeneacetic acid.

37. A method in accordance with claim 29, 4-[[-2-[2-[(2,2-dimethyl-1-oxobutoxy)methyl]-6-methylphenoxy]ethyl]oxy]-alpha-oxobenzeneacetic acid (2:1) hydrate.

38. A method in accordance with claim 29, 4-[[5-(2-naphthalenyloxy)ethyl]oxy]-alpha-oxo-2-thiophenacetic acid.

* * * * *

UNITED STATES PATENT AND TRADEMARK OFFICE
CERTIFICATE OF CORRECTION

PATENT NO. : 5,344,843
DATED : September 6, 1994
INVENTOR(S) : Guthrie, et al.

It is certified that error appears in the above-indentified patent and that said Letters Patent is hereby corrected as shown below:

- Claim 1, Column 157, line 14, after "1," insert --1--.

- Claim 3, Column 158, line 24, delete "hydrogen" and insert --- hydroxy ---.

Signed and Sealed this

Twenty-fifth Day of July, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,344,843                          Page 1 of 2

DATED : September 6, 1994

INVENTOR(S) : Guthrie, et al.

It is certified that error appears in the above-identified patent and that said Letters Patent is hereby corrected as shown below:

Claim 1, Column 157, line 9: delete " $-CR_2\equiv CR_2-$ ", insert --- $-CR_2=CR_2-$ ---.

Claim 1, Column 157, line 23: delete "alkoxaylyl", insert --- alkoxalyl ---.

Claim 2, Column 157, line 57: delete "$(-OCH_2CH_2-)_m-$", insert --- $(-OCH_2CH_2-)_m-O-$ ---.

Claim 2, Column 158, line 22: delete "alkoxaylyl", insert --- alkoxalyl ---.

Claim 3, Column 158, line 26: delete "$-NR_7=$", insert --- $-NR_7$ ---.

UNITED STATES PATENT AND TRADEMARK OFFICE
CERTIFICATE OF CORRECTION

PATENT NO. : 5,344,843
DATED : September 6, 1994
INVENTOR(S) : Guthrie, et al.

It is certified that error appears in the above-indentified patent and that said Letters Patent is hereby corrected as shown below:

Claim 20, Column 160, line 43: delete "alkoxyalyl" and insert --- alkoxalyl --- .

Signed and Sealed this

Twenty-third Day of January, 1996

Attest:

BRUCE LEHMAN

Attesting Officer

Commissioner of Patents and Trademarks